United States Patent
Crane et al.

(10) Patent No.: US 11,826,384 B2
(45) Date of Patent: Nov. 28, 2023

(54) GENETIC ENGINEERING OF MACROPHAGES FOR IMMUNOTHERAPY

(71) Applicant: Seattle Children's Hospital, Seattle, WA (US)

(72) Inventors: Courtney Crane, Seattle, WA (US); Michael C. Jensen, Bainbridge Island, WA (US); Kara White Moyes, Seattle, WA (US); Nicole Lieberman, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 542 days.

(21) Appl. No.: 16/694,024

(22) Filed: Nov. 25, 2019

(65) Prior Publication Data
US 2020/0155597 A1 May 21, 2020

Related U.S. Application Data

(63) Continuation of application No. 15/258,887, filed on Sep. 7, 2016, now Pat. No. 10,525,082.
(Continued)

(51) Int. Cl.
*A61K 35/15* (2015.01)
*A61K 35/17* (2015.01)
(Continued)

(52) U.S. Cl.
CPC .............. *A61K 35/15* (2013.01); *A61K 35/17* (2013.01); *C07K 14/47* (2013.01); *C07K 14/521* (2013.01);
(Continued)

(58) Field of Classification Search
CPC ........ A61K 35/15; A61K 35/17; C07K 14/47; C07K 14/56; C07K 14/70503;
(Continued)

(56) References Cited

U.S. PATENT DOCUMENTS 8,323,662 B1* 12/2012 Nicolai .......... A61K 39/001182
  435/320.1
8,883,507 B2 11/2014 Cambier et al.
(Continued)

FOREIGN PATENT DOCUMENTS

WO   WO 2013/040371 A2   3/2013
WO   WO 2014/031687 A1   2/2014
(Continued)

OTHER PUBLICATIONS

Kan et al., "Genetically modified macrophages expressing hypoxia regulated cytochrome P450 and P450 reductase for the treatment of cancer," International Journal of Molecular Medicine (2011) 27:173-180.
(Continued)

*Primary Examiner* — Yan Xiao
(74) *Attorney, Agent, or Firm* — Knobbe, Martens, Olson & Bear LLP

(57) ABSTRACT

Disclosed are methods of making a genetically modified immune cell for modifying a tumor microenvironment (TME) and methods of modifying a tumor microenvironment (TME). In some embodiments, the method can include delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. Methods of modulating the suppression of the immune response in a tumor microenvironment, minimizing the proliferation of tumor and suppressive cells, and increasing the efficiency of an anti-cancer therapy,
(Continued)

anti-infection therapy, antibacterial therapy, anti-viral therapy, or anti-tumoral therapy are also provided.

20 Claims, 132 Drawing Sheets

Specification includes a Sequence Listing.

Related U.S. Application Data

(60) Provisional application No. 62/361,348, filed on Jul. 12, 2016, provisional application No. 62/216,224, filed on Sep. 9, 2015.

(51) Int. Cl.
*C07K 14/47* (2006.01)
*C07K 14/56* (2006.01)
*C12N 9/22* (2006.01)
*C07K 14/52* (2006.01)
*C07K 14/705* (2006.01)
*C12N 5/0786* (2010.01)

(52) U.S. Cl.
CPC ........ *C07K 14/56* (2013.01); *C07K 14/70503* (2013.01); *C12N 5/0645* (2013.01); *C12N 9/22* (2013.01); *C07K 2319/00* (2013.01); *C12N 2510/00* (2013.01); *Y02A 50/30* (2018.01)

(58) Field of Classification Search
CPC .... C07K 2319/00; C12N 5/0645; C12N 9/22; C12N 2510/00
USPC ...................................... 424/130.1
See application file for complete search history.

(56) References Cited

U.S. PATENT DOCUMENTS

| | | |
|---|---|---|
| 9,447,194 B2 | 9/2016 | Jensen |
| 10,781,254 B2 | 9/2020 | Noelle et al. |
| 2001/0007659 A1 | 7/2001 | Wong-Staal et al. |
| 2012/0003220 A1 | 1/2012 | Chen |
| 2013/0309267 A1 | 11/2013 | Simmons et al. |
| 2014/0120622 A1 | 5/2014 | Gregory et al. |
| 2014/0314795 A1 | 10/2014 | Riddell et al. |
| 2015/0050307 A1 | 2/2015 | Nicolai et al. |
| 2017/0166657 A1 | 6/2017 | O'Neill et al. |
| 2018/0244748 A1 | 8/2018 | Gill et al. |

FOREIGN PATENT DOCUMENTS

| | | |
|---|---|---|
| WO | WO 2014/164544 A1 | 10/2014 |
| WO | WO 14/201212 | 12/2014 |
| WO | WO 2015/120363 A1 | 8/2015 |
| WO | WO 2017/044487 A1 | 3/2017 |

OTHER PUBLICATIONS

Nishihara et al., "Increased in vitro and in vivo tumoricidal activity of a macrophage cell line genetically engineered to express IFN-gamma, IL-4, IL-6, or TNF-alpha," Cancer Gene Ther. (1995) 2:113-124.
Satoh et al., "Macrophages Transduced with an adenoviral Vector Expressing Interleukin 12 Suppress Tumor Growth and Metastasis in a Preclinical Metastatic Prostate Cancer Model," Cancer Res. (Nov. 15, 2003) pp. 7853-7860.
Wu et al., "Genetically engineered macrophages expressing IFN-gamma restore alveolar immune function in scid mice," PNAS USA (Dec. 4, 2001) vol. 98, No. 25, pp. 14589-14594.
Bloch et al., Apr. 2013, Gliomas promote immunosuppression through induction of B7-H1 expression in tumor-associated macrophages, Clinical Cancer Research, 19:3165-3175.
Shalem et al., 2014, Genome-scale CRISPR-Cas9 knockout screening in human cells, Science, 343:84-87.
Andreesen et al., 1998, Adoptive immunotherapy of cancer using monocyte-derived macrophages: rationale, current status, and perspectives. J Leukoc Biol, 64:419-426.
Beatty et al., Mar. 25, 2011, CD40 agonists alter tumor stroma and show efficacy against pancreatic carcinoma in mice and humans. Science 331:1612-1616.
Beavis et al., 2016, Reprogramming the tumor microenvironment to enhance adoptive cellular therapy. Semin Immunol, 28:64-72.
Bobadilla et al., 2013, Efficient transduction of myeloid cells an HIV-1-derived lentiviral vector that packages the Vpx accessory protein, Gene Ther, 20:514-520.
Breckpot et al., 2003, Lentivirally transduced dendritic cells as a tool for cancer immunotherapy. J Gene Med, 5:654-667.
Bright et al., 1998, TGF-β inhibits IL-12-induced activation of Jak-STAT pathway in T lymphocytes. J Immunol., 161:1772-1777.
Brown et al., Dec. 1, 2009, Recognition and killing of brain tumor stem-like initiating cells by CD8+ cytolytic T cells. Cancer Res 69(23):8886-8893.
Casucci et al., 2011, Suicide gene therapy to increase the safety of chimeric antigen receptor-redirected T lymphocytes, Journal of Cancer, 2:378-382.
Chang et al., 2014, Toll-like receptor 9 agonist enhances anti-tumor immunity and inhibitis tumor-associated immunosuppressive cells numbers in a mouse cervical cancer model following recombinant lipoprotein therapy. Mol Cancer, 13:60.
Chavez et al., Apr. 2015, Highly efficient Cas9-mediated transciptional programming, Nature Methods, 12(4):326-330.
Chinnasamy et al., Sep. 1, 2000, Efficient gene transfer to human peripheral blood monocyte-derived dendritic cells using human immunodeficiency virus type 1-based lentiviral ventors. Hum Gene Ther, 11:1901-1909.
Choi et al., Apr. 2013, A novel bispecific antibody recruits T cells to eradicate tumors in the "immunologically privileged" central nervous system. Oncoimmunology, 2:e23639.
Chow et al., Mar. 2013, T cells redirected to EphA2 for the immunotherapy of glioblastoma. Mol Ther 21(3):629-637.
Cire et al., 2014, Immunization of mice with lentiviral vectors targeted to MHC class II+ cells is due to preferential transduction of dendritic cells in vivo. PLoS One, 9(7):e101644.
Crane et al., 2010, TGF-β downregulates the activating receptor NKG2D on NK cells and CD8+ T cells in glioma patients. Neuro Oncol, 12(1):7-13.
Crane et al., Aug. 7, 2012, Individual patient-specific immunity against high-grade glioma after vaccination with autologous tumor derived peptides bound to the 96 KD chaperone protein. Clin Cancer Res, 19:205-214.
Croce et al., 2015, IL-21: a pleiotropic cytokine with potential applications in oncology. J Immunol Res, 2015:696578, 15 pp.
Dunn et al., 2002, Cancer immunoediting: from immunosurveillance to tumor escape. Nat Immunol 3:991-998.
El Andaloussi et al., 2006, Stimulation of TLR9 with CpG ODN enhances apoptosis of glioma and prolongs the survival of mice with experimental brain tumors. GLIA, 54:526-535.
Escobar et al., Apr. 2014, Engineered tumor-infiltrating macrophages as gene delivery vehicles for interferon-alpha activates immunity and inhibits breast cancer progression. Oncoimmunology 3:e28696.
Fidler, May 1974, Inhibition of pulmonary metastasis by intravenous injection of specifically activated macrophages. Cancer Res 34:1074-1078.
Firat et al., 2002, Use of a lentiviral flap vector for induction of CTL immunity against melanoma. Perspectives for immunotherapy. J Gene Med, 4:38-45.
Glass et al., 2014, CNS macrophages and peripheral myeloid cells in brain tumours. Acta Neuropathol, 128:347-362.
Gorelik et a., 2001, Immune-mediated eradication of tumors through the blockade of transforming growth factor-β signaling in T cells. Nat Med 7(10):1118-1122.

(56) References Cited

OTHER PUBLICATIONS

Goyvaerts et al. 2012, Development of the Nanobody display technology to target lentiviral vectors to antigen-presenting cells. Gene Ther 19:1133-1140.

Grupp et al., 2013, Chimeric antigen receptor-modified T cells for acute lymphoid leukemia. N Engl J Med 368:1509-1518.

Hagemann et al., 2008, "Re-educating" tumor-associated macrophages by targeting NF-kappaβ. J Exp Med 205(6):1261-1268.

Hao et al., 2012, Macrophages in tumor microenvironments and the progression of tumors. Clin Dev Immunol 2012:948098, 11 pp.

Hegde et al., Nov. 2013, Combinational targeting offsets antigen escape and enhances effector functions of adoptively transferred T cells in glioblastoma. Mol Ther 21(11):2087-2101.

Huang et al., 2016, Targeted delivery of let-7b to reprogramme tumor-associated macrophages and tumor infiltrating dendritic cells for tumor rejection. Biomaterials, 90:72-84.

Kahlon et al., Dec. 15, 2004, Specific recognition and killing glioblastoma multiforme by interleukin 13-zetakine redirected cytolytic T cells. Cancer Res 64:9160-9166.

Kaiser et al., 2015, Towards a commercial process for the manufacture of genetically modified T cells for therapy. Cancer Gene Ther 22:72-78.

Kantoff et al., Jul. 29, 2010, Sipuleucel-T immunotherapy for castration-resistant prostate cancer. N Engl J Med 363(5):411-422.

Kees et al., 2012, Microglia isolated from patients with glioma gain antitumor activities on poly (I:C) stimulation. Neuro Oncol 14(1):64-78.

Kloepper et al., Apr. 19, 2016, Ang-2/VEGF bispecific antibody reprograms macrophages and resident microglia to anti-tumor phenotype and prolongs glioblastoma survival. Proc Natl Acad Sci U S A 113(16):4476-4481.

Kontermann et al., Dec. 2011, Strategies for extended serum half-life of protein therapeutics, Current Opinion in Biotechnology, 22(6):868-876.

Kostianovsky et al., 2008, Astrocytic regulation of human monocytic/microglial activation. J Immunol 181:5425-5432.

Krenciute et al., Feb. 2016, Characterization and Functional Analysis of scFv-based Chimeric Antigen Receptors to Redirect T Cells to IL13Ralpha2-positive Glioma. Mol Ther 24(2):354-363.

Lahouassa et al., Mar. 2012, SAMHD1 restricts the replication of human immunodeficiency virus type 1 by depleting the intracellular pool of deoxynucleoside triphosphates. Nat Immunol 13(3):223-228.

Langers et al., Apr. 4, 2012, Natural killer cells: role in local tumor growth and metastasis. Biologics: Targets & Therapy 6:73-82.

Lemaigre et al., 1994, Transcriptional control of genes that regulate glycolysis and gluconeogenesis in adult liver, Biochem. J. 303:1-14.

Lin et al., Feb. 26, 2008, PD-1/PD-L1 complex resembles the antigen-binding Fv domains of antibodies and T-cell receptors, Proc Natl Acad Sci U S A. 105(8):3011-3016.

Loeken et al., 1993, Effects of mutation of the CREB binding site of the somatostatin promoter on cyclic AMP responsiveness in CV-1 cells, Gene Expr. 3(3):253-264.

Long et al., Dec. 2013, Harnessing the antitumor potential of macrophages for cancer immunotherapy. Oncoimmunology 2(12):e26860.

McComb et al., 2016, Activation of concurrent apoptosis and necroptosis by SMAC mimetics for the treatment of refractory and relapsed ALL. Sci Transl Med, 8:339ra370 and Supplementary Information.

McGehee et al., 1993, Differentiation-specific element: a cis-acting developmental switch required for the sustained transcriptional expression of the angiotensinogen gene during hormonal-included differentiation of 3T3-L1 fibroblasts to adipocytes, Mol. Endocrinol. 7(4):551-560.

Miao et al., 2014, EGFRvIII-specific chimeric antigen receptor T cells migrate to and kill tumor deposits infiltrating the brain parenchyma in an invasive xenograft model of glioblastoma. PLoS One 9(4):e94281.

Omuro et al., 2013, Glioblastoma and other malignant gliomas: a clinical review. JAMA, 310:1842-1850.

O'Reilly et al., Oct. 5, 1992, Identification of an activating transcription factor (ATF) binding site in the human transforming growth factor-β2 promoter, J. Biol. Chem. 267(28):19938.

Peng et al., 2013, Inhibition of TGF-β signaling in combination with TLR7 ligation re-programs a tumoricidal phenotype in tumor-associated macrophages. Cancer Lett, 331:239-249.

Peng et al., Mar. 30, 2004, TGF-β regulates in vivo expansion of Foxp3-expressing CD4+CD25+ regulatory T cells responsible for protection against diabetes. Proc Natl Acad Sci U S A 101(13):4572-4577.

Pyonteck et al., 2013, CSF-1R inhibition alters macrophage polarization and blocks glioma progression. Nat Med, 19:1264-1272 and Supplementary Information.

Qiu et al., 2004, Mutation detection using Surveyor nuclease. Biotechniques 36(4):702-707.

Ran et al., 2013, Genome engineering using the CRISPR-Cas9 system. Nat Protoc 8(11):2281-2308.

Ransohoff et al., 2012, The anatomical and cellular basis of immune surveillance in the central nervous system. Nat Rev Immunol, 12:623-635.

Razavi et al.,Mar. 2, 2016, Immune Evasion Strategies of Glioblastoma. Front Surg 3(11):1-9.

Ries et al., Jun. 16, 2014, Targeting tumor-associated macrophages with anti-CSF-1R antibody reveals a strategy for cancer therapy. Cancer Cell 25:846-859.

Rowland-Goldsmith et al., Sep. 2001, Soluble type II transforming growth factorβ (TGF-β) receptor inhibits TGF-β signaling in COLO-357 pancreatic cancer cells in vitro and attenuates tumor formation. Clin Cancer Res 7:2931-2940.

Sanjana et al., Aug. 2014, Improved vectors and genome-wide libraries for CRISPR sceening. Nat Methods 11(9):783-784.

Sato et al., 1997, Regulation of B lymphocyte development and activation by the CD19/CD21/CD81/Leu13 complex requires the cytoplasmic domain of CD19. J Immunol, 159:3278-3287.

Schlapschy et al., Aug. 2013, PASylation: a biological alternative to PEGylation for extending the plasma half-life of pharmaceutically active protiens, Protein Eng Des Sel. 26(8):489-501.

Schulte et al., 2008, Use of albumin fusion technology to prolong the half-life of recombinant factor VIIa, Thrombosis Research 122(Suppl 4):S14-S19.

Shalem et al., 2014, Genome-scale CRISPR-Cas9 knockout screening in human cells. Science, 343:84-87 and Supplementary Materials.

Shiina et al., Jan. 2016, CAR T Cells Targeting Podoplanin Reduce Orthotopic Glioblastomas in Mouse Brains. Cancer Immunol Res 4:259-268.

Sica et al., Jan. 15, 2000, Autocrine production of IL-10 mediates defective IL-12 production and NF-kappa B activation in tumor-associated macrophages. J Immunol. 164(2):762-767.

Skak et al., 2007, Interleukin-21 activates human natural killer cells and modulates their surface receptor expression, Immunology 123:575-583.

Smyth et al., 1991, Regulation of lymphokine-activated killer activity and pore-forming protein gene expression in human peripheral blood CD8+ T lymphocytes. Inhibition by transforming growth factorβ. J Immunol, 146:3289-3297.

Spadaro et al., 2014, Recombinant human lactoferrin induces human and mouse dendritic cell maturation via Toll-like receptors 2 and 4. FASEB J 28:416-429.

Spolski et al., May 2014, Interleukin-21: a double-edged sword with therapeutic potential. Nat Rev Drug Discov 13:379-395.

Strebel et al., Dec. 2013, HIV Accessory Proteins versus Host Restriction Factors, Curr Opin Virol. 3(6):692-699.

Sunseri et al., Jul. 2011, Human immunodeficiency virus type 1 modified to package Simian immunodeficiency virus Vpx efficiently infects macrophages and dentritic cells. J Virol 85(13):6263-6274.

Suryadevara et al., Nov. 1, 2016, Immunotherapy gone viral: Bortezomib and oHSV enhance antitumor NK cell activity. Clin Cancer Res 22(21):5164-5166.

Treisman et al., 1990, The SRE: a growth factor responsive transcriptional regulator, Seminars in Cancer Biol. 1:47-58.

(56) References Cited

OTHER PUBLICATIONS

Van der Jeught et al., 2015, Targeting the tumor microenvironment to enhance antitumor immune responses. Oncotarget 6(3):1359-1381.
Wang et al., Aug. 4, 2011, A transgene-encoded cell surface polypeptide for selection, in vivo tracking, and ablation of engineering cells. Blood 118(5):1255-1263.
Watson et al., eds., 1987, Molecular Biology of the Gene, 4th ed. The Benjamin/Cummings Publishing Company, Inc., Menlo Park, California.
Xagorari et al., 2008, Toll-like receptors and viruses: induction of innate antiviral immune responses. Open Microbiol J, 2:49-59.
Xu et al., 2015, Intratumoral Delivery of IL-21 Overcomes Anti-Her2/Neu Resistance through Shifting Tumor-Associated Macrophages from M2 to M1 Phenotype. J Immunol 194:4997-5006.
Yam et al., Apr. 2002, Design of HIV vectors for efficient gene delivery into human hematopoietic cells. Mol Ther 5(4):479-484.
Ye et al., Oct. 15, 1994, Characterization of a silencer regulatory element in the human interferon-γ promoter, J. Biol. Chem. 269(41):25728.
Yee et al., Sep. 1994, A general method for the generation of high-titer, pantropic retroviral vectors: highly efficient infection of primary hepatocytes. Proc Natl Acad Sci U S A 91:9564-9568.
Yu et al., 2015, Toll-like receptor 4 mediates the antitumor host response induced by Ganoderma atrum polysaccharide. J Agric Food Chem, 63:517-525.
Bobadilla et al., 2013, Efficient transduction of myeloid cells by an HIV-1-derived lentiviral vector that packages the Vpx accessory protein, Gene Therapy, 20:514-520.

\* cited by examiner

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Guide sequence for IL-10

<400> SEQUENCE: 1
tgttgcctgg tcctcctgac                                                   20

<210> SEQ ID NO 2
<211> LENGTH: 20
<212> TYPE: DNA
<213> ORGANISM: Artificial Sequence
<220> FEATURE:
<223> OTHER INFORMATION: Guide sequence for PD-L1

<400> SEQUENCE: 2
tccagatgac ttcggccttg                                                   20

<210> SEQ ID NO 3
<211> LENGTH: 29
<212> TYPE: DNA
<213> ORGANISM: Artificial Sequence
<220> FEATURE:
<223> OTHER INFORMATION: IL-10 PCR primer forward

<400> SEQUENCE: 3
agagaggtag cccatcctaa aaatagctg                                         29

<210> SEQ ID NO 4
<211> LENGTH: 28
<212> TYPE: DNA
<213> ORGANISM: Artificial Sequence
<220> FEATURE:
<223> OTHER INFORMATION: IL-10 PCR primer reverse
```

-continued

```
<400> SEQUENCE: 4
gcaggtttcc tgcacattta ctgtatca                                        28

<210> SEQ ID NO 5
<211> LENGTH: 28
<212> TYPE: DNA
<213> ORGANISM: Artificial Sequence
<220> FEATURE:
<223> OTHER INFORMATION: PD-L1 PCR primer forward

<400> SEQUENCE: 5
ttgaattgaa ttgaggcaga gctagcag                                        28

<210> SEQ ID NO 6
<211> LENGTH: 28
<212> TYPE: DNA
<213> ORGANISM: Artificial Sequence
<220> FEATURE:
<223> OTHER INFORMATION: PD-L1 PCR primer reverse

<400> SEQUENCE: 6
atatggtttg gatgaatgga ggtgagga                                        28

<210> SEQ ID NO 7
<211> LENGTH: 76
<212> TYPE: PRT
<213> ORGANISM: Artificial Sequence
<220> FEATURE:
<223> OTHER INFORMATION: Guide PD-L1 protein fragment comprises amino
      acids 62-136

<400> SEQUENCE: 7
```

Lys Asn Ile Ile Gln Phe Val His Gly Glu Glu Asp Leu Lys Val Gln
1               5                   10                  15

His Ser Ser Tyr Arg Gln Arg Ala Arg Leu Leu Lys Asp Gln Leu Ser
            20                  25                  30

Leu Gly Asn Ala Ala Leu Gln Ile Thr Asp Val Lys Leu Gln Asp Ala
        35                  40                  45

Gly Val Tyr Arg Cys Met Ile Ser Tyr Gly Gly Ala Asp Tyr Lys Arg
    50                  55                  60

Ile Thr Val Lys Val Asn Ala Pro Tyr Asn Lys Ile
65                  70                  75

```
<210> SEQ ID NO 8
<211> LENGTH: 22
<212> TYPE: DNA
<213> ORGANISM: Artificial Sequence
<220> FEATURE:
<223> OTHER INFORMATION: WPRE-QF: Qprc primer lentiviral forward

<400> SEQUENCE: 8
actgtgtttg ctgacgcaac cc                                              22

<210> SEQ ID NO 9
<211> LENGTH: 24
<212> TYPE: DNA
<213> ORGANISM: Artificial Sequence
<220> FEATURE:
<223> OTHER INFORMATION: WPRE-QR: Qprc primer lentiviral reverse

<400> SEQUENCE: 9
caacaccacg gaattgtcag tgcc                                            24
```

<210> SEQ ID NO 10
<211> LENGTH: 25
<212> TYPE: DNA
<213> ORGANISM: Artificial Sequence
<220> FEATURE:
<223> OTHER INFORMATION: ALB-QF: Qprc primer albumin forward

<400> SEQUENCE: 10
tgaaacatac gttcccaaag agttt                                   25

<210> SEQ ID NO 11
<211> LENGTH: 26
<212> TYPE: DNA
<213> ORGANISM: Artificial Sequence
<220> FEATURE:
<223> OTHER INFORMATION: ALB-QR: Qprc primer albumin reverse

<400> SEQUENCE: 11
ctctccttct cagaaagtgt gcatat                                  26

<210> SEQ ID NO 12
<211> LENGTH: 6273
<212> TYPE: DNA
<213> ORGANISM: Artificial Sequence
<220> FEATURE:
<223> OTHER INFORMATION: Lentiviral Backbone sequence HIV7.2 with CD19t
      epitope tag

<400> SEQUENCE: 12

| | | |
|---|---|---|
| gttagaccag atctgagcct gggagctctc tggctaacta gggaacccac tgcttaagcc | 60 |
| tcaataaagc ttgccttgag tgcttcaagt agtgtgtgcc cgtctgttgt gtgactctgg | 120 |
| taactagaga tccctcagac ccttttagtc agtgtggaaa atctctagca gtggcgcccg | 180 |
| aacagggact tgaaagcgaa agggaaacca gaggagctct ctcgacgcag gactcggctt | 240 |
| gctgaagcgc gcacggcaag aggcgagggg cggcgactgg tgagtacgcc aaaaattttg | 300 |
| actagcggag gctagaagga gagagatggg tgcgagagcg tcagtattaa gcggggggaga | 360 |
| attagatcga tgggaaaaaa ttcggttaag gccaggggga agaaaaaat ataaattaaa | 420 |
| acatatagta tgggcaagca gggagctaga acgattcga gttaatcctg gcctgttaga | 480 |
| aacatcagaa ggctgtagac aaatactggg acagctacaa ccatcccttc agacaggatc | 540 |
| agaagaactt agatcattat ataatacagt agcaaccctc tattgtgtgc atcaaaggat | 600 |
| agagataaaa gacaccaagg aagctttaga caagatagag gaagagcaaa acaaaagtaa | 660 |
| gaaaaaagca cagcaagcag cagctgacac aggacacagc aatcaggtca gccaaaatta | 720 |
| ccctatagtg cagaacatcc aggggcaaat ggtacatcag gccatatcac ctagaacttt | 780 |
| aaatgcatgg gtaaaagtag tagaagagaa ggctttcagc ccagaagtga tacccatgtt | 840 |
| ttcagcatta tcagaaggag ccaccccaca agatttaaac accatgctaa acacagtggg | 900 |
| gggacatcaa gcagccatgc aaatgttaaa agagaccatc aatgaggaag ctgcaggcaa | 960 |
| agagaagagt ggtgcagaga aaaaagag cagtgggaat aggagctttg ttccttgggt | 1020 |
| tcttgggagc agcaggaagc actatgggcg cagcgtcaat gacgctgacg gtacaggcca | 1080 |
| gacaattatt gtctggtata gtgcagcagc agaacaattt gctgagggct attgaggcgc | 1140 |
| aacagcatct gttgcaactc acagtctggg gcatcaagca gctccaggca agaatcctgg | 1200 |
| ctgtggaaag atacctaaag gatcaacagc tcctggggat ttggggttgc tctggaaaac | 1260 |
| tcatttgcac cactgctgtg ccttggatct acaaatggca gtattcatcc acaatttaa | 1320 |

```
aagaaaaggg gggattgggg ggtacagtgc aggggaaaga atagtagaca taatagcaac    1380
agacatacaa actaaagaat tacaaaaaca aattacaaaa attcaaaatt ttcgggttta    1440
ttacagggac agcagagatc cagtttgggg atcaattgca tgaagaatct gcttagggtt    1500
aggcgttttg cgctgcttcg cgaggatctg cgatcgctcc ggtgcccgtc agtgggcaga    1560
gcgcacatcg cccacagtcc ccgagaagtt gggggaggg gtcggcaatt gaaccggtgc    1620
ctagagaagt tggcgcgggg taaactggga aagtgatgtc gtgtactggc tccgcctttt    1680
tcccgagggt gggggagaac cgtatataag tgcagtagtc gccgtgaacg ttcttttttcg   1740 caacgggttt gccgccagaa cacagctggc tagcgtttaa acggatccgc ggccgctcta    1800
gacccgggct gcaggaattc gatatcaagc ttatcgataa tcaacctctg gattacaaaa    1860
tttgtgaaag attgactggt attcttaact atgttgctcc ttttacgcta tgtggatacg    1920
ctgctttaat gcctttgtat catgctattg cttcccgtat ggctttcatt ttctcctcct    1980
tgtataaatc ctggttgctg tctctttatg aggagttgtg gcccgttgtc aggcaacgtg    2040
gcgtggtgtg cactgtgttt gctgacgcaa cccccactgg ttggggcatt gccaccacct    2100
gtcagctcct ttccgggact ttcgctttcc cctccctat tgccacggcg gaactcatcg    2160
ccgcctgcct tgcccgctgc tggacagggg ctcggctgtt gggcactgac aattccgtgg    2220
tgttgtcggg gaaatcatcg tccttttcctt ggctgctcgc ctgtgttgcc acctggattc    2280
tgcgcgggac gtccttctgc tacgtccctt cggccctcaa tccagcggac cttccttccc    2340
gcggcctgct gccggctctg cggcctcttc cgcgtcttcg ccttcgccct cagacgagtc    2400
ggatctccct ttgggccgcc tccccgcatc gataccgtcg actagccgta cctttaagac    2460
caatgactta caaggcagct gtagatctta gccactttt aaaagaaaag ggggactgg    2520 aagggctaat tcactcccaa agaagacaag atctgctttt tgcctgtact gggtctctct    2580
ggttagacca gatctgagcc tgggagctct ctggctaact agggaaccca ctgcttaagc    2640
ctcaataaag cttgccttga gtgcttcaag tagtgtgtgc ccgtctgttg tgtgactctg    2700
gtaactagag atccctcaga ccctttttagt cagtgtggaa aatctctagc agaattcgat    2760
atcaagctta tcgataccgt cgacctcgag ggggggcccg gtaccgagct cggatccact    2820
agtccagtgt ggtggaattc tgcagatatc cagcacagtg gcggccactc aagtctggag    2880
ggcacgttaa aacccgctga tcagcctcga ctgtgccttc tagttgccag ccatctgttg    2940
tttgcccctc ccccgtgcct tccttgaccc tggaaggtgc cactcccact gtccttcct    3000 aataaaatga ggaaattgca tcgcattgtc tgagtaggtg tcattctatt ctggggggtg    3060
gggtggggca ggacagcaag ggggaggatt gggaagacaa tagcaggcat gctggggatg    3120
cggtgggctc tatggcttct actgggcggt tttatggaca gcaagcgaac cggaattgcc    3180
agctggggcg ccctctggta aggttgggaa gccctgcaaa gtaaactgga tgctttctc    3240 gccgccaagg atctgatggc gcaggggatc aagctctgat caagacagg atgaggatc    3300 gtttcgcatg attgaacaag atggattgca cgcaggttct ccggccgctt gggtggagag    3360
gctattcggc tatgactggg cacaacagac aatcggctgc tctgatgccg ccgtgttccg    3420
gctgtcagcg caggggcgcc cggttctttt tgtcaagacc gacctgtccg gtgccctgaa    3480
tgaactgcaa gacgaggcag cgcggctatc gtggctggcc acgacgggcg ttccttgcgc    3540
agctgtgctc gacgttgtca ctgaagcggg aagggactgg ctgctattgg gcgaagtgcc    3600
ggggcaggat ctcctgtcat ctcaccttgc tcctgccgag aaagtatcca tcatggctga    3660
tgcaatgcgg cggctgcata cgcttgatcc ggctacctgc ccattcgacc accaagcgaa    3720
```

```
acatcgcatc gagcgagcac gtactcggat ggaagccggt cttgtcgatc aggatgatct   3780
ggacgaagag catcaggggc tcgcgccagc cgaactgttc gccaggctca aggcgagcat   3840
gcccgacggc gaggatctcg tcgtgaccca tggcgatgcc tgcttgccga atatcatggt   3900
ggaaaatggc cgcttttctg gattcatcga ctgtggccgg ctgggtgtgg cagaccgcta   3960
tcaggacata gcgttggcta cccgtgatat tgctgaagag cttggcggcg aatgggctga   4020
ccgcttcctc gtgctttacg gtatcgccgc tcccgattcg cagcgcatcg ccttctatcg   4080
ccttcttgac gagttcttct gaattattaa cgcttacaat tcctgatgc ggtatttttct   4140
ccttacgcat ctgtgcggta tttcacaccg catacaggtg cacttttcg gggaaatgtg   4200
cgcggaaccc ctatttgttt attttctaa atacattcaa atatgtatcc gctcatgacc   4260
aaaatccctt aacgtgagtt ttcgttccac tgagcgtcag accccgtaga aaagatcaaa   4320
ggatcttctt gagatccttt ttttctgcgc gtaatctgct gcttgcaaac aaaaaaacca   4380
ccgctaccag cggtggtttg tttgccggat caagagctac caactctttt tccgaaggta   4440
actggcttca gcagagcgca gataccaaat actgttcttc tagtgtagcc gtagttaggc   4500
caccacttca agaactctgt agcaccgcct acatacctcg ctctgctaat cctgttacca   4560
gtggctgctg ccagtggcga taagtcgtgt cttaccgggt tggactcaag acgatagtta   4620
ccggataagg cgcagcggtc gggctgaacg ggggttcgt gcacacagcc agcttggag   4680
cgaacgacct acaccgaact gagatacctta cagcgtgagc tatgagaaag cgccacgctt   4740
cccgaaggga aaaggcgga caggtatccg gtaagcggca gggtcggaac aggagagcgc   4800
acgagggagc ttccagggg aaacgcctgg tatctttata gtcctgtcgg gtttcgccac   4860
ctctgacttg agcgtcgatt tttgtgatgc tcgtcagggg ggcggagcct atggaaaaac   4920
gccagcaacg cggccttttt acggttcctg gccttttgct ggccttttgc tcacatgttc   4980
tttcctgcgt tatcccctga ttctgtggat aaccgtatta ccgcctttga gtgagctgat   5040
accgctcgcc gcagccgaac gaccgagcgc agcgagtcag tgagcgagga agcggaagag   5100
cgcccaatac gcaaaccgcc tctccccgcg cgttggccga ttcattaatg cagctggcac   5160
gacaggtttc ccgactggaa agcgggcagt gagcgcaacg caattaatgt gagttagctc   5220
actcattagg caccccaggc tttacacttt atgcttccgg ctcgtatgtt gtgtggaatt   5280
gtgagcggat aacaatttca cacaggaaac agctatgacc atgattacgc caagctcgaa   5340
attaaccctc actaaaggga acaaaagctg gagctccacc gcggtggcgg cctcgaggtc   5400
gagatccggt cgaccagcaa ccatagtccc gcccctaact ccgcccatcc cgcccctaac   5460
tccgcccagt tccgcccatt ctccgcccca tggctgacta atttttttta tttatgcaga   5520
ggccgaggcc gcctcggcct ctgagctatt ccagaagtag tgaggaggct ttttggagg   5580
cctaggcttt tgcaaaaagc ttcgacggta tcgattggct catgtccaac attaccgcca   5640
tgttgacatt gattattgac tagttattaa tagtaatcaa ttacggggtc attagttcat   5700
agcccatata tggagttccg cgttacataa cttacggtaa atggcccgcc tggctgaccg   5760
cccaacgacc cccgcccatt gacgtcaata atgacgtatg ttcccatagt aacgccaata   5820
gggactttcc attgacgtca atgggtggag tatttacggt aaactgccca cttggcagta   5880
catcaagtgt atcatatgcc aagtacgccc cctattgacg tcaatgacgg taaatggccc   5940
gcctggcatt atgcccagta catgacctta tgggactttc ctacttggca gtacatctac   6000
gtattagtca tcgctattac catggtgatg cggttttggc agtacatcaa tgggcgtgga   6060
```

```
tagcggtttg actcacgggg atttccaagt ctccacccca ttgacgtcaa tgggagtttg    6120
ttttggcacc aaaatcaacg ggactttcca aaatgtcgta acaactccgc cccattgacg    6180
caaatgggcg gtaggcgtgt acggaattcg gagtggcgag ccctcagatc ctgcatataa    6240
gcagctgctt tttgcctgta ctgggtctct ctg                                 6273

<210> SEQ ID NO 13
<211> LENGTH: 66
<212> TYPE: DNA
<213> ORGANISM: Artificial Sequence
<220> FEATURE:
<223> OTHER INFORMATION: T2A

<400> SEQUENCE: 13
ggcggcggag agggcagagg aagtcttcta acatgcggtg acgtggagga gaatcccggc    60
cctagg                                                               66

<210> SEQ ID NO 14
<211> LENGTH: 50
<212> TYPE: DNA
<213> ORGANISM: Artificial Sequence
<220> FEATURE:
<223> OTHER INFORMATION: IL21-T2A forward primer

<400> SEQUENCE: 14
ccgccagaac acagctggct agcgccacca tgagatccag tcctggcaac                50

<210> SEQ ID NO 15
<211> LENGTH: 36
<212> TYPE: DNA
<213> ORGANISM: Artificial Sequence
<220> FEATURE:
<223> OTHER INFORMATION: IL21 T2A reverse primer

<400> SEQUENCE: 15
tgtcaccagg agaagcatcc tagggccggg attctc                              36

<210> SEQ ID NO 16
<211> LENGTH: 492
<212> TYPE: DNA
<213> ORGANISM: Artificial Sequence
<220> FEATURE:
<223> OTHER INFORMATION: IL-21 nt sequence

<400> SEQUENCE: 16
gccaccatga gatccagtcc tggcaacatg gagaggattg tcatctgtct gatggtcatc    60
ttcttgggga cactggtcca caatcaagc tcccaaggtc aagatcgcca catgattaga    120
atgcgtcaac ttatagatat tgttgatcag ctgaaaaatt atgtgaatga cttggtccct    180
gaatttctgc cagctccaga agatgtagag acaaactgtg agtggtcagc ttttttcctgc    240 tttcagaagg cccaactaaa gtcagcaaat acaggaaaca tgaaaggat aatcaatgta    300 tcaattaaaa agctgaagag gaaaccacct tccacaaatg cagggagaag acagaaacac    360
agactaacat gcccttcatg tgattcttat gagaaaaaac cacccaaaga attcctagaa    420
agattcaaat cacttctcca aaagatgatt catcagcatc tgtcctctag aacacacgga    480
agtgaagatt cc                                                        492

<210> SEQ ID NO 17
<211> LENGTH: 21
<212> TYPE: DNA
<213> ORGANISM: Artificial Sequence
```

```
<220> FEATURE:
<223> OTHER INFORMATION: IL7 forward primer

<400> SEQUENCE: 17
atgcttctcc tggtgacaag c                                              21

<210> SEQ ID NO 18
<211> LENGTH: 49
<212> TYPE: DNA
<213> ORGANISM: Artificial Sequence
<220> FEATURE:
<223> OTHER INFORMATION: IL7 reverse primer

<400> SEQUENCE: 18
gcagcccggg tctagagcgg ccgctcactc gaggtgttct ttagtgccc                49

<210> SEQ ID NO 19
<211> LENGTH: 531
<212> TYPE: DNA
<213> ORGANISM: Artificial Sequence
<220> FEATURE:
<223> OTHER INFORMATION: IL-7 nucleotide sequence

<400> SEQUENCE: 19
atgcttctcc tggtgacaag ccttctgctc tgtgagttac cacacccagc attcctcctg    60
atcccagatt gtgatattga aggtaaagat ggcaaacaat atgagagtgt tctaatggtc   120
agcatcgatc aattattgga cagcatgaaa gaaattggta caattgcct gaataatgaa    180 tttaactttt ttaaaagaca tatctgtgat gctaataagg aaggtatgtt tttattccgt   240
gctgctcgca gttgaggca atttcttaaa atgaatagca ctggtgattt tgatctccac    300
ttattaaaag tttcagaagg cacaacaata ctgttgaact gcactggcca ggttaaagga   360
agaaaaccag ctgccctggg tgaagcccaa ccaacaaaga gtttggaaga aaataaatct   420
ttaaaggaac agaaaaaact gaatgacttg tgtttcctaa agagactatt acaagagata   480
aaaacttgtt ggaataaaat tttgatgggc actaaagaac acctcgagtg a            531

<210> SEQ ID NO 20
<211> LENGTH: 25
<212> TYPE: DNA
<213> ORGANISM: Artificial Sequence
<220> FEATURE:
<223> OTHER INFORMATION: PDL1.1-Forward primer

<400> SEQUENCE: 20
caccggtcca gatgacttcg gcctt                                          25

<210> SEQ ID NO 21
<211> LENGTH: 25
<212> TYPE: DNA
<213> ORGANISM: Artificial Sequence
<220> FEATURE:
<223> OTHER INFORMATION: PDL1.1-Reverse primer

<400> SEQUENCE: 21
aaacaaggcc gaagtcatct ggacc                                          25

<210> SEQ ID NO 22
<211> LENGTH: 20
<212> TYPE: DNA
<213> ORGANISM: Artificial Sequence
<220> FEATURE:
<223> OTHER INFORMATION: PD-L1 small guide RNA sequence
```

```
<400> SEQUENCE: 22
tccagatgac ttcggccttg                                                    20

<210> SEQ ID NO 23
<211> LENGTH: 22
<212> TYPE: DNA
<213> ORGANISM: Artificial Sequence
<220> FEATURE:
<223> OTHER INFORMATION: IL-10 Forward primer

<400> SEQUENCE: 23
aggaacacgc gaatgagaac cc                                                 22

<210> SEQ ID NO 24
<211> LENGTH: 22
<212> TYPE: DNA
<213> ORGANISM: Artificial Sequence
<220> FEATURE:
<223> OTHER INFORMATION: IL-10 Reverse primer

<400> SEQUENCE: 24
tgcaaggcat ggggagcatc tt                                                 22

<210> SEQ ID NO 25
<211> LENGTH: 19
<212> TYPE: DNA
<213> ORGANISM: Artificial Sequence
<220> FEATURE:
<223> OTHER INFORMATION: IL-10 small guide RNA sequence

<400> SEQUENCE: 25
ggctggccct caccccagt                                                     19

<210> SEQ ID NO 26
<211> LENGTH: 1004
<212> TYPE: DNA
<213> ORGANISM: Artificial Sequence
<220> FEATURE:
<223> OTHER INFORMATION: EF1a - Her2tG- hToll sequence
<220> FEATURE:
<221> NAME/KEY: misc_feature
<222> LOCATION: 9, 10, 685, 824, 841, 863, 933, 934, 949, 950, 968, 979,
      991, 992, 993, 994, 995
<223> OTHER INFORMATION: n = A,T,C or G

<400> SEQUENCE: 26
ggcattgann ggtgcctaga gaaggtggcg cggggtaaac tgggaaagtg atgtcgtgta        60
ctggctccgc ctttttcccg agggtggggg agaaccgtat ataagtgcag tagtcgccgt       120
gaacgttctt tttcgcaacg ggtttgccgc cagaacacag ctgggctagc atgttgctcc       180
tcgtaacctc ccttttgttg tgtgagctcc ctcacccagc ttttctgctg atcccgtgcc       240
accctgagtg tcaaccacag aatggtagcg ttacctgctt tgggcctgaa gctgatcagt       300
gcgttgcatg tgctcactat aaggatccgc catttttgcgt ggcgcggtgc ccttcgggcg       360
tgaaacctga tctaagctat atgccgatct ggaagtttcc cgatgaggag ggggcttgcc       420
agccatgtcc catcaattgt acacatagct gcgtcgactt agatgacaag gggtgcccgg       480
cggaacaacg cgcctcgccc cttactggag gcggatcggg aggcggctca ataatatcag       540
cggtagttgg tatactgctg gtggtggttc tcggagtagt atttgggata ttgataggcg       600
gcggagaggg cagaggaagt cttctaacat gcggtgacgt ggaggagaat cccggcccta       660
ggatgtgccg agccatctct cttangcgct tgctgctgct gctgctgcag ctgtcacaac       720
```

```
tcctagctgt cactcaaggg aagacgctgg tgctggggaa ggaagggaa tcagcagaac      780 tgccctgcga gagttccag aagaagatca cagtcttcac ctgnaagttc tctgaccaga      840
ngaagattct ggggcagcat ggnaaagtgt attaattaga ggaggttcgc cttcgcagtt     900
tgatcgtttt gattccaaaa aagggcatgg gannaaagga tcgtttccnn tcatcatcaa     960
taaacttnag atggaagant ctcagactta nnnnntgtga gctg                    1004
```

<210> SEQ ID NO 27
<211> LENGTH: 1610
<212> TYPE: DNA
<213> ORGANISM: Artificial Sequence
<220> FEATURE:
<223> OTHER INFORMATION: Single chain IL-12

<400> SEQUENCE: 27

```
atgtgtcacc agcagttggt catctcttgg ttttccctgg ttttctggc atctcccctc       60 gtggccatat gggaactgaa gaaagatgtt tatgtcgtag aattggattg gtatccggat      120
gcccctggag aaatggtggt cctcacctgt gacacccctg aagaagatgg tatcacctgg      180
accttggacc agagcagtga ggtcttaggc tctggcaaaa ccctgaccat ccaagtcaaa      240
gagtttggag atgctggcca gtacacctgt cacaaaggag cgaggttct aagccattcg      300 ctcctgctgc ttcacaaaaa ggaagatgga atttggtcca ctgatatttt aaaggaccag      360
aaagaaccca aaataagac cttttctaaga tgcgaggcca gaattattc tggacgtttc      420 acctgctggt ggctgacgac aatcagtact gatttgacat tcagtgtcaa aagcagcaga      480
ggctcttctg acccccaagg ggtgacgtgc ggagctgcta cactctctgc agagagagtc      540
agaggggaca caaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca acctgaccc acccaagaac      720 ttgcagctga agccattaaa gaattctcgg caggtgagg tcagctggga gtaccctgac      780
acctggagta ctccacattc ctacttctcc ctgacattct gcgttcaggt ccagggcaag      840
agcaagagag aaaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagtgttcct ggagtagggg tacctggggt gggcgccaga     1020
aacctccccg tggccactcc agacccagga atgttcccat gccttcacca ctcccaaaac     1080
ctgctgaggg ccgtcagcaa catgctccag aaggccagac aaactctaga atttacccct     1140
tgcacttctg aagagattga tcatgaagat atcacaaaag ataaaaccag cacagtggag     1200
gcctgtttac cattggaatt aaccaagaat gagagttgcc taaattccag agagaccctct    1260 ttcataacta atgggagttg cctggcctcc agaaagacct cttttatgat ggcctgtgc      1320 cttagtagta tttatgaaga cttgaagatg taccaggtgg agttcaagac catgaatgca     1380
aagctgctga tggatcctaa gaggcagatc tttctagatc aaaacatgct ggcagttatt     1440
gatgagctga tgcaggccct gaatttcaac agtgagactg tgccacaaaa atcctccctt     1500
gaagaaccgg attttataaa aactaaaatc aagctctgca tacttcttca tctttcagaa     1560
ttcgggcagt gactattgat agagtgatga gctatctgaa tgcttcctaa               1610
```

<210> SEQ ID NO 28
<211> LENGTH: 2197
<212> TYPE: DNA
<213> ORGANISM: Artificial Sequence
<220> FEATURE:
<223> OTHER INFORMATION: EGFRt-P2A-soluble VEGF Receptor

<400> SEQUENCE: 28

```
ctggggatcg gcctcttcat ggggtccggt gccaccaact tttctctcct gaagcaggcg      60
ggcgatgtcg aagagaaccc agggcctatg gtatcttact gggataccgg tgtcctgttg     120
tgtgcgctcc tttcctgctt gctgttgacg ggctctagca gcgggagcaa actgaaggac     180
cccgagcttt ctttgaaggg aacccaacac attatgcagg ccgggcagac tctccacttg     240
caatgtaggg gggaagctgc tcacaagtgg tcccttcccg aaatggttag caaagagagc     300
gaacggctct ccatcactaa gagtgcatgt ggaaggaacg gaaagcagtt ttgctcaacc     360
cttacccttaa tacggcaca ggctaaccat accgggttct attcatgtaa gtatttggct     420
gtgcctacgt caaagaaaaa agaaactgag tcagccatct acatctttat ttctgacaca     480
ggcagacctt ttgttgaaat gtactcagaa ataccggaaa ttatccatat gacagaaggt     540
cgcgaacttg tgatcccgtg tagagttacg agccccaaca tcaccgtgac gctgaagaaa     600
tttccgcttg atactcttat tccagatggg aagagaataa tttgggactc ccggaagggg     660
ttcatcattt caaatgcaac ttataaggag ataggcctcc tgacctgtga agccacagtc     720
aatggtcacc tgtataaaac caattacttg acgcaccgac aaacaaacac aatcatagac     780
gtccaaatca gtactcctcg accggtcaaa ttgctgagag ccacacact ggtcctgaat      840
tgtactgcca ctacacctct caatacgcga gttcaaatga catggtctta tcctgacgag     900
aagaacaagc gggcctctgt gcgccggcga atcgaccaaa gcaattctca tgcaaacatc     960
ttctacagtg ttctcactat cgataagatg caaaataaac tcactatcga taagatgcaa    1020
aataaagata aaggcctcta tacttgtaga gttagaagtg gccaagttt taaatctgta    1080
aatacgagcg tccatatttta tgacaaggct ttcataaccg tgaagcaccg aaagcagcag    1140
gtactggaaa ccgttgcggg caaacgatca tacagattgt caatgaaggt taaagcgttt    1200
ccttcacccg aggtagtttg gcttaaggac ggcttgcctg ccacggaaaa gagcgcacga    1260
taccttacac gcggctactc cctcatcatc aaggacgtca cggaagagga tgccggcaat    1320
tataccattc tcttgtcaat aaagcaaagt aacgttttta aaaacctcac agcaacattg    1380
attgtaaatg tcaaacccca gatttacgaa aaggcggtaa gtagcttccc tgatccggca    1440
ctctatccac tgggtagtag acaaattttg acgtgcacgg cttacggtat ccccaaccaa    1500
acaattaagt ggttttggca tccctgtaat cataatcatt cagaggcaag gtgtgacttt    1560
tgttctaata atgaagaaag tttcattctg gatgctgact ccaacatggg gaaccggata    1620
gagagcataa ctcaaaggat ggccatcata gaagggaaaa ataaaatggc ttcaacactt    1680
gtcgtggctg atagtcggat ttccgggatt tatatatgca tagcaagtaa taaggtaggg    1740
acagttggac gaaacatctc attctatatc actgacgtgc caaacggctt tcacgttaac    1800
cttgagaaaa tgccgaccga aggtgaggat ctgaagttgt catgcactgt aaacaagttt    1860
ctttatcggg acgtaacgtg gattctcctc agaactgtta ataatagaac catgcactac    1920
tctatatcca aacagaagat ggcaatcacg aaggagcata gtatcacgtt gaacttgacc    1980
attatgaatg tatcattgca agatagtgga acatacgctt gtagagcgcg caatgtctat    2040
acaggtgagg agatacttca aaaaaagaa atcaccatca gagggagca ctgtaacaaa      2100
aaagctgtat tttcaaggat aagcaaattc aagagtacta gaaatgattg cacaacgcaa    2160
agtaatgtca aacactgagc tctagacccg ggctgca                              2197
```

<210> SEQ ID NO 29
<211> LENGTH: 1641
<212> TYPE: DNA
<213> ORGANISM: Artificial Sequence
<220> FEATURE:
<223> OTHER INFORMATION: EGreen Fluorescent Protein

<400> SEQUENCE: 29

```
atggaggatg ccaagaatat taagaaaggc cctgccccat tctaccctct ggaagatggc      60
actgctggtg agcaactgca caaggccatg aagaggtatg ccctggtccc tggcaccatt     120
gccttcactg atgctcacat tgaggtggac atcacctatg ctgaatactt tgagatgtct     180
gtgaggctgg cagaagccat gaaaagatat ggactgaaca ccaaccacag gattgtggtg     240
tgctctgaga actctctcca gttcttcatg cctgtgttag gagccctgtt cattggagtg     300
gctgtggccc tgccaatga catctacaat gagagagagc tcctgaacag catgggcatc     360
agccagccaa ctgtggtctt tgtgagcaag aagggcctgc aaaagatcct gaatgtgcag     420
aagaagctgc ccatcatcca gaagatcatc atcatggaca gcaagactga ctaccagggc     480
ttccagagca tgtatacctt tgtgaccagc cacttacccc ctggcttcaa tgagtatgac     540
tttgtgcctg agagctttga cagggacaag accattgctc tgattatgaa cagctctggc     600
tccactggac tgcccaaagg tgtggctctg ccccacagaa ctgcttgtgt gagattcagc     660
catgccagag accccatctt tggcaaccag atcatccctg acactgccat cctgtctgtg     720
gttccattcc atcatggctt tggcatgttc acaacactgg ggtacctgat ctgtggcttc     780
agagtggtgc tgatgtatag gtttgaggag gagctgtttc tgaggagcct acaagactac     840
aagatccagt ctgccctgct ggtgcccact ctgttcagct ctttgccaa gagcaccctc     900
attgacaagt atgacctgag caacctgcat gagattgcct ctggaggagc accctgagc     960
aaggaggtgg gtgaggctgt ggcaaagagg ttccatctcc caggaatcag acagggctat    1020
ggcctgactg agaccacctc tgccatcctc atcaccctg aaggagatga caagcctggt    1080
gctgtgggca aggtggttcc cttttttgag gccaaggtgg tggacctgga cactggcaag    1140
accctgggag tgaaccagag gggtgagctg tgtgtgaggg gtcccatgat catgtctggc    1200
tatgtgaaca accctgaggc caccaatgcc ctgattgaca aggatggctg gctgcactct    1260
ggtgacattg cctactggga tgaggatgag cactttttca ttgtggacag gctgaagagc    1320
ctcatcaagt acaaaggcta ccaagtggca cctgctgagc tagagagcat cctgctccag    1380
caccccaaca tctttgatgc tggtgtggct ggcctgcctg atgatgatgc tggagagctg    1440
cctgctgctg ttgtggttct ggagcatgga aagaccatga ctgagaagga gattgtggac    1500
tatgtggcca gtcaggtgac cactgccaag aagctgaggg gaggtgtggt gtttgtggat    1560
gaggtgccaa agggtctgac tggcaagctg gatgccagaa agatcagaga gatcctgatc    1620
aaggccaaga agggtggcaa a                                              1641
```

<210> SEQ ID NO 30
<211> LENGTH: 1038
<212> TYPE: DNA
<213> ORGANISM: Artificial Sequence
<220> FEATURE:
<223> OTHER INFORMATION: T2A-CD19t

<400> SEQUENCE: 30

```
ggcggcggag agggcagagg aagtcttcta acatgcggtg acgtggagga gaatcccggc      60
cctaggatgc cacctcctcg cctcctcttc ttcctcctct tcctcacccc catggaagtc     120
```

```
aggcccgagg aacctctagt ggtgaaggtg gaagagggag ataacgctgt gctgcagtgc    180
ctcaagggga cctcagatgg ccccactcag cagctgacct ggtctcggga gtccccgctt    240
aaacccttct taaaactcag cctggggctg ccaggcctgg gaatccacat gaggcccctg    300
gccatctggc ttttcatctt caacgtctct caacagatgg ggggcttcta cctgtgccag    360
ccggggcccc cctctgagaa ggcctggcag cctggctgga cagtcaatgt ggagggcagc    420
ggggagctgt tccggtggaa tgtttcggac ctaggtggcc tgggctgtgg cctgaagaac    480
aggtcctcag agggcccag ctccccttcc gggaagctca tgagcccaa gctgtatgtg      540 tgggccaaag accgcctga gatctgggag ggagagcctc cgtgtgtccc accgagggac     600
agcctgaacc agagcctcag ccaggacctc accatggccc ctggctccac actctggctg    660
tcctgtgggg tacccctga ctctgtgtcc agggccccc tctcctggac ccatgtgcac      720 cccaagggc ctaagtcatt gctgagccta gagctgaagg acgatcgccc ggccagagat     780
atgtgggtaa tggagacggg tctgttgttg ccccggccca cagctcaaga cgctggaaag    840
tattattgtc accgtggcaa cctgaccatg tcattccacc tggagatcac tgctcggcca    900
gtactatggc actggctgct gaggactggt ggctggaagg tctcagctgt gactttggct    960
tatctgatct tctgcctgtg ttcccttgtg ggcattcttc atcttcaaag agccctggtc   1020
ctgaggagga aaagataa                                                 1038

<210> SEQ ID NO 31
<211> LENGTH: 972
<212> TYPE: DNA
<213> ORGANISM: Artificial Sequence
<220> FEATURE:
<223> OTHER INFORMATION: CD19t epitope tag

<400> SEQUENCE: 31
atgccacctc ctcgcctcct cttcttcctc ctcttcctca cccccatgga agtcaggccc     60
gaggaacctc tagtggtgaa ggtggaagag ggagataacg ctgtgctgca gtgcctcaag    120
gggacctcag atggccccac tcagcagctg acctggtctc gggagtcccc gcttaaaccc    180
ttcttaaaac tcagcctggg gctgccaggc ctggaatccc acatgaggcc cctggccatc    240
tggcttttca tcttcaacgt ctctcaacag atgggggct tctacctgtg ccagccgggg    300 ccccctctg agaaggcctg gcagcctggc tggacagtca atgtggaggg cagcggggag    360
ctgttccggt ggaatgtttc ggacctaggt ggcctgggct gtggcctgaa gaacaggtcc    420
tcagagggcc ccagctcccc ttccgggaag ctcatgagcc caagctgta tgtgtgggcc    480 aaagaccgcc tgagatctg gagggagag cctccgtgtg tcccaccgag gacagcctg      540 aaccagagcc tcagccagga cctcaccatg gcccctggct ccacactctg gctgtcctgt    600
ggggtacccc ctgactctgt gtccaggggc cccctctcct ggacccatgt gcaccccaag    660 ggcctaagt cattgctgag cctagagctg aaggacgatc gccggccag agatatgtgg     720 gtaatggaga cgggtctgtt gttgccccgg ccacagctc aagacgctgg aaagtattat    780
tgtcaccgtg gcaacctgac catgtcattc cacctggaga tcactgctcg gccagtacta    840
tggcactggc tgctgaggac tggtggctgg aaggtctcag ctgtgacttt ggcttatctg    900
atcttctgcc tgtgttccct tgtgggcatt cttcatcttc aaagagccct ggtcctgagg    960
aggaaaagat aa                                                       972

<210> SEQ ID NO 32
```

```
<211> LENGTH: 567
<212> TYPE: DNA
<213> ORGANISM: Artificial Sequence
<220> FEATURE:
<223> OTHER INFORMATION: T2A-sTGFBRII

<400> SEQUENCE: 32
ggcggcggag agggcagagg aagtcttcta acatgcggtg acgtggagga gaatcccggc     60
cctaggatgg gtcgggggct gctcaggggc ctgtggccgc tgcacatcgt cctgtggacg    120
cgtatcgcca gcacgatccc accgcacgtt cagaagtcgg ttaataacga catgatagtc    180
actgacaaca acggtgcagt caagtttcca caactgtgta aattttgtga tgtgagattt    240
tccacctgtg acaaccagaa atcctgcatg agcaactgca gcatcacctc catctgtgag    300
aagccacagg aagtctgtgt ggctgtatgg agaaagaatg acgagaacat aacactagag    360
acagtttgcc atgaccccaa gctcccctac catgacttta ttctggaaga tgctgcttct    420
ccaaagtgca ttatgaagga aagaaaaag cctggtgaga ctttcttcat gtgttcctgt    480
agctctgatg agtgcaatga caacatcatc ttctcagaag aatataacac cagcaatcct    540
gacttgttgc tagtcatatt tcaatga                                        567

<210> SEQ ID NO 33
<211> LENGTH: 1539
<212> TYPE: DNA
<213> ORGANISM: Artificial Sequence
<220> FEATURE:
<223> OTHER INFORMATION: CD19t-T2A-sTGFBRII

<400> SEQUENCE: 33
atgccacctc ctcgcctcct cttcttcctc ctcttcctca cccccatgga agtcaggccc     60
gaggaacctc tagtggtgaa ggtggaagag ggagataacg ctgtgctgca gtgcctcaag    120
gggacctcag atggccccac tcagcagctg acctggtctc gggagtcccc gcttaaaccc    180
ttcttaaaac tcagcctggg gctgccaggc ctggaatccc acatgaggcc cctgccatc    240
tggcttttca tcttcaacgt ctctcaacag atgggggct tctacctgtg ccagccgggg    300
ccccctctg agaaggcctg gcagcctggc tggacagtca atgtgaggg cagcggggag    360
ctgttccggt ggaatgtttc ggacctaggt ggcctgggct gtggcctgaa gaacaggtcc    420
tcagagggcc ccagctcccc ttccgggaag ctcatgagcc caagctgta tgtgtgggcc    480
aaagaccgcc ctgagatctg ggagggagag cctccgtgtg tcccaccgag ggacagcctg    540
aaccagagcc tcagccagga cctcaccatg gcccctggct ccacactctg gctgtcctgt    600
ggggtacccc ctgactctgt gtccaggggc cccctctcct ggacccatgt gcaccccaag    660
gggcctaagt cattgctgag cctagagctg aaggacgatc gccgggccag agatatgtgg    720
gtaatggaga cgggtctgtt gttgccccgg gccacagctc aagacgctgg aaagtattat    780
tgtcaccgtg gcaacctgac catgtcattc caccctggaga tcactgctcg gccagtacta    840
tggcactggc tgctgaggac tggtggctgg aaggtctcag ctgtgacttt ggcttatctg    900
atcttctgcc tgtgttccct tgtgggcatt cttcatcttc aaagagccct ggtcctgagg    960
aggaaaagat aaggcggcgg agagggcaga ggaagtcttc aacatgcgg tgacgtggag   1020
gagaatcccg gccctaggat gggtcggggg ctgctcaggg gcctgtggcc gctgcacatc   1080
gtcctgtgga cgcgtatcgc cagcacgatc ccaccgcacg ttcagaagtc ggttaataac   1140
gacatgatag tcactgacaa caacggtgca gtcaagtttc cacaactgtg taaattttgt   1200
gatgtgagat tttccacctg tgacaaccag aaatcctgca tgagcaactg cagcatcacc   1260
```

```
tccatctgtg agaagccaca ggaagtctgt gtggctgtat ggagaaagaa tgacgagaac    1320
ataacactag agacagtttg ccatgacccc aagctcccct accatgactt tattctggaa    1380
gatgctgctt ctccaaagtg cattatgaag gagaagaaaa agcctggtga ctttcttc     1440 atgtgttcct gtagctctga tgagtgcaat gacaacatca tcttctcaga agaatataac    1500
accagcaatc ctgacttgtt gctagtcata tttcaatga                          1539

<210> SEQ ID NO 34
<211> LENGTH: 1990
<212> TYPE: DNA
<213> ORGANISM: Artificial Sequence
<220> FEATURE:
<223> OTHER INFORMATION: EGFP:ffluc-T2A-CD19t

<400> SEQUENCE: 34
atggaggatg ccaagaatat taagaaaggc cctgccccat tctaccctct ggaagatggc      60
actgctggtg agcaactgca caaggccatg aagaggtatg ccctggtccc tggcaccatt    120
gccttcactg atgctcacat tgaggtggac atcacctatg ctgaatactt tgagatgtct    180
gtgaggctgg cagaagccat gaaaagatat ggactgaaca ccaaccacag gattgtggtg    240
tgctctgaga actctctcca gttcttcatg cctgtgttag gagccctgtt cattggagtg    300
gctgtggccc tgccaatga catctacaat gagagagagc tcctgaacag catgggcatc    360
agccagccaa ctgtggtctt tgtgagcaag aagggcctgc aaaagatcct gaatgtgcag    420
aagaagctgc ccatcatcca gaagatcatc atcatggaca gcaagactga ctaccagggc    480
ttccagagca tgtatacctt tgtgaccagc cacttacccc ctggcttcaa tgagtatgac    540
tttgtgcctg agagctttga cagggacaag accattgctc tgattatgaa cagctctggc    600
tccactggac tgcccaaagg tgtggctctg ccccacagaa ctgcttgtgt gagattcagc    660
catgccagag accccatctt tggcaaccag atcatccctg acactgccat cctgtctgtg    720
gttccattcc atcatggctt tggcatgttc acaaacactgg ggtacctgat ctgtggcttc    780 agtggtgc tgatgtatag gttttgaggag gagctgtttc tgaggagcct acaagactac    840
aagatccagt ctgccctgct ggtgcccact ctgttcagct tctttgccaa gagcacccatc    900 attgacaagt atgacctgag caacctgcat gagattgcct ctggaggagc accctgagc    960 aaggaggtgg gtgaggctgt ggcaaagagg ttccatctcc caggaatcag acagggctat   1020
ggcctgactg agaccaccctc tgccatcctc atcacccctg aaggagatga caagcctggt   1080
gctgtgggca agtggttcc cttttttgag gccaaggtgg tggacctgga cactggcaag   1140
accctgggag tgaaccagag gggtgagctg tgtgtgaggg gtcccatgat catgtctggc   1200
tatgtgaaca accctgaggc caccaatgcc ctgattgaca aggatggctg gctgcactct   1260
ggtgacattg cctactggga tgaggatgag cactttttca ttgtggacag gctgaagagc   1320
ctcatcaagt acaaaggcta ccaagtggca cctgctgagc tagagagcat cctgctccag   1380
caccccaaca tctttgatgc tggtgtggct ggcctgcctg atgatgatgc tggagagctg   1440
cctgctgctg ttgtggttct ggagcatgga aagaccatga ctgagaagga gattgtggac   1500
tatgtggcca gtcaggtgac cactgccaag aagctgaggg gaggtgtggt gtttgtggat   1560
gaggtgccaa agggtctgac tggcaagctg gatgccagaa agatcagaga gatcctgatc   1620
aaggccaaga agggtggcaa aggcggcgga gagggcagag aagtcttcta acatgcggt   1680 gacgtggagg agaatcccgg ccctaggatg ccacctcctc gcctcctctt cttcctcctc   1740
```

```
ttcctcaccc ccatggaagt caggcccgag gaacctctag tggtgaaggt ggaagaggga    1800
gataacgctg tgctgcagtg cctcaagggg acctcagatg gccccactca gcagctgacc    1860
tggtctcggg agtcccgct  taaacccttc ttaaaactca gctggggct  gccaggcctg    1920 ggaatccaca tgaggcccct ggccatctgg cttttcatct tcaacgtctc tcaacagatg    1980
gggggcttct                                                            1990
```

<210> SEQ ID NO 35
<211> LENGTH: 972
<212> TYPE: DNA
<213> ORGANISM: Artificial Sequence
<220> FEATURE:
<223> OTHER INFORMATION: IL-15

<400> SEQUENCE: 35

```
gccaccatgg cacttccagt cacagcgctt cttctgcctt tggcactgct tctccacgca      60
gcacgcccaa actgggtcaa tgtaatcagc gacctgaaga agattgaaga cctgattcaa     120
tcaatgcaca tagacgctac gttgtacacc gaatcagatg ttcatcctag ctgtaaagtc     180
accgcaatga atgttttttt gctggagctt aagttatat  cccttgagtc tggggacgca    240
tctatacatg acacagttga gaatttgatc atattggcaa acaatagctt gtcttccaac     300
ggtaatgtca cagagtccgg ttgtaaagag tgtgaggaac ttgaagagaa aaacattaaa     360
gaatttctcc agagtttcgt acatattgta caaatgttca taaatacttc tatctatatc     420
tgggctcctc tcgccggaac ctgtggcgtt ctgctgctgt ctttggtgat tacaggaagt     480
ggagccacaa atttcagtct gcttaaacag gcagggatg  tggaggagaa ccccggccca     540
atgcgaattt caaaaccaca tcttagatca atcagcatac agtgttatct ttgtctgctg     600
ctcaacagcc atttcttgac tgaagccaac tgggtcaacg taatttctga tcttaaaaaa     660
atcgaggatc tgatccagag tatgcacata gacgcaacgc tttacaccga agtgatgtc     720 catccgtcat gtaaagtaac ggcgatgaag tgtttccttc tcgagcttca ggtaatttca     780
ttggagtctg gagatgcctc tattcatgac acggtagaga atttgatcat tctcgctaac     840
aatagtcttt ccagtaacgg taacgttaca gagagcggat gtaaagaatg tgaggaattg     900
gaggagaaga acattaagga attccttcag tcctttgtcc acatcgttca gatgtttatt     960
aacacgagtt ga                                                         972
```

<210> SEQ ID NO 36
<211> LENGTH: 25
<212> TYPE: DNA
<213> ORGANISM: Artificial Sequence
<220> FEATURE:
<223> OTHER INFORMATION: Forward cloning primer

<400> SEQUENCE: 36

```
ctagaggcta gcgccaccat ggcac                                            25
```

<210> SEQ ID NO 37
<211> LENGTH: 23
<212> TYPE: DNA
<213> ORGANISM: Artificial Sequence
<220> FEATURE:
<223> OTHER INFORMATION: Reverse cloning primer

<400> SEQUENCE: 37

```
ctaggcggcc gctcaactcg tgt                                              23
```

-continued

<210> SEQ ID NO 38
<211> LENGTH: 1162
<212> TYPE: DNA
<213> ORGANISM: Artificial Sequence
<220> FEATURE:
<223> OTHER INFORMATION: Entolomid (TLR5 agonist)

<400> SEQUENCE: 38

```
ctggggatcg gcctcttcat ggggtccggt gccaccaact tttctctcct gaagcaggcg      60
ggcgatgtcg aagagaaccc agggcctatg ctcctgctcg taacctctct ccttttgtgc     120
gaattgcccc accctgcatt cttgcttata ccaatgcgcg gcagtcacca tcatcatcac     180
cacggtatgg cgagtatgac tggcggccag cagatgggcc gggacctgta tgatgacgat     240
gacaaagacc cgatggctca ggtcatcaat actaatagcc tgtcactgct cacccagaac     300
aacctggtta atcacagtc atccttgtca tcagcgatag agaggttgtc ttctggactc     360
cgcatcaact ctgctaagga tgatgcagct ggtcaagcaa tagcaaaccg attcacctcc     420
aatatcaaag gacttacgca ggccagtagg aatgcgaatg atggaataag catcgcacag     480
actacggaag gagcgctgaa cgaaatcaac aataacctcc agcgcgttcg cgaactctct     540
gtccaggcga caacgggcac gaattctgat agcgatctta aatcaataca agacgagata     600
cagcagcgct tggaagagat tgatagggta agcggacaaa cgcaattcaa tggcgttaaa     660
gtgctttccc aggacaatca gatgaagata caagtcggcg caaacgacgg ggagacgatt     720
acaatcgact tgcaaaaaat agatgtgaaa agcctcgggt tggatgggtt taacgtcaat     780
agtcctggca ttagtggtgg cggcggtggg attttggaca gcatgggtac tcttattaat     840
gaagatgccg cagcagctaa aaaaagtact gctaacccgc tggcatccat cgattcagcg     900
ttgagtaaag ttgacgcagt ccgcagcagt ctgggcgcga tacaaaacag atttgattcc     960
gccattacca acctcggcaa taccgtcacc aatttgaatt cagcgagatc tcggattgag    1020
gacgccgatt acgcaacaga agtgtctaac atgtctaaag ctcaaatctt gcaacaggcc    1080
ggcacctccg tactggctca ggccaatcaa gttccacaga atgtgctgag tctgcttcga    1140
taagctctag acccgggctg ca                                              1162
```

<210> SEQ ID NO 39
<211> LENGTH: 440
<212> TYPE: PRT
<213> ORGANISM: Artificial Sequence
<220> FEATURE:
<223> OTHER INFORMATION: scFV PD-1 inhibitor

<400> SEQUENCE: 39

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110
```

```
Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
        180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
        260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
        340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
        420                 425                 430

Ser Leu Ser Leu Ser Leu Gly Lys
        435                 440

<210> SEQ ID NO 40
<211> LENGTH: 214
<212> TYPE: PRT
<213> ORGANISM: Artificial Sequence
<220> FEATURE:
<223> OTHER INFORMATION: Light chain sequence

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 128
<212> TYPE: PRT
<213> ORGANISM: Artificial Sequence
<220> FEATURE:
<223> OTHER INFORMATION: Variable heavy

<400> SEQUENCE: 41

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

<210> SEQ ID NO 42
<211> LENGTH: 107
<212> TYPE: PRT
<213> ORGANISM: Artificial Sequence
<220> FEATURE:
<223> OTHER INFORMATION: Variable light -continued

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 43
<211> LENGTH: 19
<212> TYPE: PRT
<213> ORGANISM: Artificial Sequence
<220> FEATURE:
<223> OTHER INFORMATION: Optimized heavy chain

<400> SEQUENCE: 43

Met Glu Phe Gly Leu Ser Trp Val Phe Leu Val Ala Leu Phe Arg Gly
1               5                   10                  15

Val Gln Cys

<210> SEQ ID NO 44
<211> LENGTH: 57
<212> TYPE: PRT
<213> ORGANISM: Artificial Sequence
<220> FEATURE:
<223> OTHER INFORMATION: Optimized heavy chain

<400> SEQUENCE: 44

Ala Thr Gly Gly Ala Gly Thr Thr Thr Gly Gly Gly Cys Thr Gly Ala
1               5                   10                  15

Gly Cys Thr Gly Gly Gly Thr Thr Thr Thr Cys Cys Thr Cys Gly Thr
            20                  25                  30

Thr Gly Cys Thr Cys Thr Thr Thr Thr Ala Gly Ala Gly Gly Thr
        35                  40                  45

Gly Thr Cys Cys Ala Gly Thr Gly Thr
    50                  55

<210> SEQ ID NO 45
<211> LENGTH: 22
<212> TYPE: PRT
<213> ORGANISM: Artificial Sequence
<220> FEATURE:
<223> OTHER INFORMATION: Optimized light chain

<400> SEQUENCE: 45

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 46
<211> LENGTH: 66

```
-continued

<212> TYPE: PRT
<213> ORGANISM: Artificial Sequence
<220> FEATURE:
<223> OTHER INFORMATION: Optimized light chain

<400> SEQUENCE: 46

Ala Thr Gly Gly Ala Cys Ala Thr Gly Ala Gly Gly Thr Cys Cys
1               5                   10                  15

Cys Thr Gly Cys Thr Cys Ala Gly Cys Thr Cys Cys Thr Gly Gly Gly
            20                  25                  30

Gly Cys Thr Cys Cys Thr Gly Cys Thr Gly Cys Thr Cys Thr Gly Gly
            35                  40                  45

Cys Thr Cys Thr Cys Ala Gly Gly Thr Gly Cys Cys Ala Gly Ala Thr
            50                  55                  60

Gly Thr
65
```

GENETIC ENGINEERING OF MACROPHAGES FOR IMMUNOTHERAPY

CROSS-REFERENCE TO RELATED APPLICATIONS

This application is a continuation of U.S. application Ser. No. 15/258,887 filed Sep. 7, 2016 which claims priority to U.S. Prov. App. No. 62/216,224, entitled "Genetic Engineering Of Macrophages For Immunotherapy" filed Sep. 9, 2015, and U.S. Prov. App. No. 62/361,348, entitled "Genetic Engineering Of Macrophages For Immunotherapy" filed Jul. 12, 2016, the contents of which are each incorporated by reference in its entirety.

REFERENCE TO SEQUENCE LISTING

The present application is being filed along with a Sequence Listing in electronic format. The Sequence Listing is provided as a file entitled Sequence SCRI.101C1SeqListing.TXT, created Nov. 16, 2019 which is 42 kb in size. The information is the electronic format of the Sequence Listing is incorporated herein by reference in its entirety.

FIELD OF THE INVENTION

Disclosed herein are methods of modifying a tumor microenvironment (TME) in a subject in need, such that suppression of an immune response in a tumor microenvironment is modulated, and the proliferation of tumor and suppressive cells in a subject in need is minimized. Additionally, methods for improving a cancer therapy in a subject in need, is also contemplated. The methods can include administering to the subject a therapeutic dose of genetically modified immune cells or a composition of genetically modified immune cells.

BACKGROUND OF THE INVENTION

Modulation of a patient's immune system using immunotherapeutic approaches has shown remarkable success against hematological neoplasms and some solid tumors, including metastatic melanoma and colorectal carcinoma. In contrast to these successes, solid tumors, including glioblastoma (GBM) tumors have not yet responded to immunotherapy approaches. This is largely due to the fact that many solid tumors and the microenvironments that they create are highly immunosuppressive and tumor promoting, supporting tumor growth and preventing the localization and functions of cytotoxic immune cells. Therefore, an approach to overcome the influence of the tumor microenvironment (TME) and the impact on infiltrating immune cells that are responsible for the elimination of transformed cells is required as a first step in developing successful immunotherapies for GBM and other solid tumors.

For example, while childhood leukemias have shown remarkable responses to T cell-based therapeutics; treatment of solid tumors has not been nearly as successful. Along with a lack of tumor-specific antigens, the immunosuppressive microenvironment of many solid tumors has thus far been an insurmountable barrier, precluding CAR T-cell immunotherapy. Brain tumors, which represent 20% of childhood cancers, are highly infiltrated by myeloid cells that render the tumor highly resistant to the cytotoxic functions.

As such, an approach to overcome the influence of the tumor microenvironment (TME) and the impact on infiltrating immune cells that are responsible for the elimination of transformed cells is strongly needed as a first step in developing successful immunotherapies for GBM and other solid tumors.

Glioblastoma (GBM), a WHO grade IV astrocytoma, is the most aggressive primary brain tumor in adults and children, with a 5 year survival rate of <10% and 40%, respectively (Omuro A, DeAngelis L M. Glioblastoma and other malignant gliomas: a clinical review. JAMA 2013; 310:1842-1850; included by reference in its entirety herein). Standard therapy for patients with GBM includes surgery, temozolomide chemotherapy, and radiation, and provides only a modest extension of survival. For many patients, treatment associated side effects preclude a reasonable quality of life. Adoptive cellular immunotherapies are appealing for patients with GBM because these cells have the potential to efficiently home to the tumor site and specifically target tumor cells, without injury to neural and glial structures (Choi B D, Pastan I, Bigner D D et al. A novel bispecific antibody recruits T cells to eradicate tumors in the "immunologically privileged" central nervous system. Oncoimmunology 2013; 2:e23639; Grupp S A, Kalos M, Barrett D et al. Chimeric antigen receptor-modified T cells for acute lymphoid leukemia. N Engl J Med 2013; 368:1509-1518; Miao H, Choi B D, Suryadevara C M et al. EGFRvIII-specific chimeric antigen receptor T cells migrate to and kill tumor deposits infiltrating the brain parenchyma in an invasive xenograft model of glioblastoma. PLoS One 2014; 9:e94281; Ransohoff R M, Engelhardt B. The anatomical and cellular basis of immune surveillance in the central nervous system. Nat Rev Immunol 2012; 12:623-635; all incorporated by reference in their entireties herein). Like many types of solid tumors found in a variety of tissues, GBM tumor cells create a complex tumor microenvironment (TME) that includes regulatory T cells (Tregs), myeloid derived suppressor cells (MDSCs), and tumor associated macrophages (TAMs) that prevent immune surveillance by endogenous T cells and natural killer (NK) cells, reduce antigen presentation, and hinder the activity of adoptively transferred anti-tumor T cells (Razavi S M, Lee K E, Jin B E et al. Immune Evasion Strategies of Glioblastoma. Front Surg 2016; 3:11; Kostianovsky A M, Maier L M, Anderson R C et al. Astrocytic regulation of human monocytic/microglial activation. J Immunol 2008; 181:5425-5432; Beavis P A, Slaney C Y, Kershaw M H et al. Reprogramming the tumor microenvironment to enhance adoptive cellular therapy. Semin Immunol 2016; 28:64-72; all incorporated by reference in their entireties herein). Novel treatments that circumvent this suppressive milieu could greatly improve the endogenous anti-tumor response for patients harboring GBM or other types of solid tumors, as well as enhance the efficacy of immunotherapies, such as antibody-mediated checkpoint blockade, antibody-induced cytotoxicity, and engineered T cell therapies.

In spite of the successes against hematologic malignancies, immunotherapeutic interventions for glioblastoma (GBM) have thus far been unsuccessful. This is in part due to the presence of a tumor microenvironment that fosters neoplastic growth and protects the tumor from destruction by the immune system. Accordingly, new approaches to modify a tumor microenvironment (TME) in a subject in need are needed.

SUMMARY OF THE INVENTION

Described herein, are genetically engineered macrophage-based immunotherapies, which when implanted into the brain following a gross total resection, will neutralize the GBM microenvironment by supporting a pro-inflammatory innate response and enhancing tumor-directed immune activity by cytotoxic T and NK cells. The newly-described lentiviral expression system for the generation of transduced monocytes and monocyte-derived macrophages was validated and showed that transgene expression is stable over the course of weeks to months, both in vitro and in a mouse xenograft model of GBM. Furthermore, the genetically engineered macrophages (GEMs) did not cause morbidity in animals, nor did they contribute to accelerated tumor growth. The versatility of GEMs was highlighted by showing that they can be engineered to secrete proteins that either reduce immune suppression, such as the soluble TGFβRII, or promote immune cell activation, by expressing IL-21. Also disclosed, is the potential to prevent GEM-mediated immune suppression by using the CRISPR system to knock out genes responsible for dysfunction of cytotoxic cells, including IL-10 and PD-L1. Together, the results described herein provide evidence that GEMs are an ideal cell type for transforming the tumor microenvironment and enhancing anti-tumor immunity. Importantly, it is anticipated that these findings will have broad applicability to other types of tumors with microenvironments that currently preclude successful immunotherapeutic approaches.

Accordingly, disclosed herein is the first medical use of an engineered primary macrophage e.g., a genetically engineered primary macrophage for medical treatment. Aspects of the invention described herein also include a genetically engineered primary macrophage for use as a medicament to treat a cancer such as glioblastoma (GBM), breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas or ovarian cancer.

Macrophages make an ideal therapeutic cell type for restructuring the suppressive TME because they play a central role in the crosstalk between the adaptive and innate immune systems, are efficiently recruited to and retained within the tumor, and survive in the TME even after their polarization toward a pro-inflammatory phenotype (Long K B, Beatty G L. Harnessing the antitumor potential of macrophages for cancer immunotherapy. Oncoimmunology 2013; 2:e26860; Peng J, Tsang J Y, Li D et al. Inhibition of TGF-beta signaling in combination with TLR7 ligation re-programs a tumoricidal phenotype in tumor-associated macrophages. Cancer Lett 2013; 331:239-249; Beatty G L, Chiorean E G, Fishman M P et al. CD40 agonists alter tumor stroma and show efficacy against pancreatic carcinoma in mice and humans. Science 2011; 331:1612-1616; Pyonteck S M, Akkari L, Schuhmacher A J et al. CSF-1R inhibition alters macrophage polarization and blocks glioma progression. Nat Med 2013; 19:1264-1272; all included by reference in their entireties herein). Furthermore, engineered macrophages may be generated from a patient's monocyte population that is discarded during the preparation of therapeutic T Cell Receptor (TCR) or Chimeric Antigen Receptor (CAR) T cells. Described herein, is the first proposed use of engineered primary macrophages for therapeutic purposes, partly due to the difficulty in genetically manipulating these cells with clinically approved vectors such as HIV1-based lentivirus. Macrophages are refractory to lentiviral transduction because of their expression of a restriction factor, SAMHD1, which depletes the pool of nucleotide triphosphates available for reverse transcription (Lahouassa H, Daddacha W, Hofmann H et al. SAMHD1 restricts the replication of human immunodeficiency virus type 1 by depleting the intracellular pool of deoxynucleoside triphosphates. Nat Immunol 2012; 13:223-228; incorporated by reference in its entirety herein). Recent development of a lentiviral packaging system that generates virions containing viral protein X (Vpx), an SIV and HIV2-associated protein that induces the degradation of SAMHD1, has made it possible to stably deliver genes to primary human myeloid cells (Bobadilla S, Sunseri N, Landau N R. Efficient transduction of myeloid cells by an HIV-1-derived lentiviral vector that packages the Vpx accessory protein. Gene Ther 2013; 20:514-520; incorporated by reference in its entirety herein).

Also described herein, is a platform that takes advantage of this method to evaluate the use of genetically engineered macrophages (GEMs) as a potential therapeutic. Thus it can be demonstrated that GEMs: (1) survive in a xenograft model of GBM without impacting animal survival, (2) can be made resistant to reprogramming by tumor-secreted signals, and (3) stably express factors that will promote persistence and activation of endogenous or adoptively transferred NK or T cells. Described in the alternatives herein are the results from investigating the utility of GEMs as a cellular delivery vehicle that can express a multitude of factors that can overturn an immunosuppressive TME and support existing or novel immunotherapies.

Disclosed herein, is a method of developing a genetically engineered macrophage (GEM)-based immunotherapy, for example, which, when implanted into the brain following a gross total resection, serves to neutralize the GBM microenvironment through the expression of factors that simulate a pro-inflammatory immune response, allowing functional tumor-directed immune activity. Additionally, a myeloid-specific lentiviral expression system for the generation of transduced monocyte-derived macrophages has been validated, and shows that transgene expression is stable over the course of weeks to months, both in vitro and in a mouse intracranial xenograft model. Furthermore, the GEMs do not cause any morbidity in animals, nor do they contribute to accelerated tumor growth. The versatility of GEMs is highlighted by showing that they can be modified to secrete factors, such as the soluble TGFβR, IL-7, or IL-21, and can be precisely targeted by the CRISPR system to knock out genes responsible for dysfunction of cytotoxic cells, such as IL-10 and PD-L1. The results disclosed herein provide evidence that GEMs transform the tumor microenvironment to enhance immune surveillance and tumor destruction.

In a first aspect, a method of making a genetically modified immune cell for modifying a tumor microenvironment (TME) of a tumor is provided. The method can include delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1(KNIIQFVH-GEEDLKVQHSSYRQRARLLKDQLSLG-NAALQITDVKLQDAGVYRCM ISYGGA-DYKRITVKVNAPYNKI; SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the immune cell is selected from the group consisting of a macrophage, allogeneic cell, myeloid cell, a monocyte and a human monocyte. In some alternatives, the immune cell is a T cell. In some alternatives, the immune cell is an NK cell. In some alternatives, the immune cell is a genetically modified NK cell. In some alternatives, the T-cell is a genetically modified T-cell. In some alternatives, the genetically modified T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the method further comprises delivering to the immune cell, a fourth vector, wherein the fourth vector encodes a Cas9 VP64 fusion protein to activate transcription and translation of a second protein and delivering to the immune cell a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene encodes IL-12p40, IL-15, IL-6, IL-1 beta, TNF-alpha, IFN-alpha/beta/gamma, IL-12, IL-18, IL-23 or GM-CSF. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the method further comprises differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor.

In a second aspect, a genetically modified immune cell is provided. The genetically modified immune cell can comprise a first vector, wherein the first vector comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In a third aspect, a composition is provided. The composition can comprise any one or more of the genetically modified immune cells of any of the alternatives described herein and a carrier, an anti-cancer therapeutic, an anti-infection therapeutic, an antibacterial therapeutic, an anti-viral therapeutic, or an anti-tumoral therapeutic. The genetically modified immune cell can comprise a first vector that comprises a nucleic acid encoding a protein that induces T-cell proliferation, promotes persistence and/or activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/ Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In a fourth aspect, a method of modulating the suppression of the immune response in a tumor microenvironment of a subject e.g., a human is provided, wherein the method can comprise administering any one or more of the genetically modified immune cells of any one or more of the alternatives described herein or any of the compositions of any one or more of the alternatives described herein and a carrier, an anti-cancer therapeutic, an anti-infection therapeutic, an antibacterial therapeutic, an anti-viral therapeutic, or an anti-tumoral therapeutic. The genetically modified immune cell can comprise a first vector that comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 binding and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the administering is performed by adoptive cell transfer. In some alternatives, the genetically modified immune cells are administered by direct delivery to a tumor bed by injection. In some alternatives, the subject in need e.g., a human suffers from cancer or a subject having cancer is selected to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. The composition can comprise any one or more of the genetically modified immune cells of any one or more of the alternatives described herein and a carrier, anti-cancer therapeutic, anti-infection therapeutic, antibacterial therapeutic, anti-viral therapeutic, or anti-tumoral therapeutic. In some alternatives, the method further comprises administering a cellular therapy to the subject in need thereof before, after or simultaneous to introducing, providing, or administering any one or more of the cells of any of the alternatives described herein or the composition of any of the alternatives described herein. In some alternatives, the cellular therapy is CAR T-cell therapy. In some alternatives, the method further comprises delivering antibodies, small molecules, heat shock protein-peptide complexes or oncolytic polio virus to the subject in need thereof before, after, or simultaneous to introducing, providing, or administering any one or more of the cells of any of the alternatives described herein or the composition of any of the alternatives described herein into the subject for therapy. In some alternatives, the antibodies are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of anyone of the alternatives described herein or the composition of anyone of the alternatives described herein. In some alternatives, the subject is identified or selected to receive an anti-cancer therapy, an anti-infection therapy, an antibacterial therapy, an anti-viral therapy, or an anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of anyone of the alternatives described herein or the composition of anyone of the alternatives described herein. In some alternatives, the additional therapeutic agent is an anti-cancer therapy comprising a hormone blocking therapy, chemotherapy, a small molecule, monoclonal antibodies, or binding fragments thereof, and/or radiation. In some alternatives, the monoclonal antibody is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In a fifth aspect, a method of minimizing the proliferation of tumor and suppressive cells in a subject in need thereof is provided. The method can comprise administering any one or more of the genetically modified immune cells or any of the compositions of any one or more of the alternatives described herein to a subject in need thereof and, optionally, selecting or identifying said subject to receive said genetically modified immune cells and/or measuring the proliferation of tumor and suppressive cells in said subject after administration of said genetically modified immune cells. The composition can comprise any one or more of the genetically modified immune cells of any one or more of the alternatives described herein and a carrier, anti-cancer therapeutic, anti-infection therapeutic, antibacterial therapeutic, anti-viral therapeutic, or anti-tumoral therapeutic. The genetically modified immune cell can comprise a first vector that comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 binding and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the administering is performed by adoptive cell transfer. In some alternatives, the genetically modified immune cells are administered by direct delivery to a tumor bed by injection. In some alternatives, the subject in need e.g., a human suffers from cancer or a subject having cancer is selected to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the method further comprises administering a cellular therapy to the subject in need thereof before, after or simultaneous to introducing, providing, or administering any one or more of the cells of any of the alternatives described herein or the composition of any of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any of the alternatives described herein or the composition of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of anyone of the alternatives described herein or the composition of anyone of the alternatives described herein. In some alternatives, the subject is identified or selected to receive anti-cancer therapy, anti-infection therapy, antibacterial therapy, anti-viral therapy, or anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of anyone of the alternatives described herein or the composition of anyone of the alternatives described herein. In some alternatives, the additional therapeutic agent is an anti-cancer therapy comprising a hormone blocking therapy, chemotherapy, a small molecule, monoclonal antibodies, or binding fragments thereof and/or radiation. In some alternatives, the monoclonal antibody is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In a sixth aspect, a method of increasing the efficiency of an anti-cancer therapy, anti-infection therapy, antibacterial therapy, anti-viral therapy, or anti-tumoral therapy in a subject in need thereof is provided. The method can comprise administering any one or more of the genetically modified immune cells or any of the compositions of any one or more of the alternatives described herein to a subject in need thereof and, optionally, selecting or identifying said subject to receive said genetically modified immune cells and/or measuring the proliferation of the cancer, infection, bacteria, virus, or tumor in said subject after administration of said genetically modified immune cells. The composition can comprise any one or more of the genetically modified immune cells of any one or more of the alternatives described herein and a carrier, anti-cancer therapeutic, anti-infection therapeutic, antibacterial therapeutic, anti-viral therapeutic, or anti-tumoral therapeutic. The genetically modified immune cell can comprise a first vector that comprises a nucleic acid encoding a protein that promotes persistence and activation of endogenous or adoptively transferred NK or T cells, induces T-cell proliferation and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from a group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 binding and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the administering is performed by adoptive cell transfer. In some alternatives, the genetically modified immune cells are administered by direct delivery to a tumor bed by injection. In some alternatives, the subject in need e.g., a human suffers from cancer or a subject having cancer is selected to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the method further comprises administering a cellular therapy to the subject in need thereof before, after or simultaneous to introducing, providing, or administering any one or more of the cells of any of the alternatives described herein or the composition of any of the alternatives described herein. In some alternatives, the cellular therapy is a CAR T-cell therapy. In some alternatives, the method further comprises delivering antibodies, or binding fragments thereof small molecules, heat shock protein-peptide complexes or oncolytic polio virus to the subject in need thereof before, after, or simultaneous to introducing, providing, or administering any one or more of the cells of any of the alternatives described herein or the composition of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the subject is identified or selected to receive anti-cancer therapy, anti-infection therapy, antibacterial therapy, antiviral therapy, or anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of anyone of the alternatives described herein or the composition of anyone of the alternatives described herein. In some alternatives, the additional therapeutic agent is an anti-cancer therapy comprising a hormone blocking therapy, chemotherapy, a small molecule, monoclonal antibodies, or binding fragments thereof and/or radiation. In some alternatives, the monoclonal antibody is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor. More alternatives concern any one or more of the aforementioned genetically modified immune cells, alone or in combination, for use as a medicament.

In a seventh aspect, the genetically modified immune cell of any one of the alternatives described herein is for use as a medicament. The genetically modified immune cell can comprise a first vector wherein the first vector comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

BRIEF DESCRIPTION OF THE DRAWINGS

FIG. 1A shows representative tissue sections stained with CD163, a macrophage cell marker (right) and analyzed using Nuance quantitative software for number of cells/field (left) (FIG. 1B). FIG. 1C shows representative flow cytometry of GBM patient tumor-infiltrating macrophages analyzed immediately after tumor resection as defined by CD11b and HLA-DR expression (left). Summary of all patients analyzed (MNGn=13, GBMn=17) (FIG. 1D).

FIG. 4A: MDMs transduced with a GFP and luciferase-encoding lentivirus and evaluated for expression of GFP. FIG. 4B: Results of NSG mice intracranially injected with $2\times10^5$ wild-type U87 cells. FIG. 4C: Longitudinal GEM luminescence signals.

As shown in FIG. 6A, Top panel, are macrophages derived from primary monocytes using GM-CSF and stained with antibodies to HLA-DR-PE-Cy7 and TGFβRII-488 and analyzed by FCM. (Bottom panel, FIG. 6C). MFI of HLA-DR+ cells (~98% of the population. As shown in FIG. 6B, are 293 Ts expressing a SBE (SMAD binding element) luciferase reporter and/or dnTGFβRII were treated with 1 ng/mL TGFβ1 for 3 hours.

As shown in FIG. 7A, supernatant from parental or PD1:IFNα-transduced H9 cells was concentrated, electrophoresed and Western blotted, using monoclonal antibodies to either a 2A tag, which is retained by the IFNa protein (left, 1:5000), or PD1 (right, 1:250). FIG. 7B: Parental or PD1:IFNα-transduced H9 cells were cultured with Brefeldin A, fixed and permeablized, and an intracellular stain performed with fluorophore-conjugated antibodies. Cells were analyzed by FCM for anti-IFNa (left) and anti-PD1 (right).

(FIG. 13C) Similar to FIG. 13A, but infection was performed concurrent with differentiation, and analysis performed 14 days after isolation/infection. (FIG. 13D) Yield of GM-CSF and M-CSF macrophages differentiated in the presence or absence of 250 LP/cell of virus. Percentage is relative to the number of input CD14+ cells, and error bars represent the standard deviation of 3 independent replicates. (t-test, *, $p<0.05$. 209×218 mm (300×300 DPI)).

(FIG. 15B) Percentage cells positive, or (FIGS. 15C-15G) mean fluorescence intensity (MFI), and overlaid histograms of macrophage surface protein expression following, viral infection, and/or LPS/IFNγ stimulation. Error bars represent the standard deviation of independent experiments using monocytes from 3 healthy donors. One-way ANOVA with Dunnet's multiple comparisons test. *$p<0.05$, $p<0.01$, *$p<0.001$, ****$p<0.0001$.

(FIG. 16A) Experimental schema: Animals were injected with unlabeled U87s, Six days later; animals were injected in the same site with GFP-ffluc-expressing GEMs. (FIG. 16B) Bioluminescent images 15 minutes after the subcutaneous injection of luciferin. (FIG. 16C) Longitudinal analysis of bioluminescence in luciferin treated animals injected with U87 tumor cells and PBS only (circles), GM-CSF differentiated GEMs (squares), or GM-CSF differentiated, LPS/IFNγ stimulated GEMs (triangles) (FIG. 16D) Survival curve for animals injected with U87 tumor cells and PBS only, GM-CSF differentiated GEMs or GM-CSF differentiated, LPS/IFNγ stimulated GEMs (n=4 each group, Mantel-Cox: $p=0.2542$).

(FIG. 17A) Experimental schema: Animals were injected with GFP-ffluc-expressing U87s. Seven days later, animals were injected in the same site with mCherry-expressing (non-bioluminescent) GEMs. (FIG. 17B) Bioluminescent images 15 minutes after the subcutaneous injection of luciferin. (FIG. 17C) Longitudinal analysis of bioluminescence in luciferin treated animals injected with U87 tumor cells and PBS only (circles), GM-CSF differentiated GEMs (squares), or GM-CSF differentiated, LPS/IFNγ stimulated GEMs (triangles) (FIG. 17D) Survival curve for animals injected with U87 tumor cells and PBS only, GM-CSF differentiated GEMs or GM-CSF differentiated, LPS/IFNγ stimulated GEMs, n=5 each group, (Mantel-Cox: p=0.4491). (FIGS. 17E-17G) To identify GEMs in tumor tissue, formalin-fixed, paraffin-embedded whole brain sections were immunostained with an antibody against human CD45. Tumor area is denoted with * and is bounded with a dotted line.

FIG. 19A) Amplified and annealed genomic DNA isolated from GEMs infected with a Cas9/IL-10gRNA-expressing virus, but not Cas9 only control, is cleaved by the Surveyor endonuclease. FIGS. 19B, 19C) GEMs expressing Cas9 and IL-10gRNA produce less IL-10 in response to LPS+IFNγ stimulation. FIG. 19D) Amplified and annealed genomic DNA isolated from GEMs infected with a Cas9/PD-L1gRNA-expressing virus, but not Cas9 only control, is cleaved by the Surveyor endonuclease. FIG. 19E) Representative flow plot showing decreased LPS+IFNγ induced PD-L1 expression on GEMs expressing Cas9/PD-L1gRNA relative to Cas9 only control. FIG. 19F) MFI differences in PD-L1 expression after Cas9-mediated PD-L1 gene disruption. FIG. 19G) GM-CSF-differentiated macrophages were seeded at 500,000 cells per well in a 12 well plate were transduced with 250 or 500 LP/cell of lentivirus encoding sTGFβRII. Media was collected on days 3, 5, 12, and 15 following 24 hours of conditioning and protein secretion was detected by ELISA. GEMs express sTGFβRII in a manner that is dependent on the dose of virus. Expression peaks around day 5 post transduction, but persists for at least 2 weeks. Error bars represent the standard deviation of independent experiments using monocytes from 3 healthy donors. FIG. 19H) GM-CSF-differentiated macrophages were seeded at 200,000 cells per well in a 24 well plate were transduced with 1000 LP/cell of lentivirus encoding IL-21. Media was collected on days 6 following 24 hours of conditioning and protein secretion was detected by Bioplex. Error bars represent the standard deviation of independent experiments using monocytes from 2 healthy donors. FIG. 19I) GM-CSF-differentiated macrophages were seeded at 500,000 cells per well in a 12 well plate were transduced with 250 or 500 LP/cell of lentivirus encoding sTGFβRII. Media was collected on days 3, 5, 12, and 15 following 24 hours of conditioning and protein secretion was detected by ELISA. GEMs express sTGFβRII in a manner that is dependent on the dose of virus. Expression peaks around day 5 post transduction, but persists for at least 2 weeks. Error bars represent the standard deviation of independent experiments using monocytes from 3 healthy donors.

FIG. 21A: Representative section from a mouse injected with U87 only and mock injected with PBS 5 days later, FIG. 21B: Representative section from a mouse injected with U87 cells, and 5 days later with CD45 expressing GEMs.

(FIG. 24E) CD19t epitope tag surface expression analyzed by flow cytometry following infection with lentiviruses encoded in (FIG. 24C). (FIG. 24F) EGFRt epitope tag surface expression by flow cytometry following infection with lentiviruses encoded in (24D).

(FIG. 25A) Following 7 days of GM-CSF differentiation, macrophages were infected with 20, 50, 100, 250, 500, 750, or 1000 GFP-ffluc-encoding lentiviral particles (LP) per cell containing Vpx, or 1000 LP/cell without Vpx. Seven days after infection (14 days after isolation), the frequency of the population positive for both HLA-DR and GFP (upper right quadrant) was quantified by flow cytometry. Data are representative of 3 independent replicates. (FIG. 25B) Similar to A, but infection was performed concurrently with differentiation, and analysis performed 14 days later. Yields of cells infected as macrophages (FIG. 25C) or monocytes (FIG. 25D) relative to the number of uninfected cells recovered. (FIG. 25E) Yield of macrophages recovered following differentiation with GM-CSF or M-CSF, as a percentage of the number of CD14+ monocytes originally isolated. Error bars represent the standard deviation of independent experiments using CD14+ monocytes isolated from 3 healthy donors. Unpaired t-test, ns: p>0.05. ns: not significant.

(FIG. 26A) GEMs transduced with Cas9 and IL-10gRNA were evaluated for IL-10 secretion in response to LPS+IFNγ stimulation using Bioplex. IL-10 expression for each patient was expressed as percent of the EGFRt vector control. Error bars represent the standard deviation of independent experiments using CD14+ monocytes isolated from 3 healthy donors. Unpaired t-test, *p<0.001. (FIG. 26B) Representative flow cytometry dot plot showing LPS+IFNγ induced PD-L1 expression on GEMs expressing Cas9/PD-L1gRNA relative to Cas9 only control (EGFRt vector). (FIG. 26C) Mean fluorescence intensity of PD-L1 surface expression after Cas9-mediated PD-L1 gene disruption. Error bars represent the standard deviation of independent experiments using CD14+ monocytes isolated from 3 healthy donors. PD-L1 expression for each patient was expressed as percent of the EGFRt vector control. Unpaired t-test, **p<0.0001. (FIG. 26D) GM-CSF-differentiated macrophages were transduced on day 7 with 250 LP/cell lentivirus encoding CD19t-T2A-sTβRII or CD19t vector control. Media was collected on days 5, 6, and 7, following 24 hours of conditioning at each time point, and secreted sTβRII was detected using ELISA. Error bars represent the standard deviation of independent experiments using monocytes from 3 healthy donors. One-way ANOVA with Dunnet's multiple comparisons test. p>0.05. ns: not significant. n/d: not detected. (26E) GM-CSF-differentiated macrophages were transduced with 250 LP/cell of lentivirus encoding IL-21-T2A-CD19t or CD19t vector control. Media was replaced on day 6, and collected 24 hours later for quantification of secreted protein using Bioplex for IL-21. Error bars represent the standard deviation of independent experiments using monocytes from 3 healthy donors. n/d: not detected.

(FIG. 27A) GEMs infected with viruses encoding sTβRII and PD-L1gRNA can be selected for co-expression of the CD19t and EGFRt epitope tags (Q2, EGFRt and CD19t positive). (FIG. 27B) Representative flow cytometry dot plot showing decreased LPS+IFNγ induced PD-L1 expression on GEMs expressing Cas9/PD-L1gRNA relative to Cas9 only control, gated on both EGFRt and CD19t expression to select for dually infected cells. (FIG. 27C) MFI differences in PD-L1 expression after Cas9-mediated PD-L1 gene disruption and selection for co-expression of EGFRt and CD19t. Error bars represent the standard deviation of independent experiments using CD14+ monocytes isolated from 3 healthy donors. Unpaired t-test, ***p<0.001. (FIG. 27D) GEMs infected with two viruses produce sTβRII. Conditioned media was collected from doubly transduced cells as above and analyzed for sTβRII expression by ELISA. Error bars represent the standard deviation of independent experiments using CD14+ monocytes isolated from 3 healthy donors. n/d: not detected. (27E) GEMs infected with viruses encoding IL-21 and Cas9/IL-10gRNA identified using antibodies specific for non-signaling epitope tags CD19t and EGFRt (Q2, EGFRt and CD19t positive). Conditioned media was collected from doubly transduced cells as above and analyzed for IL-21 and IL-10 expression using Bioplex. (FIG. 27F) GEMs infected with IL-21 and IL-10gRNA viruses secrete reduced IL-10 in response to LPS+IFNγ. Error bars represent the standard deviation of independent experiments using CD14+ monocytes isolated from 3 healthy donors. One-way ANOVA with Dunnet's multiple comparisons test. *p<0.05, p<0.01, *p<0.001, ****p<0.0001. (FIG. 27G) GEMs infected with IL-21 and IL-10gRNA viruses still secrete high levels of IL-21. Error bars represent the standard deviation of independent experiments using CD14+ monocytes isolated from 3 healthy donors. Unpaired t test, p>0.05. ns: not significant. n/d: not detected.

(FIG. 29A) Following 7 days of M-CSF differentiation, macrophages were infected with 20, 50, 100, 250, 500, 750, or 1000 GFP-ffluc-encoding lentiviral particles (LP) per cell containing Vpx, or 1000 LP/cell without Vpx. Seven days after infection (14 days after isolation), the frequency of the population positive for both HLA-DR and GFP (upper right quadrant) was quantified by flow cytometry. Data are representative of 3 independent replicates. (FIG. 29B) Similar to FIG. 29A, but infection was performed concurrent with differentiation, and analysis performed 14 days after isolation/infection. (FIG. 29C) Yields of cells infected as monocytes relative to the number of uninfected cells recovered. Error bars represent the standard deviation of independent experiments using CD14+ monocytes isolated from 3 healthy donors. Unpaired t-test, *p<0.05.

DEFINITIONS

In the description that follows, a number of terms are used extensively. The following definitions are provided to facilitate understanding of the present alternatives.

As used herein, "a" or "an" may mean one or more than one.

As used herein, the term "about" indicates that a value includes the inherent variation of error for the method being employed to determine a value, or the variation that exists among experiments.

As described herein, the "tumor microenvironment" (TME) is the surrounding microenvironment that constantly interacts with tumor cells which is conducive to allow cross-talk between tumor cells and its environment. A tumor microenvironment plays a role in disrupting the cancer immunity cycle and plays a critical role in multiple aspects of cancer progression. For example, the TME can decrease drug penetration, confer proliferative and anti-apoptotic advantages to surviving cells, facilitate resistance without causing genetic mutations and epigenetic changes, and collectively modify disease modality and distort clinical indices. Without being limiting, the tumor microenvironment can include the cellular environment of the tumor, surrounding blood vessels, immune cells, fibroblasts, bone marrow derived inflammatory cells, lymphocytes, signaling molecules and the extracellular matrix. The tumor environment can include tumor cells or malignant cells that are aided and influenced by the tumor microenvironment to ensure growth and survival. The tumor microenvironment can also include tumor-infiltrating immune cells such as lymphoid and myeloid cells, which can stimulate or inhibit the antitumor immune response and stromal cells such as tumor-associated fibroblasts and endothelial cells that contribute to the tumor's structural integrity. Without being limiting, stromal cells can include cells that make up tumor-associated blood vessels, such as endothelial cells and pericytes, which are cells that contribute to structural integrity (fibroblasts), as well as tumor-associated macrophages (TAMs) and infiltrating immune cells including monocytes, neutrophils (PMN), dendritic cells (DCs), T and B cells, mast cells, and natural killer (NK) cells. The stromal cells make up the bulk of tumor cellularity while the dominating cell type in solid tumors is the macrophage.

The tumor microenvironment can also comprise microniches in which the niches are well perfused and oxygenated or poorly perfused and hypoxic. In the case in which the niche is poorly perfused and hypoxic, the niche can be particularly dangerous to the host as it can harbor resistant tumor cells that can survive a nutrient and oxygen deprived environment.

The tumor can influence its surrounding environment to be immunosuppressive by the release of extracellular signals, promoting tumor angiogenesis, for example, by the upregulation of VEGF, and induce peripheral immune tolerance.

Figure 9:
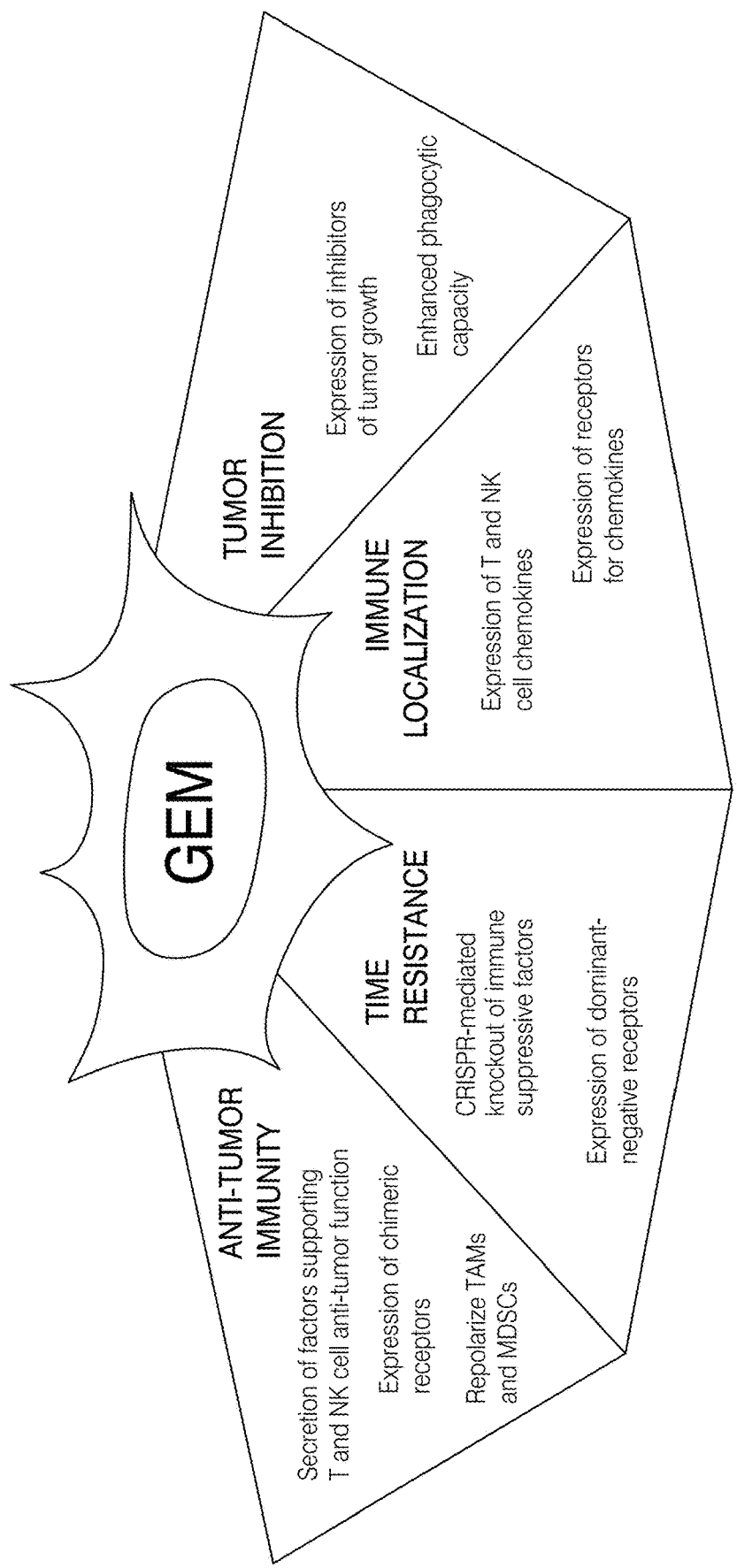
FIG. 9 shows genetically engineered macrophage (GEM) Functions. It is believed that GEMs derived from modified MMCs have diverse functions dependent on the method of modification, including 1) enhancing recruitment and functions of anti-tumor immune cells, 2) resisting functional modifications mediated by components of the tumor microenvironment that suppress immune responses, or 3) inhibiting tumor growth directly.

In some alternatives described herein, a method of making a genetically modified immune cell for modifying a tumor microenvironment (TME) is provided, wherein the method comprising delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, a method of modulating the suppression of the immune response in a tumor microenvironment of a subject in need thereof is provided, wherein the method comprises administering any one or more of the genetically modified immune cells of any one or more of the alternatives described herein to a subject in need thereof e.g., a human and, optionally, selecting or identifying said subject to receive said genetically modified immune cells and/or measuring a modulation of suppression of the immune response in the tumor microenvironment of said subject after administration of said genetically modified immune cells. In some alternatives, a method of minimizing the proliferation of tumor and suppressive cells in a subject in need thereof is provided, wherein the method comprises administering any one or more of the genetically modified immune cells of any one or more of the alternatives described herein to a subject in need thereof e.g., a human and, optionally, selecting or identifying said subject to receive said genetically modified immune cells and/or measuring the proliferation of tumor and suppressive cells in said subject after administration of said genetically modified immune cells. In some alternatives, the T-cells that are proliferated are selected from the group consisting of T-helper Cells, memory T-cells, cytotoxic T-cells, suppressor T-cells, natural killer T cells, and gamma delta T-cells. Shown in FIG. 9, is the use of some of the genetically modified immune cells described herein for increasing anti-tumor immunity.

In some alternatives, small designer proteins are used to occupy the PD-1 binding site without delivery of an agonist signal. Computational programs, mutagenesis and other methods to determine binding sites can be utilized. The PD-L1 residues 62-136, as described by Lin et al. ("The PD-1/PD-L1 complex resembles the antigen-binding Fv domains of antibodies and T-cell receptors," Proc Natl Acad Sci USA. 2008 Feb. 26; 105(8): 3011-3016; incorporated by reference in its entirety herein) can be used to occupy the PD-1 binding site in some alternatives described herein. Additionally, multiple PD-1 binding molecules can be tested for antagonist function upon binding of PD-1. PD-1 binding molecules that do not deliver an inhibitory signal can be used to inhibit PD-1/PD-L1 complex agonist activity or PD-1/PD-L2 agonist activity. Additionally in some alternatives, single chain antibody or antibody-like proteins generated using the sequence of monoclonal antibodies developed to inhibit PD-1 signaling can be used to prevent complex agonist activity. Examples are described in U.S. Pat. No. 8,008,449 B2 (hereby expressly incorporated by reference in its entirety).

"Protein" as described herein refers to a macromolecule comprising one or more polypeptide chains. A protein can therefore comprise of peptides, which are chains of amino acid monomers linked by peptide (amide) bonds, formed by any one or more of the amino acids. A protein or peptide can contain at least two amino acids, and no limitation is placed on the maximum number of amino acids that can comprise the protein or peptide sequence. Without being limiting, the amino acids are, for example, arginine, histidine, lysine, aspartic acid, glutamic acid, serine, threonine, asparagine, glutamine, cysteine, cystine, glycine, proline, alanine, valine, hydroxyproline, isoleucine, leucine, pyrolysine, methionine, phenylalanine, tyrosine, tryptophan, ornithine, S-adenosylmethionine, and selenocysteine. A protein can also comprise non-peptide components, such as carbohydrate groups, for example. Carbohydrates and other non-peptide substituents can be added to a protein by the cell in which the protein is produced, and will vary with the type of cell. Proteins are defined herein in terms of their amino acid backbone structures; substituents such as carbohydrate groups are generally not specified, but can be present nonetheless. In some alternatives described herein, a method of making a genetically modified immune cell for modifying a tumor microenvironment (TME) is provided, wherein the method comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the gene delivery polynucleotide further comprises a sequence for at least one protein. In some alternatives, the protein induces or promotes T-cell proliferation. In some alternatives, the protein induces production of an interleukin, an interferon, a PD-1 checkpoint binding protein, HMGB1, MyD88, a cytokine or a chemokine. In some alternatives, the protein is a fusion of PD-1 binding and interferon alpha, interferon beta, or interferon gamma. In some alternatives, the T-cells that are proliferated are selected from the group consisting of T-helper Cells, memory T-cells, cytotoxic T-cells, suppressor T-cells, natural killer T cells, and gamma delta T-cells.

Proteins that can be expressed by the genetically modified immune cell can also be genetically modified to enhance therapeutic effects, such as, for example, a longer half-life, and resistance to proteases. Methods such as fusion of a protein to a polypeptide such as PAS, albumin, and XTEN is described in the literature (Schlapschy et al., Protein Eng Des Sel. 2013 August; 26(8): 489-501; Kontermann et al., Current Opinion in Biotechnology Volume 22, Issue 6, December 2011, 868-876; Schulte et al., Thrombosis Research Volume 122, Supplement 4, 2008, Pages S14S19; all incorporated by reference in their entireties herein). Methods to increase a protein half-life can include, but is not limited to fusion of the protein of interest to albumin or a portion thereof to extend the half-life by recombinant techniques, fusion of a protein to an IgG Fc region to prolong the half-life of a protein by recombinant techniques, fusion of an antibody Fc domains onto the protein of interest in order to extend the half-life by recombinant techniques, fusion of the protein of interest to the 864 amino acid polypeptide, XTEN, in order to extend the protein half-life by recombinant techniques, and fusion of the protein of interest to the polypeptide, PAS (XL-protein GmbH)9), in order to extend the protein half-life by recombinant techniques. The genetic fusions with Fc, human serum albumin (HSA), the designed polypeptide fusions XTEN and PAS, are known to those skilled in the art and can be fused to the protein of interest by recombinant techniques in order add a longer half-life to a protein or to resist proteolysis. In some alternatives described herein, a method of making a genetically modified immune cell for modifying a tumor microenvironment (TME) is provided, wherein the method comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the protein is fused to a polypeptide by recombinant techniques in order to increase the half-life of the protein and/or to increase the resistance of the protein to degradation. In some alternatives, the polypeptide comprises an antibody Fc domain or portion thereof, an IgG Fc domain or portion thereof, XTEN or a portion thereof, PAS or a portion thereof, or human serum albumin or a portion thereof.

In some alternatives, the vectors encoding the protein for inducing T-cell proliferation and/or inducing production of an interleukin, an interferon, a PD-1 checkpoint binding protein, HMGB1, MyD88, a cytokine or a chemokine can be an RNA or a nucleic acid encoding an RNA for translation of the protein. The RNA can be constructed so that it is modified to contain different codons to optimize expression in a selected host cell e.g., human, as is known in the art. The RNA can be constructed to increase its half-life in the cell and to increase efficiency of translation of the protein. In some alternatives, polyadenylation can be used to increase the stability of an RNA in a cell and increase the half-life of an RNA. In some alternatives, the RNA is modified to increase the half-life of the RNA or to increase the translation levels in the cell. In some alternatives, the RNA can comprise a poly(A) tail of 50, 100, 150, 200, 250, 300, 350, 400, 450, or 500 covalently linked adenosine residues, or an amount of residues within a range defined by any two of the aforementioned values.

In some alternatives, an immune cell comprises a first vector, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the protein supports or promotes T-cell and/or NK-cell anti-tumor activity. Examples of proteins that can promote anti-tumor activity are described and are not limited to p53 (a tumor suppressor), ribosome inactivating proteins (RIPs; inhibition of protein synthesis and anti-tumor activities) and cytokines. In some alternatives, the protein is p53, a ribosome inactivating protein, a cytokine or a chemokine. Cytokines can include but are not limited to IL-2 (proliferation and development of NK cells), IL-1β (increases lytic activity of immune cells), IFNγ, IL-1, IL-7 (promote T-cell proliferation/survival and development of cytolytic effector functions), IL-15 (promote T-cell proliferation/survival and development of cytolytic effector functions), IL12 (promote T-cell proliferation/survival and development of cytolytic effector functions), IL-18 (promote CD8 and Th1 effector functions), IL-21 (regulatory effects on cells of the immune system, including natural killer (NK) cells and cytotoxic T-cells that can destroy virally infected or cancerous cells) or IL-33 (promote CD8 and Th1 effector functions). In some alternatives of the proteins expressed by the immune cells, the protein is a cytokine. In some alternatives, the cytokine is IL-2, IL-1β, IFNγ, IL-1, IL-7, IL-15, IL12, IL-18, IL-21 or IL-33. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35 (GCCACCATGGCACTTCCAGT-CACAGCGCTTCTTCTGCCTTTGGCACTGCTTCTCC ACGCAGCACGCCCAAACTGGGT-CAATGTAATCAGCGACCTGAAGAAGATTGAAG ACCTGATTCAATCAATGCACATAGACGC-TACGTTGTACACCGAATCAGATGTTCA TCCTAGCTGTAAAGTCACCGCAAT-GAAATGTTTTTTGCTGGAGCTTCAAGTTATA TCCCTTGAGTCTGGGGACGCATCTATA-CATGACACAGTTGAGAATTTGATCATAT TGGCAAACAATAGCTTGTCTTCCAACGGTAATGT-CACAGAGTCCGGTTGTAAAG AGTGTGAGGAACTT-GAAGAGAAAAACATTAAAGAAT-TTCTCCAGAGTTTCGTAC ATATTGTACAAATGTTCATAAATACTTCTATC-TATATCTGGGCTCCTCTCGCCGGA ACCTGTGGCGTTCTGCTGCTGTCTTTGGTGATTA-CAGGAAGTGGAGCCACAAATT TCAGTCTGCT-TAAACAGGCAGGGATGTGGAG-GAGAACCCCGGCCCAATGCGAA TTTCAAAACCACATCTTAGATCAATCAGCATA-CAGTGTTATCTTTGTCTGCTGCTC AACAGCCAT-TTCTTGACTGAAGCCAACTGGGTCAACGTAAT-TTCTGATCTTAAAA AAATCGAGGATCTGATCCAGAGTATGCACATA-GACGCAACGCTTTACACCGAAA GTGATGTC-CATCCGTCATGTAAAGTAACGGCGAT-GAAGTGTTTCCTTCTCGAGCT TCAGGTAATTTCATTGGAGTCTGGAGATGCCTCTAT-TCATGACACGGTAGAGAAT TTGATCAT-TCTCGCTAACAATAGTCTTTCCAGTAACGGTAACGT-TACAGAGAGCG GATGTAAAGAATGTGAGGAATTGGAGGAGAAGAA-CATTAAGGAATTCCTTCAGT CCTTTGTCCA-CATCGTTCAGATGTTTATTAACACGAGTTGA). In some alternatives, the protein comprises interferon alpha, interferon beta, or interferon gamma. More alternatives concern any one or more of the aforementioned genetically modified immune cells, alone or in combination, for use as a medicament e.g., to treat or inhibit a cancer such as breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

"Modulate immune response" or "modulation of an immune response" refers to the adjustment of an immune response to a desired level, such as, for example, in immunopotentiation, immunosuppression or induction of immunological tolerance. In the alternatives described herein, the genetically modified immune cells are provided to modulate the tumor microenvironment with secreted proteins that can alter immunity. These proteins or immunomodulators can include but is not limited to interleukins, cytokines, immunomodulatory antibodies, and chemokines. Without being limiting the immunomodulators can be IL-2, G-CSF, Imiquimod, CCL3, CCL26, CSCL7, TGFBRII, IL-1, IL-6, IL-7, IL-15, IL-2, IL12, IL-18, IL21, interferon alpha, interferon beta, interferon gamma, PD-1 checkpoint binding inhibitor, CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15.

Immunomodulators can either enhance an immune response or suppress it. In some alternatives, the immunomodulatory can enhance the activity of the immune system to increase the body's natural defense mechanism against a disease. Immunomodulators can also modulate immunosuppression in order to increase the efficacy of anti-cancer treatments. In a tumor environment, the tumor can inhibit or suppress the anti-tumor effect of the immune response. In some alternatives described herein, in cancer and/or "Chemokines" as described herein are a family of small cytokines, or signaling proteins secreted by cells. Chemokines can be either basal or inflammatory. Inflammatory chemokines are formed upon inflammatory stimuli such as IL-1, TNF-alpha, LPS or by viruses, and participate in the inflammatory response attracting immune cells to the site of inflammation. Without being limiting, inflammatory chemokines can include CXCL-8, CCL2, CCL3, CCL4, CCL5, CCL11 or CXCL10. In some alternatives, an immune cell comprises a first vector, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a T-cell or NK-cell chemokine. In some alternatives, the chemokine is CXCL-8, CCL2, CCL3, CCL4, CCL5, CCL11 or CXCL10. In some alternatives, the chemokine comprises CCL1, CCL2, CCL3, CCR4, CCL5, CCL7, CCL8, CCL11, CCL13, CCL17, CCL22, CCL24, or CCL26. In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokines are selected from the group consisting of EGF, Eotaxin, FGF-2, FLT-3L, Fractalkine, G-CSF, GM-CSF, GRO, IL-10, IL-12(p40), IL-12(p70), IL-13, IL-13, IL-15, Il18A, IL-1RA, Il-1a, IL-1b, Il-2, Il-3, Il-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, 1309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, IL-15 is encoded by a sequence set forth in SEQ ID NO: 35

(GCCACCATGGCACTTCCAGTCACAGCGCTTCTTCTGCCTTTGGCACTGC

TTCTCCACGCAGCACGCCCAAACTGGGTCAATGTAATCAGCGACCTGAAG

AAGATTGAAGACCTGATTCAATCAATGCACATAGACGCTACGTTGTACAC

CGAATCAGATGTTCATCCTAGCTGTAAAGTCACCGCAATGAAATGTTTTT

TGCTGGAGCTTCAAGTTATATCCCTTGAGTCTGGGGACGCATCTATACAT

GACACAGTTGAGAATTTGATCATATTGGCAAACAATAGCTTGTCTTCCAA

CGGTAATGTCACAGAGTCCGGTTGTAAAGAGTGTGAGGAACTTGAAGAGA

AAAACATTAAAGAATTTCTCCAGAGTTTCGTACATATTGTACAAATGTTC

```
ATAAATACTTCTATCTATATCTGGGCTCCTCTCGCCGGAACCTGTGGCGT

TCTGCTGCTGTCTTTGGTGATTACAGGAAGTGGAGCCACAAATTTCAGTC

TGCTTAAACAGGCAGGGGATGTGGAGGAGAACCCCGGCCCAATGCGAATT

TCAAAACCACATCTTAGATCAATCAGCATACAGTGTTATCTTTGTCTGCT

GCTCAACAGCCATTTCTTGACTGAAGCCAACTGGGTCAACGTAATTTCTG

ATCTTAAAAAAATCGAGGATCTGATCCAGAGTATGCACATAGACGCAACG

CTTTACACCGAAAGTGATGTCCATCCGTCATGTAAAGTAACGGCGATGAA

GTGTTTCCTTCTCGAGCTTCAGGTAATTTCATTGGAGTCTGGAGATGCCT

CTATTCATGACACGGTAGAGAATTTGATCATTCTCGCTAACAATAGTCTT

TCCAGTAACGGTAACGTTACAGAGAGCGGATGTAAAGAATGTGAGGAATT

GGAGGAGAAGAACATTAAGGAATTCCTTCAGTCCTTTGTCCACATCGTTC

AGATGTTTATTAACACGAGTTGA).
```

"Interferons" (IFNs) as described herein, are signaling proteins synthesized and released by host cells in response to the presence of pathogens, such as viruses, bacteria, parasites, or tumor cells. For example, a virus-infected cell will release interferons causing nearby cells to heighten their anti-viral defenses. Interferons, such as Type I IFN has been shown to inhibit tumor growth in animals. Interferons can also increase p53 activity, which can promote apoptosis of cancer cells. IFN in combination with p53 has been linked to a protective role against several cancers. Interferon beta 1a, interferon beta 1b, interferon alfa and interferon beta have been used as a treatment for some cancers. In some alternatives, an immune cell comprises a first vector, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the interferon is a Type I IFN. In some alternatives, the interferon is interferon beta 1a, interferon beta 1b, interferon alfa or interferon beta.

"Programmed cell death protein 1," or PD-1 is a protein that functions as an immune checkpoint and plays a role in down regulating the immune system by preventing the activation of T cells to reduce autoimmunity and promote self-tolerance. PD-1 has an inhibitory effect of programming apoptosis in antigen specific T cells in the lymph nodes and simultaneously reducing apoptosis in regulatory T cells. PD-1 inhibitors can be used however to activate the immune system to attack tumors and can be used to treat some types of cancers. PD-1 has two ligands PD-L1 and PD-L2. Binding of PD-L1 to PD-1 allows the transmittal of an inhibitory signal which reduces the proliferation of CD8+ T cells at lymph nodes. PD-L1 can also bind PD-1 on activated T cells, B cells and myeloid cells to modulate activation or inhibition. The upregulation of PD-L1 may also allow cancers to evade the host immune system. Therefore, inhibitors to PD-L1 or PD-1 to prevent formation of a PD-L1-PD-1 complex, is important for suppression of some cancers.

In some alternatives, a PD-1 inhibitor is provided. In some alternatives, the inhibitor is an scFv. scFv PD1-inhibitor (Nivolimumab) comprises an amino acid sequence set forth in SEQ ID NO: 39 (QVQLVES-GGGVVQPGRSLRLDCK-ASGITFSNSGMHWVRQAPGKGLEWVAVIWYD GSKRYYADSVKGRFTISRDNSKNTLFLQMNSLRAED-TAVYYCATNDDYWGQGTLV TVSSASTKGPSVF-PLAPCSRSTSESTAALGCLVKDYF-PEPVTVSWNSGALTSGVHTFP AVLQSSGLYS-LSSVVTVPSSSLGTKTYTCNVDHKPSNTKVDKRVES KYGPPCPPCPA PEFLGGPSVFLFPPKPKDTLMISRTPE-VTCVVVDVSQEDPEVQFNWYVDGVEVHNA KTKPREEQFN-STYRVVSVLTVLHQDWLNGKEYKCKVSNKGLPSSIE KTISKAKGQPR EPQVYTLPPSQEEMTKNQVSLT-CLVKGFYPSDIAVEWESNGQPENNYKTTPPVLDSD GSFFLYSRLTVDKSRWQEGNVFSCSVMHEALHN-HYTQKSLSLSLGK). The light chain comprises a sequence set forth in SEQ ID NO: 40 (EIVLTQSPATLSLSPGER-ATLSCRASQSVSSYLAWYQQKPGQAPRLLIYDASN-RATGI PARFSGSGSGTDFTLTISSLEPED-FAVYYCQQSSNWPRTFGQGTKVEIKRTVAAPSVFI FPPSDEQLKSGTASVVCLLNNFYPREAKVQWKVD-NALQSGNSQESVTEQDSKDSTY SLSSTLTL-SKADYEKHKVYACEVTHQGLSSPVTKSFNRGEC).

The variable heavy chain comprises a sequence set forth in SEQ ID NO: 41 (QVQLVESGGGVVQPGRSLRLDCK-ASGITFSNSGMHWVRQAPGKGLEWVAVIWYD GSKRYYADSVKGRFTISRDNSKNTLFLQMNSLRAED-TAVYYCATNDDYWGQGTLV TVSSGGGGSGGGGSGGGGS). The variable light chain comprises a sequence in SEQ ID NO: 42

```
(EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTFG

QGTKVEIK).
```

In some alternatives, the heavy and the light chain are optimized. The optimized heavy chain comprises a sequence set forth in SEQ ID NO: 43 (MEFGLSWVFLVAL-FRGVQC), which is encoded by a sequence set forth in SEQ ID NO: 44 (ATGGAGTTTGGGCT-GAGCTGGGTTTTCCTCGTTGCTCTTTT-TAGAGGTGTCCAGT GT). The optimized light chain comprises a sequence set forth in SEQ ID NO: 45 (MDMRVPAQLLGLLLLWLSGARC), which is encoded by a sequence set forth in SEQ ID NO: 46

```
(ATGGACATGAGGGTCCCTGCTCAGCTCCTGGGGCTCCTGCTGCTCTGGC

TCTCAGGTGCCAGATGT).
```

"PD-L2" as described herein, is a second ligand for PD-1 that can inhibit T-cell activation. Therefore inhibitors that bind PD1, PD-L1 or PD-L2 to prevent a PD1-PD-L1 complex or PD1-PDL2 complex formation can suppress some cancers. In some alternatives of the methods described herein, the protein is an inhibitor that can bind PD1, PD-L1 or PD-L2 to prevent a PD1-PD-L1 complex or PD1-PDL2 complex.

In some alternatives, an immune cell comprises a first vector, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the protein is a PD-1 checkpoint binding inhibitor. In some alternatives, the PD-1 checkpoint inhibitor binds to PD1, PD-L1 or PD-L2 to prevent a PD1-PD-L1 complex or PD1-PDL2 complex formation or persistence. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. More alternatives concern any one or more of the aforementioned genetically modified immune cells, alone or in combination, for use as a medicament e.g., to inhibit or treat a cancer such as breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes "peptide nucleic acids," which comprise naturally-occurring or modified nucleic acid bases attached to a polyamide backbone. Nucleic acids can be either single stranded or double stranded.

A "vector" or "construct" is a nucleic acid used to introduce heterologous nucleic acids into a cell that can also have regulatory elements to provide expression of the heterologous nucleic acids in the cell. Vectors include but are not limited to plasmid, minicircles, yeast, and viral genomes. In some alternatives, the vectors are plasmid, minicircles, viral vectors, DNA or mRNA. In some alternatives, the vector is a lentiviral vector or a retroviral vector. In some alternatives, the vector is a lentiviral vector.

"Vpx" as described herein, is a virion associated protein that is encoded by HIV type 2 and in some simian immunodeficiency virus strains. Vpx can enhance HIV-2 replication in humans. Lentiviral vectors packaged with Vpx protein can led to an increase in the infection of myeloid cells, when used in transfections. In some alternatives described herein, the lentiviral vector is packaged with a Vpx protein.

"Vpr" protein as described herein refers to Viral Protein R, which is a 14 kDa protein, which plays an important role in regulating nuclear import of the HIV-1 pre-integration complex, and is required for virus replication in non-dividing cells. Non dividing cells can include macrophages, for example. In some alternatives described herein, the lentiviral vector can be packaged with a Vpr protein, or a Vpr protein portion thereof. In some alternatives, the lentiviral vector is packaged with a viral accessory protein. In some alternatives, the viral accessory protein is selected from the group consisting of Vif, Vpx, Vpu, Nef and Vpr. These accessory proteins such as, for example vif, Vpx, vpu and nef interact with cellular ligands to act as an adapter molecule to redirect the normal function of host factors for virus-specific purposes. HIV accessory proteins are described in Strebel et al. ("HIV Accessory Proteins versus Host Restriction Factors, Curr Opin Virol. 2013 December; 3(6): 10.1016/j.coviro.2013.08.004; incorporated by reference in its entirety herein).

"CRISPRs" (clustered regularly interspaced short palindromic repeats), as described herein, are segments of prokaryotic DNA containing short repetitions of base sequences. Each repetition is followed by short segments of "spacer DNA" from previous exposures to a bacterial virus or plasmid. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. CRISPR/Cas system has been used for gene editing (adding, disrupting or changing the sequence of specific genes) and gene regulation in species throughout the tree of life. By delivering the Cas9 protein and appropriate guide RNAs into a cell, the organism's genome can be cut at any desired location. One can use CRISPR to build RNA-guided gene editing tools capable of altering the genomes of entire populations. In some alternatives, a system for editing at least one target gene in a cell is provided. In some alternatives described herein, a method of making a genetically modified immune cell for modifying a tumor microenvironment (TME) is provided, wherein the method comprises delivering a first vector to an immune cell, wherein the first vector comprises a nucleic acid encoding a protein that induces T-cell proliferation, promotes persistence and/or activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the method further comprises delivering to the cell, a second vector, wherein the second vector comprises a nucleic acid encoding a Cas9 endonuclease and delivering to the cell a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the target gene in the cell encodes TGF-beta or IL-10. In some alternatives, the target gene is PD-L1, TGF-beta, IL-10, Arginase, HIF-1 alpha, RAGE, CD206, IL-4, CCL22, CCL17, VEGF, EGF, WNT7beta, and/or PGE.

The CRISPR/Cas system has been used for gene editing (e.g., adding, disrupting or changing the sequence of specific genes) and gene regulation in a variety of species. "Cas9" as described herein, is an RNA-guided DNA endonuclease enzyme associated with the CRISPR adaptive immunity system in bacteria. By delivering the Cas9 protein and appropriate guide RNAs into a cell, the organism's genome is cut at any desired location. The basic components of CRISPR/Cas9 system comprise a target gene, a guide RNA, and a Cas9 endonuclease, derivative, or fragment thereof. An important aspect of applying CRISPR/Cas9 for gene editing is the need for a system to deliver the guide RNAs efficiently to a wide variety of cell types. This could for example involve delivery of an in vitro generated guide RNA as a nucleic acid (the guide RNA generated by in vitro transcription or chemical synthesis). In some alternatives the nucleic acid encoding the guide RNA is rendered nuclease resistant by incorporation of modified bases, such as 2'O-methyl bases. Furthermore, an important system for expressing guide RNAs in this context is based on the use of adeno-associated virus (AAV) vectors because AAV vectors are able to transduce a wide range of primary cells. AAV vectors do not cause infection and are not known to integrate into the genome. Therefore, the use of AAV vectors has the benefits of being both safe and efficacious. In some alternatives, the vector is an AAV vector. In some alternatives, the vector is a lentivector.

The CRISPR/Cas9 system can also be used as a modular protein effector recruitment system that can be used for gene activation when coupled with transcriptional activators. Cas9 can be genetically engineered as a fusion protein with a domain of a transcriptional activator. Without being limiting, activation domains can comprise a single or multiple domains from the transcriptional activator VP16, VP64 or a p65 activation domain, for example. Thus, the Cas9 fusion can serve as an RNA guided DNA binding protein to target any protein to any DNA sequence and provides a general platform for targeting proteins to DNA. A Cas9 fusion protein can also be used to target enhancers, introns and other noncoding elements to map the regulatory functions of these elements on transcription. In some alternatives described herein, a method of making a genetically modified immune cell for modifying a tumor microenvironment (TME) is provided, wherein the method comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the method further comprises delivering to the cell, a fourth vector, wherein the fourth vector encodes a Cas9 protein fused to a transcriptional activator domain to activate transcription and translation of a second protein and delivering to the cell a fifth vector, wherein the fifth vector comprises a CRISPR guide RNA complimentary to at least one target gene in the cell. In some alternatives, the cell is a myeloid cell. In some alternatives, the transcriptional activation domain comprises a VP16, VP64 or a p65 activation domain. In some alternatives, the method further comprises delivering to the cell, a fourth vector, wherein the fourth vector encodes a Cas9 VP64 fusion protein to activate transcription and translation of a second protein and delivering to the cell a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-
CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA-GACTTGAAGATGTACCAGGTG GAGTTCAAGAC-CATGAATGCAAAGCTGCTGATG-GATCCTAAGAGGCAGATCTTT CTAGATCAAAACATGCTGGCAGTTATTGATGAGCT- GATGCAGGCCCTGAATTTCA ACAGTGAGACTGTGCCACAAAAATCCTCCCTTGAAGAACCGGATTTTTATAAAACTAAAATCAAGCTCTGCATACTTCTTCATCTTTCAGAATTCGGGCAGTGACTATTGATAGAGTGATGAGCTATCTGAATGCTTCCTAA). In some alternatives, the second protein is IL-12p40, IL-15, IL-6, IL-1 beta, TNF-alpha, IFN-alpha/beta/gamma, IL-12, IL-18, IL-23 or GM-CSF. In some alternatives the at least one target gene is an endogenous pro-inflammatory gene. In some alternatives, the pro-inflammatory gene encodes IL-12p40, IL-15, IL-6, IL-1 beta, TNF-alpha, IFN-alpha/beta/gamma, IL-12, IL-18, IL-23 or GM-CSF.

Another factor for maximal protein selection is adaptation of codons of the transcript gene to the typical codon usage of a host e.g. a human. In this aspect, many synthetic genes can be designed to increase their protein expression level. The design process of codon optimization can be to alter rare codons to codons known to increase maximum protein expression efficiency. In some alternatives, codon selection is described, wherein codon selection can be performed by using algorithms to create synthetic genetic transcripts optimized for high protein yield. Programs containing algorithms for codon optimization are available and include e.g., OptimumGene™, and GeneGPS®. In some alternatives of the methods provided herein, the vectors provided for the methods are codon optimized for expression in humans.

"Genetically modified immune cells" or "Genetically engineered cells" are made by a process called genetic engineering, which can include but is not limited to manipulating a cells own genome or inserting a new nucleic acid into a cell. In some alternatives, these cells can be macrophages and can also be referred to as genetically engineered macrophages (GEMs). These techniques can be used to change the genetic makeup of the cell, and can include inserting a vector encoding a gene of interest into a cell, and genome editing using RNAi systems, meganucleases, zinc finger nucleases, transcription activator like effector nucleases (TALENS), or CRISPRs. Without being limiting, the vectors encoding the gene of interest can be a viral vector, DNA or an mRNA. In some alternatives, described herein, genetically modified immune cells are provided. In some alternatives, the genetically modified immune cells are made using genome editing proteins or systems, such as for example, meganucleases, zinc finger nucleases, transcription activator like effector nucleases (TALENS), CRISPR/VP64-Cas9 systems or CRISPR/CAS9 systems. In some alternatives, wherein the genetically modified immune cells are made using vectors, the vectors are viral vectors, DNA or mRNA. In some alternatives, the T-cell is a genetically modified T-cell. In some alternatives, the T-cell is genetically modified to express a chimeric antigen receptor. In some alternatives the genetically modified T-cell is genetically modified to express a chimeric antigen receptor (CAR) or T-cell receptor (Tcr). More alternatives concern any one or more of the aforementioned genetically modified immune cells, alone or in combination, for use as a medicament e.g., to treat or inhibit a cancer such as breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

"Chimeric receptor" as used herein refers to a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). These receptors can be used to graft the specificity of a monoclonal antibody or binding fragment thereof onto a T-cell with transfer of their coding sequence facilitated by viral vectors, such as a retroviral vector or a lentiviral vector. CARs are genetically engineered T-cell receptors designed to redirect T-cells to target cells that express specific cell-surface antigens. T-cells can be removed from a subject and modified so that they can express receptors that can be specific for an antigen by a process called adoptive cell transfer. The T-cells are reintroduced into the patient where they can then recognize and target an antigen. These CARs are engineered receptors that can graft an arbitrary specificity onto an immune receptor cell. The term chimeric antigen receptors or "CARs" are also considered by some investigators to include the antibody or antibody fragment, the spacer, signaling domain, and transmembrane region. Due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements. The variation of the different elements of the CAR can, for example, lead to stronger binding affinity for a specific epitope or antigen. In some alternatives, the CARs provided herein comprise a T2A cleavage sequence. The cleavage sequence is encoded by the sequence set forth in SEQ ID NO: 13

(Ggcggcggagagggcagaggaagtcttctaacatgcggtgacgtggagg agaatcccggccctagg).

"T-cell receptors" or Tcr is a molecule on the surface of a T lymphocyte that is responsible for recognizing and binding antigens that are bound to major histocompatibility complex molecules. In some alternatives, the genetically modified T-cell expresses a Tcr.

"Suicide gene therapy," "suicide genes" and "suicide gene systems" as described herein, can refer to methods to destroy a cell through apoptosis, which requires a suicide gene that will cause a cell to kill itself by apoptosis. Due to safety concerns for the patients in need of using genetically modified immune cells for treatment or modification of a tumor environment, strategies are being developed in order to prevent or abate adverse events. Adverse effects of incorporation of genetically modified immune cells into a subject for a pretreatment step can include "cytokine storms," which is a cytokine release syndrome, wherein the infused T-cells release cytokines into the bloodstream, which can lead to dangerously high fevers, as well as, a precipitous drop in blood pressure.

A "prodrug" as described herein, is a compound, formulation or a medication that can be metabolized by the body in order to become a pharmacologically active drug. Prodrugs are derivatives of drug molecules that can under an enzymatic and/or chemical modification in vivo to release an active parent drug in order to exert a desired pharmacological effect. As such, these inactive prodrugs become an activated form once they are metabolized. Without being limiting, a prodrug can be used to improve how a medicine is absorbed, distributed, metabolized, excreted, improve bioavailability of a drug, or improve how selectively a drug can interact with cells or processes that are not its intended targets.

There are several types of prodrugs that are further defined depending on how the body converts the prodrug into a final active form of drug. Type I prodrugs are bioactivated within a cell (intracellularly) and Type II prodrugs are bioactivated outside of a cell (extracellularly). Both of these types can also be further categorized into subtypes based on factors such as whether the intracellular bioactivation location is also the site of the therapeutic action or whether or not the bioactivation can occur in the gastrointestinal fluids or in the circulatory system.

Using a prodrug in a cancer therapy is also described herein. During cancer therapy, the main challenge is the destruction of cancer cells and malignant tumors or tumor cells without the destruction of healthy host cells. This can be accomplished, for example, by the use of a suicide gene. A suicide gene can be used to cause a cell to kill itself by apoptosis. Two methods of using a suicide gene include gene-directed enzyme producing therapy and virus directed enzyme prodrug therapy.

For gene-directed enzyme producing therapy, a gene is taken from a cancer cell then modified with other genes to form enzymes that are harmless to healthy cells. The foreign enzyme is then inserted into the tumor cells, where it can release a prodrug that is harmless to healthy cells but causes harm in cancer cells. The modified suicide gene can then convert the non-toxic prodrug into a cytotoxic substance.

In virus-directed enzyme prodrug therapy, a carrier can be used to deliver the modified genes to the cancer cells. Without being limiting, the carrier can be a virus, such as a herpes virus or a vector to deliver the modified gene.

Suicide gene therapy can be used to increase the safety of the genetically modified immune cells and manage the adverse events that can occur following infusion of genetically modified immune cells. Pharmacologic therapies, suicide genes or novel strategies are needed to limit the cytotoxic effect only to malignant cells. There are several methods for suicide gene therapy. Without being limiting, methods can include gene-directed enzyme producing therapy or virus directed enzyme prodrug therapy. For gene-directed enzyme producing therapy (GDEPT), a gene is taken from the cancer cell and then modified with other genes to form enzymes that are harmless to healthy cells. This foreign enzyme is inserted into the tumor cells where it releases a prodrug, which is a small molecule harmless to healthy cells, but destructive to cancerous cells. The modified suicide gene converts the non-toxic prodrug into a cytotoxic substance. For virus directed enzyme prodrug therapy, a virus, such as herpes simplex or cold virus, as the carrier, or vector, is used to deliver the modified genes to the cancer cells. Suicide gene therapy is not necessarily expected to completely eliminate the need for chemotherapy and radiation treatment for all cancerous tumors. The damage inflicted upon the tumor cells, however, makes them more susceptible to the chemotherapy or radiation. This approach has already proven effective against prostate and bladder cancers. The application of suicide gene therapy is being expanded to several other forms of cancer, as well. Cancer patients often experience depressed immune systems, so they can suffer some side effects of the use of a virus as a delivery agent. Management of adverse effects of genetically modified immune cells can be performed by expressing the genetically modified immune cells under the control of a promoter. As previously described in several reviews, genetically modified immune cells can further be genetically modified ex vivo with a suicide gene. Without being limiting, the suicide gene can be a gene encoding for a factor that is able to convert at a cellular level a non-toxic prodrug into a toxic compound. During adverse effect that may follow infusion of genetically modified immune cells by adoptive cell transfer, the prodrug can be administrated to the subject suffering from adverse effects, and the prodrug can selectively eliminate suicide gene modified genetically modified immune cells without interfering with the process of immune reconstitution operated by the non-modified T-cells. Suicide systems using the herpes simplex thymidine kinase (Hsv-tk)/ganciclovir (GCV) suicide system have been described. (Casucci et al. 2011, Journal of Cancer 2011, 2; hereby expressly incorporated by reference in its entirety). In some alternatives, a method of modifying a tumor microenvironment (TME) is provided, wherein the method comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system.

In some alternatives, the suicide gene system is an EGFRt suicide gene system, wherein the patient is administered Erbitux as the prodrug. In some alternatives, the subject is administered 0.04 mg/cm$^2$ Erbitux a day. In some alternatives, wherein Erbitux is the prodrug, 0.04 mg/cm$^2$ can be considered the initial dose and in some alternatives a weekly dose of 0.025 mg/cm$^2$ of Erbitux is administered after the initial dose. In some alternatives, wherein a rash develops on the patient, the weekly dose can go down to 0.03 mg/cm$^2$, 0.02 mg/cm$^2$ or 0.01 mg/cm$^2$, or any other dosage between any two of the aforementioned values described. In some alternatives, the suicide gene system is a Her2tG suicide gene system, wherein the patient is administered Herceptin as the prodrug. In some alternatives, the subject is administered 2 mg/kg, 3 mg/kg or 4 mg/kg Herceptin or any dosage between any two of the aforementioned values described.

A "regulatory element" as described herein, can refer to a regulatory sequence, which is any DNA sequence that is responsible for the regulation of gene expression, such as promoters and operators. The regulatory element can be a segment of a nucleic acid molecule, which is capable of increasing or decreasing the expression of specific genes within an organism. In some alternatives described herein, the protein is under a control of a regulatory element.

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. Without being limiting, these promoter elements can include RNA polymerase binding sites, TATA sequences, CAAT sequences, differentiation-specific elements (DSEs; McGehee et al., Mol. Endocrinol. 7:551 (1993); hereby expressly incorporated by reference in its entirety), cyclic AMP response elements (CREs), serum response elements (SREs; Treisman et al., Seminars in Cancer Biol. 1:47 (1990); incorporated by reference in its entirety), glucocorticoid response elements (GREs), and binding sites for other transcription factors, such as CRE/ATF (O'Reilly et al., J. Biol. Chem. 267:19938 (1992); incorporated by reference in its entirety), AP2 (Ye et al., J. Biol. Chem. 269:25728 (1994); incorporated by reference in its entirety), SP1, cAMP response element binding protein (CREB; Loeken et al., Gene Expr. 3:253 (1993); hereby expressly incorporated by reference in its entirety) and octamer factors (see, in general, Watson et al., eds., Molecular Biology of the Gene, 4th ed. (The Benjamin/Cummings Publishing Company, Inc. 1987; incorporated by reference in its entirety)), and Lemaigre and Rousseau, Biochem. J. 303:1 (1994); incorporated by reference in its entirety). As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives described herein, a method of making a genetically modified immune cell for modifying a tumor microenvironment (TME) is provided, wherein the method comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites.

In some alternatives, promoters used herein can be inducible or constitutive promoters. Without being limiting, inducible promoters can include, for example, a tamoxifen inducible promoter, tetracycline inducible promoter, or a doxocycline inducible promoter (e.g. tre) promoter. Constitutive promoters can include, for example, SV40, CMV, UBC, EF1alpha, PGK, or CAGG. In some alternatives, the regulatory element is a promoter. In some alternatives, the promoter is a tamoxifen inducible promoter, a tetracycline inducible promoter, or a doxocycline inducible promoter (e.g. tre) promoter. In some alternatives provided herein, expression of a protein is induced by tamoxifen and/or its metabolites. Metabolites for tamoxifen are active metabolites such as 4-hyroxytamoxifen (afimoxifene) and N-desmethyl-4-hydroxytamoxifen (endoxifen), which can have 30-100 times more affinity with an estrogen receptor than tamoxifen itself. In some alternatives, the tamoxifen metabolites are 4-hyroxytamoxifen (afimoxifene) and/or N-desmethyl-4-hydroxytamoxifen (endoxifen).

"Immune cells" as described herein are cells of the immune system that are involved in the protection of infectious disease and protection from cancer cells. In some alternatives described herein, a method of making a genetically modified immune cell for modifying a tumor microenvironment (TME) is provided, wherein the method comprising delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a myeloid cell. In some alternatives, the myeloid cell is a macrophage. In some alternatives, the myeloid cell is a microglial cell.

Cancer is associated with uncontrolled or dysregulated cell growth. Cancer can present as malignant tumors or malignant neoplasmas having abnormal cell growth, which can invade and spread to other parts of the body. In some alternatives described herein, a method of modulating the suppression of the immune response in a tumor microenvironment of a subject in need thereof e.g., a human is provided, wherein the method comprises administering any one or more of the genetically modified immune cells of any one or more of the alternatives described herein to a subject in need thereof e.g., a human and, optionally, selecting or identifying said subject to receive said genetically modified immune cells and/or measuring a modulation of suppression of the immune response in the tumor microenvironment of said subject after administration of said genetically modified immune cells. In some alternatives, the tumor within the tumor environment is a glioma. In some alternatives, the tumor is a glioblastoma. In some alternatives, the tumor is lung tumor. In some alternatives, the tumor is a prostate tumor. In some alternatives, the tumor is a stomach tumor. In some alternatives, the tumor is a breast tumor. In some alternatives, the tumor is a colorectal tumor. In some alternatives, the tumor is a brain tumor.

"Natural killer cells" or NK cells are a type of cytotoxic lymphocyte important to the innate immune system. The role NK cells play is analogous to that of cytotoxic T cells in the vertebrate adaptive immune response. NK cells provide rapid responses to viral-infected cells and respond to tumor formation. The function of NK cells is important to the prevention of de novo tumor growth through a process known as immune surveillance (Dunn et al., Cancer immunoediting: from immunosurveillance to tumor escape. Nat Immunol 3, 991-998 (2002); Langers et al., Natural killer cells: role in local tumor growth and metastasis. Biologics: targets & therapy 6, 73-82 (2012); both references incorporated by reference in their entireties herein).

"Myeloid cells" can refer to a granulocyte or monocyte precursor cell in bone marrow or spinal cord, or a resemblance to those found in the bone marrow or spinal cord. The myeloid cell lineage includes circulating monocytic cells in the peripheral blood and the cell populations that they become following maturation, differentiation, and/or activation. These populations include non-terminally differentiated myeloid cells, myeloid derived suppressor cells, and differentiated macrophages. Differentiated macrophages include non-polarized and polarized macrophages, resting and activated macrophages. Without being limiting, the myeloid lineage can also include granulocytic precursors, polymorphonuclear derived suppressor cells, differentiated polymorphonuclear white blood cells, neutrophils, granulocytes, basophils, eosinophils, monocytes, macrophages, microglia, myeloid derived suppressor cells, dendritic cells and erythrocytes. For example, microglia can differentiate from myeloid progenitor cells.

"Microglial cells" as described herein are glial cells that are resident macrophages of the brain and spinal cord, and thus act as the first and main form of active immune defense in the central nervous system (CNS).

"Combination therapy" as described herein, refers to a therapy that uses more than one medication or modality for a treatment. Combination therapy, for example can also refer to multiple therapies to treat a single disease, and often all the therapies are pharmaceutical product combinations. Combination therapy can also involve prescribing and administering separate drugs in which the dosage can also have more than one active ingredient. In some alternative, a combination therapy is provided. In some alternatives, the combination therapy comprises administering a genetically modified immune cell for modifying a tumor microenvironment. In some alternatives, the combination therapy comprises administering a genetically modified immune cell for modulating the suppression of the immune response in a tumor microenvironment. In some alternatives, the combination therapy comprises administering a genetically modified immune cell for minimizing the proliferation of tumor and suppressive cells in a subject in need thereof e.g. a human. In some alternatives, the combination therapy comprises administering a genetically modified immune cell for increasing the efficiency of an anti-cancer therapy, anti-infection therapy, antibacterial therapy, anti-viral therapy, or anti-tumoral therapy in a subject in need thereof e.g., a human. In some alternatives, the combination therapy further comprises administration of an inhibitor. In some alternatives, the inhibitor is not an enzymatic inhibitor. In some alternatives, the inhibitor is an enzymatic inhibitor. In some alternatives, the combination therapy comprises administering a therapeutic dose of an inhibitor or an antibody or a binding fragment thereof. These antibodies or binding fragments thereof can be humanized in some alternatives. In some alternatives, the combination therapy can further comprise administering a CAR bearing T-cell to a subject in need e.g., a human.

"Chemotherapeutic drugs" are category of anti-cancer medicaments that can use, for example, chemical substances, such as anti-cancer drugs (chemotherapeutic agents) that can be given as part of a standardized chemotherapy regimen. Chemotherapeutic drugs can be given with a curative intent, or it can aim to prolong life or to reduce symptoms (palliative chemotherapy). Additional chemotherapies can also include hormonal therapy and targeted therapy, as it is one of the major categories of medical oncology (pharmacotherapy for cancer). These modalities are often used in conjunction with other cancer therapies, such as radiation therapy, surgery, and/or hyperthermia therapy. In few cases, cancer has been known to spread due to surgery. In some alternatives, a genetically modified immune cell is administered to the tumor site prior to or after a surgical procedure.

Some newer anticancer drugs (for example, various monoclonal antibodies, humanized versions thereof and binding fragments thereof) are not indiscriminately cytotoxic, but rather target proteins that are abnormally expressed in cancer cells and that are essential for their growth. Such treatments are often referred to as targeted therapy (as distinct from classic chemotherapy) and are often used alongside traditional chemotherapeutic agents in antineoplastic treatment regimens. In some alternatives, the methods described herein can further comprise administering any one or more of these targeted anti-cancer therapies (for example, various monoclonal antibodies, humanized versions thereof and binding fragments thereof).

Chemotherapy, in which chemotherapeutic drugs are administered, can use one drug at a time (single-agent chemotherapy) or several drugs at once (combination chemotherapy or polychemotherapy). The combination of chemotherapy and radiotherapy is chemoradiotherapy. Chemotherapy using drugs that convert to cytotoxic activity only upon light exposure is called photochemotherapy or photodynamic therapy. In some alternatives of administering the genetically modified immune cell described herein, the method can further comprise administering to a subject having cancer, photochemotherapy or photodynamic therapy after receiving the genetically modified immune cells or genetically engineered macrophages (GEMs).

Chemotherapuetic drugs can include but are not limited to antibody-drug conjugates (for example, an antibody attached to a drug by a linker), nanoparticles (for example a nanoparticle can be 1-1000 nanometer sized particle for promoting tumor selectivity and aid in delivering low-solubility drugs), electochemotherapy, alkylating agents, antimetabolites (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and Thioguanine), anti-tumor antibiotics, topoisomerase inhibitors, mitotic inhibitors, corticosteroids, DNA intercalating agents, or checkpoint inhibitors (for example checkpoint kinases CHK1, or CHK2). In some alternatives of the methods described herein, the genetically modified immune cells or compositions comprising genetically modified immune cells are administered in combination with one or more anti-cancer agents, such as any one or more of the foregoing compounds or therapies. In some alternatives, the one or more anti-cancer agent that is co-administered or administered in conjunction with the genetically modified immune cells, comprises antibody-drug conjugates, nanoparticles, electrochemotherapy, alkylating agents, antimetabolites, anti-tumor antibiotics, topoisomerase inhibitors, mitotic inhibitors, corticosteroids, DNA intercalating agents, or checkpoint inhibitors. In some alternatives, the antimetabolites comprises 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, or Thioguanine.

"Checkpoint blockades" refers to a form of immunotherapy, meaning it aims to help the patient's own immune system fight cancer. It can use substances such as monoclonal antibodies or binding fragments thereof, which can be designed to target extremely specific molecules on cell surfaces. For example, the antibodies unblock a reaction that stops the immune system's natural attack on invading cancer cells. In another example, a ligand-receptor interaction that has been investigated as a target for cancer treatment is the interaction between the transmembrane programmed cell death 1 protein (PDCD1, PD-1; also known as CD279) and its ligand, PD-1 ligand 1 (PD-L1, CD274). In normal physiology PD-L1 on the surface of a cell binds to PD1 on the surface of an immune cell, which inhibits the activity of the immune cell. It appears that upregulation of PD-L1 on the cancer cell surface can allow them to evade the host immune system by inhibiting T cells that might otherwise attack the tumor cell. Antibodies that bind to either PD-1 or PD-L1 and therefore block the interaction can allow the T-cells to attack the tumor. In some alternatives, the checkpoint blockade therapeutics comprises anti-PD-1 antibodies or binding fragments thereof (e.g., monoclonal antibodies or humanized versions thereof or binding fragments thereof). In some alternatives, the checkpoint blockade therapeutics comprises PD-L1. In some alternatives, the one or more anti-cancer agents that is co-administered or administered in conjunction with the genetically modified immune cells or genetically engineered macrophages (GEMs) comprises one or more of such checkpoint blockades.

"Small molecule inhibitors" as described herein refers to small inhibitors that can target proteins of interest. The proteins can be proteins that are secreted by tumor cells or proteins secreted during cellular stress. Small molecule inhibitors can include but are not limited to kinase inhibitors, inhibitors of Bcl-2 family proteins for cancer therapy, MCl-1 inhibitors, or tyrosine kinase inhibitors. Tyrosine kinase inhibitors can include but are not limited to Imatinib mesylate (approved for chronic myelogenous leukemia, gastrointestinal stromal tumor and some other types of cancer), Gefitinib (Iressa, also known as ZD1839); targets the epidermal growth factor receptor (EGFR) tyrosine kinase) Erlotinib (marketed as Tarceva), Sorafenib, Sunitinib (Sutent), Dasatinib (Srycel), Lapatinib (Tykerb), Nilotinib (Tasigna), Bortezomib (Velcade), Janus kinase inhibitors, ALK inhibitors, crizotinib Bcl-2 inhibitors, obatoclax, navitoclax, gossypol, PARP inhibitors, Iniparib, Olaparib, PI3K inhibitors, perifosine, Apatinib, VEGF Receptor 2 inhibitors, AN-152, Braf inhibitors, vemurafenib, dabrafenib, LGX818, MEK inhibitors, trametinib, MEK162, CDK inhibitors, PD-0332991, Hsp90 inhibitors, or salinomycin. In some alternatives, the one or more anti-cancer agents that is co-administered or administered in conjunction with the genetically modified immune cells or genetically engineered macrophages (GEMs) comprises one or more of such small molecule inhibitors. In some alternatives, the small molecule inhibitors that are used comprise kinase inhibitors. In some alternatives, the small molecule inhibitors comprise inhibitors of Bcl-2 family proteins. In some alternatives, the small molecule inhibitors comprise MCl-1 inhibitors. In some alternatives, the small molecule inhibitors comprise tyrosine kinase inhibitors. In some alternatives, the small molecule inhibitor is Imatinib. In some alternatives, the small molecule inhibitor is mesylate. In some alternatives, the small molecule inhibitor is Gefitinib. In some alternatives, the small molecule inhibitor is Erlotinib. In some alternatives, the small molecule inhibitor is Sorafenib. In some alternatives, the small molecule inhibitor is Sunitinib (Sutent). In some alternatives, the small molecule inhibitor is Dasatinib. In some alternatives, the small molecule inhibitor is Lapatinib (Tykerb). In some alternatives, the small molecule inhibitor is Nilotinib (Tasigna). In some alternatives, the small molecule inhibitor is Bortezomib (Velcade). In some alternatives, the small molecule inhibitors are Janus kinase inhibitors. In some alternatives, the small molecule inhibitor is an ALK inhibitor. In some alternatives, the small molecule inhibitor is crizotinib. In some alternatives, the small molecule inhibitors are Bcl-2 inhibitors. In some alternatives, the small molecule inhibitor is obatoclax. In some alternatives, the small molecule inhibitor is navitoclax. In some alternatives, the small molecule inhibitor is gossypol. In some alternatives, the small molecule inhibitors are PARP inhibitors. In some alternatives, the small molecule inhibitor is Iniparib. In some alternatives, the small molecule inhibitor is Olaparib. In some alternatives, the small molecule inhibitor is PI3K inhibitors. In some alternatives, the small molecule inhibitor is perifosine. In some alternatives, the small molecule inhibitor is Apatinib. In some alternatives, the small molecule inhibitors are tyrosine VEGF Receptor 2 inhibitors. In some alternatives, the small molecule inhibitor is AN-152. In some alternatives, the small molecule inhibitors are Braf inhibitors. In some alternatives, the small molecule inhibitor is vemurafenib. In some alternatives, the small molecule inhibitor is dabrafenib. In some alternatives, the small molecule inhibitor is LGX818. In some alternatives, the small molecule inhibitors are MEK inhibitors. In some alternatives, the small molecule inhibitor is trametinib. In some alternatives, the small molecule inhibitor is MEK162. In some alternatives, the small molecule inhibitors are CDK inhibitors. In some alternatives, the small molecule inhibitor is PD-0332991. In some alternatives, the small molecule inhibitors are Hsp90 inhibitors. In some alternatives, the small molecule inhibitor is salinomycin.

In some alternatives, of the methods provided herein, the method further comprises administering in combination or conjunction with the genetically modified immune cells or genetically engineered macrophages (GEMs), immunotherapy treatments, wherein the immunotherapy treatments modulate immune cells, wherein the treatments or therapies comprise at least one of checkpoint blockades, small molecule inhibitors, and/or adoptive cellular therapies. In some alternatives, the immunotherapy treatments modulate immune cells, wherein the treatments or therapies comprise at least one of checkpoint blockades, small molecule inhibitors, and/or adoptive cellular therapies. In some alternatives, the checkpoint blockade therapeutics comprises anti-PD-1 antibodies or binding fragments thereof. In some alternatives, the checkpoint blockade therapeutics comprises PD-L1. In some alternatives, the genetically modified immune cells can be combined with adoptive cellular therapy. In some alternatives, adoptive cellular therapy comprises administering T cells comprising chimeric antigen receptors. In some alternatives, the adoptive cellular therapies comprise administering T-cells comprising chimeric antigen receptors. In some alternatives, the chimeric antigen receptors target epitopes on tumors. In some alternatives, the adoptive cellular therapies comprise administering T cells comprising specific Tcrs. In some alternatives, the small molecule inhibitors are kinase inhibitors. In some alternatives, the small molecules are Chk1, 2 inhibitors. In some alternatives, the small molecule inhibitors comprise inhibitors of Bcl-2 family proteins. In some alternatives, the small molecule inhibitors comprise MCl-1 inhibitors. In some alternatives, the small molecule inhibitors comprise tyrosine kinase inhibitors. In some alternatives, the small molecule inhibitor is Imatinib. In some alternatives, the small molecule inhibitor is mesylate. In some alternatives, the small molecule inhibitor is Gefitinib. In some alternatives, the small molecule inhibitor is Erlotinib. In some alternatives, the small molecule inhibitor is Sorafenib. In some alternatives, the small molecule inhibitor is Sunitinib (Sutent). In some alternatives, the small molecule inhibitor is Dasatinib. In some alternatives, the small molecule inhibitor is Lapatinib (Tykerb). In some alternatives, the small molecule inhibitor is Nilotinib (Tasigna). In some alternatives, the small molecule inhibitor is Bortezomib (Velcade). In some alternatives, the small molecule inhibitors are Janus kinase inhibitors. In some alternatives, the small molecule inhibitor is an ALK inhibitor. In some alternatives, the small molecule inhibitor is crizotinib. In some alternatives, the small molecule inhibitors are Bcl-2 inhibitors. In some alternatives, the small molecule inhibitor is obatoclax. In some alternatives, the small molecule inhibitor is navitoclax. In some alternatives, the small molecule inhibitor is gossypol. In some alternatives, the small molecule inhibitors are PARP inhibitors. In some alternatives, the small molecule inhibitor is Iniparib. In some alternatives, the small molecule inhibitor is Olaparib. In some alternatives, the small molecule inhibitor is PI3K inhibitors. In some alternatives, the small molecule inhibitor is perifosine. In some alternatives, the small molecule inhibitor is Apatinib. In some alternatives, the small molecule inhibitors are tyrosine VEGF Receptor 2 inhibitors. In some alternatives, the small molecule inhibitor is AN-152. In some alternatives, the small molecule inhibitors are Braf inhibitors. In some alternatives, the small molecule inhibitor is vemurafenib. In some alternatives, the small molecule inhibitor is dabrafenib. In some alternatives, the small molecule inhibitor is LGX818. In some alternatives, the small molecule inhibitors are MEK inhibitors. In some alternatives, the small molecule inhibitor is trametinib. In some alternatives, the small molecule inhibitor is MEK162. In some alternatives, the small molecule inhibitors are CDK inhibitors. In some alternatives, the small molecule inhibitor is PD-0332991. In some alternatives, the small molecule inhibitors are Hsp90 inhibitors. In some alternatives, the small molecule inhibitor is salinomycin.

Small inhibitors can also include serine/threonine kinase inhibitors. Without being limiting, examples include Temsirolimus (Torisel), Everolimus (Afinitor), Vemurafenib (Zelboraf), Trametinib (Mekinist) or Dabrafenib (Tafinlar). In some alternatives, the small molecule inhibitor is Temsirolimus (Torisel). In some alternatives, the small molecule inhibitor is Everolimus (Afinitor). In some alternatives, the small molecule inhibitor is Vemurafenib (Zelboraf). In some alternatives, the small molecule inhibitor is Trametinib (Mekinist). In some alternatives, the small molecule inhibitor is Dabrafenib (Tafinlar).

In some alternatives of the methods provided herein, particularly in combination or in conjunction with treatments or therapies predicated on the activation of immune cells, the genetically modified immune cells or genetically engineered macrophages (GEMs), can be administered with checkpoint blockades, small molecule inhibitors, and/or adoptive cellular therapies, such as anti-CTLA-4 antibodies or binding fragments thereof, anti-PD1 antibodies or binding fragments thereof, anti-PD-L1 antibodies or binding fragments thereof, Chk1,2 inhibitors, CAR's, or TCR's. In some alternatives, the small molecule inhibitor is Temsirolimus (Torisel). In some alternatives, the small molecule inhibitor is Everolimus (Afinitor). In some alternatives, the small molecule inhibitor is Vemurafenib (Zelboraf). In some alternatives, the small molecule inhibitor is Trametinib (Mekinist). In some alternatives, the small molecule inhibitor is Dabrafenib (Tafinlar). In some alternatives, the small molecule inhibitors are kinase inhibitors. In some alternatives, the small molecules are Chk1, 2 inhibitors. In some alternatives, the small molecule inhibitors comprise inhibitors of Bcl-2 family proteins. In some alternatives, the small molecule inhibitors comprise MCl-1 inhibitors. In some alternatives, the small molecule inhibitors comprise tyrosine kinase inhibitors. In some alternatives, the small molecule inhibitor is Imatinib. In some alternatives, the small molecule inhibitor is mesylate. In some alternatives, the small molecule inhibitor is Gefitinib. In some alternatives, the small molecule inhibitor is Erlotinib. In some alternatives, the small molecule inhibitor is Sorafenib. In some alternatives, the small molecule inhibitor is Sunitinib (Sutent). In some alternatives, the small molecule inhibitor is Dasatinib. In some alternatives, the small molecule inhibitor is Lapatinib (Tykerb). In some alternatives, the small molecule inhibitor is Nilotinib (Tasigna). In some alternatives, the small molecule inhibitor is Bortezomib (Velcade). In some alternatives, the small molecule inhibitors are Janus kinase inhibitors. In some alternatives, the small molecule inhibitor is an ALK inhibitor. In some alternatives, the small molecule inhibitor is crizotinib. In some alternatives, the small molecule inhibitors are Bcl-2 inhibitors. In some alternatives, the small molecule inhibitor is obatoclax. In some alternatives, the small molecule inhibitor is navitoclax. In some alternatives, the small molecule inhibitor is gossypol. In some alternatives, the small molecule inhibitors are PARP inhibitors. In some alternatives, the small molecule inhibitor is Iniparib. In some alternatives, the small molecule inhibitor is Olaparib. In some alternatives, the small molecule inhibitors are PI3K inhibitors. In some alternatives, the small molecule inhibitor is perifosine. In some alternatives, the small molecule inhibitor is Apatinib. In some alternatives, the small molecule inhibitors are tyrosine VEGF Receptor 2 inhibitors. In some alternatives, the small molecule inhibitor is AN-152. In some alternatives, the small molecule inhibitors are Braf inhibitors. In some alternatives, the small molecule inhibitor is vemurafenib. In some alternatives, the small molecule inhibitor is dabrafenib. In some alternatives, the small molecule inhibitor is LGX818. In some alternatives, the small molecule inhibitors are MEK inhibitors. In some alternatives, the small molecule inhibitor is trametinib. In some alternatives, the small molecule inhibitor is MEK162. In some alternatives, the small molecule inhibitors are CDK inhibitors. In some alternatives, the small molecule inhibitor is PD-0332991. In some alternatives, the small molecule inhibitors are Hsp90 inhibitors. In some alternatives, the small molecule inhibitor is salinomycin. In some alternatives, the methods described herein further comprise adoptive cellular therapies, wherein the adoptive cellular therapies comprise administering T cells comprising chimeric antigen receptors (CARs). In some alternatives, the CARs are engineered to bind to an epitope on a tumor cell.

DETAILED DESCRIPTION

Although the invention is described in various exemplary alternatives and implementations as provided herein, it should be understood that the various features, aspects, and functionality described in one or more of the individual alternatives are not limited in their applicability to the particular alternative with which they are described. Instead, they can be applied alone or in various combinations to one or more of the other alternatives of the invention, whether the alternatives are described or whether the features are presented as being a part of the described alternative. The breadth and scope of the present invention should not be limited by any exemplary alternatives described or shown herein.

Aspects of the present invention relate to methods, genetically modified immune cells and compositions for modifying the tumor environment. In particular, methods, cells and compositions for modifying the tumor environment comprise immune cells that can encode a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma.

The immune response has an important role in cancer, for identification and elimination of tumors. For example, transformed cells of tumors can express antigens that are not found on normal cells. To the immune system, these antigens appear foreign, and their presence causes immune cells to attack the transformed tumor cells. The antigens expressed by tumors have several sources, for example, some are derived from oncogenic viruses like human papillomavirus, which can cause cervical cancer, while in other examples, the organisms own proteins that occur at low levels in normal cells can reach high levels in tumor cells. One example is an enzyme called tyrosinase that, when expressed at high levels, transforms certain skin cells (e.g. melanocytes) into tumors called melanomas. A third possible source of tumor antigens are proteins normally important for regulating cell growth and survival, that commonly mutate into cancer inducing molecules called oncogenes.

The main response of the immune system to tumors is to destroy the abnormal cells using killer T cells, sometimes with the assistance of helper T cells. Tumor antigens are presented on MHC class I molecules in a similar way to viral antigens. This allows killer T cells to recognize the tumor cell as abnormal. NK cells also kill tumorous cells in a similar way, especially if the tumor cells have fewer MHC class I molecules on their surface than normal; this is a common phenomenon with tumors. Sometimes antibodies are generated against tumor cells allowing for their destruction by the complement system.

In the alternatives described herein, there are several novel approaches to genetically engineer pro-inflammatory macrophages for allogeneic transplantation into the brain. The transplanted macrophages then transform the tumor microenvironment (TME), including reverting the immunosuppressive myeloid cell phenotype. It is expected that these genetically engineered macrophages (GEMs) will support cytotoxic immune function and support effective CAR T-cell immunotherapy in brain and other solid tumors.

The alternatives described herein utilize novel genetically modified macrophage (GEM) technology to develop a broadly applicable therapy that will modulate or inhibit the suppression of an anti-tumor immune response in patients with solid tumors and/or promote or enhance the anti-tumor response, as well as those with metastatic or inoperable disease, chronic viral infections, or autoimmunity, and encompasses a new use and one or more new products. It is anticipated that these alternatives can be used as a stand-alone therapy or as an adjuvant or "pre-conditioning step" to modify and modulate local immune suppression and set the stage for further response and addition therapy.

In some alternatives, wherein a subject suffers from autoimmune disorders, genetically modified myeloid cells are used to modulate the immune response to reduce or inhibit the autoimmune response.

The alternatives described herein encompasses a novel approach to modify the TME by adoptively transferring macrophages engineered to express factors that enhance T-cell proliferation and function, and/or minimize the proliferation of tumor and suppressive cells. Primary human monocytes and macrophages are notoriously resistant to genetic engineering. However, using a myeloid cell-specific lentivirus packaging system, primary human monocytes isolated from peripheral blood, and monocyte-derived macrophages can be infected. The alternatives described herein have demonstrated stable gene integration and robust, stable expression from these vectors. Additionally, in the alternatives described herein, the GEMs have persisted in the TME.

Although the current practice uses lentiviral vectors to generate GEMs, alternatives of the GEMS can be generated by a variety of gene transfer methods, including direct delivery of mRNA. Furthermore, although the current iteration encompasses GBM tumors, it is not restricted to GBM or any specific cancer and would likely be beneficial for any condition in which modulation of immune responses is a barrier to treatment.

Treatment options for patients with GBM lag far behind other cancers: few drugs have shown efficacy and standard of care treatment (surgical resection followed by radiation and temozolomide chemotherapy) has changed little in several decades, indicating the urgent need for new approaches to treat patients with GBM. Previous cellular immunotherapy approaches for GBM have been largely ineffective, due in large part to the immunosuppressive TME. One of the defining characteristics of GBM and other high-grade gliomas is a massive infiltration of regulatory myeloid cells that have a tumor-promoting, anti-inflammatory phenotype.

In some alternatives, GEMs to overcome local immune suppression in the TME are provided. The recent development of a lentivirus capable of infecting myeloid cells provides a unique opportunity to engineer GEMs in which a construct is stably integrated and results in robust, stable protein expression. Embodiments described herein use several approaches to modify gene expression in these GEMS. In one approach, GEMs are engineered to provide a local source of small molecules and proteins that enhance NK cell and T-cell proliferation and function. Examples of these include IL-7, IL-15, IL-2, IL-12, IL-21, type 1 interferons (alpha and beta), PD-1 checkpoint blockade, or a variety of cytokines or chemokines produced in response to TLR-mediated activation using the HMGB1 B box domain, or an endogenous constitutively active MyD88 signal (Medzhitov MTA). Another approach utilizes Cas9/CRISPR-mediated gene editing to delete immune suppressive genes, such as TGF-beta and IL-10, making GEMs resistant to polarization once injected. Likewise, the Cas9/CRISPR system has been utilized to achieve constitutive or inducible expression of endogenous pro-inflammatory genes to support macrophage, NK cell and T-cell functions and/or inhibition of tumor cell growth. Examples of the genes targeted include IFN-gamma, IL-12 and IL-18 using a VP64 transactivating Cas9/CRISPR vector.

The alternatives described herein can be used to develop a catalog of vectors for establishing GEMs that allow for modification of cells as needed. In the alternatives described herein, there are currently developed 10 vectors but by utilizing the approaches described herein many more can be developed.

In some alternatives described herein, data have been generated that demonstrate that these GEMs infiltrate tumor, persist, and stably produce transgenes in an intracranial model of GBM. Furthermore, in some alternatives it has been demonstrated that these GEMs exhibit a stable pro-inflammatory cytokine profile after genetic manipulation, providing evidence that GEMs are an ideal vehicle for restructuring the TEM to support anti-tumor immune responses.

The alternatives described herein will be utilized as a stand-alone therapy or as an adjunct to other cancer therapies or immunotherapies so as to modulate the suppression of the immune response in the tumor microenvironment. As such, these alternatives can be used in combination or in conjunction with a multitude of cellular immune therapies including, but not limited to, CAR T-cell therapy, antibodies or binding fragments thereof, small molecules, tetanus toxin, heat shock protein-peptide complexes, or oncolytic polio virus.

In some embodiments, the therapy utilizes autologous cells and direct injection into tumor beds, however, in other alternatives allogeneic cells and I.V. administration is utilized. Tumor beds, as described herein, refer to the vascular and stromal tissue that surrounds a cancerous tumor and provides it with oxygen, growth factors, and nutrients. Accordingly, the utility of embodiments of the invention includes non-surgically addressed tumors and other immune suppressive conditions and aspects described herein provide off-the-shelf, ready to administer, allogeneic macrophage products tailored to specific conditions, which support other forms of immunotherapy. In some alternatives of the methods described herein, the genetically modified cells or compositions are injected directly into the tumor beds. In some alternatives, $1\times10^5$-$2\times10^7$ genetically modified cells are injected into a tumor bed. In some alternatives, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, or $7\times10^7$ genetically modified cells or any other amount between any two aforementioned values are injected into a tumor bed. In some alternatives, the genetically modified cells or compositions are injected within a 1, 2, 5, 10, 20, 30, 40, 50, 60, 70, 80, 90, 100, 110, 120, 130, 140, 150, 160, 170, 180, 190 or 200 mm radius of the tumor bed, or any other radius between any two aforementioned values.

Use of these GEMs described in the alternatives herein provides considerable therapeutic benefit through restoration of critical immune functions, such as T-cell or NK cell cytotoxicity and cytokine production, myeloid cell function in the tumor microenvironment and tumor cell growth and modification of the tumor microenvironment. Treating patients with genetically modified macrophages, either as a stand-alone therapeutic or as an adjuvant or adjunct therapy with other immunotherapies, can improve overall survival and such embodiments are described herein.

Methods for Making a Genetically Modified Immune Cell for Modifying a Tumor Microenvironment (TME) of a Tumor Described herein are methods for making a genetically modified immune cell for modifying a tumor microenvironment (TME). The tumor microenvironment can comprise a tumor. The method can include delivering a first vector to an immune cell, wherein the first vector comprises a nucleic acid encoding a protein that induces T-cell proliferation, promotes persistence and/or activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (KNIIQFVH-GEEDLKVQHSSYRQRARLLKDQLSLG-NAALQITDVKLQDAGVYRCMIS YGGA-DYKRITVKVNAPYNKI (SEQ ID NO: 7)). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the immune cell is selected from the group consisting of a macrophage, allogeneic cell, myeloid cell and a monocyte. In some alternatives, the immune cell is a T-cell. In some alternatives, the immune cell is an NK cell. In some alternatives, the immune cell is a genetically modified NK cell. In some alternatives, the T cell is a genetically modified T-cell, genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the method further comprises delivering to the immune cell, a fourth vector, wherein the fourth vector encodes a Cas9 VP64 fusion protein to activate transcription and translation of a second protein and delivering to the immune cell a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene encodes IL-12p40, IL-15, IL-6, IL-1 beta, TNF-alpha, IFN-alpha/beta/gamma, IL-12, IL-18, IL-23 or GM-CSF. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the method further comprises differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor.

Cells Expressing a Protein that Induces T-Cell Proliferation, Promotes Persistence and Activation of Endogenous or Adoptively Transferred NK or T Cells and/or Induces Production of an Interleukin, an Interferon, a PD-1 Checkpoint Binding Protein, HMGB1, MyD88, a Cytokine or Chemokine.

In accordance with some preferred alternatives, there are genetically modified immune cells provided, wherein the cells comprise a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, a genetically modified immune cell comprising a first vector is provided. The first vector can comprise a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, there are methods provided of making the genetically modified immune cell for modifying a tumor microenvironment (TME). In some alternatives, the method comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma.

In some alternatives, the immune cell is a T-cell. In some alternatives, the immune cell is an NK cell. In some alternatives, the immune cell is a genetically modified NK cell. In some alternatives, the immune cell is a modified T-cell. In some alternatives, the immune cell is genetically modified to express a chimeric antigen receptor (CAR) or T-cell receptor (Tcr). In some alternatives, the cell is selected from the group consisting of a macrophage, allogeneic cell, myeloid cell, a monocyte and a primary human monocyte. In some alternatives, the cell is a primary human monocyte. In some alternatives, the immune cell is a myeloid cell. In some alternatives, the myeloid cell is a macrophage. In some alternatives, the myeloid cell is a microglial cell. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35 (GC-CACCATGGCACTTCCAGT-CACAGCGCTTCTTCTGCCTTTGGCACTGCTTCTCC ACGCAGCACGCCCAAACTGGGT-CAATGTAATCAGCGACCTGAAGAAGATTGAAG ACCTGATTCAATCAATGCACATAGACGC-TACGTTGTACACCGAATCAGATGTTCA TCCTAGCTGTAAAGTCACCGCAAT-GAAATGTTTTTTGCTGGAGCTTCAAGTTATA TCCCTTGAGTCTGGGGACGCATCTATA-CATGACACAGTTGAGAATTTGATCATAT TGGCAAACAATAGCTTGTCTTCCAACGGTAATGT-CACAGAGTCCGGTTGTAAAG AGTGTGAGGAACTT-GAAGAGAAAAACATTAAAGAAT-TTCTCCAGAGTTTCGTAC ATATTGTACAAATGTTCATAAATACTTCTATC-TATATCTGGGCTCCTCTCGCCGGA ACCTGTGGCGTTCTGCTGCTGTCTTTGGTGATTA-CAGGAAGTGGAGCCACAAATT TCAGTCTGCT-TAAACAGGCAGGGGATGTGGAG-GAGAACCCCGGCCCAATGCGAA TTTCAAAACCACATCTTAGATCAATCAGCATA-CAGTGTTATCTTTGTCTGCTGCTC AACAGCCAT-TTCTTGACTGAAGCCAACTGGGTCAACGTAAT-TTCTGATCTTAAAA AAATCGAGGATCTGATCCAGAGTATGCACATA-GACGCAACGCTTTACACCGAAA GTGATGTC-CATCCGTCATGTAAAGTAACGGCGAT-GAAGTGTTTCCTTCTCGAGCT TCAGGTAATTTCATTGGAGTCTGGAGATGCCTCTAT-TCATGACACGGTAGAGAAT TTGATCAT-TCTCGCTAACAATAGTCTTTCCAGTAACGGTAACGT-TACAGAGAGCG GATGTAAAGAATGTGAGGAATTGGAGGAGAAGAA-CATTAAGGAATTCCTTCAGT CCTTTGTCCA-CATCGTTCAGATGTTTATTAACACGAGTTGA). In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein or an active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, the first vector is a viral vector. In some alternatives, the viral vector is a retroviral vector or a lentiviral vector. In some alternatives, the lentiviral vector is packaged with a Vpx protein. In some alternatives, the lentiviral vector packaged with the Vpx protein is used to provide efficient transfection of myeloid cells. In some alternatives, the protein supports or promotes T-cell and/or NK-cell anti-tumor activity. In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8, CCL11, CCL13, CCL17, CCL22, CCL24, or CCL26. In some alternatives, the T-cell is a genetically modified T-cell. In some alternatives, the genetically modified T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the method further comprises delivering to the immune cell, a fourth vector, wherein the fourth vector encodes a Cas9 VP64 fusion protein and delivering to the immune cell a fifth vector, wherein the fifth vector comprises a CRISPR guide RNA complimentary to at least one target gene in the cell.

In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGAG AAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA- GACTTGAAGATGTACCAGGTG GAGTTCAAGAC-CATGAATGCAAAGCTGCTGATG-GATCCTAAGAGGCAGATCTTT CTAGATCAAAACATGCTGGCAGTTATTGATGAGCT-GATGCAGGCCCTGAATTTCA ACAGTGA-GACTGTGCCACAAAAATCCTCCCTTGAAGAACCG-GATTTTTATAAAA CTAAAATCAAGCTCTGCATACTTCTT-CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte.

In some alternatives, the method further comprises differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor.

In some alternatives, a genetically modified immune cell is provided wherein the genetically modified immune cell comprises a first vector that comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, beta, or gamma. In some alternatives, the protein comprises a PD-1 checkpoint binding inhibitor. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCCTGGAGAAATGGTGGTCCT-CACCTGTGACACCCCTGAAGA AGATGGTATCACCTGGACCTTGGACCAGAGCAGT-GAGGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC- CATGCCTTCACCACTCCCAAAACCTGCTG AGGGCCGTCAGCAACATGCTCCAGAAGGCCA- GACAAACTCTAGAATTTTACCCT TGCACTTCT- GAAGAGATTGATCATGAAGATATCACAAAAGA- TAAAACCAGCACA GTGGAGGCCTGTTTACCATTGGAATTAAC- CAAGAATGAGAGTTGCCTAAATTCCA GAGA- GACCTCTTTCATAACTAATGG- GAGTTGCCTGGCCTCCAGAAAGACCTCTTT TATGATGGCCCTGTGCCTTAGTAGTATTTATGAA- GACTTGAAGATGTACCAGGTG GAGTTCAAGAC- CATGAATGCAAAGCTGCTGATG- GATCCTAAGAGGCAGATCTTT CTAGATCAAAACATGCTGGCAGTTATTGATGAGCT- GATGCAGGCCCTGAATTTCA ACAGTGA- GACTGTGCCACAAAAATCCTCCCTTGAAGAACCG- GATTTTTATAAAA CTAAAATCAAGCTCTGCATACTTCTT- CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the immune cell is selected from the group consisting of a macrophage, allogeneic cell, myeloid cell and a monocyte. Methods of Expressing Myeloid Cell Surface Markers in GEMs In accordance with some preferred alternatives, there are genetically modified immune cells provided, wherein the cells comprise a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, a genetically modified immune cell comprising a first vector is provided. The first vector can comprise a nucleic acid encoding a protein that induces T-cell proliferation, promotes persistence and/or activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, there are methods provided of making the genetically modified immune cell for modifying a tumor microenvironment (TME). In some alternatives, the method comprises delivering a first vector to an immune cell, wherein the first vector comprises a nucleic acid encoding a protein that induces T-cell proliferation, promotes persistence and/or activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma.

In some alternatives, the immune cell is a T-cell. In some alternatives, the immune cell is an NK cell. In some alternatives, the immune cell is a genetically modified NK cell. In some alternatives, the immune cell is a modified T-cell. In some alternatives, the immune cell is genetically modified to express a chimeric antigen receptor (CAR) or T-cell receptor (Tcr). In some alternatives, the cell is selected from the group consisting of a macrophage, allogeneic cell, myeloid cell, a monocyte and a primary human monocyte. In some alternatives, the cell is a primary human monocyte. In some alternatives, the immune cell is a myeloid cell. In some alternatives, the myeloid cell is a macrophage. In some alternatives, the myeloid cell is a microglial cell. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, the first vector is a viral vector. In some alternatives, the viral vector is a retroviral vector or a lentiviral vector. In some alternatives, the lentiviral vector is packaged with a Vpx protein. In some alternatives, the lentiviral vector packaged with the Vpx protein is used to provide efficient transfection of myeloid cells. In some alternatives, the protein supports or promotes T-cell and/or NK-cell anti-tumor activity. In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8, CCL11, CCL13, CCL17, CCL22, CCL24, or CCL26. In some alternatives, the T-cell is a genetically modified T-cell. In some alternatives, the genetically modified T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the method further comprises delivering to the immune cell, a fourth vector, wherein the fourth vector encodes a Cas9 VP64 fusion protein and delivering to the immune cell a fifth vector, wherein the fifth vector comprises a CRISPR guide RNA complimentary to at least one target gene in the cell.

In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA-GACTTGAAGTATGCCAGGTG GAGTTCAAGAC-CATGAATGCAAAGCTGCTGATG-GATCCTAAGAGGCAGATCTTT CTAGATCAAAACATGCTGGCAGTTATTGATGAGCT- GATGCAGGCCCTGAATTTCA ACAGTGAGACTGTGCCACAAAAATCCTCCCTTGAAGAACCGGATTTTTATAAAACTAAAATCAAGCTCTGCATACTTCTTCATCTTTCAGAATTCGGGCAGTGACTATTGATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte.

In some alternatives, the method further comprises further comprising differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor.

In some alternatives, a genetically modified immune cell is provided wherein the genetically modified immune cell comprises a first vector that comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35 (GCCACCATGGCACTTCCAGTCACAGCGCTTCTTCTGCCTTTGGCACTGCTTCTCCACGCAGCACGCCCAAACTGGGTCAATGTAATCAGCGACCTGAAGAAGATTGAAGACCTGATTCAATCAATGCACATAGACGCTACGTTGTACACCGAATCAGATGTTCATCCTAGCTGTAAAGTCACCGCAATGAAATGTTTTTTGCTGGAGCTTCAAGTTATATCCCTTGAGTCTGGGGACGCATCTATACATGACACAGTTGAGAATTTGATCATATTGGCAAACAATAGCTTGTCTTCCAACGGTAATGTCACAGAGTCCGGTTGTAAAG AGTGTGAGGAACTTGAAGAGAAAAACATTAAAGAATTTCTCCAGAGTTTCGTACATATTGTACAAATGTTCATAAATACTTCTATCTATATCTGGGCTCCTCTCGCCGGAACCTGTGGCGTTCTGCTGCTGTCTTTGGTGATTACAGGAAGTGGAGCCACAAATT TCAGTCTGCTTAAACAGGCAGGGGATGTGGAGGAGAACCCCGGCCCAATGCGAATTTCAAAACCACATCTTAGATCAATCAGCATACAGTGTTATCTTTGTCTGCTGCTC AACAGCCATTCTTGACTGAAGCCAACTGGGTCAACGTAATTTCTGATCTTAAAAAAATCGAGGATCTGATCCAGAGTATGCACATAGACGCAACGCTTTACACCGAAA GTGATGTCCATCCGTCATGTAAAGTAACGGCGATGAAGTGTTTCCTTCTCGAGCTTCAGGTAATTTCATTGGAGTCTGGAGATGCCTCTATTCATGACACGGTAGAGAAT TTGATCATTCTCGCTAACAATAGTCTTTCCAGTAACGGTAACGTTACAGAGAGCGGATGTAAAGAATGTGAGGAATTGGAGGAGAAGAACATTAAGGAATTCCTTCAGT CCTTTGTCCACATCGTTCAGATGTTTATTAACACGAGTTGA). In some alternatives, the protein comprises interferon alpha, beta, or gamma. In some alternatives, the protein comprises a PD-1 checkpoint binding inhibitor. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGTCATCTCTTGGTTTTCCCTGGTTTTTCTGGCATCTCCCCTCGTGGCCATATGGGAACTGAAGAAAGATGTTTATGTCGTAGAATTGGATTG GTATCCGGATGCCCCTGGAGAAATGGTGGTCCT CACCTGTGACACCCCTGAAGA
AGATGGTATCACCTGGACCTTGGACCAGAGCAGT-
GAGGTCTTAGGCTCTGGCAA AACCCTGACCATC-
CAAGTCAAAGAGTTTGGAGATGCTGGCCAGTA-
CACCTGTCA
CAAAGGAGGCGAGGTTCTAAGCCAT-
TCGCTCCTGCTGCTTCACAAAAAGGAAGA
TGGAATTTGGTCCACTGATATTT-
TAAAGGACCAGAAAGAACCCAAAAATAAGAC
CTTTCTAAGATGCGAGGCCAAGAATTAT-
TCTGGACGTTTCACCTGCTGGTGGCTG
ACGACAATCAGTACTGATTTGACATTCAGTGT-
CAAAAGCAGCAGAGGCTCTTCTG ACCCC-
CAAGGGGTGACGTGCGGAGCTGCTA-
CACTCTCTGCAGAGAGAGTCAGAG
GGGACAACAAGGAGTATGAGTACTCAGTG-
GAGTGCCAGGAGGACAGTGCCTGCC CAGCTGCT-
GAGGAGAGTCTGCCCATTGAGGTCATGGTG-
GATGCCGTTCACAAGC
TCAAGTATGAAAACTACACCAGCAGCTTCTT-
CATCAGGGACATCATCAAACCTG ACCCACC-
CAAGAACTTGCAGCTGAAGCCATTAAAGAAT-
TCTCGGCAGGTGGAGG
TCAGCTGGGAGTACCCTGACACCTGGAGTACTC-
CACATTCCTACTTCTCCCTGAC
ATTCTGCGTTCAGGTCCAGGGCAAGAGCAAGAGA
GAAAAGAAAGATAGAGTCTT CACGGACAA-
GACCTCAGCCACGGT-
CATCTGCCGCAAAAATGCCAGCATTAGCGT
GCGGGCCCAGGACCGCTACTATAGCTCATCTTG-
GAGCGAATGGGCATCTGTGCC
CTGCAGTGTTCCTG-
GAGTAGGGGTACCTGGGGTGGGCGCCAGAAACCT
CCCCGT GGCCACTCCAGACCCAGGAATGTTCC-
CATGCCTTCACCACTCCCAAAACCTGCTG
AGGGCCGTCAGCAACATGCTCCAGAAGGCCA-
GACAAACTCTAGAATTTTACCCT TGCACTTCT-
GAAGAGATTGATCATGAAGATATCACAAAAGA-
TAAAACCAGCACA
GTGGAGGCCTGTTTACCATTGGAATTAAC-
CAAGAATGAGAGTTGCCTAAATTCCA GAGA-
GACCTCTTTCATAACTAATGG-
GAGTTGCCTGGCCTCCAGAAAGACCTCTTT
TATGATGGCCCTGTGCCTTAGTAGTATTTATGAA-
GACTTGAAGATGTACCAGGTG GAGTTCAAGAC-
CATGAATGCAAAGCTGCTGATG-
GATCCTAAGAGGCAGATCTTT
CTAGATCAAAACATGCTGGCAGTTATTGATGAGCT-
GATGCAGGCCCTGAATTTCA ACAGTGA-
GACTGTGCCACAAAAATCCTCCCTTGAAGAACCG-
GATTTTATAAAA
CTAAAATCAAGCTCTGCATACTTCTT-
CATCTTTCAGAATTCGGGCAGTGACTATT
GATAGAGTGATGAGCTATCTGAATGCTTCCTAA). In
some alternatives, the first vector further comprises a nucleic
acid encoding a suicide gene system. In some alternatives,
the suicide gene system is a Herpes Simplex Virus Thymi-
dine Kinase (HSVTK)/Ganciclovir (GCV) suicide gene sys-
tem or an inducible Caspase suicide gene system. In some
alternatives, the nucleic acid encoding said protein is under
the control of a regulatory element. In some alternatives, the
regulatory element is a promoter that is inducible by a drug.
In some alternatives, the regulatory element is a promoter
that is inducible by a steroid, such as a ligand for the
estrogen receptor. In some alternatives, the regulatory ele-
ment is a promoter inducible by tamoxifen and/or its
metabolites. In some alternatives, the immune cell is
selected from the group consisting of a macrophage, allo-
geneic cell, myeloid cell and a monocyte. In some alterna-
tives, the immune cells are differentiated. In some alterna-
tives, the immune cells are differentiated to a pro-
inflammatory phenotype by culturing the cells with
granulocyte macrophage colony stimulating factor. In some
alternatives, the immune cells are differentiated to an anti-
inflammatory phenotype by culturing the cells with a mac-
rophage colony stimulating factor. In some alternatives, the
cells have a decrease in CD11b expression in comparison to
an immune cells that have not been induced with the said
vectors. In some alternatives, the immune cell is selected
from the group consisting of a macrophage, allogeneic cell,
myeloid cell and a monocyte. In some alternatives, the
immune cell has an increased expression of anti-inflamma-
tory macrophage markers. In some alternatives, the anti-
inflammatory macrophage markers are CD163 and CD80. In
some alternatives, the immune cell expresses a higher con-
centration of anti-inflammatory macrophage markers in
comparison to an immune cell that has not been transduced
with the said vectors.

Compositions

In some alternatives, the methods and compositions
described herein are used to modify a tumor environment in
a subject suffering from cancer, disease or an infection e.g.,
a human. In some alternatives of the methods and compo-
sitions provided herein, the patients in need are people of
pediatric age with relapsed refractory neuroblastoma. In
some alternatives, the cancer is a solid tumor. In some
alternatives, the solid tumor is selected from the group
consisting of a breast cancer, brain cancer, lung cancer, liver
cancer, stomach cancer, spleen cancer, colon cancer, renal
cancer, pancreatic cancer, prostate cancer, uterine cancer,
skin cancer, head cancer, neck cancer, sarcomas, neuroblas-
tomas and ovarian cancer.

In some alternatives, the composition provided to said
subject is used for modifying a tumor environment in said
subject. In some alternatives, the composition is used to
modulate the suppression of the immune response in a tumor
microenvironment of a subject in need thereof e.g., a subject
that has a cancer such as a breast cancer, brain cancer, lung
cancer, liver cancer, stomach cancer, spleen cancer, colon
cancer, renal cancer, pancreatic cancer, prostate cancer,
uterine cancer, skin cancer, head cancer, neck cancer, sar-
comas, neuroblastomas and ovarian cancer. In some alter-
natives, the composition is used to minimize the prolifera-
tion of tumor and suppressive cells in a subject in need
thereof e.g., a subject that has a cancer such as a breast
cancer, brain cancer, lung cancer, liver cancer, stomach
cancer, spleen cancer, colon cancer, renal cancer, pancreatic
cancer, prostate cancer, uterine cancer, skin cancer, head
cancer, neck cancer, sarcomas, neuroblastomas and ovarian
cancer. In some alternatives, the composition is used to of
increase the efficiency of an anti-cancer therapy, anti-infec-
tion therapy, antibacterial therapy, anti-viral therapy, or
anti-tumoral therapy in a subject in need thereof e.g., a
subject that has a cancer such as a breast cancer, brain
cancer, lung cancer, liver cancer, stomach cancer, spleen
cancer, colon cancer, renal cancer, pancreatic cancer, pros-
tate cancer, uterine cancer, skin cancer, head cancer, neck
cancer, sarcomas, neuroblastomas and ovarian cancer.

In some alternatives, the composition comprises any one
or more of the genetically modified immune cells of any of
the alternatives described herein or any one of more of the
genetically modified immune cells manufactured by any one
of the alternatives described herein and a carrier, an anti-
cancer therapeutic, an anti-infection therapeutic, an antibacterial therapeutic, an anti-viral therapeutic, or an anti-tumoral therapeutic. In some alternatives, the genetically modified immune cells of the composition comprises a nucleic acid encoding a protein that induces T-cell proliferation, promotes persistence and/or activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma.

In some alternatives, the method of making the genetically modified immune cell comprises delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma.

In some alternatives, the vector is a viral vector. In some alternatives, the viral vector is a retroviral vector or a lentiviral vector. In some alternatives, the lentiviral vector is packaged with a Vpx protein. In some alternatives, the lentiviral vector packaged with the Vpx protein is used to provide efficient transfection of myeloid cells. In some alternatives, the protein supports or promotes T-cell and/or NK-cell anti-tumor activity. In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokine comprises CCL1, CCL2, CCL3, CCR4, CCL5, CCL7, CCL8, CCL11, CCL13, CCL17, CCL22, CCL24, or CCL26. In some alternatives, the T-cell is a genetically modified T-cell. In some alternatives, the genetically modified T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the method further comprises delivering to the immune cell, a fourth vector, wherein the fourth vector encodes a Cas9 VP64 fusion protein and delivering to the immune cell a fifth vector, wherein the fifth vector comprises a CRISPR guide RNA complimentary to at least one target gene in the cell.

In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGTCATCTCTTGGTTTTCCCTGGTTTTTCTGGCATCTCCCCTCGTGGCCATATGGGAACTGAAGAAAGATGTTTATGTCGTAGAATTGGATTG GTATCCGGATGCCCCTGGAGAAATGGTGGTCCTCACCTGTGACACCCCTGAAGA AGATGGTATCACCTGGACCTTGGACCAGAGCAGTGAGGTCTTAGGCTCTGGCAA AACCCTGACCATCCAAGTCAAAGAGTTTGGAGATGCTGGCCAGTACACCTGTCA CAAAGGAGGCGAGGTTCTAAGCCATTCGCTCCTGCTGCTTCACAAAAAGGAAGA TGGAATTTGGTCCACTGATATTTTAAAGGACCAGAAAGAACCCAAAAATAAGAC CTTTCTAAGATGCGAGGCCAAGAATTATTCTGGACGTTTCACCTGCTGGTGGCTG ACGACAATCAGTACTGATTTGACATTCAGTGTCAAAAGCAGCAGAGGCTCTTCTG ACCCCCAAGGGGTGACGTGCGGAGCTGCTACACTCTCTGCAGAGAGAGTCAGAG GGGACAACAAGGAGTATGAGTACTCAGTGGAGTGCCAGGAGGACAGTGCCTGCC CAGCTGCTGAGGAGAGTCTGCCCATTGAGGTCATGGTGGATGCCGTTCACAAGC TCAAGTATGAAAACTACACCAGCAGCTTCTTCATCAGGGACATCATCAAACCTG ACCCACCCAAGAACTTGCAGCTGAAGCCATTAAAGAATTCTCGGCAGGTGGAGG TCAGCTGGGAGTACCCTGACACCTGGAGTACTCCACATTCCTACTTCTCCCTGAC ATTCTGCGTTCAGGTCCAGGGCAAGAGCAAGAGAGAAAAGAAAGATAGAGTCTT CACGGACAAGACCTCAGCCACGGTCATCTGCCGCAAAAATGCCAGCATTAGCGT GCGGGCCCAGGACCGCTACTATAGCTCATCTTGGAGCGAATGGGCATCTGTGCC CTGCAGTGTTCCTGGAGTAGGGGTACCTGGGGTGGGCGCCAGAAACCTCCCCGT GGCCACTCCAGACCCAGGAATGTTCCCATGCCTTCACCACTCCCAAAACCTGCTG AGGGCCGTCAGCAACATGCTCCAGAAGGCCAGACAAACTCTAGAATTTTACCCT TGCACTTCTGAAGAGATTGATCATGAAGATATCACAAAAGATAAAACCAGCACA GTGGAGGCCTGTTTACCATTGGAATTAACCAAGAATGAGAGTTGCCTAAATTCCA GAGAGACCTCTTTCATAACTAATGGGAGTTGCCTGGCCTCCAGAAAGACCTCTTT TATGATGGCCCTGTGCCTTAGTAGTATTTATGAAGACTTGAAGATGTACCAGGTG GAGTTCAAGACCATGAATGCAAAGCTGCTGATGGATCCTAAGAGGCAGATCTTT CTAGATCAAAACATGCTGGCAGTTATTGATGAGCTGATGCAGGCCCTGAATTTCA ACAGTGAGACTGTGCCACAAAAATCCTCCCTTGAAGAACCGGATTTTTATAAAA CTAAAATCAAGCTCTGCATACTTCTT- CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte.

In some alternatives, the method further comprises differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor.

In some alternatives, the genetically modified cells comprise a first vector, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35 (GCCACCATGGCACTTCCAGTCACAGCGCTTCTTCTGCCTTTGGCACTGCTTCTCC ACGCAGCACGCCCAAACTGGGT-CAATGTAATCAGCGACCTGAAGAAGATTGAAG ACCTGATTCAATCAATGCACATAGACGC-TACGTTGTACACCGAATCAGATGTTCA TCCTAGCTGTAAAGTCACCGCAAT-GAAATGTTTTTTGCTGGAGCTTCAAGTTATA TCCCTTGAGTCTGGGGACGCATCTATA-CATGACACAGTTGAGAATTTGATCATAT TGGCAAACAATAGCTTGTCTTCCAACGGTAATGT-CACAGAGTCCGGTTGTAAAG AGTGTGAGGAACTT-GAAGAGAAAAACATTAAAGAAT-TTCTCCAGAGTTTCGTAC ATATTGTACAAATGTTCATAAATACTTCTATC-TATATCTGGGCTCCTCTCGCCGGA ACCTGTGGCGTTCTGCTGCTGTCTTTGGTGATTA-CAGGAAGTGGAGCCACAAATT TCAGTCTGCT-TAAACAGGCAGGGGATGTGGAG-GAGAACCCCGGCCCAATGCGAA TTTCAAAACCACATCTTAGATCAATCAGCATA-CAGTGTTATCTTTGTCTGCTGCTC AACAGCCAT-TTCTTGACTGAAGCCAACTGGGTCAACGTAAT-TTCTGATCTTAAAA AAATCGAGGATCTGATCCAGAGTATGCACATA-GACGCAACGCTTTACACCGAAA GTGATGTC-CATCCGTCATGTAAAGTAACGGCGAT-GAAGTGTTTCCTTCTCGAGCT TCAGGTAATTTCATTGGAGTCTGGAGATGCCTCTAT-TCATGACACGGTAGAGAAT TTGATCAT-TCTCGCTAACAATAGTCTTTCCAGTAACGGTAACGT-TACAGAGAGCG GATGTAAAGAATGTGAGGAATTGGAGGAGAAGAA-CATTAAGGAATTCCTTCAGT CCTTTGTCCA-CATCGTTCAGATGTTTATTAACACGAGTTGA). In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT- TCTGGACGTTTCACCTGCTGGTGGCTGACGACAATCAGTACTGATTTGACATTCAGTGTCAAAAGCAGCAGAGGCTCTTCTG ACCCCCAAGGGGTGACGTGCGGAGCTGCTACACTCTCTGCAGAGAGAGTCAGAG GGGACAACAAGGAGTATGAGTACTCAGTGGAGTGCCAGGAGGACAGTGCCTGCC CAGCTGCTGAGGAGAGTCTGCCCATTGAGGTCATGGTGGATGCCGTTCACAAGC TCAAGTATGAAAACTACACCAGCAGCTTCTTCATCAGGGACATCATCAAACCTG ACCCACCCAAGAACTTGCAGCTGAAGCCATTAAAGAATTCTCGGCAGGTGGAGG TCAGCTGGGAGTACCCTGACACCTGGAGTACTCCACATTCCTACTTCTCCCTGAC ATTCTGCGTTCAGGTCCAGGGCAAGAGCAAGAGAGAAAAGAAAGATAGAGTCTT CACGGACAAGACCTCAGCCACGGTCATCTGCCGCAAAAATGCCAGCATTAGCGT GCGGGCCCAGGACCGCTACTATAGCTCATCTTGGAGCGAATGGGCATCTGTGCC CTGCAGTGTTCCTGGAGTAGGGGTACCTGGGGTGGGCGCCAGAAACCT CCCCGT GGCCACTCCAGACCCAGGAATGTTCCCATGCCTTCACCACTCCCAAAACCTGCTG AGGGCCGTCAGCAACATGCTCCAGAAGGCCAGACAAACTCTAGAATTTTACCCT TGCACTTCTGAAGAGATTGATCATGAAGATATCACAAAAGATAAAACCAGCACA GTGGAGGCCTGTTTACCATTGGAATTAACCAAGAATGAGAGTTGCCTAAATTCCA GAGAGACCTCTTTCATAACTAATGGGAGTTGCCTGGCCTCCAGAAAGACCTCTTT TATGATGGCCCTGTGCCTTAGTAGTATTTATGAAGACTTGAAGATGTACCAGGTG GAGTTCAAGACCATGAATGCAAAGCTGCTGATGGATCCTAAGAGGCAGATCTTT CTAGATCAAAACATGCTGGCAGTTATTGATGAGCTGATGCAGGCCCTGAATTTCA ACAGTGAGACTGTGCCACAAAAATCCTCCCTTGAAGAACCGGATTTTTATAAAA CTAAAATCAAGCTCTGCATACTTCTTCATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

The composition can further comprise a pharmaceutical vehicle or pharmaceutical excipient. "Pharmaceutical excipient," or pharmaceutical vehicle as described herein can refer to a carrier or inert medium used as a solvent in which the medicinally active agent or T-cells for treatment or therapy is formulated and or administered. Vehicles can include polymeric micelles, liposomes, lipoprotein-based carriers, nano-particle carriers, dendrimers, and/or other vehicles.

"Vehicles" as described herein can refer to a substance of no therapeutic value that is used to convey an active medicine or cells for administration. Pharmaceutical vehicle as described herein can refer to a carrier or inert medium used as a solvent in which the medicinally active agent is formulated and or administered. An ideal vehicle can be non-toxic, biocompatible, non-immunogenic, biodegradable, and can avoid recognition by the host's defense mechanisms. In several alternatives, compositions are provided which comprise vehicles or excipients that promote or enhance or stabilize the integrity of the genetically modified immune cells. In some alternatives, the vehicles are pharmaceutical vehicles. In some alternatives, the pharmaceutical vehicles include pharmaceutical compositions. In some alternatives, the composition further comprises a pharmaceutical excipient and at least one population of genetically modified immune cells of any of the alternatives described herein.

Methods of Modulating the Suppression of the Immune Response in a Tumor Microenvironment of a Subject in Need Thereof In some alternatives, a method of modulating the suppression of the immune response in a tumor microenvironment of a subject in need thereof e.g., a human is provided, wherein the method comprises administering any one or more of the genetically modified immune cells of any one or more of the alternatives described herein or any one or more of the compositions of any of the alternatives described herein to said subject in need thereof and, optionally, selecting or identifying said subject to receive said genetically modified immune cells and/or measuring a modulation of suppression of the immune response in the tumor microenvironment of said subject after administration of said genetically modified immune cells.

In some alternatives, the genetically modified cells comprise a first vector wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokine comprises CCL1, CCL2, CCL3, CCR4, CCL5, CCL7, CCL8, CCL11, CCL13, CCL17, CCL22, CCL24, or CCL26. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA-GACTTGAAGATGTACCAGGTG GAGTTCAAGAC-CATGAATGCAAAGCTGCTGATG-GATCCTAAGAGGCAGATCTTT CTAGATCAAAACATGCTGGCAGTTATTGATGAGCT-GATGCAGGCCCTGAATTTCA ACAGTGA-GACTGTGCCACAAAAATCCTCCCTTGAAGAACCG-GATTTTTATAAAA CTAAAATCAAGCTCTGCATACTTCTT-CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, the composition is used for modulating the suppression of the immune response in a tumor microenvironment. In some alternatives of the genetically modified cells of the composition, the genetically modified cells comprise a first vector that comprises a nucleic acid encoding a protein that induces T-cell proliferation, promotes persistence and/or activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA-GACTTGAAGATGTACCAGGTG GAGTTCAAGAC-CATGAATGCAAAGCTGCTGATG-GATCCTAAGAGGCAGATCTTT CTAGATCAAAACATGCTGGCAGTTATTGATGAGCT-GATGCAGGCCCTGAATTTCA ACAGTGA-GACTGTGCCACAAAAATCCTCCCTTGAAGAACCG-GATTTTTATAAAA CTAAAATCAAGCTCTGCATACTTCTT-CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives of the method, administering is performed by adoptive cell transfer. In some alternatives, the genetically modified immune cells are administered by direct delivery to a tumor bed by injection. In some alternatives, the subject in need suffers from cancer. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

In some alternatives, the method further comprises administering a cellular therapy to the subject in need thereof e.g., a human before, after or simultaneous to introducing, providing, or administering any one or more of the cells described in any of the alternatives herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of any of the alternatives described herein. In some alternatives, the drug is tamoxifen and/or its metabolites. In some alternatives, the subject is identified or selected to receive an anti-cancer therapy, an anti-infection therapy, an antibacterial therapy, an anti-viral therapy, or an anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of any of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragment thereof is specific for Her2, CD52, CD20, CD25, VEGF or EGRF and such antibodies or binding fragments thereof can be humanized. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor. In some alternatives, the method does not negatively affect survival of the subject. In some alternatives, the method does not cause detrimental side effects.

A Method of Minimizing the Proliferation of Tumor and Suppressive Cells

In some alternatives, a method of minimizing the proliferation of tumor and suppressive cells in a subject in need thereof e.g., a human is provided, wherein the method comprises administering any one or more of the genetically modified immune cells of any one or more of the alternatives described herein or any one or more of the compositions of any of the alternatives described herein to said subject in need thereof and, optionally, selecting or identifying said subject to receive said genetically modified immune cells and/or measuring the proliferation of tumor and suppressive cells in said subject after administration of said genetically modified immune cells.

In some alternatives, the genetically modified cells comprise a first vector that comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell antitumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokine comprises CCL1, CCL2, CCL3, CCR4, CCL5, CCL7, CCL8, CCL11, CCL13, CCL17, CCL22, CCL24, or CCL26. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGTCATCTCTTGGTTTTCCCTGGTTTTTCTGGCATCTCCCCTCGTGGCCATATGGGAACTGAAGAAAGATGTTTATGTCGTAGAATTGGATTG GTATCCGGATGCCCCTGGAGAAATGGTGGTCCTCACCTGTGACACCCCTGAAGAAGATGGTATCACCTGGACCTTGGACCAGAGCAGTGAGGTCTTAGGCTCTGGCAA AACCCTGACCATCCAAGTCAAAGAGTTTGGAGATGCTGGCCAGTACACCTGTCACAAAGGAGGCGAGGTTCTAAGCCATTCGCTCCTGCTGCTTCACAAAAAGGAAGATGGAATTTGGTCCACTGATATTTTAAAAGGACCAGAAAGAACCCAAAAATAAGACCTTTCTAAGATGCAGGCCAAGAATTATTCTGGACGTTTCACCTGCTGGTGGCTGACGACAATCAGTACTGATTTGACATTCAGTGTCAAAAGCAGCAGAGGCTCTTCTG ACCCCCAAGGGGTGACGTGCGGAGCTGCTACACTCTCTGCAGAGAGAGTCAGAGGGGACAACAAGGAGTATGAGTACTCAGTGGAGTGCCAGGAGGACAGTGCCTGCC CAGCTGCTGAGGAGAGTCTGCCCATTGAGGTCATGGTGGATGCCGTTCACAAGCTCAAGTATGAAAACTACACCAGCAGCTTCTTCATCAGGGACATCATCAAACCTG ACCCACCCAAGAACTTGCAGCTGAAGCCATTAAAGAATTCTCGGCAGGTGGAGGTCAGCTGGGAGTACCCTGACACCTGGAGTACTCCACATTCCTACTTCTCCCTGACATTCTGCGTTCAGGTCCAGGGCAAGAGCAAGAGAGAAAAGAAAGATAGAGTCTT CACGGACAAGACCTCAGCCACGGTCATCTGCCGCAAAAATGCCAGCATTAGCGTGCGGGCCCAGGACCGCTACTATAGCTCATCTTGGAGCGAATGGGCATCTGTGCCCTGCAGTGTTCCTGGAGTAGGGGTACCTGGGGTGGGCGCCAGAAACCT CCCCGT GGCCACTCCAGACCCAGGAATGTTCCCATGCCTTCACCACTCCCAAAACCTGCTGAGGGCCGTCAGCAACATGCTCCAGAAGGCCAGACAAACTCTAGAATTTTACCCT TGCACTTCTGAAGAGATTGATCATGAAGATATCACAAAAGATAAAACCAGCACAGTGGAGGCCTGTTTACCATTGGAATTAACCAAGAATGAGAGTTGCCTAAATTCCA GAGAGACCTCTTTCATAACTAATGGGAGTTGCCTGGCCTCCAGAAAGACCTCTTTTATGATGGCCCTGTGCCTTAGTAGTATTTATGAAGACTTGAAGATGTACCAGGTG GAGTTCAAGACCATGAATGCAAAGCTGCTGATGGATCCTAAGAGGCAGATCTTTCTAGATCAAAACATGCTGGCAGTTATTGATGAGCTGATGCAGGCCCTGAATTTCA ACAGTGAGACTGTGCCACAAAAATCCTCCCTTGAAGAACCGGATTTTTATAAAACTAAAATCAAGCTCTGCATACTTCTTCATCTTTCAGAATTCGGGCAGTGACTATTGATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, the composition is used for minimizing the proliferation of tumor and suppressive cells in a subject in need. In some alternatives of the genetically modified cells of the composition, the genetically modified cells comprise a first vector that comprises a nucleic acid encoding a protein that induces T-cell proliferation, promotes persistence and/or activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-6, IL-7, IL-15, IL-2, IL-12, IL-18 or IL-21. In some alternatives, the protein comprises interferon alpha, beta, or gamma. In some alternatives, IL-15 is encoded by a sequence set forth in SEQ ID NO: 35. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokine is CCL1, CCL2, CCL3, CCR4, CCL5, CCL7, CCL8, CCL11, CCL13, CCL17, CCL22, CCL24, or CCL26. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGTCATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG-GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA-GACTTGAAGATGTACCAGGTG GAGTTCAAGAC-CATGAATGCAAAGCTGCTGATG-GATCCTAAGAGGCAGATCTTT CTAGATCAAAACATGCTGGCAGTTATTGATGAGCT-GATGCAGGCCCTGAATTTCA ACAGTGA-GACTGTGCCACAAAAATCCTCCCTTGAAGAACCG-GATTTTTATAAAA CTAAAATCAAGCTCTGCATACTTCTT-CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. The composition can further comprise a vehicle, or pharmaceutical vehicle.

In some alternatives of the method, the administering is performed by adoptive cell transfer. In some alternatives, the genetically modified immune cells are administered by direct delivery to a tumor bed by injection. In some alternatives, the subject in need suffers from cancer. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

In some alternatives, the method further comprises administering a cellular therapy to the subject in need thereof before, after or simultaneous to introducing, providing, or administering any one or more of the cells described in any of the alternatives herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of any of the alternatives described herein. In some alternatives, the drug is tamoxifen and/or its metabolites. In some alternatives, the subject is identified or selected to receive an anti-cancer therapy, an anti-infection therapy, an antibacterial therapy, an anti-viral therapy, or an anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of any of the alternatives described herein. In some alternatives, the additional therapeutic agent is an anti-cancer therapy comprising a hormone blocking therapy, chemotherapy, a small molecule, monoclonal antibodies or binding fragments thereof, which can be humanized, and/or radiation. In some alternatives, the monoclonal antibody or binding fragment thereof or humanized variants thereof, is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

Method of Increasing the Efficiency of an Anti-Cancer Therapy, Anti-Infection Therapy, Antibacterial Therapy, Anti-Viral Therapy, or Anti-Tumoral Therapy in a Subject In some alternatives, a method of increasing the efficiency of an anti-cancer therapy, anti-infection therapy, antibacterial therapy, anti-viral therapy, or anti-tumoral therapy in a subject in need thereof e.g., a human is provided, wherein the method comprises administering any one or more of the genetically modified immune cells of any one or more of any one of the alternatives described herein or a composition of any one of the alternatives described herein to s subject in need thereof e.g., a human and, optionally, selecting or identifying said subject to receive said genetically modified immune cells and/or measuring the proliferation of the cancer, infection, bacteria, virus, or tumor in said subject after administration of said genetically modified immune cells.

In some alternatives of the genetically modified immune cells used for increasing the efficiency of an anti-cancer therapy, anti-infection therapy, antibacterial therapy, anti-viral therapy, or anti-tumoral therapy in said subject in need, the genetically modified immune cells comprise a first vector, wherein the first vector comprises a nucleic acid encoding a protein that induces T-cell proliferation, promotes persistence and/or activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the genetically modified immune cell is a T-cell. In some alternatives, the immune cell is an NK cell. In some alternatives, the immune cell is a genetically modified NK cell. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, beta, or gamma. In some alternatives, IL-15 is encoded by a sequence set forth in SEQ ID NO: 35. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT-TCGCTCCTGCTGCTTCACAAAAAGGAAGA TGGAATTTGGTCCACTGATATTT-TAAAGGACCAGAAAGAACCCAAAAATAAGAC CTTTCTAAGATGCGAGGCCAAGAATTAT-TCTGGACGTTTCACCTGCTGGTGGCTG ACGACAATCAGTACTGATTTGACATTCAGTGT-CAAAAGCAGCAGAGGCTCTTCTG ACCCC-CAAGGGGTGACGTGCGGAGCTGCTA-CACTCTCTGCAGAGAGAGTCAGAG GGGACAACAAGGAGTATGAGTACTCAGTG-GAGTGCCAGGAGGACAGTGCCTGCC CAGCTGCT-GAGGAGAGTCTGCCCATTGAGGTCATGGTG- GATGCCGTTCACAAGC TCAAGTATGAAAACTACACCAGCAGCTTCTT-CATCAGGGACATCATCAAACCTG ACCCACC-CAAGAACTTGCAGCTGAAGCCATTAAAGAAT-TCTCGGCAGGTGGAGG TCAGCTGGGAGTACCCTGACACCTGGAGTACTC-CACATTCCTACTTCTCCCTGAC ATTCTGCGTTCAGGTCCAGGGCAAGAGCAAGAGA GAAAAGAAAGATAGAGTCTT CACGGACAA-GACCTCAGCCACGGT-CATCTGCCGCAAAAATGCCAGCATTAGCGT GCGGGCCCAGGACCGCTACTATAGCTCATCTTG-GAGCGAATGGGCATCTGTGCC CTGCAGTGTTCCTG-GAGTAGGGGTACCTGGGGTGGGCGCCAGAAACCT CCCCGT GGCCACTCCAGACCCAGGAATGTTCC-CATGCCTTCACCACTCCCAAAACCTGCTG AGGGCCGTCAGCAACATGCTCCAGAAGGCCA-GACAAACTCTAGAATTTTACCCT TGCACTTCT-GAAGAGATTGATCATGAAGATATCACAAAAGA-TAAAACCAGCACA GTGGAGGCCTGTTTACCATTGGAATTAAC-CAAGAATGAGAGTTGCCTAAATTCCA GAGA-GACCTCTTTCATAACTAATGG-GAGTTGCCTGGCCTCCAGAAAGACCTCTTT TATGATGGCCCTGTGCCTTAGTAGTATTTATGAA-GACTTGAAGATGTACCAGGTG GAGTTCAAGAC-CATGAATGCAAAGCTGCTGATG-GATCCTAAGAGGCAGATCTTT CTAGATCAAAACATGCTGGCAGTTATTGATGAGCT-GATGCAGGCCCTGAATTTCA ACAGTGA-GACTGTGCCACAAAAATCCTCCCTTGAAGAACCG-GATTTTTATAAAA CTAAAATCAAGCTCTGCATACTTCTT-CATCTTTCAGAATTCGGGCAGTGACTATT GATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, the composition is used for increasing the efficiency of or improving an anti-cancer therapy, an anti-infection therapy, an antibacterial therapy, an anti-viral therapy, or an anti-tumoral therapy in a subject in need e.g., a human. In some alternatives, the genetically modified cells comprise a first vector that comprises a nucleic acid encoding a protein that induces T-cell proliferation, promotes persistence and/or activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the genetically modified cell is a T-cell. In some alternatives, the T-cell is a modified T-cell. In some alternatives, the T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is TGF-beta or IL-10. In some alternatives, the genetically modified immune cell further comprises a fourth vector, wherein the fourth vector encodes a Cas9 VP64 fusion protein and a fifth vector, wherein the fifth vector comprises a CRISPR guide RNA complimentary to at least one target gene in the cell. In some alternatives, the fourth vector is an mRNA. In some alternatives, the mRNA is codon optimized for expression in a eukaryotic cell, such as a human cell. In some alternatives, the protein supports or promotes T-cell and/or NK-cell anti-tumor activity. In some alternatives, the at least one target gene is an endogenous pro-inflammatory gene. In some alternatives, the pro-inflammatory gene is IFN-gamma, IL-12 and/or IL-18. In some alternatives, IL-12 is encoded by a sequence set forth in SEQ ID NO: 27 (ATGTGTCACCAGCAGTTGGT-CATCTCTTGGTTTTCCCTGGTTTTTCTGGCATCTCC CCTCGTGGCCATATGGGAACTGAAGAAAGATGTT-TATGTCGTAGAATTGGATTG GTATCCG-GATGCCCTGGAGAAATGGTGGTCCT-CACCTGTGACACCCCTGAAGA AGATGGTATCACCTGGACCTTGGACCAGAGCAGT-GAGGTCTTAGGCTCTGGCAA AACCCTGACCATC-CAAGTCAAAGAGTTTGGAGATGCTGGCCAGTA-CACCTGTCA CAAAGGAGGCGAGGTTCTAAGCCAT- TCGCTCCTGCTGCTTCACAAAAAGGAAGATGGAATTTGGTCCACTGATATTTTAAAGGACCAGAAAGAACCCAAAAATAAGACCTTTCTAAGATGCGAGGCCAAGAATTATTCTGGACGTTTCACCTGCTGGTGGCTGACGACAATCAGTACTGATTTGACATTCAGTGTCAAAAGCAGCAGAGGCTCTTCTG ACCCCCAAGGGGTGACGTGCGGAGCTGCTACACTCTCTGCAGAGAGAGTCAGAGGGGACAACAAGGAGTATGAGTACTCAGTGGAGTGCCAGGAGGACAGTGCCTGCC CAGCTGCTGAGGAGAGTCTGCCCATTGAGGTCATGGTGATGCCGTTCACAAGCTCAAGTATGAAAACTACACCAGCAGCTTCTTCATCAGGGACATCATCAAACCTG ACCCACCCAAGAACTTGCAGCTGAAGCCATTAAAGAATTCTCGGCAGGTGGAGGTCAGCTGGGAGTACCCTGACACCTGGAGTACTCCACATTCCTACTTCTCCCTGACATTCTGCGTTCAGGTCCAGGGCAAGAGCAAGAGAGAAAAGAAAGATAGAGTCTT CACGGACAAGACCTCAGCCACGGTCATCTGCCGCAAAAATGCCAGCATTAGCGTGCGGGCCCAGGACCGCTACTATAGCTCATCTTGGAGCGAATGGGCATCTGTGCCCTGCAGTGTTCCTGGAGTAGGGGTACCTGGGGTGGGCGCCAGAAACCT CCCCGT GGCCACTCCAGACCCAGGAATGTTCCCATGCCTTCACCACTCCCAAAACCTGCTGAGGGCCGTCAGCAACATGCTCCAGAAGGCCAGACAAACTCTAGAATTTTACCCT TGCACTTCTGAAGAGATTGATCATGAAGATATCACAAAAGATAAAACCAGCACAGTGGAGGCCTGTTTACCATTGGAATTAACCAAGAATGAGAGTTGCCTAAATTCCA GAGAGACCTCTTTCATAACTAATGGGAGTTGCCTGGCCTCCAGAAAGACCTCTTTTATGATGGCCCTGTGCCTTAGTAGTATTTATGAAGACTTGAAGATGTACCAGGTG GAGTTCAAGACCATGAATGCAAAGCTGCTGATGGATCCTAAGAGGCAGATCTTTCTAGATCAAAACATGCTGGCAGTTATTGATGAGCTGATGCAGGGCCCTGAATTTCA ACAGTGAGACTGTGCCACAAAAATCCTCCCTTGAAGAACCGGATTTTTATAAAACTAAAATCAAGCTCTGCATACTTCTTCATCTTTCAGAATTCGGGCAGTGACTATTGATAGAGTGATGAGCTATCTGAATGCTTCCTAA). In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. The composition can further comprise a pharmaceutical vehicle or pharmaceutical excipient. Vehicles can include polymeric micelles, liposomes, lipoprotein-based carriers, nano-particle carriers, dendrimers, and/or other vehicles for T-cells that are known to one skilled in the art. In some alternatives of the method, the administering is performed by adoptive cell transfer. In some alternatives, the genetically modified immune cells are administered by direct delivery to a tumor bed by injection. In some alternatives, the subject in need suffers from cancer.

In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the method further comprises administering a cellular therapy to the subject in need thereof e.g., a human before, after or simultaneous to introducing, providing, or administering any one or more of the cells described in any of the alternatives herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof e.g., a human before, after, or simultaneous to introducing, providing, or administering any one or more of the cells of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of any of the alternatives described herein. In some alternatives, the drug is tamoxifen and/or its metabolites. In some alternatives, the subject is identified or selected to receive an anti-cancer therapy, an anti-infection therapy, an antibacterial therapy, an anti-viral therapy, or an anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of any of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragments thereof is specific for Her2, CD52, CD20, CD25, VEGF or EGRF. In some alternatives, the hormone blocking therapy comprises delivery of tamoxifen, anastrozole, and/or letrozole.

Growth of an Intracranial Tumor after Administration of GEMs in Mice.

In some experiments that were conducted, CD14+ monocytes were isolated from donor PBMCs and differentiated into Ml-like macrophages, then infected with a myeloid cell-specific lentivirus. Infected macrophages were tested by qPCR, Bioplex assay, and flow cytometry for upregulation of expression of pro-inflammatory cytokines such as IL12, TNFα, and/or type I interferons. The GEMs were also tested in a mouse model of glioblastoma for their ability to slow the growth of an intracranial tumor, both in the presence and absence of CART cells.

Macrophages are notoriously difficult to engineer to express transgenes, owing to their immunologic function of detection and elimination of foreign genetic material. The recent development of a lentivirus capable of infecting myeloid cells therefore affords the opportunity to use several approaches to genetically engineer macrophages to transform the brain TME. In the first approach, GEMs overexpress and secrete a TLR agonist, high mobility group box 1 (HMGB1) that will serve both as an autocrine signal for continued expression of pro-inflammatory factors, as well as a paracrine signal to the immunosuppressive myeloid cells within the TME. Quantitative PCR suggests that HMGB-treated macrophages upregulate their expression of ILβ and TNFα. The second approach involves the development and expression of novel PD1-binding proteins; upon secretion by transplanted GEMs, these PD1 binders block the interaction between PD1 and its natural ligands, reducing the exhaustion of CAR T cells. Finally, using the Cas9-CRISPR system to knock out genes for anti-inflammatory cytokines, this rendered the transplanted GEMs less susceptible to the influence of the TME. The in vivo data shows that macrophages transplanted into mouse brain tumors persist and express transgene for the life of the animal without any additional delivery of cytokines or growth factors.

Entolomid, which is a TLR agonist is encoded by a sequence set forth in SEQ ID NO: 38

```
(CTGGGGATCGGCCTCTTCATGGGGTCCGGTGCCACCAACTTTTCTCTCC

TGAAGCAGGCGGGCGATGTCGAAGAGAACCCAGGGCCTATGCTCCTGCTC

GTAACCTCTCTCCTTTTGTGCGAATTGCCCCACCCTGCATTCTTGCTTAT

ACCAATGCGCGGCAGTCACCATCATCATCACCACGGTATGGCGAGTATGA

CTGGCGGCCAGCAGATGGGCCGGGACCTGTATGATGACGATGACAAAGAC

CCGATGGCTCAGGTCATCAATACTAATAGCCTGTCACTGCTCACCCAGAA

CAACCTGGTTAAATCACAGTCATCCTTGTCATCAGCGATAGAGAGGTTGT

CTTCTGGACTCCGCATCAACTCTGCTAAGGATGATGCAGCTGGTCAAGCA

ATAGCAAACCGATTCACCTCCAATATCAAAGGACTTACGCAGGCCAGTAG

GAATGCGAATGATGGAATAAGCATCGCACAGACTACGGAAGGAGCGCTGA

ACGAAATCAACAATAACCTCCAGCGCGTTCGCGAACTCTCTGTCCAGGCG

ACAACGGGCACGAATTCTGATAGCGATCTTAAATCAATACAAGACGAGAT

ACAGCAGCGCTTGGAAGAGATTGATAGGGTAAGCGGACAAACGCAATTCA

ATGGCGTTAAAGTGCTTTCCCAGGACAATCAGATGAAGATACAAGTCGGC

GCAAACGACGGGGAGACGATTACAATCGACTTGCAAAAAATAGATGTGAA

AAGCCTCGGGTTGGATGGGTTTAACGTCAATAGTCCTGGCATTAGTGGTG

GCGGCGGTGGGATTTTGGACAGCATGGGTACTCTTATTAATGAAGATGCC

GCAGCAGCTAAAAAAAGTACTGCTAACCCGCTGGCATCCATCGATTCAGC

GTTGAGTAAAGTTGACGCAGTCCGCAGCAGTCTGGGCGCGATACAAAACA

GATTTGATTCCGCCATTACCAACCTCGGCAATACCGTCACCAATTTGAAT

TCAGCGAGATCTCGGATTGAGGACGCCGATTACGCAACAGAAGTGTCTAA

CATGTCTAAAGCTCAAATCTTGCAACAGGCCGGCACCTCCGTACTGGCTC

AGGCCAATCAAGTTCCACAGAATGTGCTGAGTCTGCTTCGATAA

GCTCTAGACCCGGGCTGCA).
```

Macrophage Infiltration

Figure 1A:
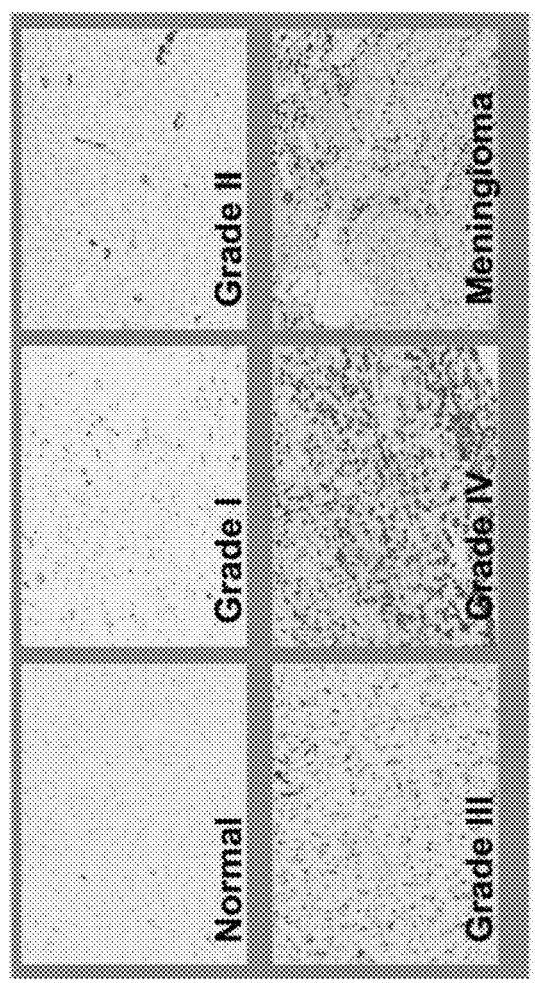
FIGS. 1A, 1B, 1C and 1D show high grade gliomas having significant macrophage infiltration.
Figure 1B:
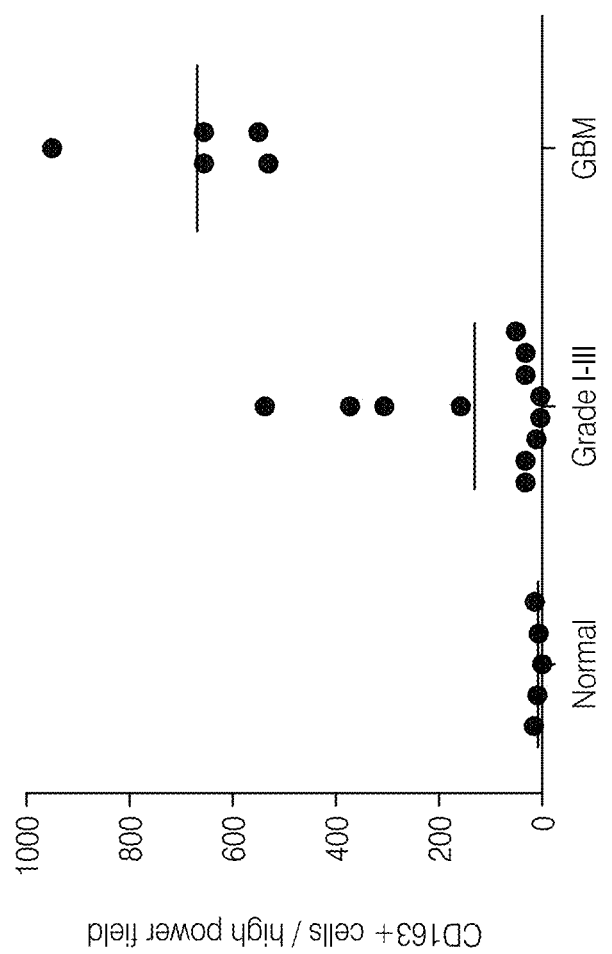
Figure 1C:
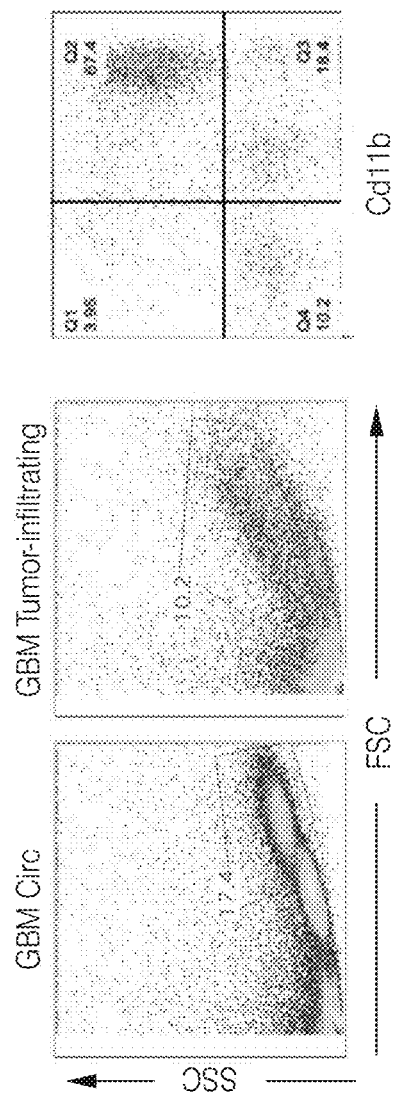
Figure 1D:
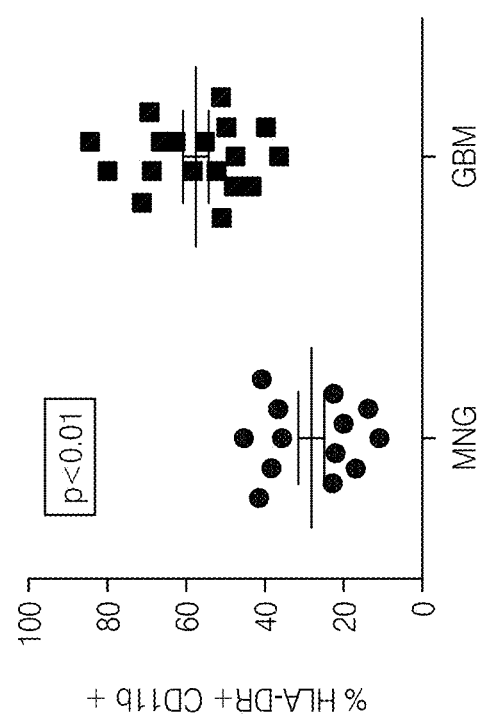

Experiments were performed on high grade gliomas in mice to examine macrophage infiltration. Shown in FIG. 1A are normal cells, Grade 1 glioma, Grade 2 glioma, Grade 3 glioma, Grade 4 glioma, and Meningloma. As shown in FIGS. 1A-1D, the high grade gliomas have significant macrophage infiltration.

Mouse Macrophages Recruited to U87 Tumors

Figure 2:
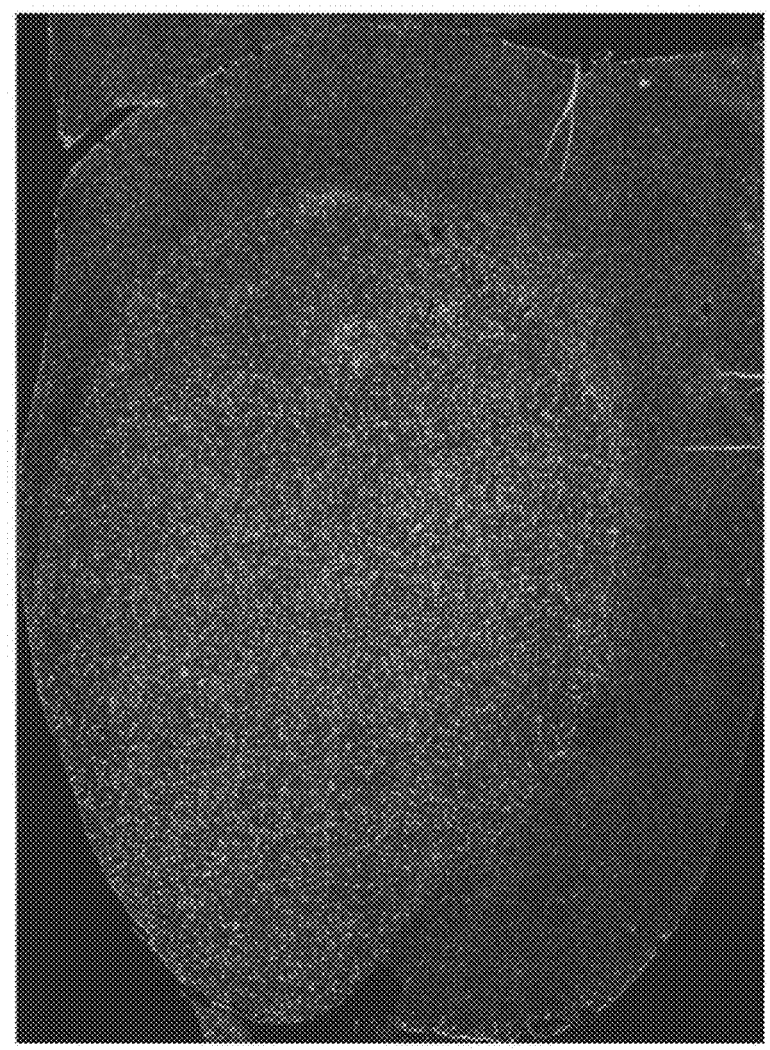
FIG. 2 shows mouse macrophages recruited to engrafted U87 tumors.

An 8 week old NSG mouse was intracranially injected with 200,000 U87 tumor cells. 28 days later, the brain was harvested, fixed embedded in paraffin in coronal orientation. A 5 μm section was stained with rat antiF4/80 (Sigma) at 1:100 followed by goat anti-rat-HRP (Life technologies), and detected using tyramide signal amplification—Alexa488. Slide was imaged by tiling 10×1720×images with a Nikon Eclipse Ci. Illustrated in FIG. 2 is a stained slide showing the mouse macrophages recruited to the engrafted U87 tumors.

HLA-DR+ Macrophages Successfully Transduced with VPX-Containing Lentivirus

Figure 3:
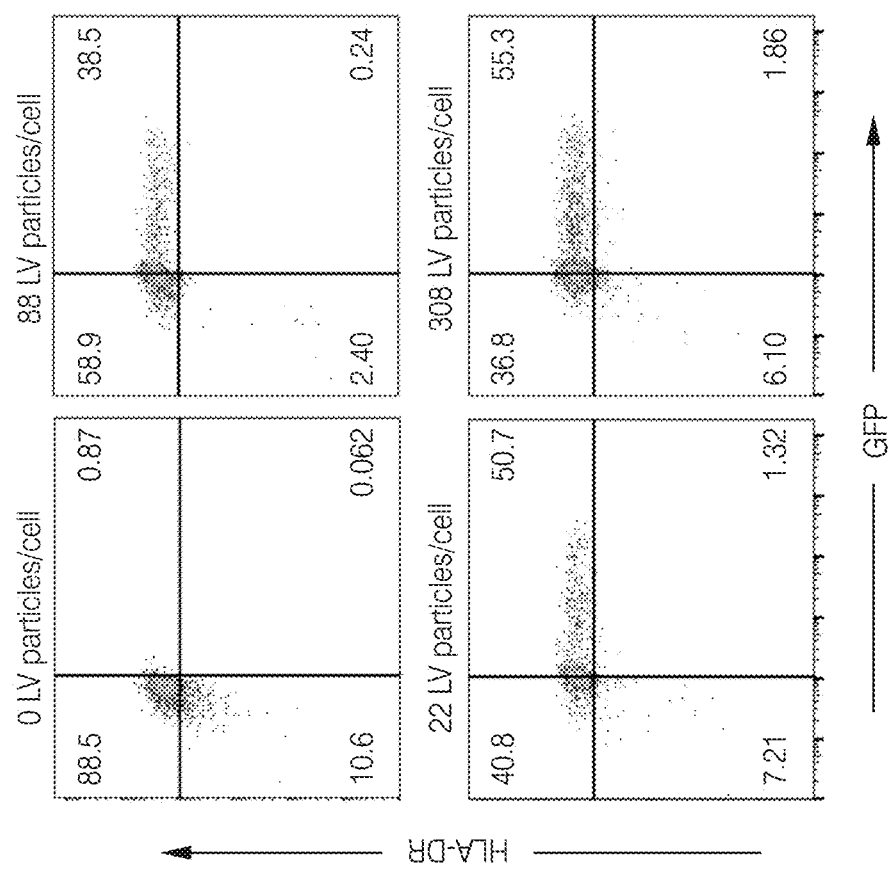
FIG. 3 shows HLA-DR+ macrophages successfully transduced with VPX-containing lentivirus.

CD14+ cells were isolated from normal human PBMCs and treated with 25 nm/ml M-CSF for 6 days. The resulting monocyte-derived macrophages (MDMs) were transduced with a GFP reporter lentivirus (pLenti-CMV-eGFP) containing Vpx at 0, 88, 220 and 308 lentiviral (LV) particles per cell. On day 13, MDMs were harvested with trypsin, stained with anti-HLA-DR-PE Cy7 and analyzed for GFP expression by flow cytometry. Shown in FIG. 3, are the results of the flow cytometry in which the MDMs were analyzed in which they had 0, 88, 220 or 308 LV particles per cell.

Figure 4A:
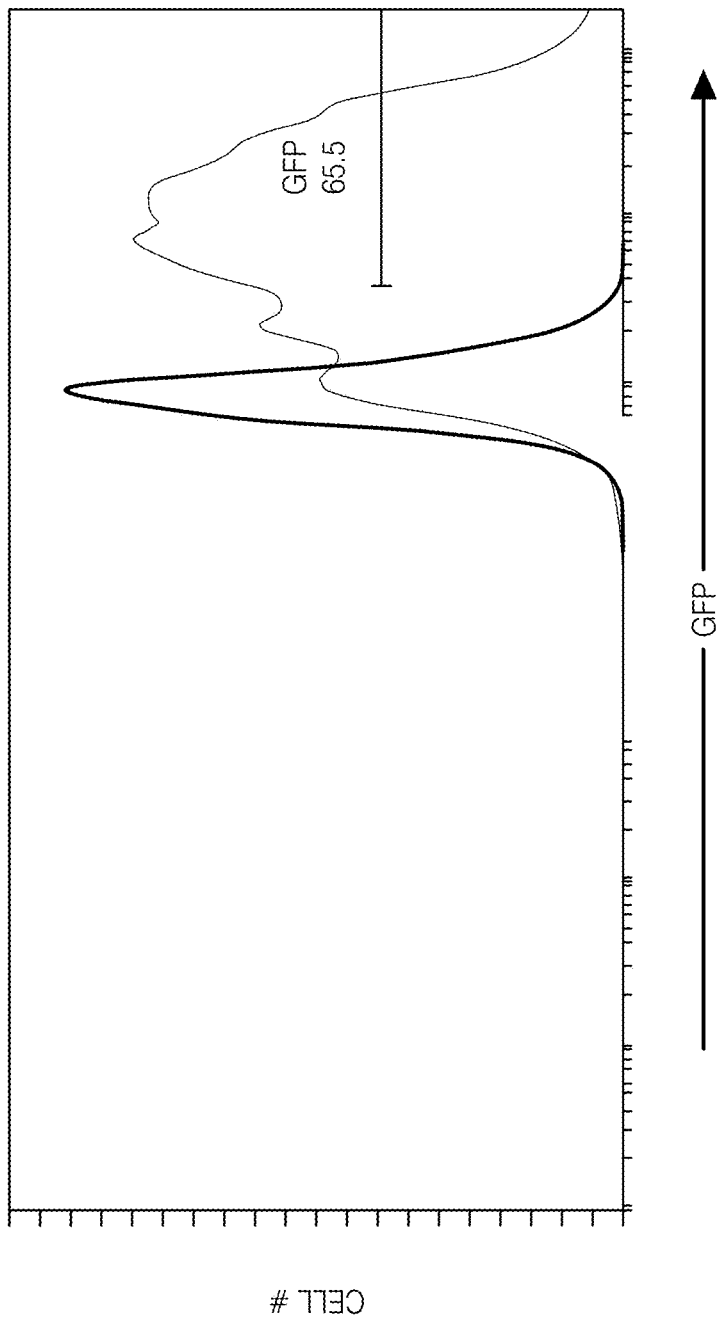
FIGS. 4A, 4B and 4C show that MDMs transduced with a lentivirus encoding GFP and firefly luciferase persist in a mouse model of GBM.
Figure 4B:
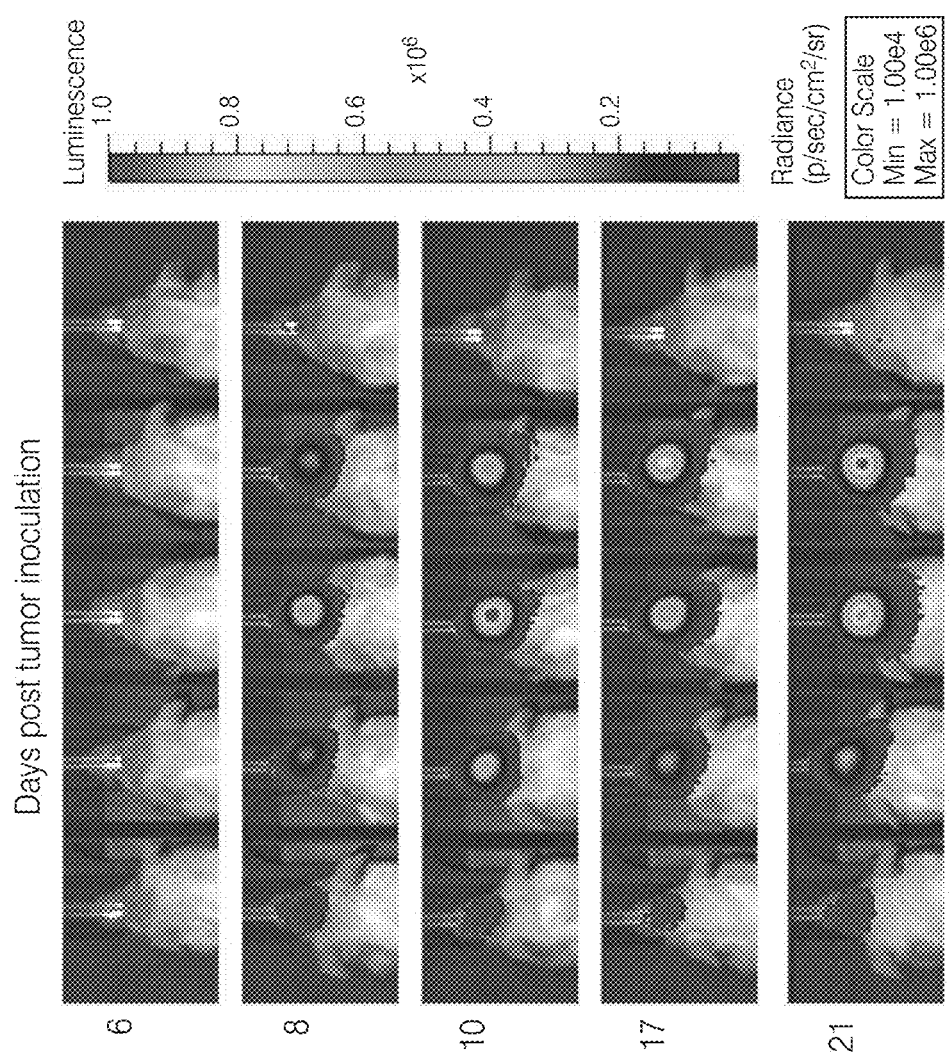
Figure 4C:
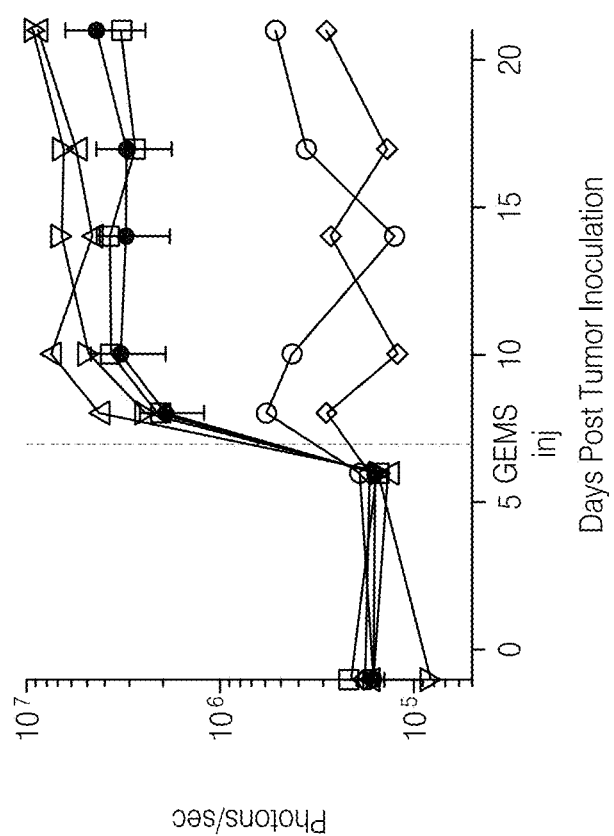

MDMs Transduced with a Lentivirus Encoding GFP and Firefly Luciferase Persist in a Mouse Model of GBM MDMs were transduced with a GFP and luciferase-encoding lentivirus and evaluated for expression of GFP by flow cytometry 30 days later (FIG. 4A). Shown in FIG. 4B, are the results of NSG mice intracranially injected with $2×10^5$ wild-type U87 cells on Day 0. Background luminescence was measured at Day 6. On Day 7 post U87 injection, 1.44×105 luciferase expressing GEMs (65.5% GFP+from Panel A) were injected, and images collected twice weekly. FIGS. 4B and 4C show Longitudinal GEM luminescence signals.

Figure 5:
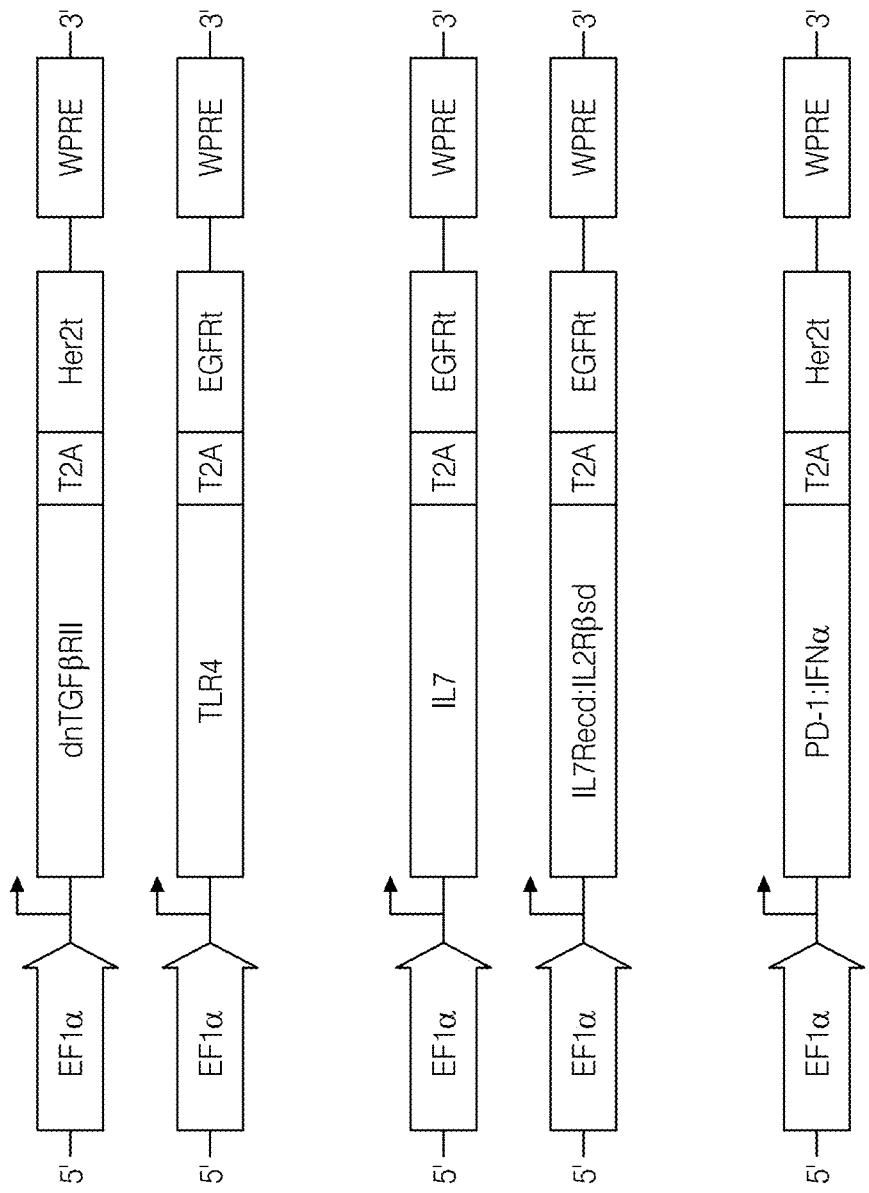
FIG. 5 shows a schematic of representative lentiviral constructs. Gene regulatory elements are indicated by the arrows and include the EF1a promoter and the Woodchuck Hepatitis Virus Posttranscriptional Regulatory Element (WPRE) enhancer. The open reading frame of each includes the transgene of interest shown after the promoter symbol), a T2A co-translational cleavage site, and a Her2t or EGFRt cell-surface epitope tag for detection of infected cells by binding of Herceptin or Erbitux, respectively.

Several lentiviral constructs used in other experiments are shown in FIG. 5.

TGFβRII Expression in MDMs and Signaling Inhibition

Figure 6A:
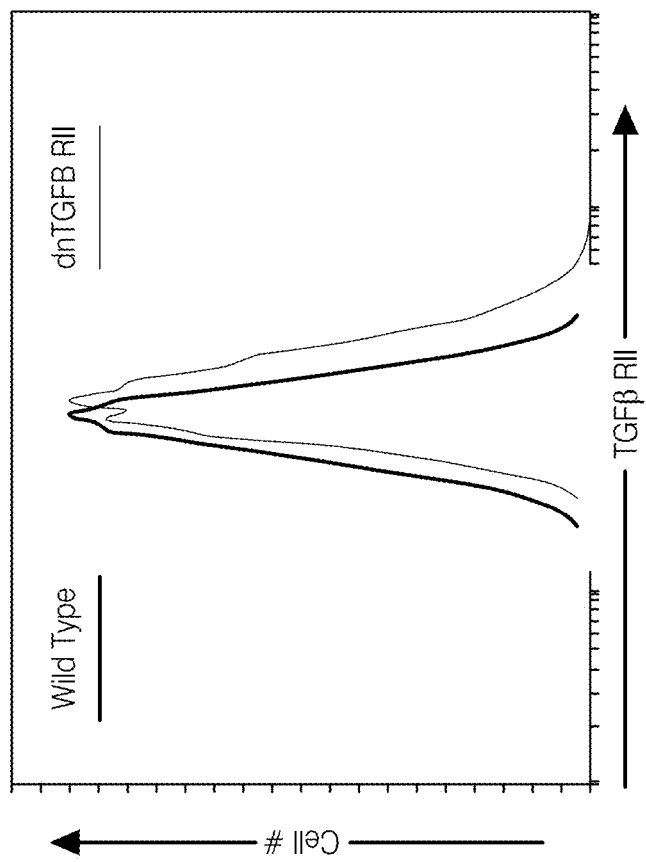
FIGS. 6A, 6B and 6C show TGFβRII expression in MDMs and signaling inhibition.
Figure 6B:
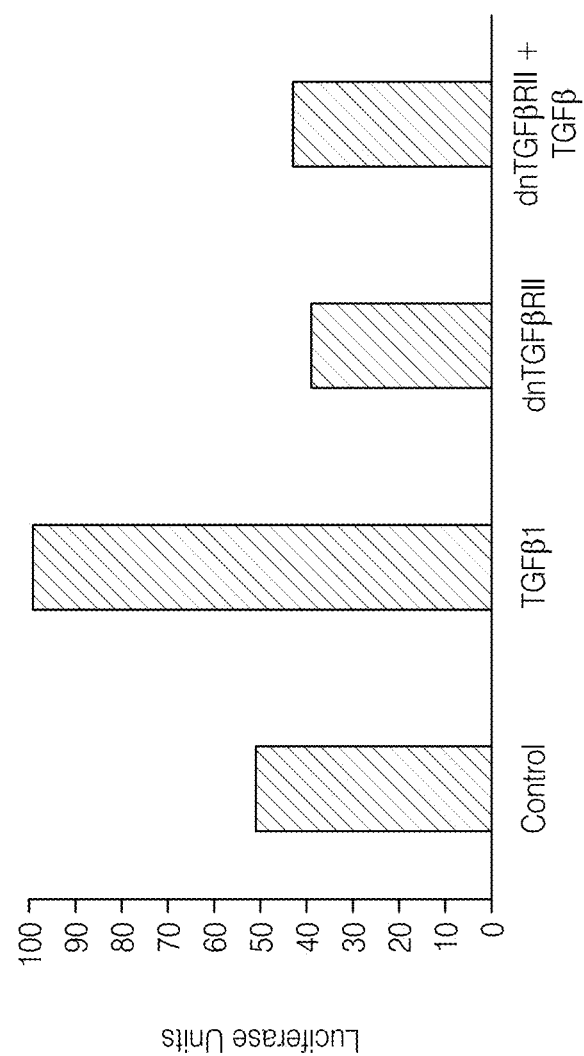
Figure 6C:
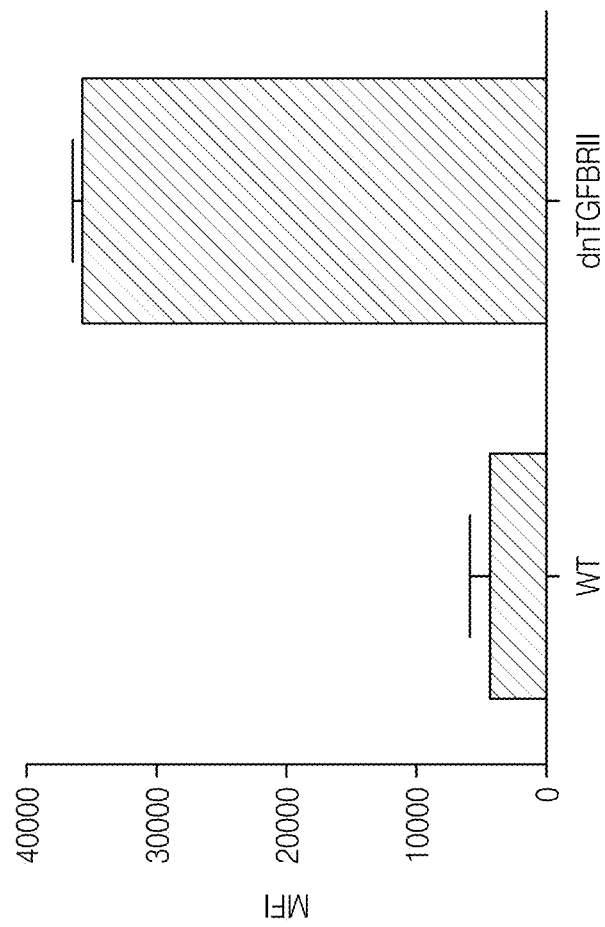
Figure 7A:
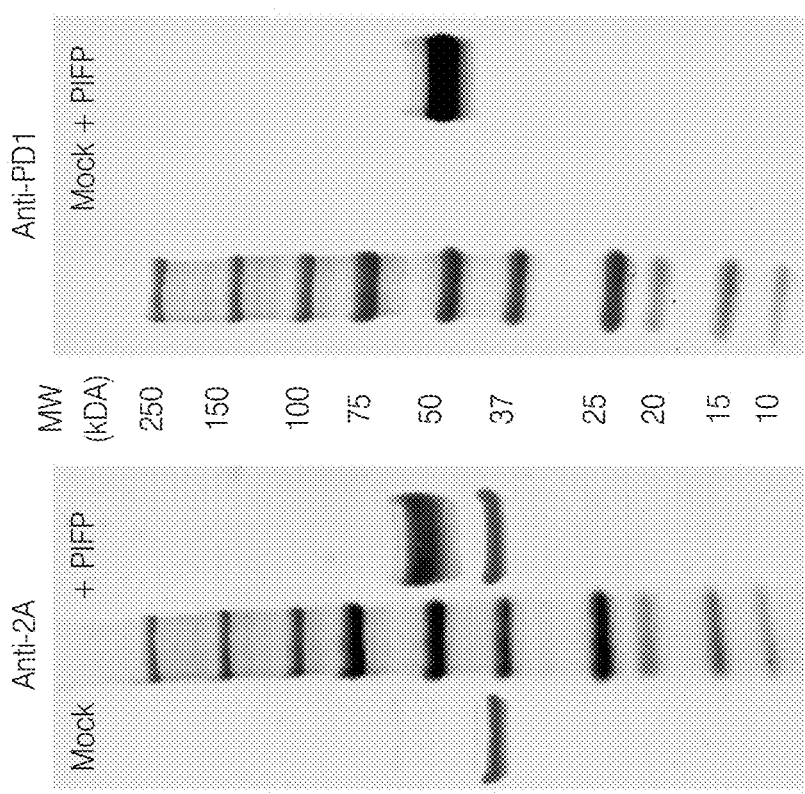
FIGS. 7A and 7B show that transduced H9 cells secrete PD-1/IFNα fusion protein (PIFP).
Figure 7B:
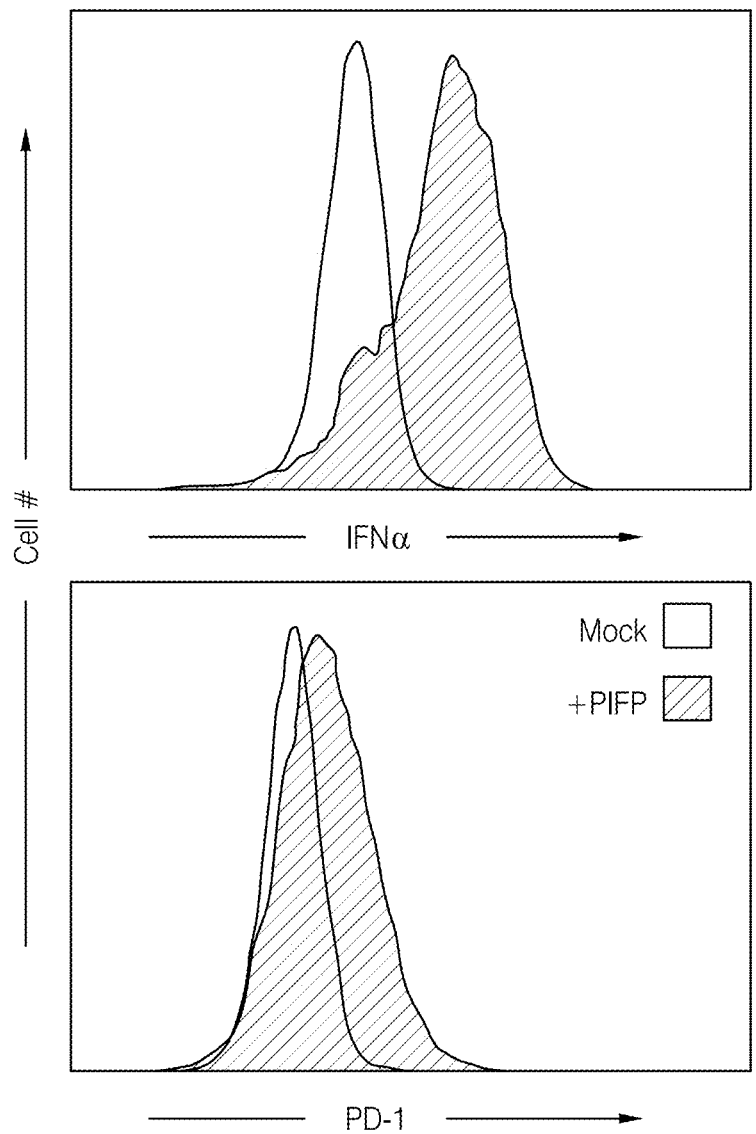

The vector for TGFβRII expression in MDMs shown in FIG. 5 was used to transfect an immune cell. Shown in FIG. 6A, in the top panel, are macrophages derived from primary monocytes using GM-CSF and stained with antibodies to HLA-DR-PE-Cy7 and TGFβRII-488 and analyzed by FCM. (Bottom panel, FIG. 6C). MFI of HLA-DR+cells (~98% of the population). As shown in FIG. 6B, 293 Ts expressing a SBE (SMAD binding element) luciferase reporter and/or dnTGFβRII were treated with 1 ng/mL TGFβ1 for 3 hours.
PD-1/IFNα Fusion Protein Expression in Genetically Modified Immune Cells The vector shown in FIG. 5 for PD-1/IFNα fusion protein expression in MDMs was used to transfect an immune cell. As shown in FIG. 7A, transduced H9 cells secrete PD-1/IFNα fusion protein (PIFP). Supernatant from parental or PD1:IFNα-transduced H9 cells was concentrated, electrophoresed and Western blotted, using monoclonal antibodies to either a 2A tag, which is retained by the IFNα protein (left, 1:5000), or PD1 (right, 1:250). Shown in FIG. 7B are Parental or PD1: IFNα-transduced H9 cells cultured with Brefeldin A, fixed and permeablized, and an intracellular stain performed with fluorophore-conjugated antibodies. Cells were analyzed by FCM for anti-IFNα (left) and anti-PD1 (right).

VPX Virus Production

Figure 8:
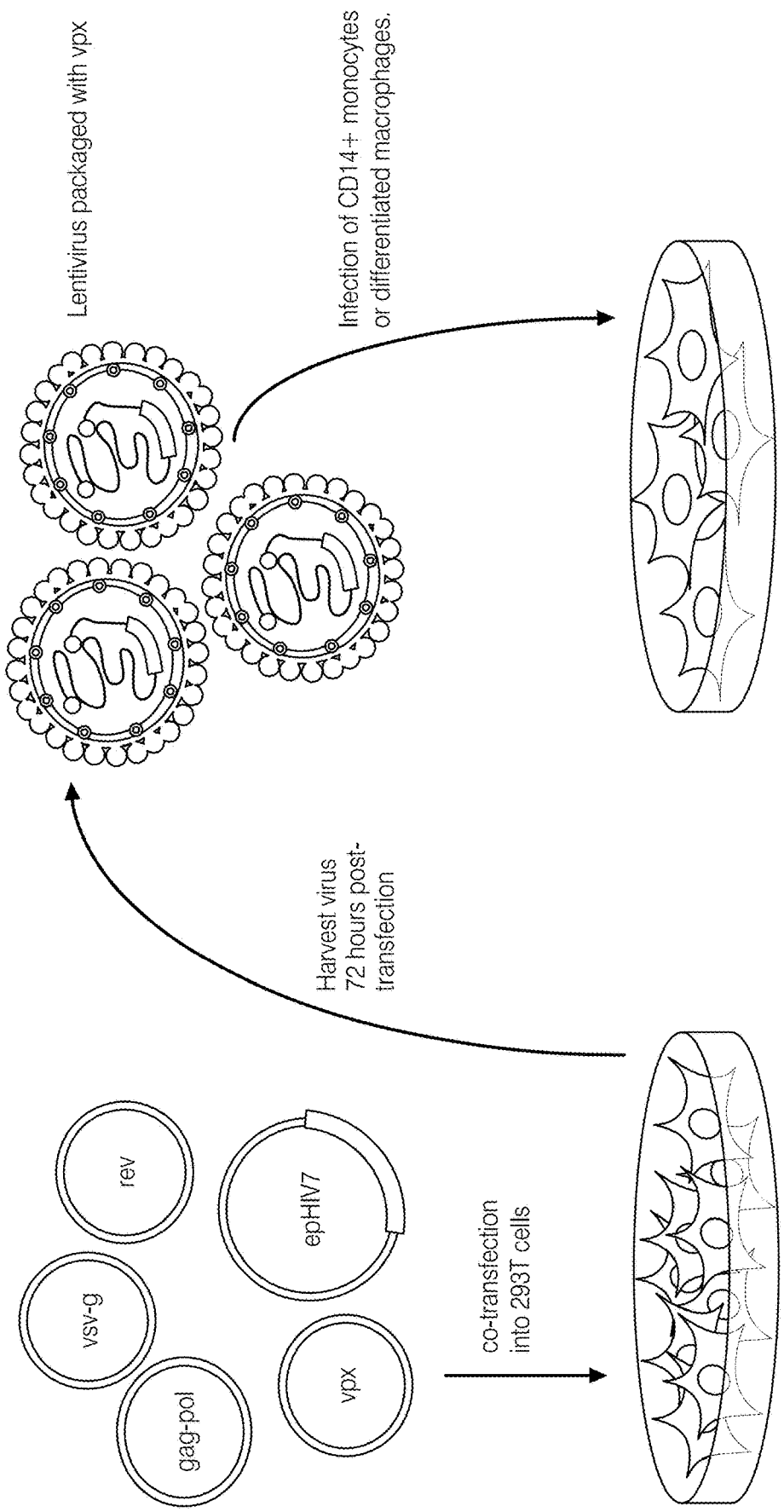
FIG. 8 shows co-transfection of viruses into 293T cells used for harvesting viruses for infection of CD14+ monocytes or differentiated macrophages.

As shown in FIG. 8, plasmids encoding lentiviral packaging components (gag-pol, vsv-g, and rev), the transgene of interest (pink) in the epHIV7 lentiviral backbone, and the factor allowing myeloid cell transduction, Vpx, were co-transfected into the 293T-cell line. 72 hours after transfection, virions packaged to include the Vpx protein were purified from the 293T culture supernatant. Vpx-containing virus was used to infect myelomonocytic cells (MNICs—primary, human monocytes or in vitro differentiated macrophages). Vpx-mediated degradation of SAMHD1, a restriction factor expressed by MMCs inactivates viral reverse transcriptase as allows stable gene integration and expression as previously described. Lentivirus vectors packaged with the Vpx protein lead allow stable transfection of myeloid cells.

Infection Strategies

Figure 10A:
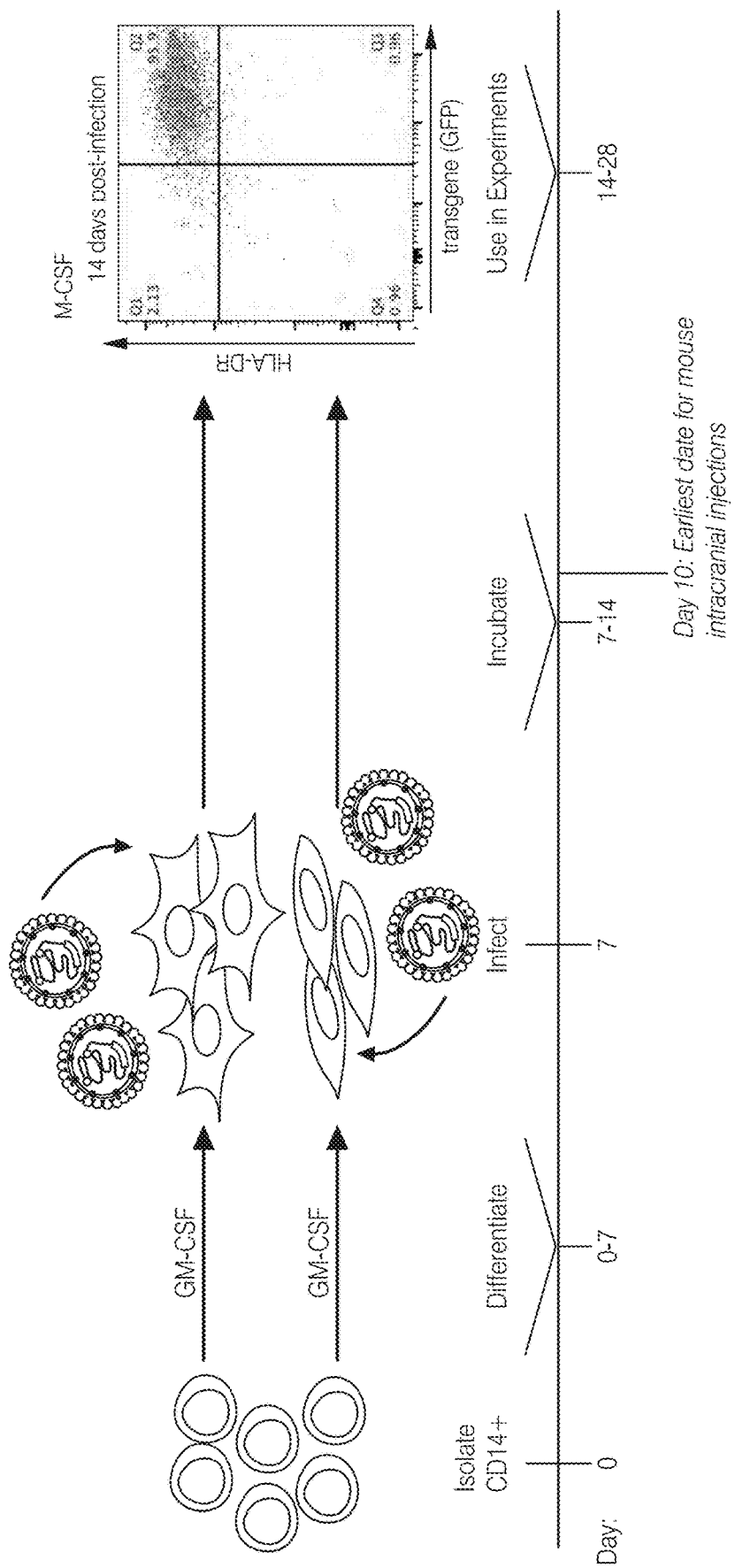
FIGS. 10A-10B shows infection strategies.
Figure 10B:
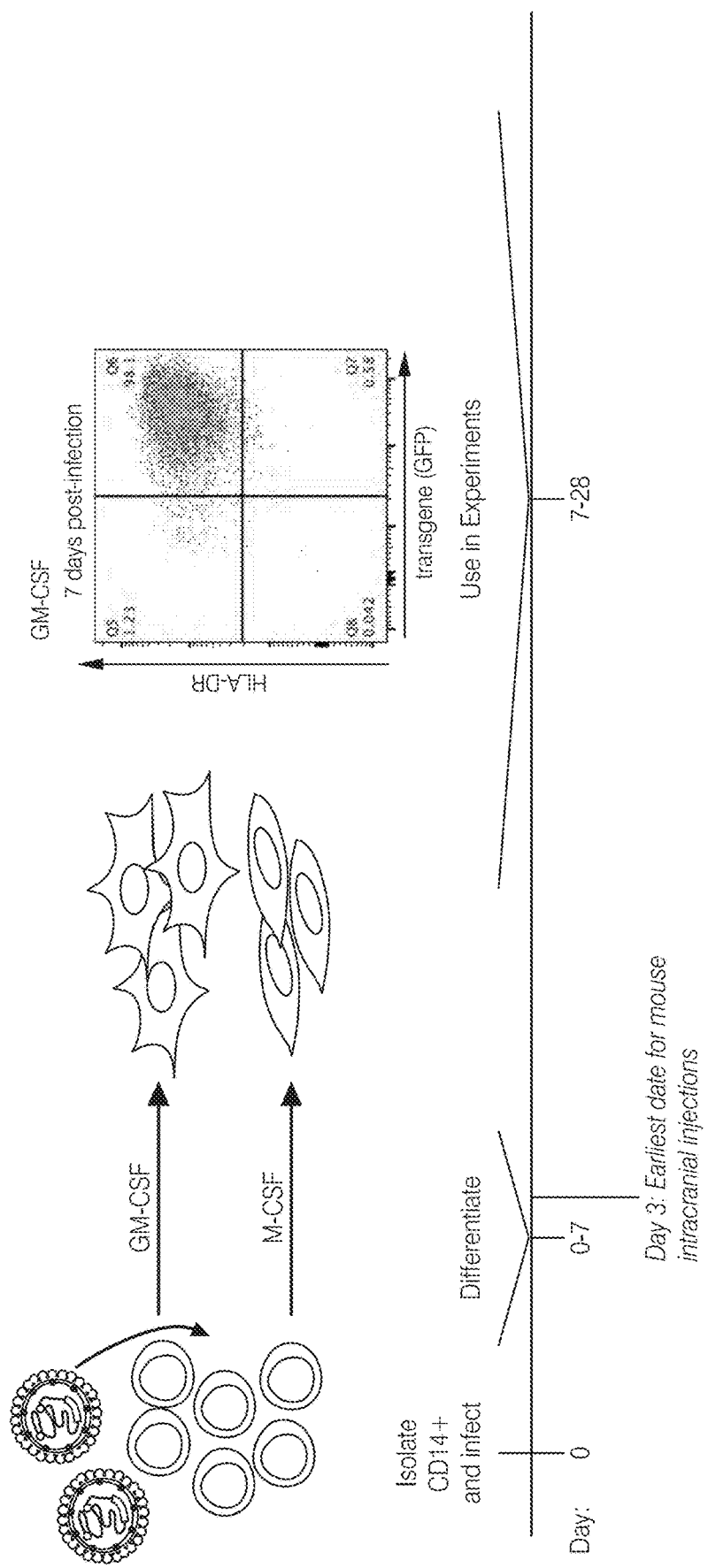

MMCs, including both primary, human peripheral blood monocytes and monocyte-derived macrophages can be infected with lentivirus. As shown in FIG. 10A, in the first protocol, CD14+ monocytes are isolated by magnetic separation of peripheral blood mononuclear cells (PBMCs), followed by differentiation to a pro-inflammatory phenotype by culture with 10 ng/mL granulocyte-macrophage colony stimulating factor (GM-CSF), or an anti-inflammatory phenotype with 25 ng/mL macrophage colony stimulating factor (M-CSF). After 7 days of differentiation, macrophages were infected with Vpx-containing lentivirus, and used for experiments after transgene is being stably expressed one week later. By 7 days post-infection (14 days after CD14+ isolation), greater than 95% of macrophages are positive for transgene expression. As shown in FIG. 10B, CD14+ monocytes were isolated from PBMCs and infected with Vpx-containing lentivirus the same day, followed by differentiation with GM-CSF or M-CSF for 7 days, when greater than 95% of macrophages are positive for transgene expression.

GM-CSF Differentiation

Figure 11A:
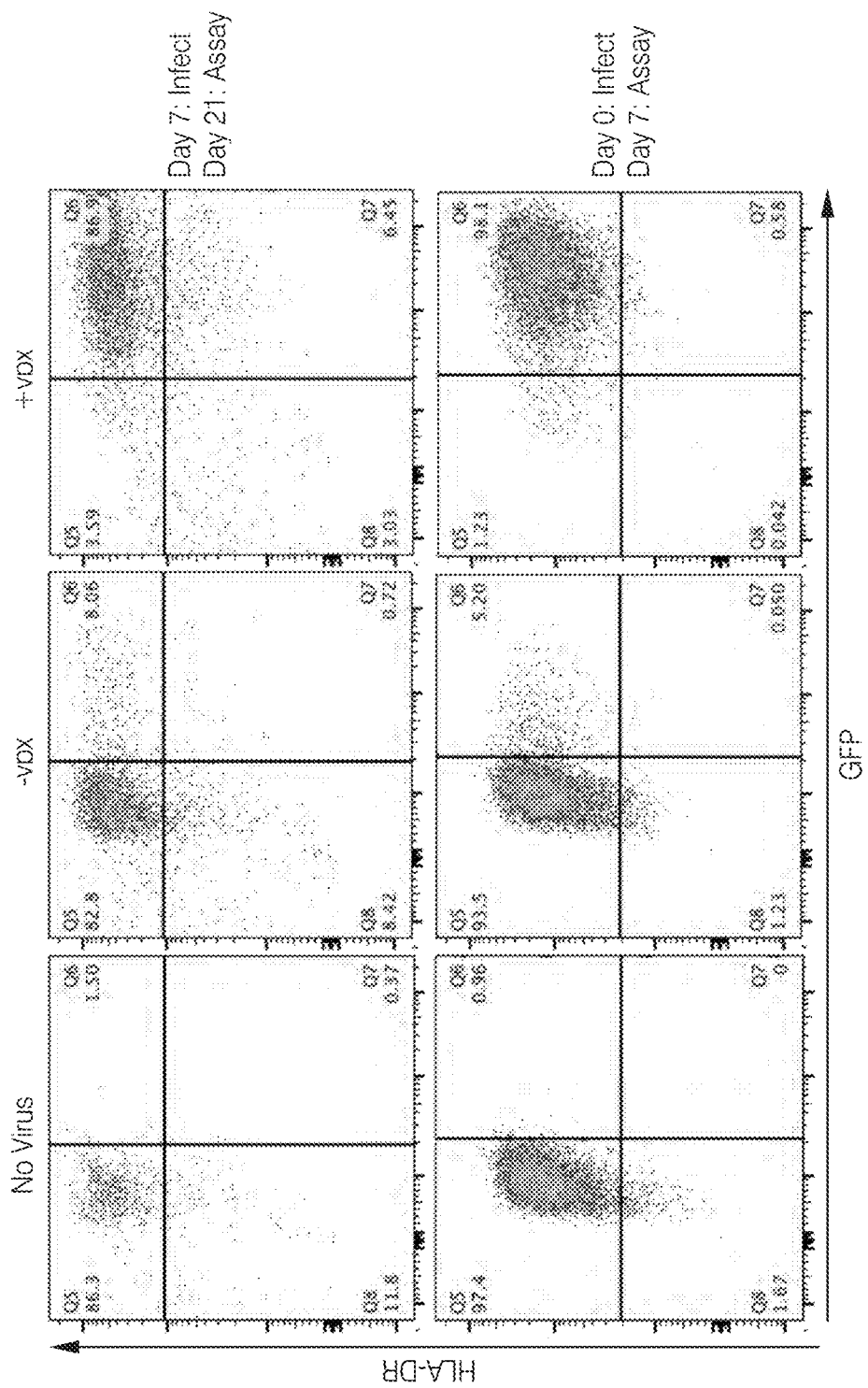
FIGS. 11A and 11B shows GM-CSF Differentiation Plots. Packaging of lentivirus with Vpx is required for successful infection of GM-CSF-derived macrophages.
Figure 11B:
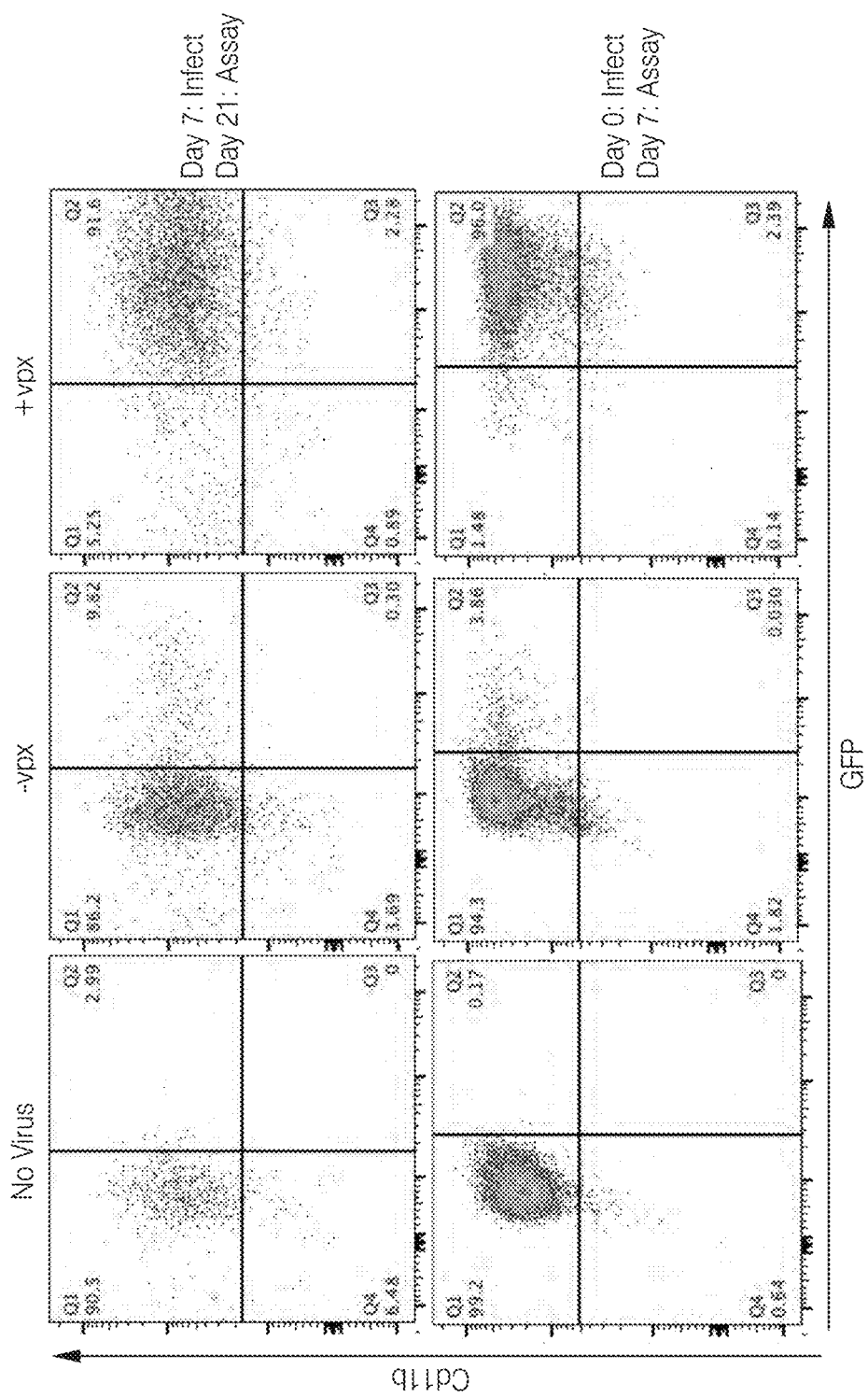

Packaging of lentivirus with Vpx is required for successful infection of GM-CSF-derived macrophages. Macrophages or monocytes were infected with no virus, GFP-lentivirus packaged without Vpx, or GFP-lentivirus packaged with Vpx, then assayed by flow cytometry for co-expression of GFP and HLA-DR (FIG. 11A) or CD11b (FIG. 11B) at the time points indicated to the right of the plots, which show infection of MMCs-monocytes (Day 0 infection) and macrophages (Day 7 infection).

M-CSF Differentiation Plots

Figure 12A:
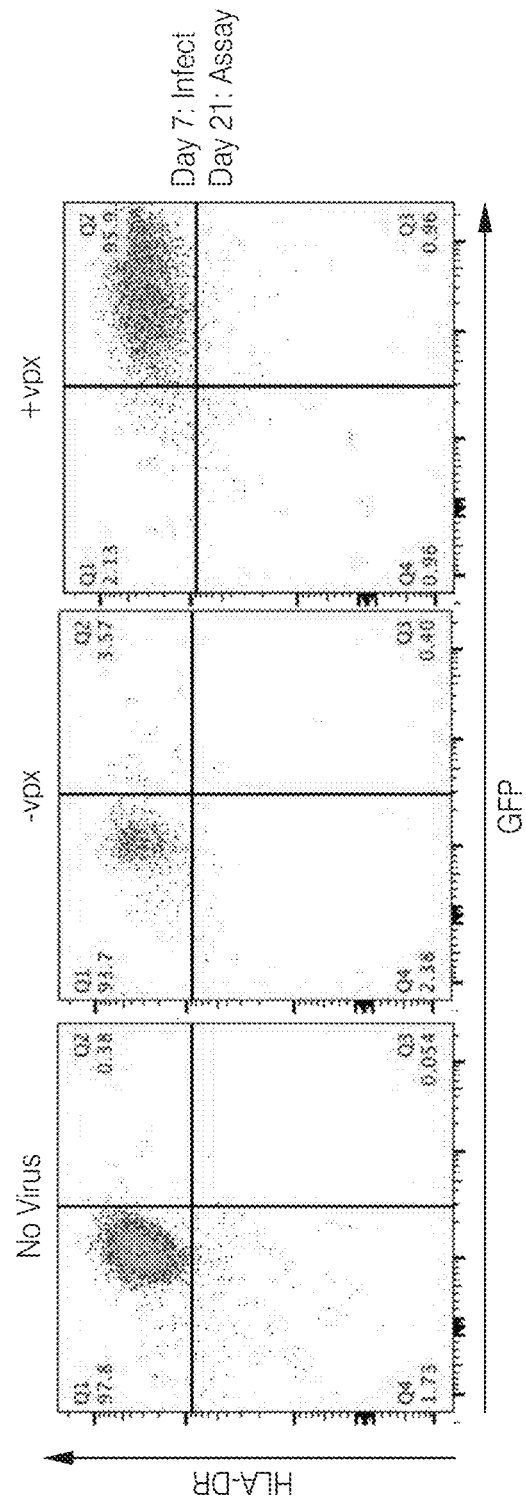
FIGS. 12A and 12B shows M-CSF Differentiation Plots. Packaging of lentivirus with Vpx is required for successful infection of M-CSF-derived macrophages.
Figure 12B:
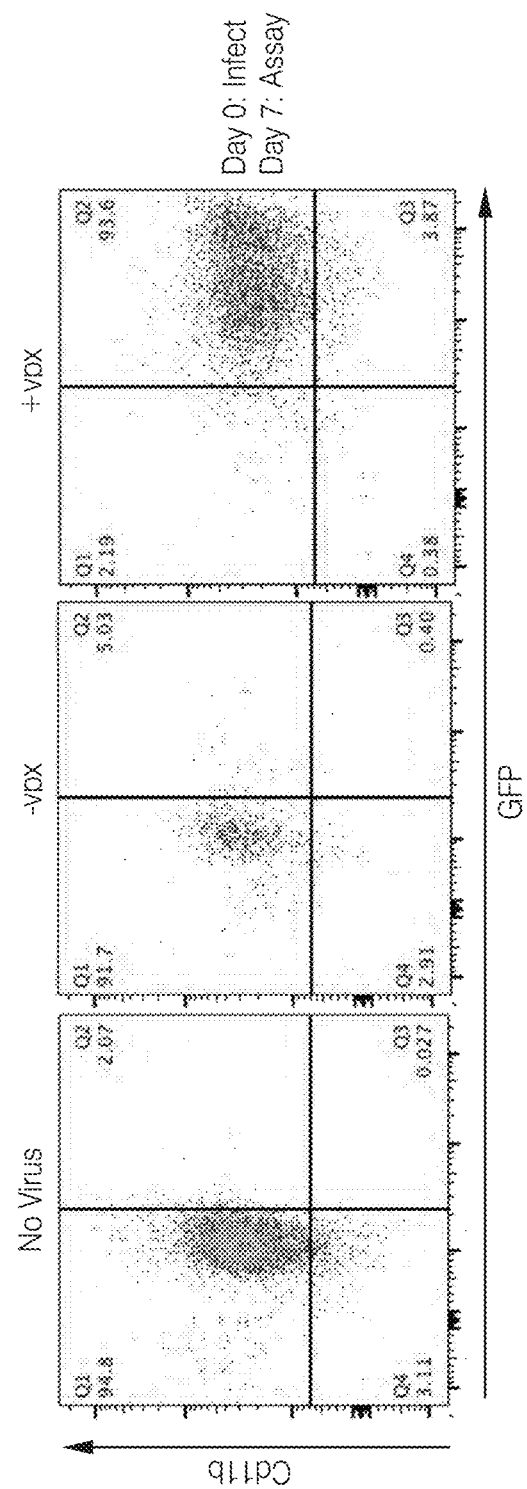

Packaging of lentivirus with Vpx is required for successful infection of M-CSF-derived macrophages. Macrophages were infected on Day 7 after CD14+ isolation with no virus, GFP-lentivirus packaged without Vpx, or GFP-lentivirus packaged with Vpx, then assayed by flow cytometry at Day 21 for co-expression of GFP and HLA-DR (FIG. 12A) or CD11b (FIG. 12B).

Isolation of CD14+ Monocytes from Peripheral Blood Mononuclear Cells (PBMCs)

Healthy donor whole blood and apheresis product was acquired from Bloodworks Northwest (Seattle Children's Research Institute IRB #14412). PBMCs were isolated with a Ficoll-Paque density gradient (GE Healthcare) using standard protocols[15]. CD14+ monocytes were purified from PBMCs with the EasySep Human CD14 Positive Selection Kit (Stemcell Technologies) according to manufacturer's protocols (Noble P B, Cutts J H. Separation of blood leukocytes by Ficoll gradient. Can Vet J 1967; 8:110-111; incorporated by reference in its entirety herein).

Macrophage Differentiation

Isolated CD14+ monocytes were plated in macrophage media (RPMI1640 medium (Gibco) supplemented with 10% FBS (Hyclone)) on tissue culture-treated plastic dishes (Corning) at a density not exceeding 250,000 cells/cm$^2$ in the presence of either 25 ng/mL M-CSF or 10 ng/mL GM-CSF (R&D Systems) at 37° C., 5% $CO_2$. 72 hours after plating, half the medium was replaced with fresh macrophage media supplemented with M- or GM-CSF or GM-CSF at final concentrations of 25 and 10 ng/ml, respectively. Monocytes were considered fully differentiated to macrophages six days after isolation, and could be replated as necessary following detachment with 0.25% trypsin (Gibco) and gentle scraping.

Dendritic Cell Differentiation

Isolated CD14+ monocytes were differentiated to dendritic cells (DCs) following the protocol of Spadaro et al (Spadaro M, Montone M, Arigoni M et al. Recombinant human lactoferrin induces human and mouse dendritic cell maturation via Toll-like receptors 2 and 4. FASEB J 2014; 28:416-429; incorporated by reference in its entirety herein). Briefly, CD14+ cells were plated in RPMI-1640 supplemented with 10% FBS, 100 ng/mL GM-CSF, and 50 ng/mL IL-4 (R&D Systems). Media was replaced and fresh cytokines added 72 hours later.

Lentiviral Vectors

Unless otherwise stated, all constructs utilized the epHIV7 or epHIV7.2 lentiviral backbones, gifts of Dr. Michael Jensen (Seattle Children's Research Institute). In epHIV7 the CMV promoter of pHIV7 (Yam P Y, Li S, Wu J et al. Design of HIV vectors for efficient gene delivery into human hematopoietic cells. Mol Ther 2002; 5:479-484; incorporated by referenced in its entirety herein) has been replaced with the EF1a promoter. For epHIV7.2 the EF1a promoter has been replaced with a minimal EF1a (lacking the HTLV-1 domain) and the gene for ampicillin resistance has been exchanged for kanamycin resistance. The green fluorescent protein-firefly luciferase (GFP-ffluc) fusion protein has been previously described (Brown C E, Starr R, Martinez C et al. Recognition and killing of brain tumor stem-like initiating cells by CD8+ cytolytic T cells. Cancer Res 2009; 69:8886-8893; incorporated by referenced in its entirety herein). GFP-ffluc in the epHIV7 backbone was a gift from Dr. Michael Jensen. The green fluorescent protein-firefly luciferase (GFP-ffluc) fusion protein is encoded by a sequence set forth in SEQ ID NO: 29 (atggaggatgccaagaat-attaagaaaggccctgccccattctaccctctggaagatggcactgctggt-gagcaactgcacaaggc catgaagaggtatgccctggtecctggcaccat-tgccttcactgatgctcacattgaggtggacatcacctatgctgaatactttgagatg tctgtgaggctggcagaagccatgaaaagatatggactgaacaccaaccacag-gattgtggtgtgctctgagaactctctccagttctt catgcctgtgttaggagccctgttcattggagtggctgtggcccctgccaatgacatctacaatgagagagagctcctgaacagcatgg
gcatcagccagccaactggtcgtgagcaagaagggcctgcaaaagatcctgaatgtgcagaagaagctgcccatcatccaga agatcatcatcatggacagcaagactgactaccagggcttccagagcatgtatacctttgtgaccagccacttaccccctggcttcaatg
agtatgactttgtgcctgagagctttgacagggacaagaccattgctctgattataatgaacagctctggctccactggactgcccaaaggtg tggcgccccacagactgcttgtgtgagattcagccatgccagagaccccatcttggcaaccagatcatccctgacactgccatc
ctgccggttccattccatcatggctggcatgttcacaacactggggtacctgatctgtggcttcagagtggtgctgatgtataggttt gaggaggagctgtttctgaggagcctacaagactacaagatccagtctgccctgctggtgcccactctgttcagcttctttgccaagag
caccctcattgacaagtatgacctgagcaacctgcatgagattgcctctggaggagcaccccctgagcaaggaggtgggtgaggctgt ggcaaagaggttcatctcccaggaatcagacagggctatggcctgactgagaccacctctgccatcctcatcacccctgaaggaga
tgacaagcctggtgcgggcaaggtgttccctttgaggccaaggtggtggacctggacactggcaagaccctgggagtgaa ccagaggggtgaggtgaggggtcccatgatcatgtctggctatgtgaacaaccctgaggccaccaatgccctgattgacaag
gatggctggctgcactctggtgacattgcctactgggatgaggatgagcactttttcattgtggacaggctgaagagcctcatcaagtac aaaggctaccaagtggcacctgctgagctagagagcatcctgctccagcaccccaacatctttgatgctggtgtggctggcctgcctg
atgatgatgctggagagctgcctgctgctgttgtggttctggagcatggaaagaccatgactgagaaggagattgtggactatgtggcc agtcggtgaccactgccaagaagctgaggggaggggtgtttgtggatgaggtgcaaagggtctgactggcaagctggatgc
cagaaagatcagagagatcctgatcaaggccaagaagggtggcaaa). EGFP:ffluc-T2A-CD19t is encoded by a sequence set forth in SEQ ID NO: 34 (atggaggatgccaagaatattaagaaaggccctgccccattctaccctctggaagatggcactgctggtgagcaactgcacaaggc catgaagaggtatgccctggtccctggcaccattgccttcactgatgctcacattgaggtggacatcacctatgctgaatactttgagatg
tctgtgaggctggcagaagccatgaaaagatatggactgaacaccaaccacagattgtggtgtgctctgagaactctctccagttctt catgcctgttaggagccctgtcattggagtggctgtggcccctgccaatgacatctacaatgagagagagctcctgaacagcatgg
gcatcagccagccaactggtcgtgagcaagaagggcctgcaaaagatcctgaatgtgcagaagaagctgcccatcatccaga agatcatcatcatggacagcaagactgactaccagggcttccagagcatgtatacctttgtgaccagccacttaccccctggcttcaatg
agtatgactttgtgcctgagagctttgacagggacaagaccattgctctgattataatgaacagctctggctccactggactgcccaaaggtg tggcgccccacagactgcttgtgtgagattcagccatgccagagaccccatcttggcaaccagatcatccctgacactgccatc
ctgccggttccattccatcatggctggcatgttcacaacactggggtacctgatctgtggcttcagagtggtgctgatgtataggttt gaggaggagctgtttctgaggagcctacaagactacaagatccagtctgccctgctggtgcccactctgttcagcttctttgccaagag
caccctcattgacaagtatgacctgagcaacctgcatgagattgcctctggaggagcaccccctgagcaaggaggtgggtgaggctgt ggcaaagaggttcatctcccaggaatcagacagggctatggcctgactgagaccacctctgccatcctcatcacccctgaaggaga
tgacaagcctggtgcgggcaaggtgttccctttgaggccaaggtggtggacctggacactggcaagaccctgggagtgaa ccagaggggtgagctgtgtgaggggtcccatgatcatgtctggctatgtgaacaaccctgaggccaccaatgccctgattgacaag
gatggctggctgcactctggtgacattgcctactgggatgaggatgagcactifitcattgtggacaggctgaagagcctcatcaagtac aaaggctaccaagtggcacctgctgagctagagagcatcctgctccagcaccccaacatctttgatgctggtgtggctggcctgcctg
atgatgatgctggagagctgcctgctgctgttgtggttctggagcatggaaagaccatgactgagaaggagattgtggactatgtggcc agtcaggtgaccactgccaagaagctgaggggaggtgtggtgtttgtggatgaggtgc-
caaagggtctgactggcaagctggatgc
cagaaagatcagagagatcctgatcaaggc-
caagaagggtggcaaaGgcggcggagagggcagaggaagtcttctaacatgcg
gtgacgtggaggagaatcccggccctaggatgc-
cacctcctcgcctcctcttcttcctcctcttcctcaccccccatggaagtcaggccc
gaggaacctctagtggtgaaggtggaagagggaga-
taacgctgtgctgcagtgcctcaagggaacctcagatggccccactcagc
agctgacctggtctcgggagtccccgcttaaaccttct-
taaaactcagcctggggctgccaggcctgggaatccacatgaggcccct ggc-
catctggcttttcatcttcaacgtctctcaacagatgggggcttct). The epHIV7.2 lentiviral vector and epHIV7:GFP-ffluc, dnTGFBRII-t2a-Her2tg, and sTGFBRII-t2a-Her2tg were kind gifts from Dr. Michael Jensen. T2A-sTGFBRII is encoded by a sequence set forth in SEQ ID NO: 32 (Ggcggcggagagggcagaggaagtcttctaacatgcggtgacgtggag-
gagaatcccggccctaggatgggtcggggggctgct
caggggcctgtggccgctgcacatcgtcctgtggacgcgtatcgccagcac-
gatcccaccgcacgttcagaagtcggttaataacga catgatagt-
cactgacaacaacggtgcagtcaagtttccacaactgtgtaaattttgtgatgt-
gagattttccacctgtgacaaccagaaa
tcctgcatgagcaactgcagcatcacctccatctgtgagaagccacag-
gaagtctgtgtggctgtatggagaaagaatgacgagaac ataacactaga-
gacagtttgccatgacccccaagctcccctaccatgactttattctggaa-
gatgctgcttctccaaagtgcattatgaaggg
agaagaaaaagcctggtgagacttttctcatgtgttcctgtagctctgat-
gagtgcaatgacaacatcatcttctcagaagaatataacac
cagcaatcctgacttgttgctagtcatatttcaatga). The mCherry construct was created by Gibson cloning into NheI/NotI of HIV7.2. To generate the soluble transforming growth factor β receptor II (sTβRII) construct described previously (Rowland-Goldsmith M A, Maruyama H, Kusama T et al. Soluble type II transforming growth factor-beta (TGF-beta) receptor inhibits TGF-beta signaling in COLO-357 pancreatic cancer cells in vitro and attenuates tumor formation. Clin Cancer Res 2001; 7:2931-2940; incorporated by reference in its entirety herein) the extracellular portion of human TGFβRII isoform A (aa 1-159; NCBI accession #NP_001020018.1) was cloned into the NheI/NotI sites of epHIV7.2. The truncated CD19 (CD19t) (Sato S, Miller A S, Howard M C et al. Regulation of B lymphocyte development and activation by the CD19/CD21/CD81/Leu 13 complex requires the cytoplasmic domain of CD19. J Immunol 1997; 159:3278-3287; incorporated by reference in its entirety herein) was inserted by Gibson cloning upstream of the sTIβRII gene, separated by a T2A sequence. The IL-21 plasmid was purchased from Origene (plasmid RC215235, containing the coding sequence of NCBI RefSeq NM_021803) and cloned into NheI/NotI of epHIV7.2. CD19t (Sato S, Miller A S, Howard M C et al. Regulation of B lymphocyte development and activation by the CD19/CD21/CD81/Leu 13 complex requires the cytoplasmic domain of CD19. J Immunol 1997; 159:3278-3287; incorporated by reference in its entirety herein) was inserted by Gibson cloning downstream of the IL-21 gene, separated by a T2A sequence. The IL-21-T2A sequence (SEQ ID NO: 16; Gccaccatgagatccagtcctggcaacatggagaggattgtcatctgtctgatggt-
catcttcttggggacactggtccacaaatcaag ctcccaaggtcaagatcgcca-
catgattagaatgcgtcaacttatagatattgttgatcagctgaaaaattatgtgaatg
acttggtccctg aatttctgccagctccagaagatgtagagacaaactgt-
gagtggtcagattttctgctttcagaaggcccaactaaagtcagcaaata cag-
gaaacaatgaaaggataatcaatgtatcaattaaaaagctgaagaggaaac-
caccttccacaaatgcagggagaagacagaaa
cacagactaacatgccatcatgtgattatatgagaaaaaaccacccaaagaat-
tcctagaaagattcaaatcacttctccaaaagatg attcatcag-
catctgtcctctgtagaacacacggaagtgaagattcc) was closed with the forward primer, SEQ ID NO: 14 (ccgccagaacacagctggctagcgccaccatgagatccagtcctggcaac)

and the reverse primer, SEQ ID NO: 15 (tgtcaccaggagaagcatcctagggccgggattctc). Cells can also be manufactured to express an EGFRt-P2A-soluble VEGF receptor (encoded by a sequence set forth in SEQ ID NO: 28). The LentiCRISPRv2 vector was a gift from Feng Zhang (Addgene plasmid #52961), and guide sequences for IL-10 (TGTTGCCTGGTCCTCCTGAC (SEQ ID NO: 1)) and PD-L1 (TCCAGATGACTTCGGCCTTG (SEQ ID NO: 2)) were inserted into the BsmB1 site using standard protocols (Sanjana N E, Shalem O, Zhang F. Improved vectors and genome-wide libraries for CRISPR screening. Nat Methods 2014; 11:783-784 and Shalem O, Sanjana N E, Hartenian E et al. Genome-scale CRISPR-Cas9 knockout screening in human cells. Science 2014; 343:84-87; both references incorporated in their entireties herein). The truncated epidermal growth factor receptor (EGFRt) (Wang X, Chang W C, Wong C W et al. A transgene-encoded cell surface polypeptide for selection, in vivo tracking, and ablation of engineered cells. Blood 2011; 118:1255-1263; incorporated by reference in its entirety herein) epitope tag was inserted to replace the puromycin resistance sequence. To generate soluble TGFβRII (sTGFβRII) construct, the extracellular portion of human TGFβRII isoform A (aa 1-166; NCBI accession #NP_001020018.1) was purchased from Gen9 and cloned into the NheI/NotI sites of epHIV7.2. The IL-21 plasmid was purchased from Origene (plasmid RC215235, containing the coding sequence of NCBI RefSeq NM_021803) and cloned into NheI/NotI of epHIV7.2.

Lentivirus Production

All viral preparation was conducted in a BSL-2 laminar flow hood. pcVpx and pMDL-X were kind gifts of the Landau lab (Bobadilla, Gene Therapy 2013) (Bobadilla S, Sunseri N, Landau N R. Efficient transduction of myeloid cells by an HIV-1-derived lentiviral vector that packages the Vpx accessory protein. Gene Ther 2013; 20:514-520; incorporated by reference in its entirety herein). RSV-Rev was purchased from Addgene (plasmid #12253). pCMV-G was a gift from Dr. Michael Jensen (Yee J K, Miyanohara A, LaPorte P et al. A general method for the generation of high-titer, pantropic retroviral vectors: highly efficient infection of primary hepatocytes. Proc Natl Acad Sci USA 1994; 91:9564-9568; incorporated by reference in its entirety herein). 293T cells were purchased from ATCC (CRL-3216), and used at below passage 20. 293T cells were plated at $10^7$ cells per 15 cm dish in 293T media (DMEM supplemented with 10 mM HEPES and 1% Glutamax (Gibco) and 10% FBS). After overnight growth, each plate was transfected with pcVpx (4.6 μg), pMDL-X (13.5 μg), RSV-Rev (6.8 μg), pCMV-G (9.5 μg), and the transgene vector (37.8 μg) using the CalPhos Mammalian Transfection Kit (Clontech). After 16 hours, media was changed to fresh 293T media. Virus-containing supernatant was collected at 48 hours, followed by filtration with a 0.45 μm filter to remove debris and ultracentrifugation at 108,000×g in a Beckman Coulter Optima L-90K ultracentrifuge using the SW-28 rotor for 90 minutes at 4 C. The viral pellet was resuspended in serum-free DMEM and the concentration of intact lentiviral particles (LP) was determined by the Quick Titer Lentivirus titer kit, an ELISA for lentivirus associated p24 (Cell Biolabs).

High MOI Transduction of Partially Differentiated Macrophages and DCs

To determine the titering units (TU) per mL of lentivirus packaged with or without Vpx, H9 cells were transduced with a range of concentrations of virus encoding GFP-ffluc and analyzed by flow cytometry. TU/mL=(# of H9 cells at time of transduction)×(proportion of GFP positive cells)/ (volume of virus added (mL)). This value was used to determine MOI for infection of dendritic cells or macrophages at day 3 of differentiation (Breckpot K, Dullaers M, Bonehill A et al. Lentivirally transduced dendritic cells as a tool for cancer immunotherapy. J Gene Med 2003; 5:654-667; incorporated by reference in its entirety herein). Virus was added with fresh media and cytokines as above. Protamine sulfate (100 ug/mL) was added to enhance transduction by lentivirus packaged without Vpx.

Lentiviral Infection of Monocytes or Macrophages

Freshly isolated monocytes or differentiated macrophages were infected with 20-1000 LP/cell in macrophage media (supplemented with M- or GM-CSF as appropriate for concurrent differentiation of monocytes). Media was refreshed every three days.

U87 Cell Culture

The wild-type U87 glioma cell line was purchased from ATCC (HTB-14). U87 cells stably transduced with epHIV7: GFP-ffluc were a gift from Dr. Michael Jensen's lab. All U87s were cultured in DMEM supplemented with 1% Glutamax and 10% FBS at 37° C., 5% CO2, and passaged prior to the formation of neurospheres. GFP-ffluc-expressing U87s were not used for more than five passages, and GFP expression was verified using fluorescent microscopy before use.

Lentiviral Copy Number Assay

To determine the number of lentiviral integrations per cell, CD14+ cells were transduced on day 0 of differentiation, or after 7 days of differentiation in 10 ng/mL GM-CSF, with 100 or 250 LP/cell encoding GFP-ffluc. On day 10 of differentiation, genomic DNA was isolated using the Qiagen DNA Mini Kit. qPCR for WPRE and the albumin gene on the BioRad CFX96 Real Time System using 2× Power SYBR Green Master Mix (Thermo Fisher). Picograms of lentiviral (WPRE) and genomic DNA (albumin) was determined by comparing Cq values to those obtained from respective standard curves of known concentrations of plasmid DNA. Viral integrations per cell=2×(pg WPRE)/(pg ALB).

```
WPRE-QF:
                                    (SEQ ID NO: 8)
ACTGTGTTTGCTGACGCAACCC

WPRE-QR:
                                    (SEQ ID NO: 9)
CAACACCACGGAATTGTCAGTGCC

ALB-QF:
                                    (SEQ ID NO: 10)
TGAAACATACGTTCCCAAAGAGTTT

ALB-QR:
                                    (SEQ ID NO: 11)
CTCTCCTTCTCAGAAAGTGTGCATAT.
```

Flow Cytometry

GEMs were harvested for flow cytometry by treatment with Versene (Gibco) followed by gentle scraping. Detached cells were treated with Fc Block (BD Biosciences) to eliminate non-specific antibody binding, stained with fluorophore-conjugated antibodies, fixed with 2% paraformaldehyde, and run on a BD LSR Fortessa flow cytometer with FACS DIVA software. Analysis was performed with FlowJo for Mac, v10 (Treestar). Anti-human antibodies included CD16-V500, CD163-Alexa647, and CD80-BV786 (BD Biosciences), and CD11b-APC-Cy7, CD19-APC, HLA-DR-BV605 or HLA-DR-APC, CD45-BV785, and PD-L1-PECy7 (Biolegend), as well as the Live/Dead fixable blue stain (Thermo Fisher). Erbitux (Bristol-Myers Squibb) was biotinylated using the EZ-link biotinylation kit (Thermo Scientific) and used in conjunction with streptavidin-FITC (Biolegend).

Figure 21B:
FIGS. 21A and 21B show that human GEMs disperse from the injection site and infiltrate tumor tissue. 25 days after GEM injection (30 days post-U87 injection), brains were harvested, sectioned, and stained for DAPI (blue) and human CD45. CD45 expression is restricted to engineered macrophages and does not cross react with mouse myeloid cells.
Figure 21A:
Figure 22A:
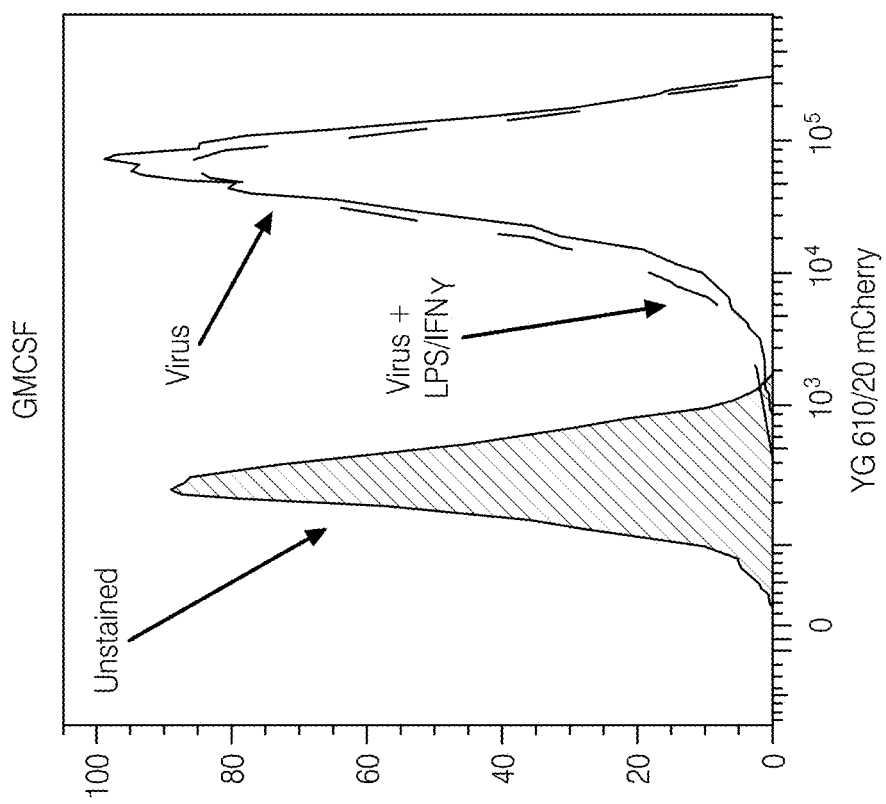
FIGS. 22A, 22B, 22C, 22D, 22E, 22F, 22G and 22H show that GEMs express standard myeloid cell surface markers and respond to LPS/IFNγ stimulation. GM-CSF (22A) or M-CSF (22B) monocyte-derived macrophages were infected on day 0 of differentiation with 250 vpx-containing LP/cell of lentivirus encoding mCherry. Cells analyzed for expression on Day 7 were found to be 100% positive, regardless of treatment. These cells were also analyzed for surface expression of the common myeloid markers CD11b, CD16, C80, HLADR, PD-L1, and CD163 (FIG. 22C-22H).
Figure 22B:
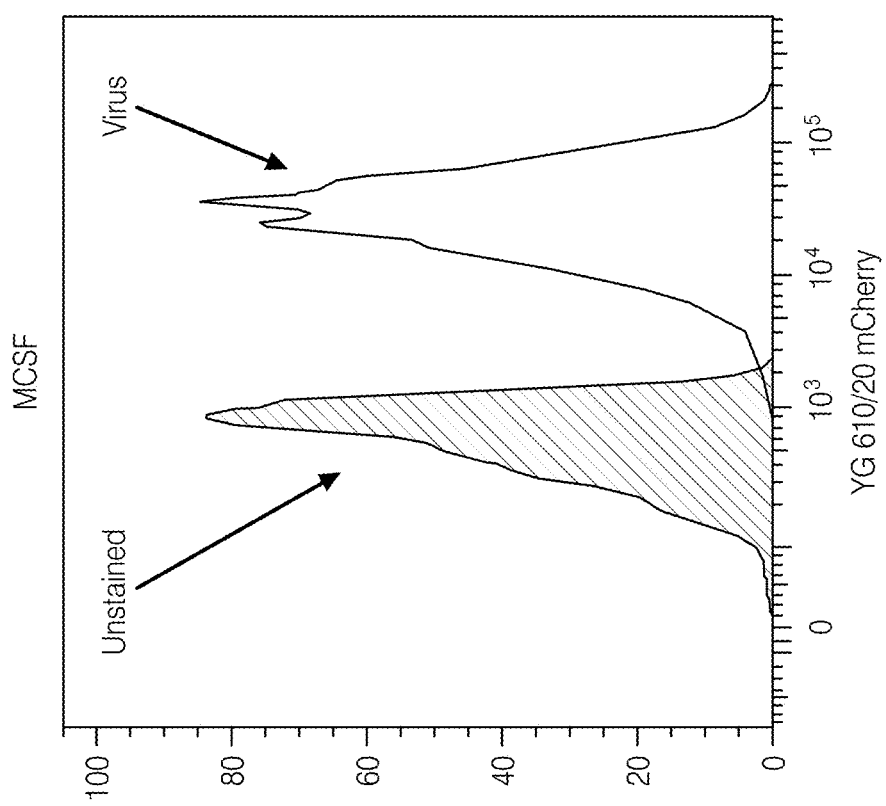
Figure 22C:
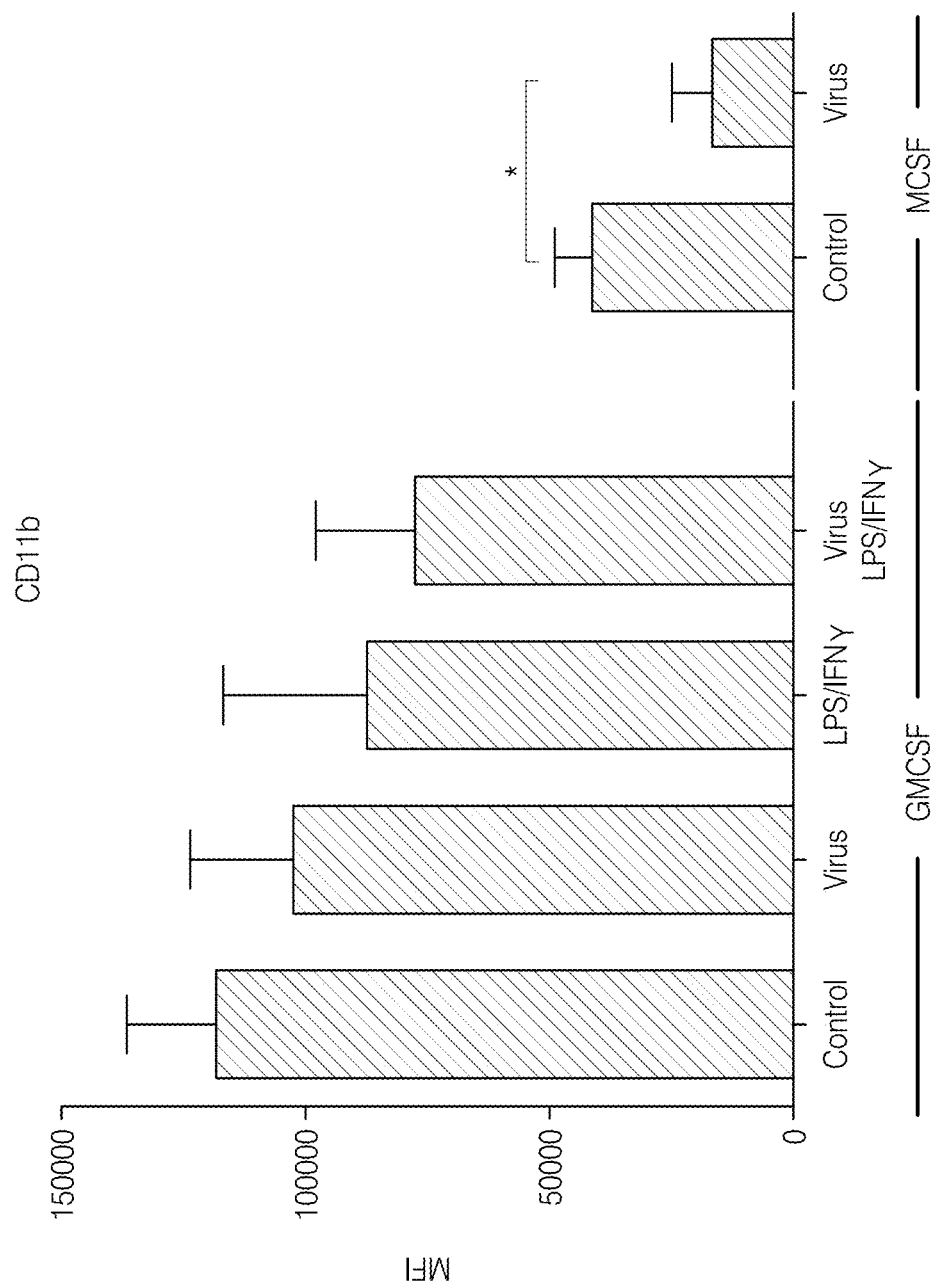
Figure 22D:
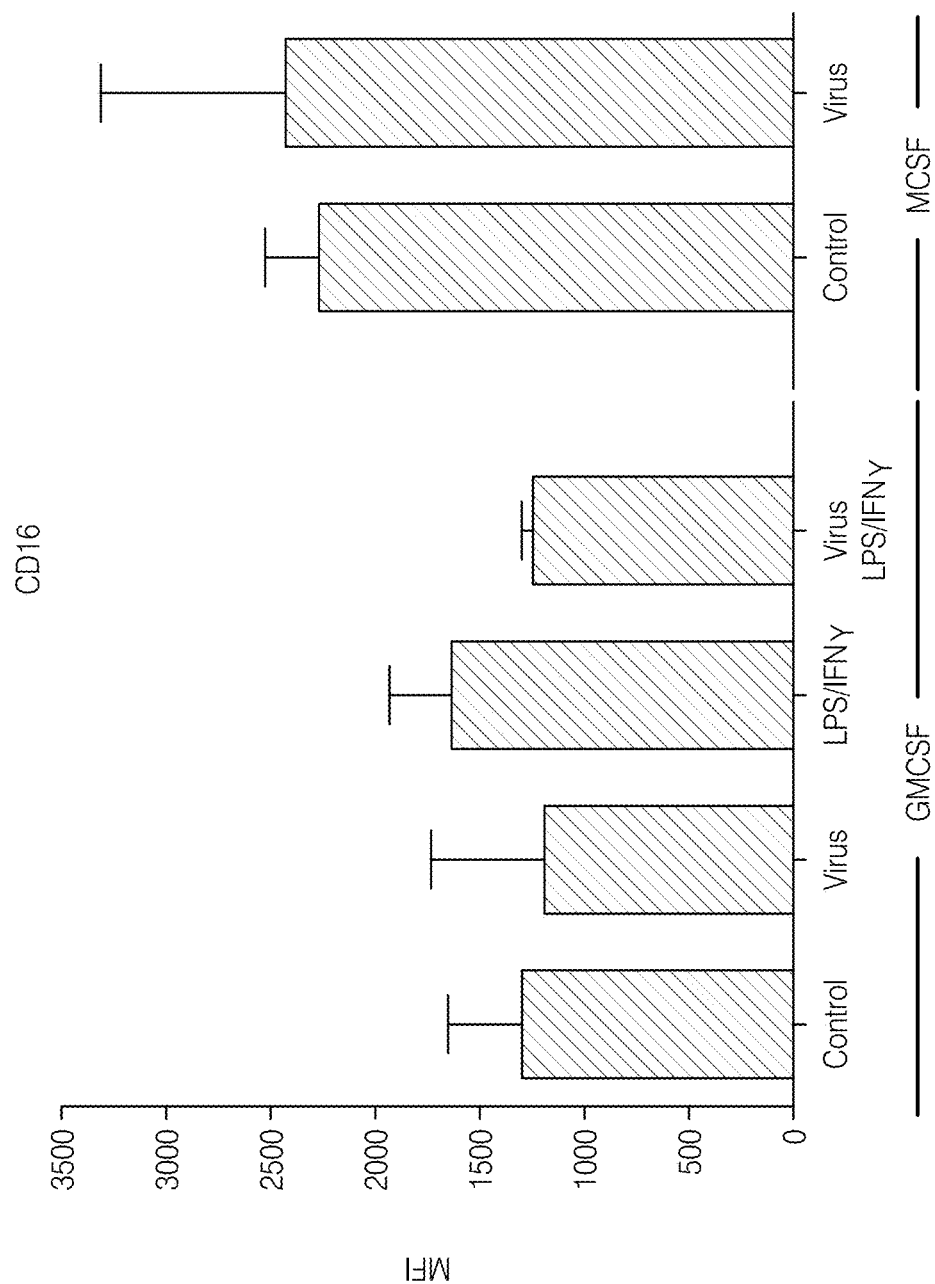
Figure 22E:
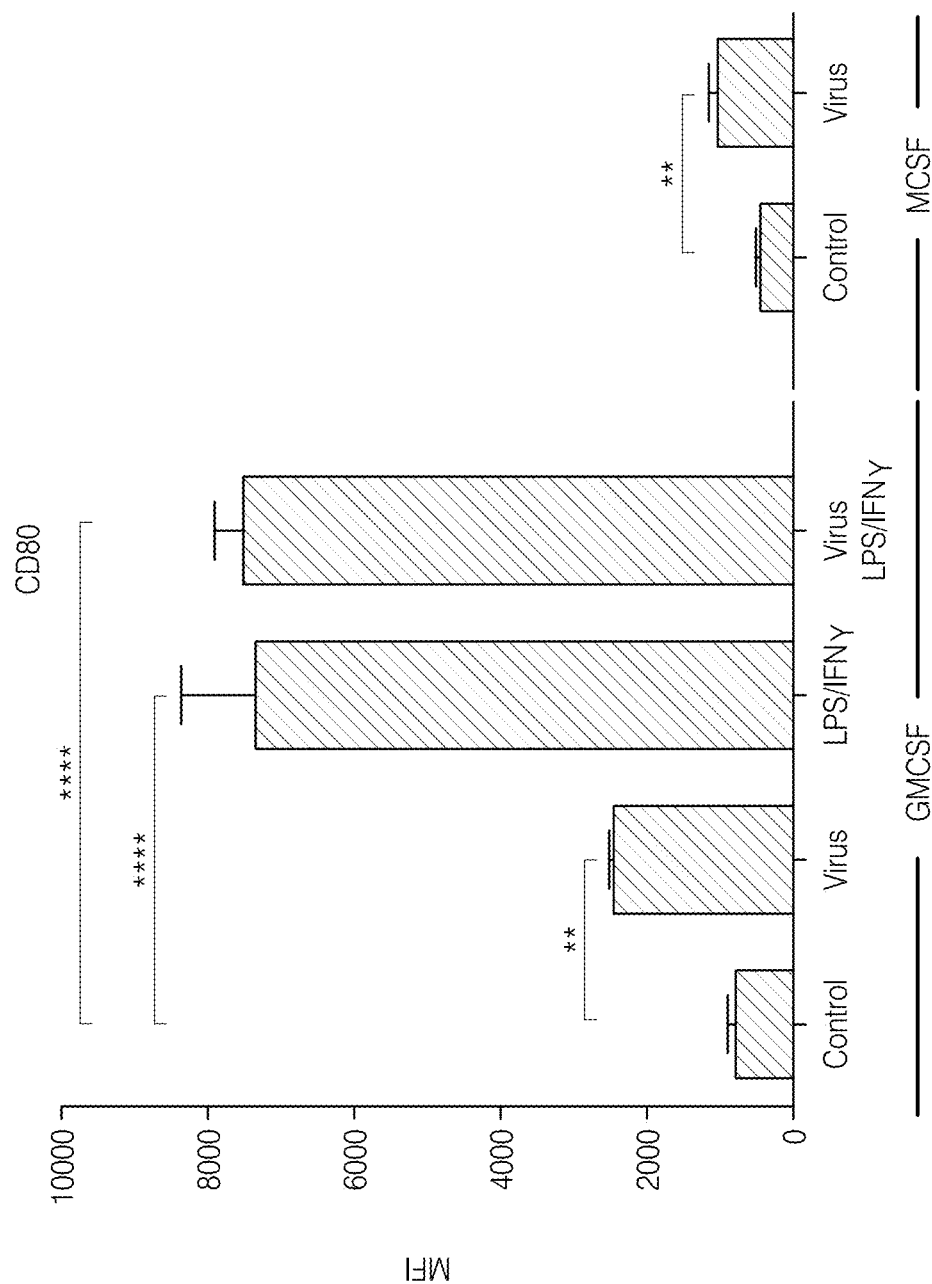
Figure 22F:
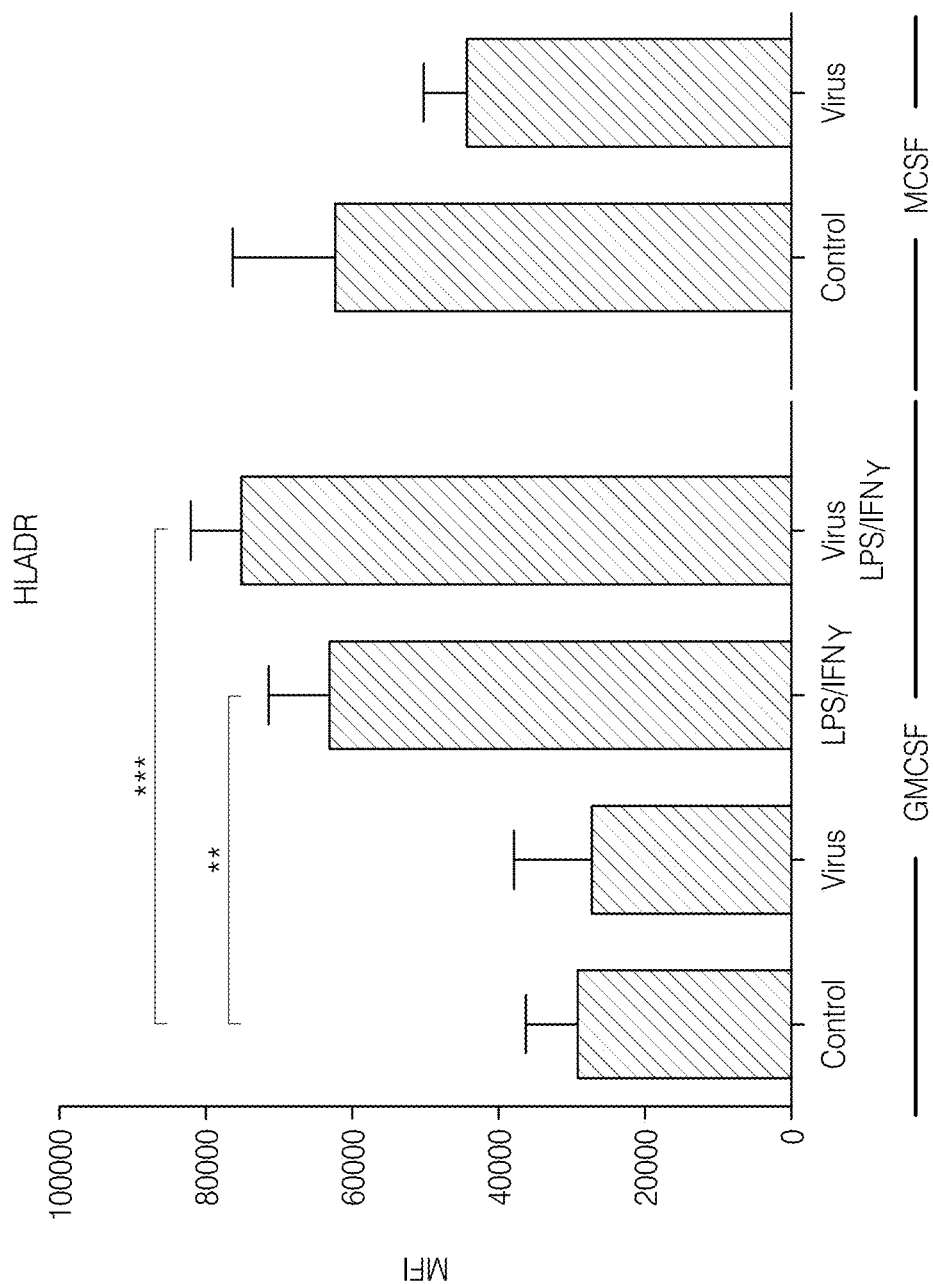
Figure 22G:
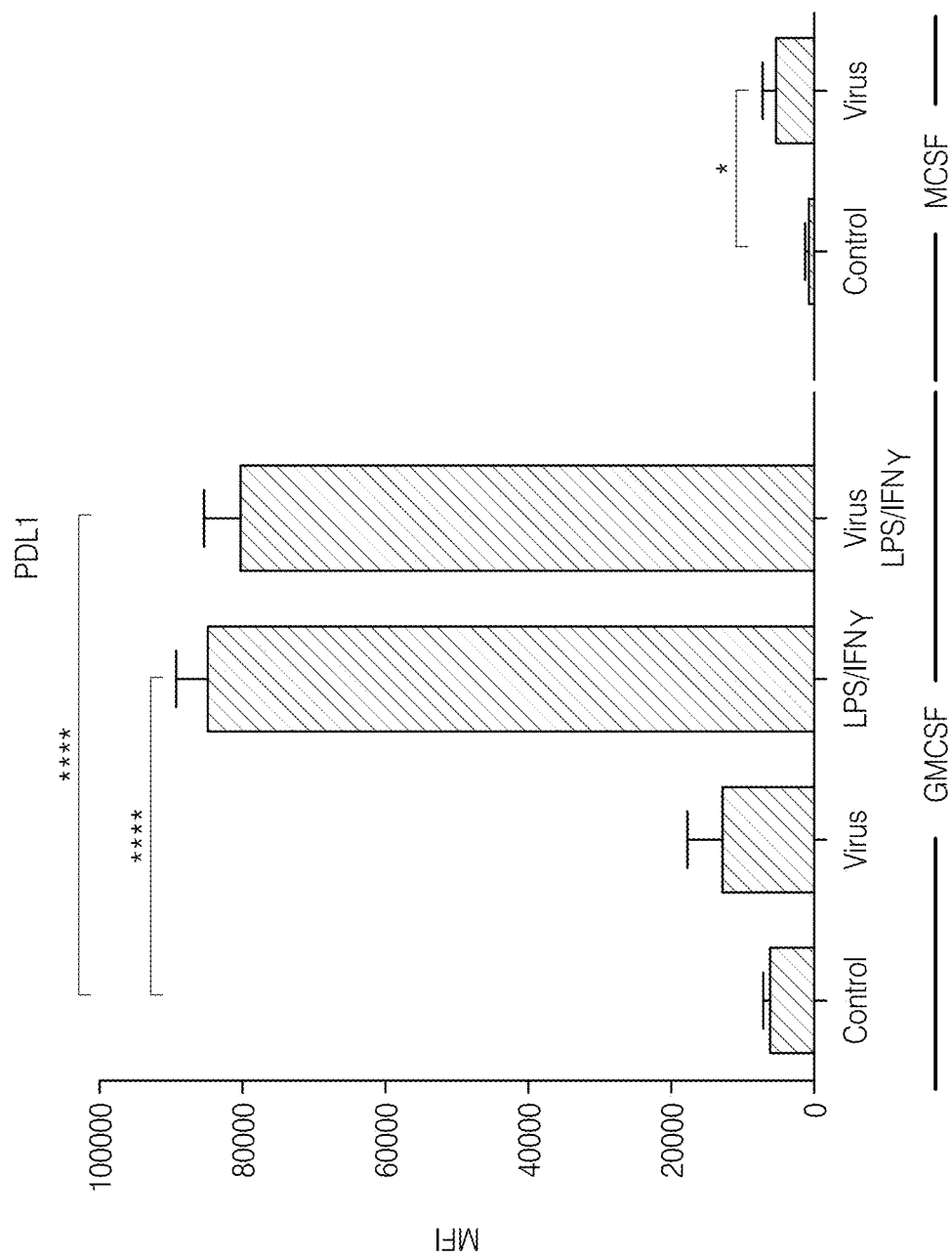
Figure 22H:
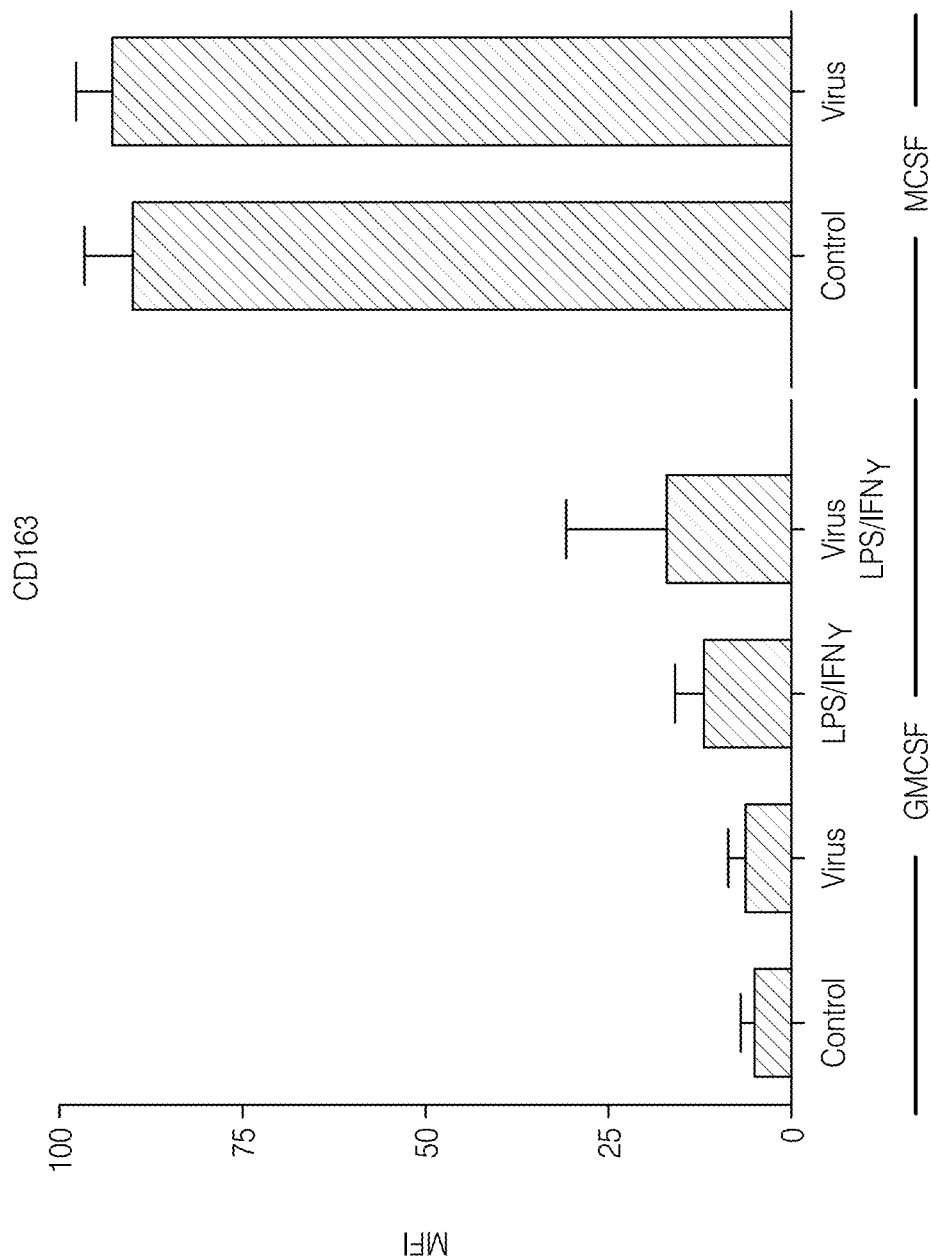
Figure 23A:
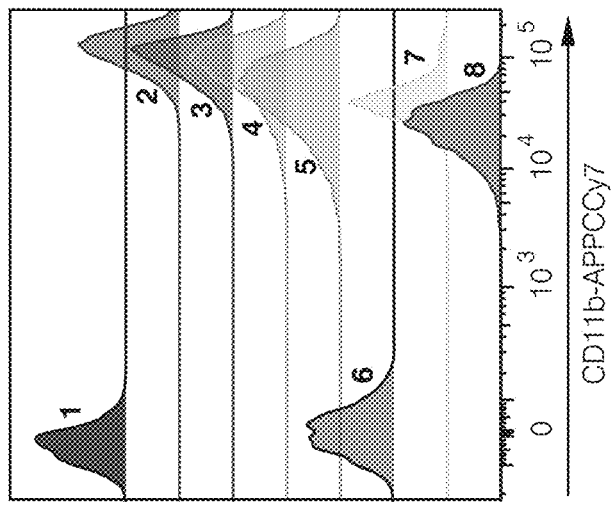
FIG. 23A-23F shows GM-CSF and M-CSF macrophages were transduced on Day 0 (at the time of CD14 isolation) and stained and analyzed for myeloid surface markers on Day 7
Figure 23B:
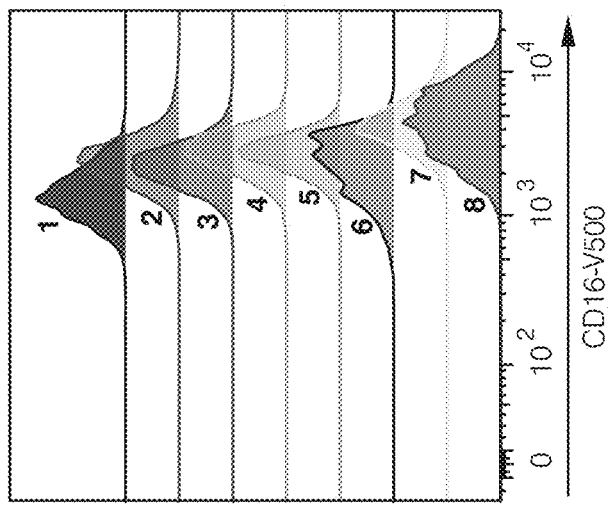
Figure 23C:
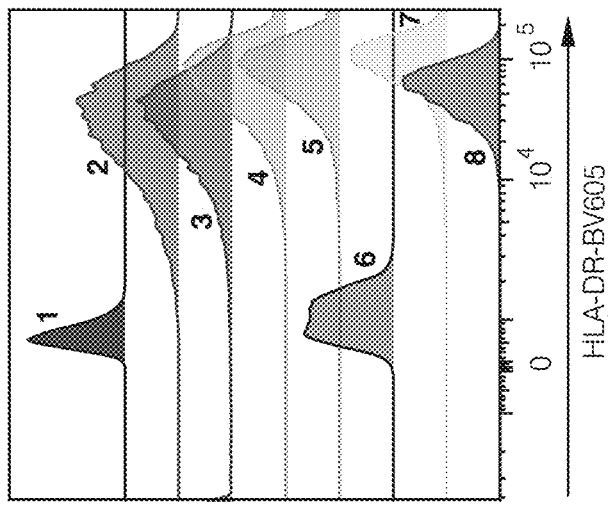
Figure 23D:
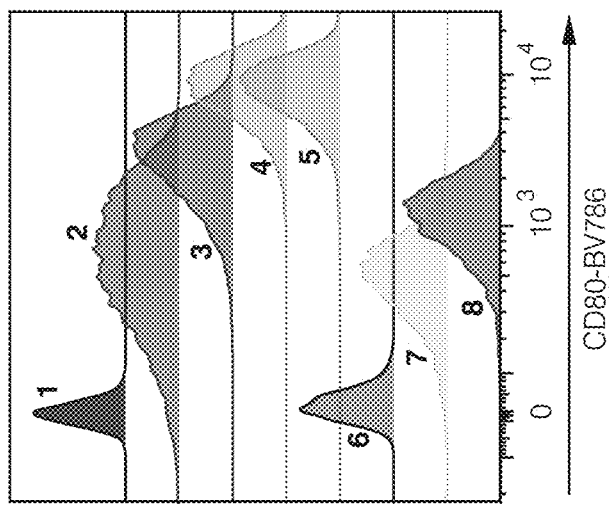
Figure 23E:
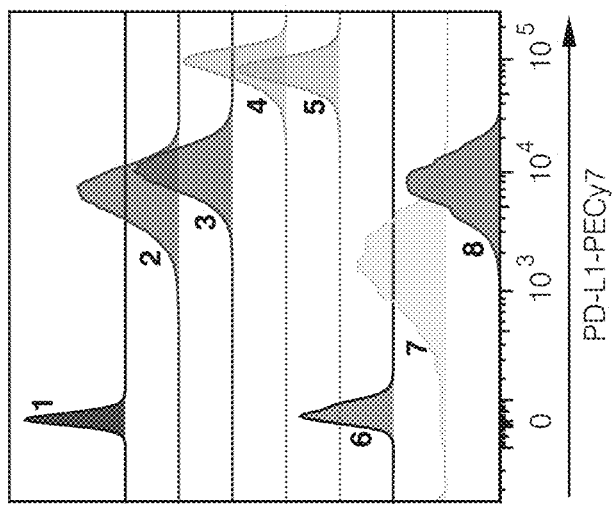
Figure 23F:
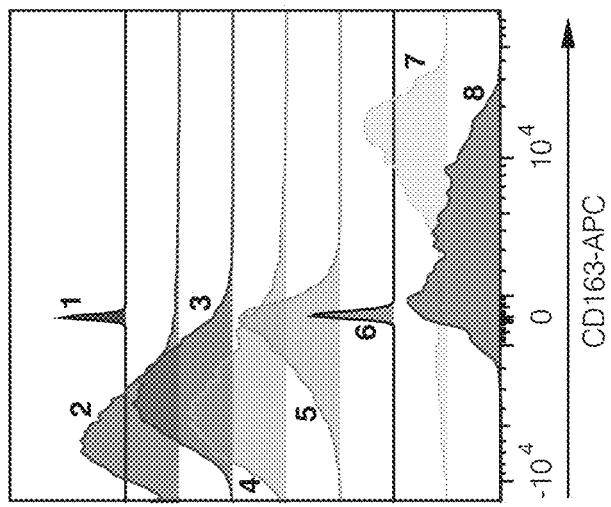

The immunohistochemistry results are shown in FIGS. 21A and 21B. Shown in FIG. 21A is the representative section from a mouse injected with U87 only and mock injected with PBS 5 days later. Shown in FIG. 21B is the representative section from a mouse injected with U87 cells, and 5 days later with CD45 expressing GEMs.

Viral Induced Cytokine Production

CD14+ monocytes were isolated from healthy donor PBMCs and transduced with 0 or 250 LP/cell mCherry Vpx+ lentivirus and differentiated in GM-CSF for 7 days. Following 24 hours of conditioning, media was collected at a ratio of 1 mL per 500,000 cells at 24 hours and 7 days post-transduction. Media samples were then used undiluted on a Luminex kit that included IL-12 (p40/p70), TNF, and IFNα (Life Technologies).

Surveyor Assay

GM-CSF-differentiated macrophages were infected with 1000 LP/cell Vpx+ LentiCRISPRv2 virus containing control (no gRNA), IL-10 gRNA, or PD-L1 gRNA. After 5 days in culture, genomic DNA was isolated using the DNeasy Kit (Qiagen) following manufacturer's protocols. Genomic regions surrounding the Cas9-cleaved sites were PCR amplified with the following primer sets, and the Surveyor Assay (Integrated DNA Technologies) carried out according to the manufacturer's protocol.

```
IL-10 PCR primers:
F:
                                        (SEQ ID NO: 3)
5'-AGAGAGGTAGCCCATCCTAAAAATAGCTG, R:
                                        (SEQ ID NO: 4)
5'-GCAGGTTTCCTGCACATTTACTGTATCA.

PD-L1 PCR primers:
F:
                                        (SEQ ID NO: 5)
5'-TTGAATTGAATTGAGGCAGAGCTAGCAG, R:
                                        (SEQ ID NO: 6)
5'-ATATGGTTTGGATGAATGGAGGTGAGGA.
```

Validation of PD-L1 Expression Downregulation

GM-CSF-differentiated macrophages were infected with 1000 LP/cell Vpx+ LentiCRISPRv2-EGFRt virus containing control (no gRNA) or PD-L1 gRNA. After 6 days in culture, GEMs were stimulated with 100 ng/mL lipopolysaccharide (LPS) and 20 ng/mL interferon gamma (IFNγ) for 24 hours, and stained for flow cytometry with anti-PD-L1 and Erbitux to determine transduction efficiency based on expression of the epitope tag EGFRt.

Validation of IL-10 Expression Downregulation

GM-CSF-differentiated macrophages were infected with 1000 LP/cell Vpx+ LentiCRISPRv2:EGFRt virus containing control (no gRNA) or IL-10 gRNA. After 6 days in culture, GEMs were stimulated with 100 ng/mL LPS and 20 ng/mL IFNγ for 24 hours at 1 mL/500,000 cells. Conditioned media was collected and used undiluted for Bio-Rad's IL-10 BioPlex Pro Assay on a Bio-Plex 200 instrument. Cells were stained for flow cytometry with Erbitux to determine transduction efficiency based on expression of the epitope tag EGFRt.

Validation of Soluble TGFβRII Expression

To verify the expression of sTβRII, GM-CSF-differentiated macrophages were transduced on day 7 with 250 LP/cell of lentivirus encoding CD19t-T2A-sTβRII (SEQ ID NO: 33; Atgccacctectcgcctectcttcttcctcctcttcctcaccccccatg-gaagtcaggcccgaggaacctctagtggtgaaggtggaaga gggaga-taacgctgtgctgcagtgcctcaaggggacctcagatggccc-cactcagcagctgacctggtctcgggagtccccgcttaa acccttcttaaaactcagcctggggctgccaggcctgggaatctgc-catctggcttttcatcttcaacgtctctca acagatgggggcttc-tacctgtgccagccggggccccccctct-gagaaggcctggcagcctggctggacagtcaatgtggagggc agcggggagctgttccggtg-gaatgtttcggacctaggtggcctgggctgtggcct-gaagaacaggtcctcagagggccccagctc ccct tccgggaagctcat-gagccccaagctgtatgtgtgggccaaagaccgccctgagatctgggagggaga gcctccgtgtgtcc caccgagggacagcct-gaaccagagcctcagccaggacctcaccatggcccctggctc-cacactctggctgtcctgtggggtaccc Cctgactctgtgtccgtgtgcaccc-caaggggcctaagtcattttggaatgctgagcctagagctgaaggac gatcgcccggccagagatatgtgggtaatggagacgggtgttgttgccccgggc-cacagctcaagacgctggaaagtatttgtc accgtggcaacctgaccatgtcattc-cacctggagatcactgctcggccagtactatggcactggctgct-gaggactggtggctggaa ggtctcagctgtgacttggcttatctgatcttctgcctgtgttcccttgtgggcat-tcttcatcttcaaagagccctggttgaggaggaa aagataaGgcggcg-gagagggcagaggaagtcttctaacatgcggtgacgtggag-gagaatcccggccctaggatgggtcggg ggctgctcaggggcctgtggacgcgtatcgccagcacgatcc-caccgcacgttcagaagtcggtgta ataacgacatgatagt-cactgacaacaacggtgcagtcaagtttccacaactgtgtaaattttgtgatgt-gagattttccacctgtgacaa ccagaaatcctgcatgagcaactgcagcatcacctccatctgtgagaagccacag-gaagtctgtggctgtgtatggagaaagaatga cgagaacataacactaga-gacagtttccatgaccccaagctcccctaccatgactttattctggaa-gatgctgcttctccaaagtgcatt atgaaggagaagaaaaagcctggtgagactttcttcatgtgttcctgtagctctgat-gagtgcaatgacaacatcatcttctcagaagaat ataacaccagcaatcctgacttgttgctagtcatatttcaatga) or CD19t vector control. Media was collected following 24 hours of conditioning in 1 mL/500,000 cells on days 5, 6, and 7 post-transduction. Secreted protein was detected by the human TGFβRII DuoSet ELISA (R&D Systems). T2A-CD19t is encoded by a sequence set forth in SEQ ID NO: 30 (Ggcggcggagagggcagaggaagtcttctaacatgcggtgacgtggag-gagaatcccggccctaggatgccacctcctcgcctc ctcttcttcctcctctt-cacccccatggaagtcaggcccgaggaaccccccccatgtagtggt-gaagagtcggcccggagataacgctgtgct gcagtgcctcaaggggacctcagatggccc-cactcagcagctgacctggtctcgggagtccccgcttaaacccttct-taaaactcagc ctggggctgccaggcctgggaatccacatgaggccccctggc-catctggcttttcatcttcaacgtctctcaacagatgggggettta cctgtgccagccggggcccctctgagaaggcctctgtggacagtcaatgtg-gaggcagcggggagctgttccgg tggaatgtttcggacctaggtggcctgggctgtggcct-gaagaacaggtcctcagagggcccccagctccccttccgggaagctcatg agccccaagctgtatgtgtgggccaaagaccgccctgagatctgggagg-gagagcctccgtgtgtcccaccgagggacagcctga accagagcctcagccaggacctcaccatggcccctggctc-cacactctggctgtcctgtggggtacccctgactctgtgtcaggg gccccctctcctggacccatgtgcacccaaggggcctaagtcattgct-gagcctagagctgaaggacgatcgcccggccagagat atgtgggtaatgga-gacgggtctgttgttgccccgggccacagctcaagacgctggaaagtattattgt-caccgtggcaacctgacca tgtcattccacctggagatcactgctcggccagtactatggcactggctgct-gaggactggtggctggggttcagctgtgactttg gatatct-gatcttctgcctgtgttcccttgtgggcattcttcatcttcaaagagccctggtcct-gaggaggaaaagataaa). The CD19t epitope tag is encoded by a sequence set forth in SEQ ID NO: 31

(Atgccacctcctcgcctcctcttcttcctcctcttcctcaccoccatg gaagtcaggcccgaggaacctctagtggtgaaggtggaagagggagata acgctgtgctgcagtgcctcaaggggacctcagatggccccactcagca gctgacctggtctcgggagtccccgcttaaaccettcttaaaactcagc ctggggctgccaggcctgggaatccacatgaggccoctggccatctggc ttttcatcttcaacgtctctcaacagatgggggcttctacctgtgcca gccggggccccctctgagaaggcctggcagcctggctggacagtcaat gtggagggcagcggggagctgttccggtggaatgtttcggacctaggtg gcctgggctgtggcctgaagaacaggtcctcagagggcccagctcccc ttccgggaagctcatgagcccaagctgtatgtgtgggccaaagaccgc cctgagatctgggagggagagcctccgtgtgtcccaccgagggacagcc tgaaccagagcctcagccaggacctcaccatggccoctggctccacact ctggctgtcctgtggggtaccccctgactctgtgtccaggggcccctc tcctggacccatgtgcaccccaagggcctaagtcattgctgagcctag agctgaaggacgatcgcccggccagagatatgtgggtaatggagacggg tctgttgttgccccgggccacagctcaagacgctggaaagtattattgt caccgtggcaacctgaccatgtcattccacctggagatcactgctcggc cagtactatggcactggctgctgaggactggtggctggaaggtctcagc tgtgactttggcttatctgatcttctgcctgtgttccettgtgggcatt cttcatcttcaaagagccctggtcctgaggaggaaaagataa).

Validation of IL-10 Expression

GM-CSF-differentiated macrophages were infected with 1000 LP/cell Vpx+ LentiCRISPRv2 virus containing control (no gRNA) or IL-10 gRNA. Monocytes were also infected with 1000 LP/cell and differentiated with GM-CSF concurrently. After 6 days in culture, GEMs were replated to include equal cell numbers (100,000-200,000 per well of a 24 well plate) and stimulated with 100 ng/mL LPS and 20 ng/mL IFNγ for 48 hours. Conditioned media was collected and used undiluted for Bio-Rad's IL-10 BioPlex Pro Assay on a Bio-Plex 200 instrument.

IL-10 Bioplex Assay

GM-CSF-differentiated macrophages were infected with 1000 LP/cell Vpx+ lentiCRISPRv2 virus containing control (no gRNA) or IL-10 gRNA. Monocytes were also infected with 1000 LP/cell and differentiated concurrently. After 6 days in culture, GEMs were replated to include equal cell numbers (100,000-200,000 per well of a 24 well plate) and stimulated with 100 ng/mL LPS/20 ng/mL IFNγ for 48 hours. Conditioned media was collected and used undiluted for Bio-Rad's IL-10 BioPlex Pro Assay on a Bio-Plex 200 instrument.

Validation of sTGFβRII Expression

The TGFBRII construct and the IL-21 plasmid were cloned in to the HIV7.2 backbone previously described. Soluble TGFβ receptor or IL-21 expression was detected in GEM-conditioned media that was collected in 24 hour intervals using the TGFβR duoset kit DY241 (R&D) or the IL-21 Bioplex pro kit (Biorad), respectively. For these assays, GM-CSF derived macrophages were transduced on Day 7 of differentiation.

To verify the expression of soluble TGFβ receptor, GM-CSF-differentiated macrophages seeded on day 6 in 700 µL at 500,000 cells per well in a 12 well plate. Cells were transduced on day 7 with 250 or 500 LP/cell of lentivirus encoding sTGFβRII. Media was collected following 24 hours of conditioning on days 2, 5, 12, and 15-post-transduction. Secreted protein was detected by the human TGFβRII DuoSet ELISA (R&D).

Validation of IL-21 Expression

In some alternatives, to verify the expression of IL-21, GM-CSF-differentiated macrophages were transduced on day 7 with 250 LP/cell of lentivirus encoding IL-21-T2A-CD19t or CD19t vector control. Media was collected 7 days post-transduction (day 14 of differentiation) following 24 hours of conditioning in 1 mL/500,000 cells. IL-21 secretion was detected using the BioPlex Pro assay (Bio-Rad).

In some alternatives, to verify the expression of IL-21, GM-CSF-differentiated macrophages were seeded on day 6 following isolation and differentiated in 500 µL of macrophage media at 200,000 cells per well in a 24 well plate. Cells were transduced on day 7 with 1000 LP/cell of lentivirus encoding IL-21 and media was collected 6 days post-transduction (day 13 of differentiation) following 24 hours of conditioning. IL-21 secretion was detected using the BioPlex Pro assay (Bio-Rad).

Co-Infections with epHIV7.2 and LentiCRISPRv2 Vpx+ Lentivirus

GM-CSF differentiated macrophages were infected with 250 LP/cell epHIV7.2:CD19t vector control (SEQ ID NO: 12), CD19t-T2A-sTβRII, or IL-21-T2A-CD19t virus concurrently with 1000 LP/cell lentiCRISPRv2:EGFRt vector control, PD-L1gRNA-EGFRt, or IL-10gRNA-EGFRt virus. Flow cytometry for epitope tags was used to determine the percent of cells double positive, and assays performed for each factor as above.

Detection of LPS/IFNγ-Induced Factors

To determine the longitudinal expression of interleukins, cytokines, chemokines, and growth factors elicited by lipopolysaccharide/interferon-γ (LPS/IFNγ) stimulation, GM-CSF differentiated macrophages were seeded on day 6 at 200,000 cells per well in a 24 well plate. On day 7, macrophages were stimulated with 100 ng/mL LPS, 20 ng/mL IFNγ or LPS+IFNγ for 18 hours in 500 µL media. Conditioned media was collected at 18 h (Day 1) and replaced with fresh media without cytokines. Media was harvested every 24 hours for a total of 10 days. Cytokine release was detected using the Luminex Human 30-plex cytokine kit (Life Tech).

Animal Studies

All mouse studies were conducted with the oversight of the Seattle Children's IACUC (Protocol #15181) and efforts made to minimize use in accordance with Institute policies. Animals were euthanized following the appearance of symptoms secondary to tumor engraftment, including cachexia, lethargy, hindlimb paralysis, or when they reached 80% of their original body weight. Eight week old male NOD.Cg-Prkdc$^{scid}$ Il2rg$^{tm1Wjt}$SzJ (NSG) mice were purchased from The Jackson Laboratory. Ketamine/xylazine-anesthetized animals were immobilized in stereotactic apparatus (Stoelting), a 0.5 cm incision made on the skin covering the skull, and a burr hole drilled 2 mm lateral and 0.5 mm anterior to the bregma. 200,000 wild-type or GFP-ffluc-expressing U87 cells were injected in a 2 µL volume at a rate of 1 µL/minute at 2.5 and 2.25 µL beneath the dura, 1 µL at each location. After wound closure, mice received lactated Ringer's solution for fluid recovery and buprenorphine as an analgesic. Surgery for injection of GEMs was similar to that for U87s, except that 150,000 GEMs were injected in a 3 µL total volume at 3 steps of 2.5, 2.35, and 2.25 mm below the dura. Bioluminescent imaging of GEMs or U87s expressing ffluc was conducted three times weekly. Mice were anesthetized with isoflurane, injected with 150 μL of a 28.57 mg/mL solution of D-luciferin (Perkin Elmer) intraperitoneally or subcutaneously in the scruff. Bioluminescent images were collected with a Xenogen IVIS Spectrum Imaging System (Perkin Elmer) and Living Image Software (Perkin Elmer) used to analyze the data.

Immunohistochemistry (IHC) of Human CD45+ Cells in Brain Tumor Xenografts

After reaching the defined experimental endpoint (above), animals were deeply anesthetized with 4% isoflurane, the chest cavity opened, and 15 mL PBS perfused through the heart and vasculature followed by 15 mL 10% neutral buffer formalin (NBF). Mouse brains were harvested, formalin-fixed and paraffin-embedded using standard protocols. To identify injected GEMs within the tumor xenograft, brain sections were immunostained with anti-human CD45 (clone HI30, BioLegend) at a 1:100 dilution and detected with the iVIEW DAB Detection Kit on the Ventana Ultra automated platform. Images were acquired on a Nikon Eclipse Ci with a 20× PlanApo objective (0.75 NA) with a DS-Ri1 color camera. Tile scanned images were stitched together using Nikon Elements software.

Isolation and Flow Cytometry of Human Cells from Brain Xenografts

After reaching the defined experimental endpoint (above), animals were deeply anesthetized with 4% isoflurane, the chest cavity opened, and 15 mL PBS perfused through the heart and vasculature. The brain and tumor were dissected with 1 mm surrounding normal tissue isolated. Dissociation of the brain tumor was performed with the human Tumor Dissociation Kit (Miltenyi), followed by removal of mouse cells with the Mouse Cell Depletion kit (Miltenyi) using manufacturer's protocols. Single-cell suspensions of human cells were stained for flow cytometry as described above.

Statistics and Reproducibility

Unless otherwise stated, all experiments were performed a minimum of three times using macrophages isolated from different donors. Results were analyzed in Prism software (GraphPad) and appropriate tests (paired T tests or ANOVA) performed. Statistical significance (p<0.05) is denoted with an asterisk.

Monocyte-Derived Macrophages can Stably Express Lentivirally-Encoded Genes

Figure 28A:
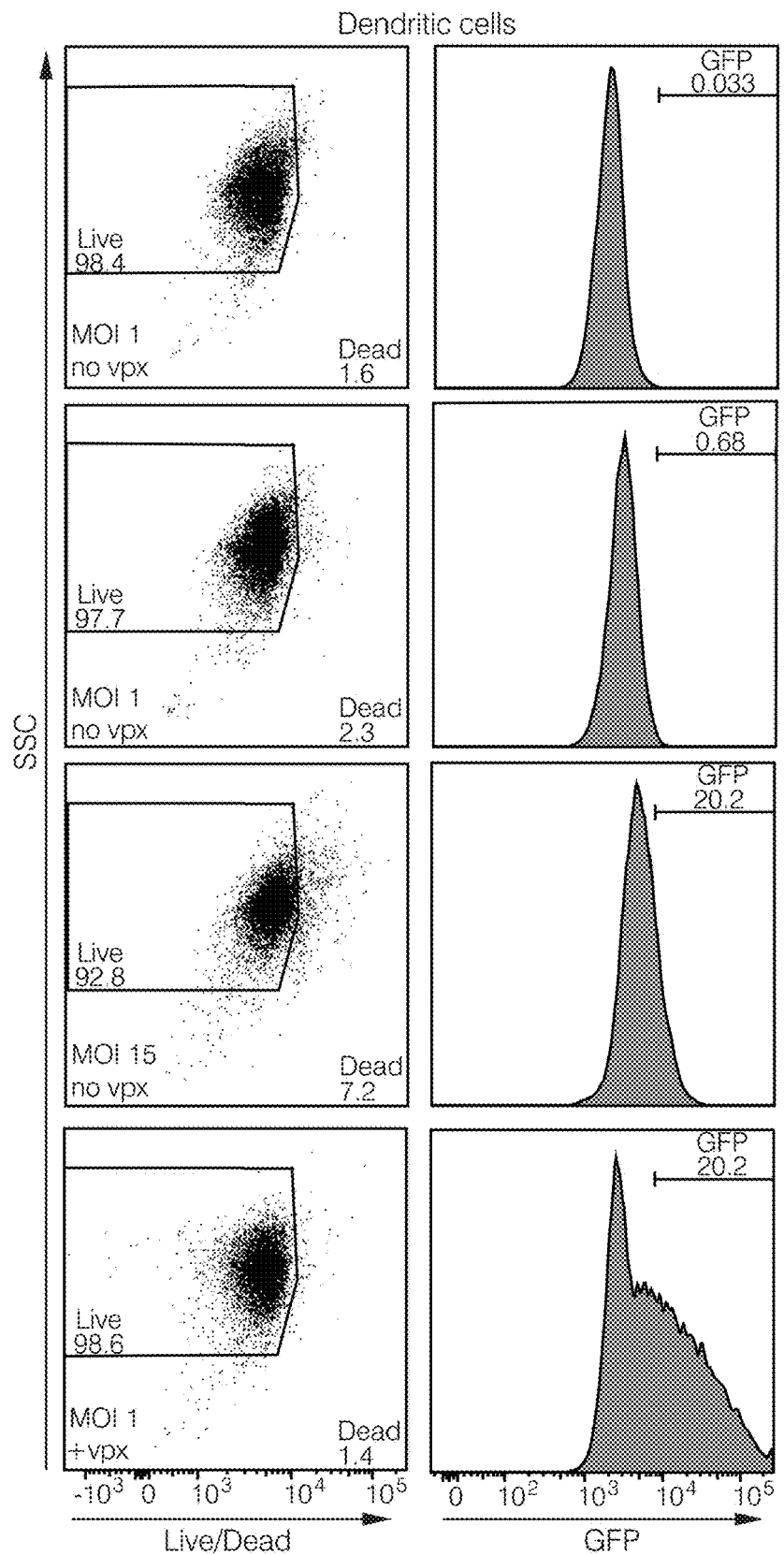
FIGS. 28A and 28B show that lentivirus packaged with Vpx is more efficient at transducing dendritic cells and macrophages. On day 3 of differentiation, monocyte-derived dendritic cells (FIG. 28A) and macrophages (FIG. 28B) were infected with an MOI of 0, 1, or 15 of GFP-ffluc-containing lentivirus packaged without Vpx, or MOI of 1 of GFP-ffluc-encoding lentivirus packaged with Vpx. A viability cell stain was included (left column), and those cells falling in the "live" gate were analyzed for GFP expression (right).
Figure 28B:
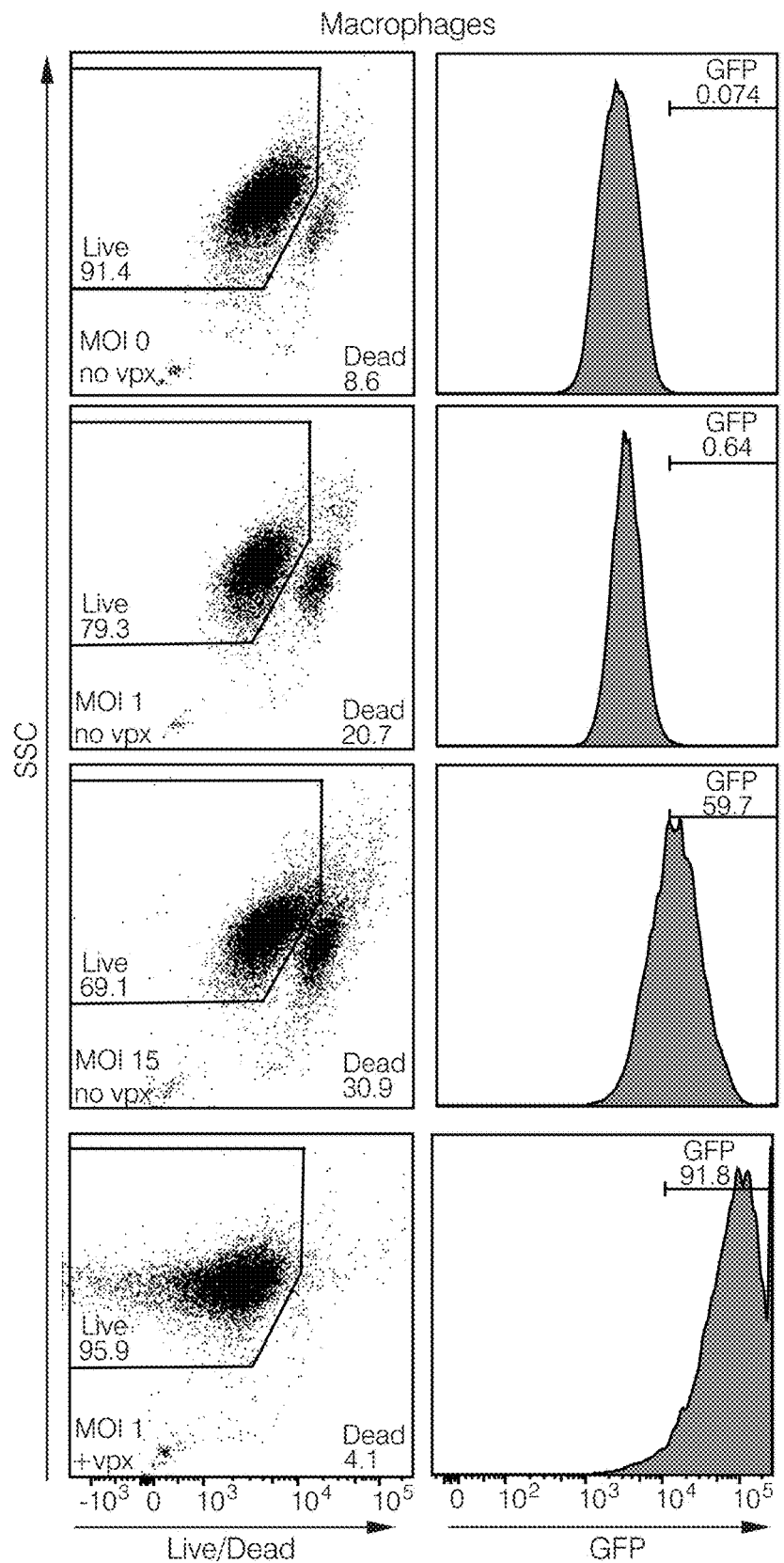

The use of lentivirus to stably transduce T cells for cancer immunotherapy has become routine in recent years. In contrast, no standard system for infection of myeloid cells exists. Recent reports have demonstrated that dendritic cells (DCs) derived from monocytes using granulocyte macrophage colony stimulating factor (GM-CSF) and IL-4, or pro-inflammatory macrophages differentiated using GM-CSF alone, can be transduced at high efficiency when lentiviral particles are packaged with Vpx (Bobadilla S, Sunseri N, Landau N R. Efficient transduction of myeloid cells by an HIV-1-derived lentiviral vector that packages the Vpx accessory protein. Gene Ther 2013; 20:514-520 and Sunseri N, O'Brien M, Bhardwaj N et al. Human immunodeficiency virus type 1 modified to package Simian immunodeficiency virus Vpx efficiently infects macrophages and dendritic cells. J Virol 2011; 85:6263-6274; both incorporated by reference in their entireties herein). Prior studies reported that DCs can be successfully transduced without Vpx, if they are exposed to high multiplicities of infection (MOI) earlier in the differentiation process (Breckpot K, Dullaers M, Bonehill A et al. Lentivirally transduced dendritic cells as a tool for cancer immunotherapy. J Gene Med 2003; 5:654-667 and Chinnasamy N, Chinnasamy D, Toso J F et al. Efficient gene transfer to human peripheral blood monocyte-derived dendritic cells using human immunodeficiency virus type 1-based lentiviral vectors. Hum Gene Ther 2000; 11:1901-1909; both incorporated by reference in their entireties herein). To determine if Vpx is necessary for successful transduction of monocyte derived macrophages, epHIV7:GFP-ffluc, a lentiviral backbone currently in use in clinical trials (NCT01683279, NCT02311621), was packaged with and without Vpx using a standard lentivirus production protocol. CD14+ cells isolated from healthy donor PBMCs were differentiated to DCs or macrophages using GM-CSF and IL-4, or GM-CSF only, respectively. Three days after isolation and initiation of differentiation, cells were counted and replated in fresh media containing cytokines and GFP-ffluc-encoding lentivirus packaged with or without Vpx. Cells infected with virus that did not contain Vpx also received 100 ug/mL protamine sulfate to aid viral entry. Following six days of in vitro differentiation, cells were analyzed by flow cytometry. Using an MOI of 15 as demonstrated in DCs[25] and 100 ug/mL protamine sulfate, we observed that 20% of DCs and 60% of macrophages expressed lentivirally encoded GFP (FIGS. 28A and 28B). However, the combination of high viral dose and a high concentration of protamine sulfate had a detrimental effect on macrophage viability, with more than 30% of cells examined staining positive for a dye that marks dead or dying cells (FIG. 28B). The same effect was not observed for DCs (FIG. 28A). In contrast, when lentivirus was packaged with Vpx, an MOI of 1 was sufficient to infect nearly 100% of day 3 macrophages, without the negative impact on viability. For these reasons, it was opted to proceed with Vpx+ lentivirus for the remainder of the studies.

Figure 25A:
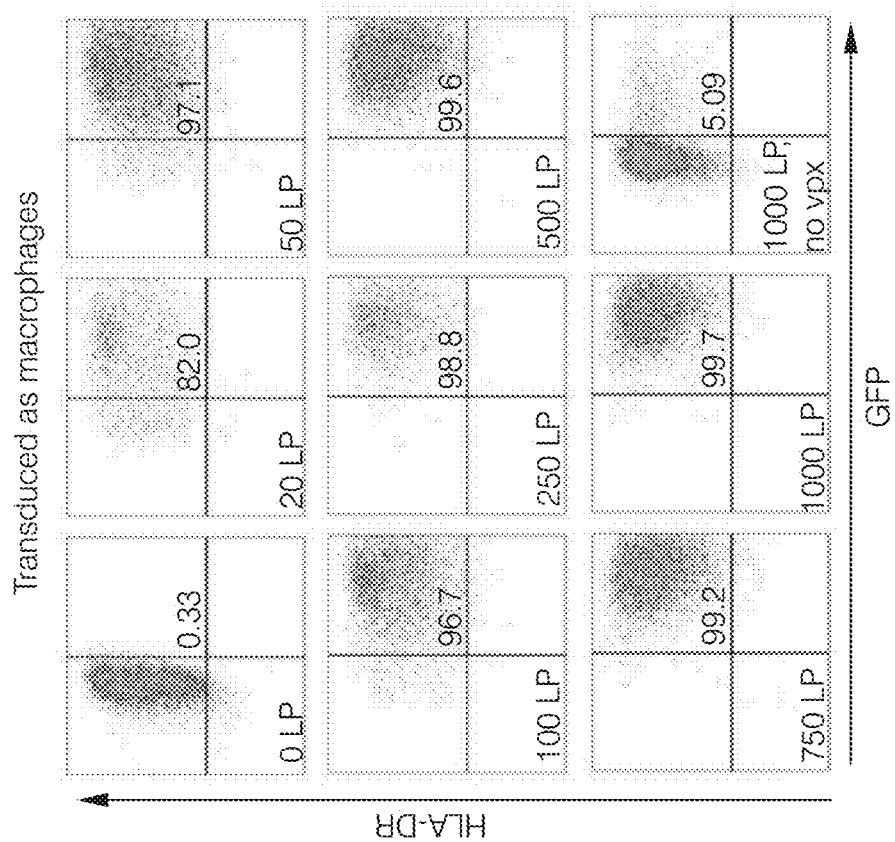
FIGS. 25A, 25B, 25C, 25D and 25E show that GM-CSF-differentiated macrophages and monocytes can be infected with Vpx+ lentivirus in a dose-dependent fashion.
Figure 25B:
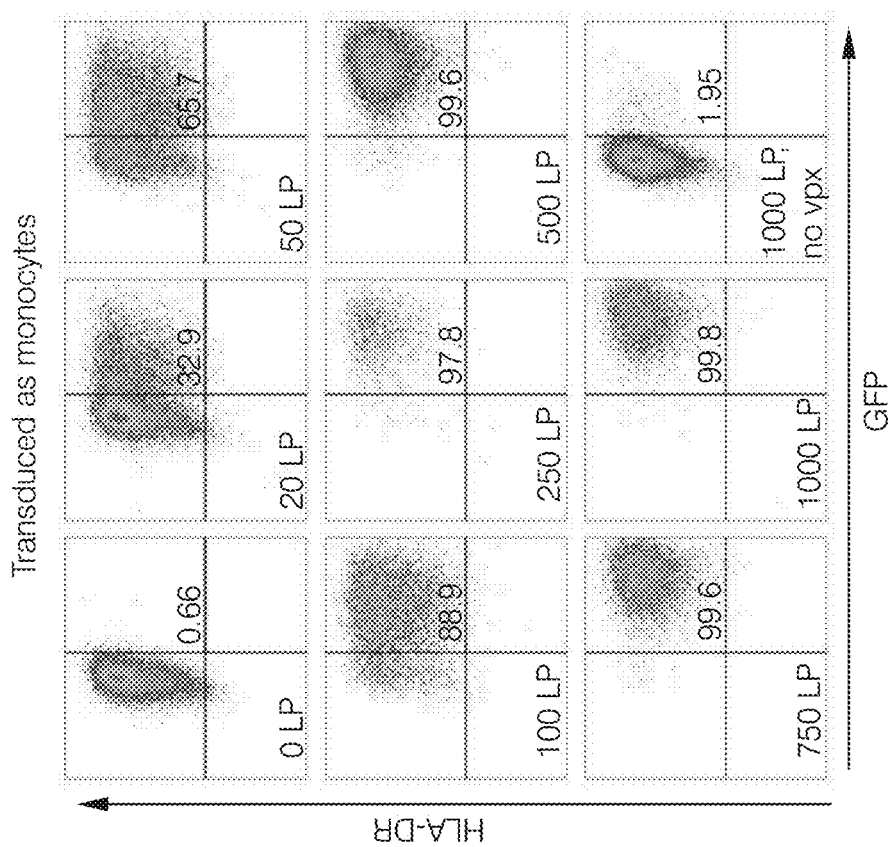
Figure 25C:
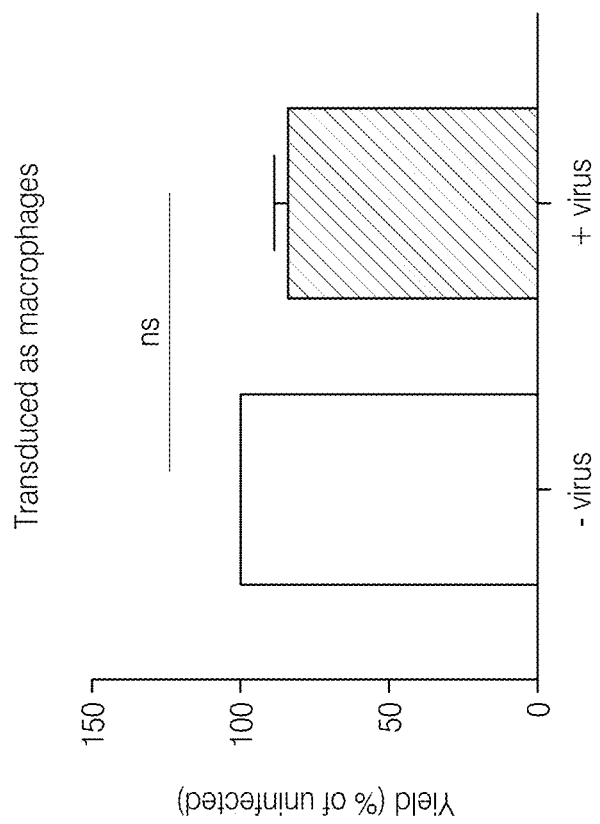
Figure 29A:
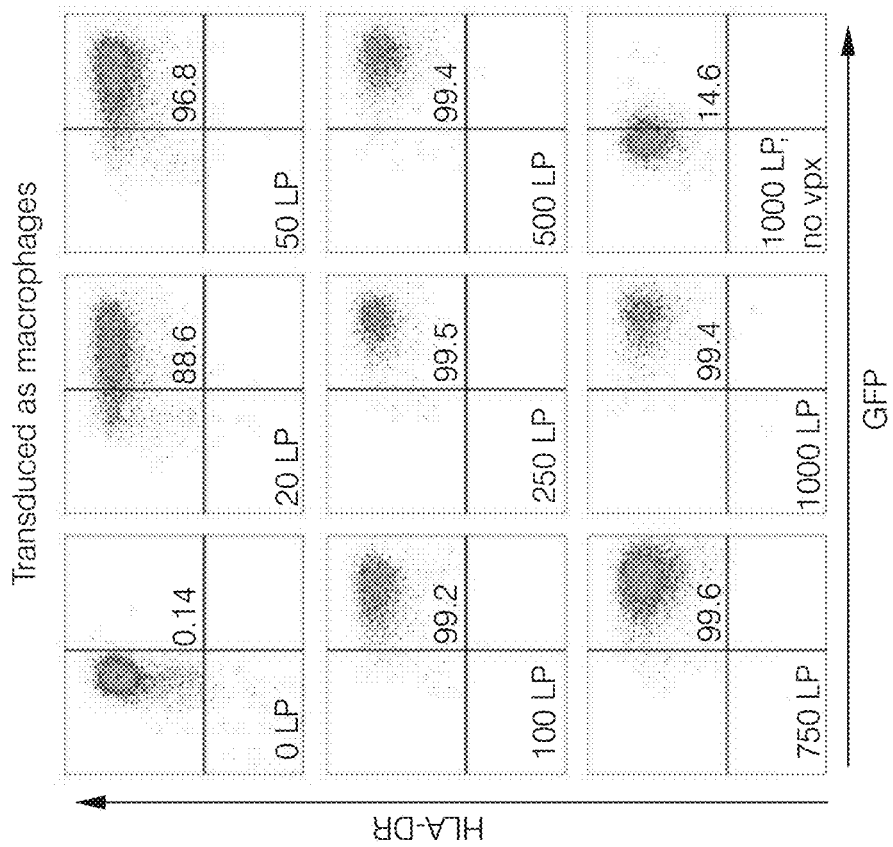
FIGS. 29A, 29B and 29C show that M-CSF-differentiated macrophages and monocytes can be infected with Vpx+ lentivirus in a dose-dependent manner.

Because all subsequent experiments evaluated GEM expression of varied viral payloads that can't be normalized using traditional flow cytometry-based titering, the viral dose was standardized based on the amount of virus-associated p24, where 1 ng p24 is equivalent to $1.25 \times 10^7$ lentiviral particles (LP). To determine the minimal dose of Vpx-containing virus necessary to consistently achieve high transgene expression, both pro-inflammatory macrophages differentiated in GM-CSF were transduced (FIG. 25A, representative of 3 independent experiments) and anti-inflammatory macrophages differentiated in M-CSF (FIG. 29A) on day 7 of differentiation with a range of lentiviral particles per cell (LP/cell). GFP expression was evaluated after an additional seven days in culture (FIG. 25A, FIG. 29A). It was found that the two phenotypes have similar transduction efficiencies following infection with Vpx-containing virions at all doses tested, nearing 100% at concentrations as low as 250 LP/cell. Importantly, infection with 250 LP/cell following differentiation with GM-CSF did not significantly impact viability (FIG. 25C). Virions packaged without Vpx had very poor transduction efficiency in both GM-CSF (5.09%) and M-CSF (14.6%) differentiated macrophages at the highest concentration tested (1000 LP/cell) (FIG. 25A, FIG. 29A).

Figure 25D:
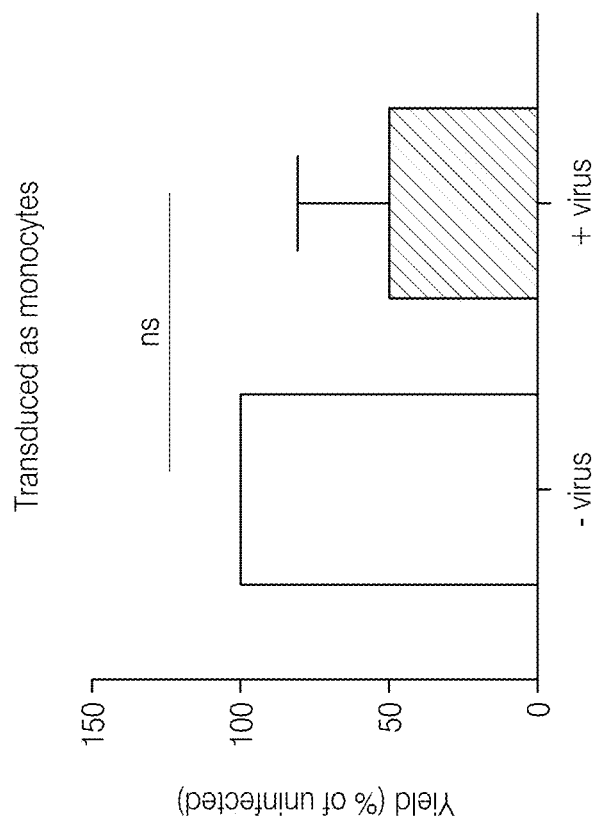
Figure 25E:
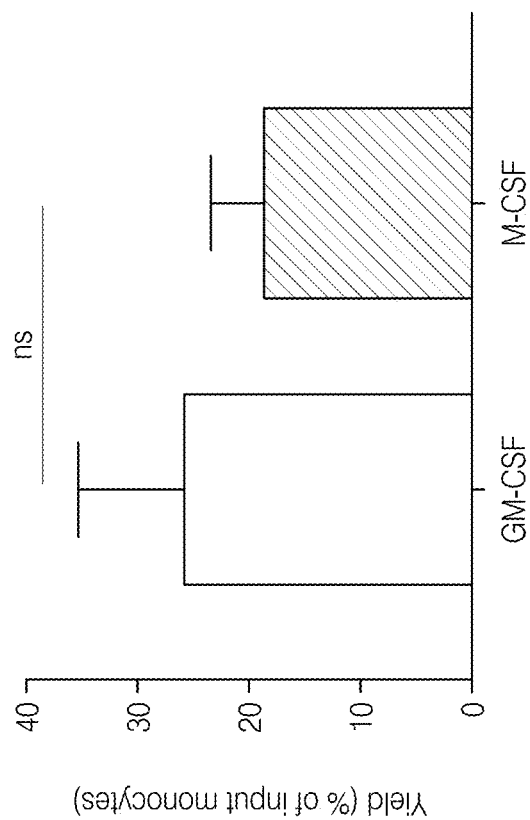
Figure 29B:
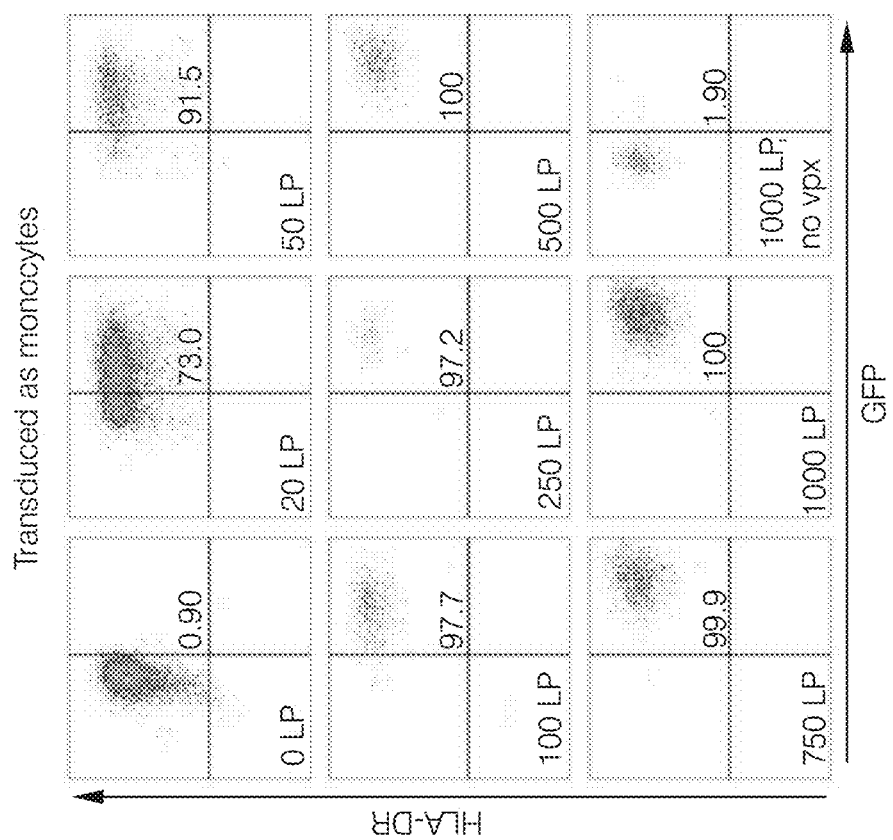
Figure 29C:
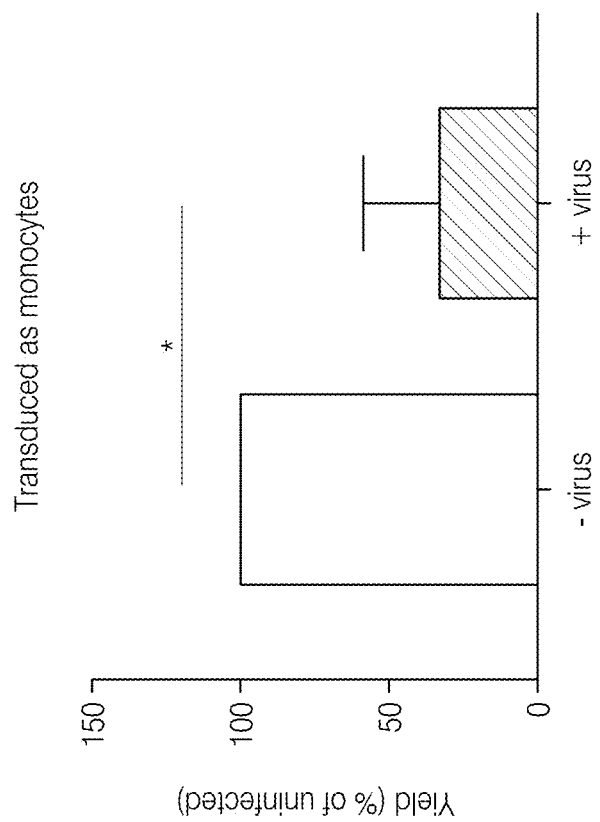

One of the challenges of treating patients with relapsed disease is the time between apheresis to delivery of an autologous cellular therapy, which can be several days to weeks for CAR T cell products (Kaiser A D, Assenmacher M, Schroder B et al. Towards a commercial process for the manufacture of genetically modified T cells for therapy. Cancer Gene Ther 2015; 22:72-78; incorporated by reference in its entirety herein). To determine if time and cost of developing a clinical monocyte-derived cell product for patients could be reduced, it was tested whether freshly isolated CD14+ monocytes could be concurrently transduced and differentiated. It was found that transduction of monocytes at the time of selection and induction in GM-CSF or M-CSF (day 0) resulted in similar dose-dependent proportions of GFP+ macrophages as consecutive differentiation and transduction (FIG. 25B, FIG. 29B). However, this approach had a significant impact on macrophage viability. Although differentiation in GM-CSF or M-CSF without virus resulted in approximately 20-30% yields relative to the original number of CD14+ cells (FIG. 25E), differentiation in combination with infection with 250 LP/cell further reduced yields by 49.7% in GM-CSF, and 67.4% in M-CSF differentiated macrophages (FIG. 25D, FIG. 29C, respectively).

Figure 30A:
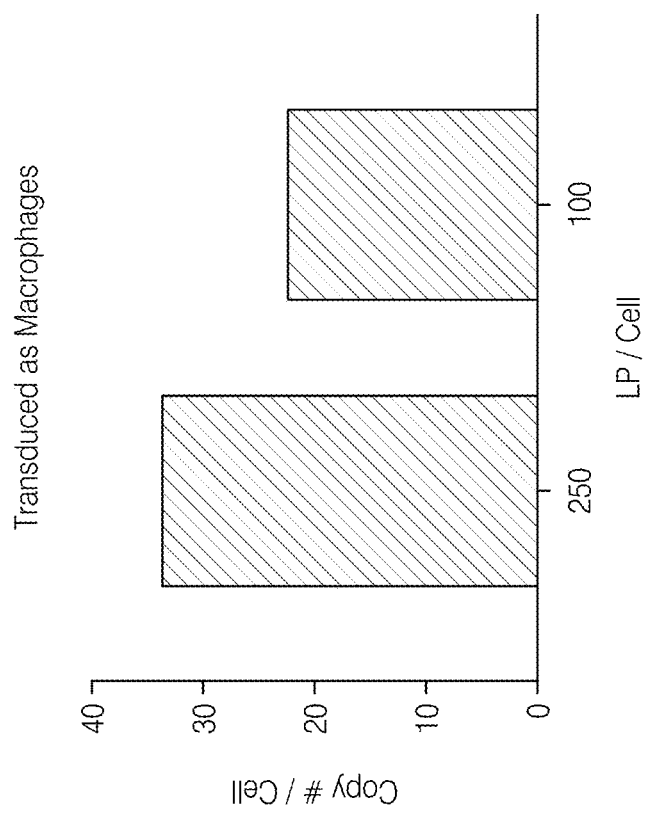
FIGS. 30A and 30B shows lentiviral integration events per cell. Cells were transduced (FIG. 30A) as macrophages (Day 7) or (FIG. 30B) as monocytes (Day 0) with 100 or 250 GFP-ffluc-encoding LP/cell. Genomic DNA was isolated 3 days post transduction. To calculate the number of vector integration sites per cell qPCR was performed for WPRE and the albumin gene. Lentiviral copy number per cell was calculated by multiplying the ratio of pg of WPRE/Albumin by two.
Figure 30B:
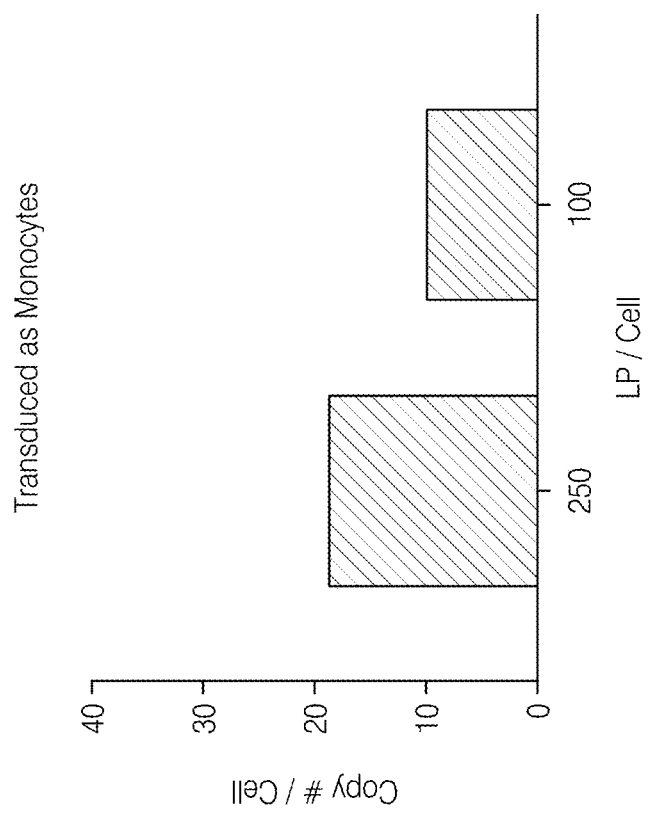

Successful clinical development of a virally-transduced adoptive cellular therapy should balance efficacy and safety. High transgene expression and transduction efficiency is often associated with a high rate of lentiviral integration into the host cell genome. It is important to control the integration rate because increased vector copy numbers increase the likelihood of insertional mutagenesis or toxic levels of transgene synthesis. To determine the number of lentiviral copies per cell, genomic DNA was isolated from macrophages that had been transduced on day 0 of differentiation, or after 7 days of differentiation with Vpx-containing lentivirus encoding GFP-ffluc. In a representative experiment, the number of lentiviral copies per cell was found to be 34 and 22 when cells were transduced with 250 or 100 LP/cell, respectively, as macrophages (FIG. 30A) and 18 and 10 when the cells were transduced as monocytes (FIG. 30B).

Monocyte-Derived Macrophages can Stably Express Lenti-virally-Encoded Genes

Figure 13A:
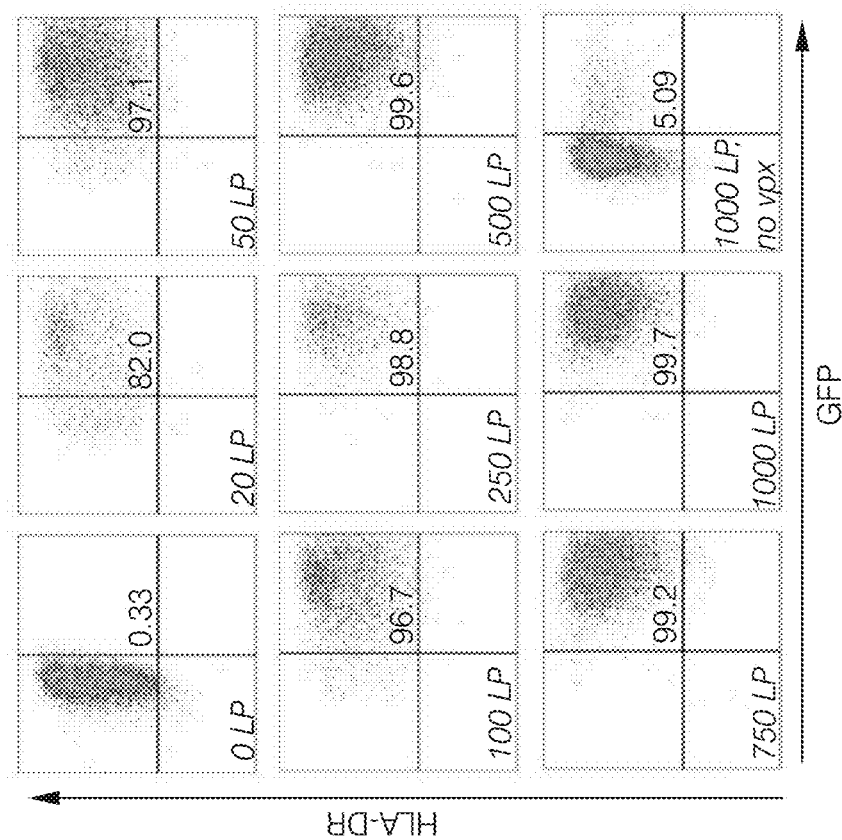
FIGS. 13A, 13B, 13C and 13D show that macrophages and monocytes can be infected with Vpx+ lentivirus in a dose-dependent fashion. GM-CSF (FIG. 13A) or M-CSF (FIG. 13B) monocyte-derived macrophages were infected on day 7 of differentiation with 20, 50, 100, 250, 500, 750, or 1000 GFP-encoding lentiviral particles (LP) per cell containing Vpx, or 1000 LP/cell without Vpx. Seven days after infection (14 days after isolation), the frequency of the population positive for both HLA-DR and GFP (upper right quadrant) was quantified by flow cytometry. Data are representative of 3 independent replicates.
Figure 13B:
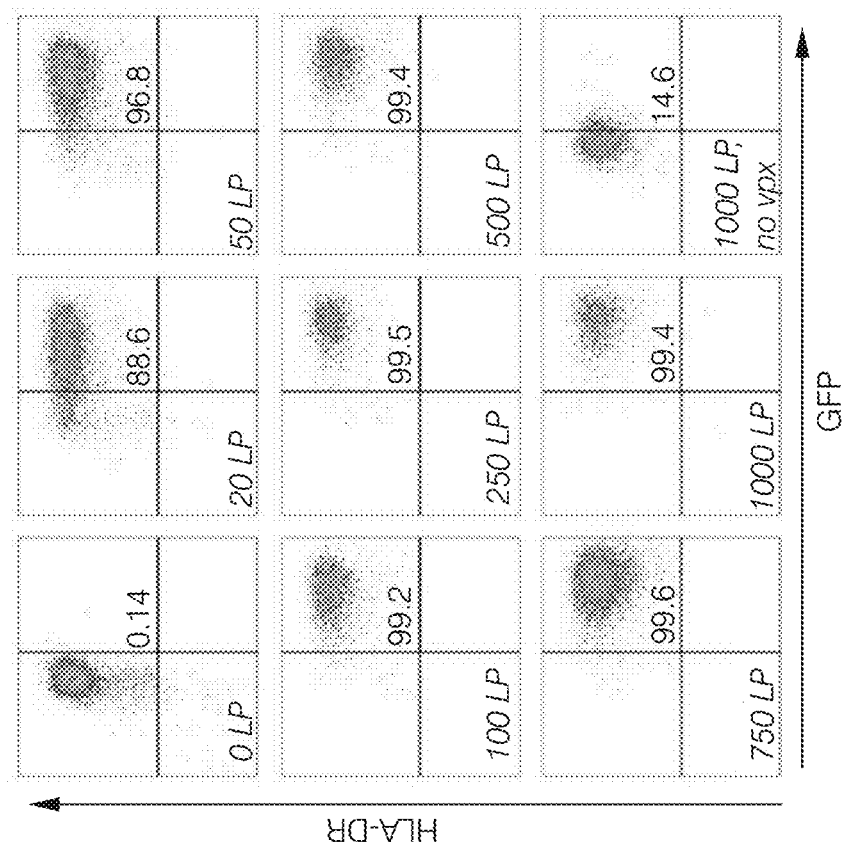

Previous reports have demonstrated that monocyte-derived dendritic cells that are differentiated using granulocyte macrophage colony stimulating factor (GM-CSF) and IL-4 or pro-inflammatory macrophages differentiated using GM-CSF alone, can be transduced at high efficiency when lentiviral particles are packaged with Vpx. To determine if this system was applicable to monocytes differentiated to an anti-inflammatory population using macrophage colony stimulating factor (M-CSF), epHIV7:GFP-ffluc was packaged, which is a lentiviral backbone currently in use in clinical trials (NCT01683279, NCT02311621), with Vpx using a standard lentivirus production protocol. Monocyte-derived macrophages were transduced after seven days of culture in the presence of GM-CSF or M-CSF with a range of lentiviral particles (LP) per cell, and evaluated GFP expression after an additional seven days in culture (FIG. 13A, 13B). It was found that the two phenotypes have similar transduction efficiencies following infection with Vpx-containing virions at all doses tested, nearing 100% at concentrations as low as 250 LP/cell. In contrast, virions packaged without Vpx had very poor transduction efficiency in both GM-CSF (5.09%) and M-CSF (14.6%) differentiated macrophages, even at 1000 LP/cell.

Figure 13C:
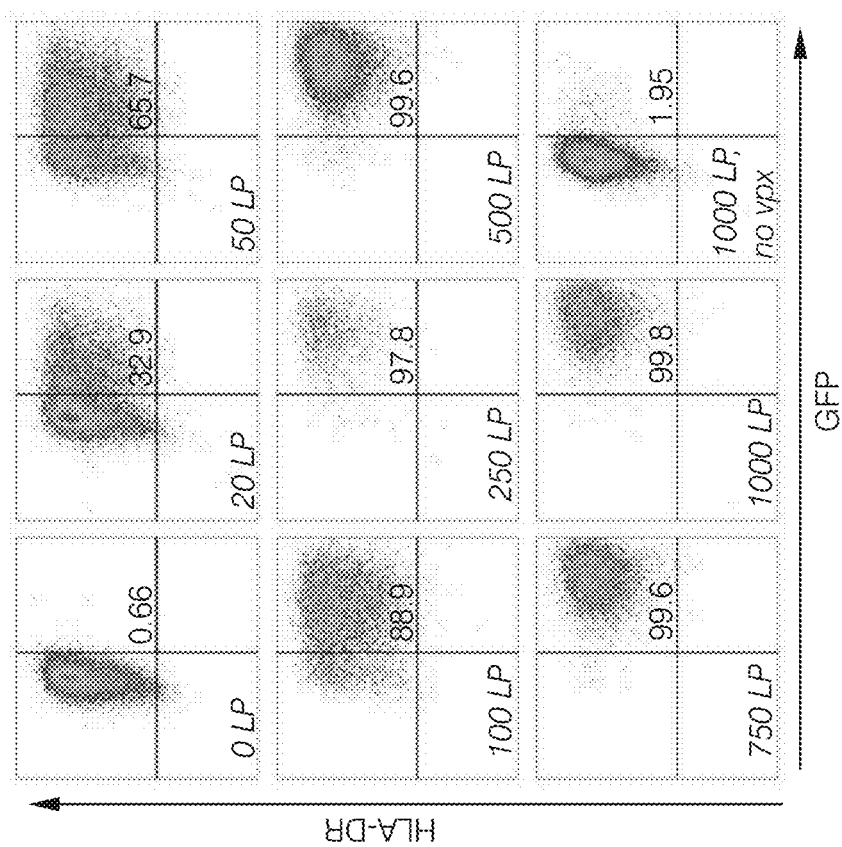
Figure 13D:
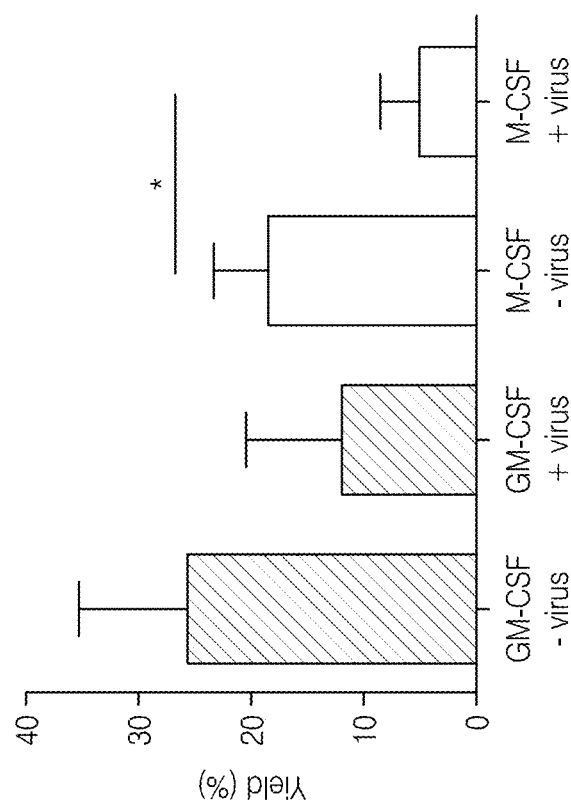
Figure 14:
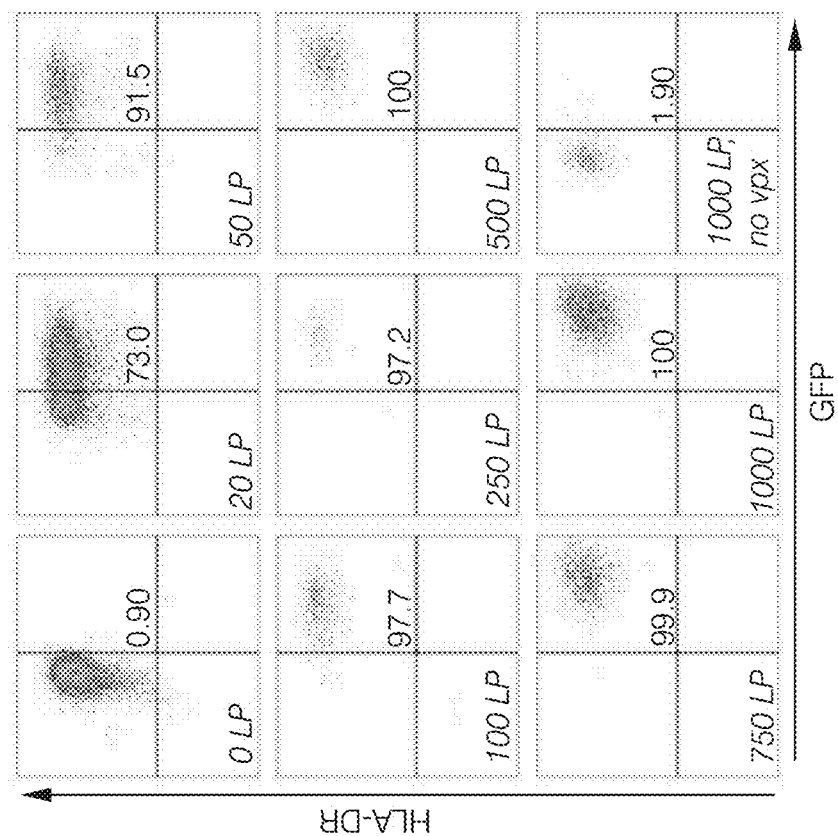
FIG. 14 shows that concurrent differentiation with M-CSF and lentiviral infection results in dose-dependent GFP expression but low yields. Monocytes were concurrently differentiated in M-CSF and infected with 20, 50, 100, 250, 500, 750, or 1000 GFP-encoding LP/cell containing vpx, or 1000 LP/cell without vpx. Cells were analyzed by flow cytometry 14 days after isolation/infection. Percentage positive for HLA-DR and GFP are shown in the upper right quadrant.

One of the challenges of treating patients with relapsed disease is the time between apheresis to delivery of an autologous cellular therapy, which can be several days to weeks for CAR T cell products. To determine if the time and cost of developing a clinical product for patients could be reduced, it was determined whether freshly isolated CD14+ monocytes could be infected and differentiated concurrently. It was found that transduction of monocytes at the time of selection on day 0, during differentiation in GM-CSF or M-CSF resulted in similar dose-dependent proportions of GFP+ macrophages as consecutive differentiation and infection (FIG. 13C and FIG. 14).

GEMs Express Myeloid Cell Surface Markers and Respond to LPS/IFNγ Stimulation

Figure 15A:
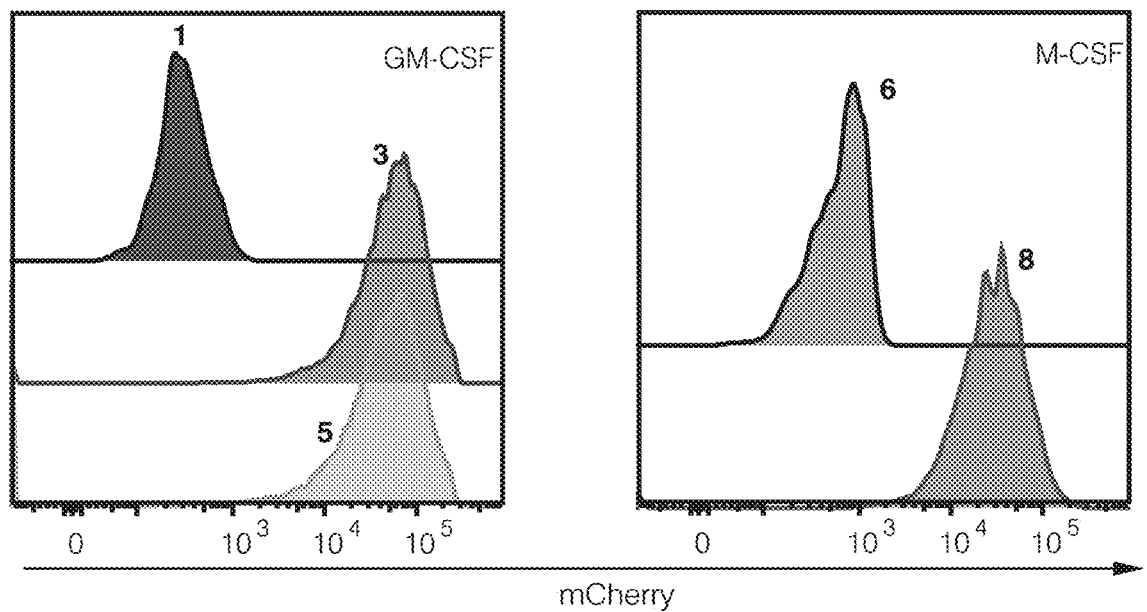
FIGS. 15A, 15B, 15C, 15D, 15E, 15F and 15G show that GEMs express standard myeloid cell surface markers and respond to LPS/IFNγ stimulation. GM-CSF or M-CSF monocyte-derived macrophages were infected on day 0 of differentiation with 250 LP/cell of lentivirus encoding mCherry. On day 6 cells were treated with fresh media or LPS/IFNγ for 18 hours then analyzed by flow cytometry. Macrophages were found to be 100% positive for mCherry expression (FIG. 15A) regardless of treatment.
Figure 15B:
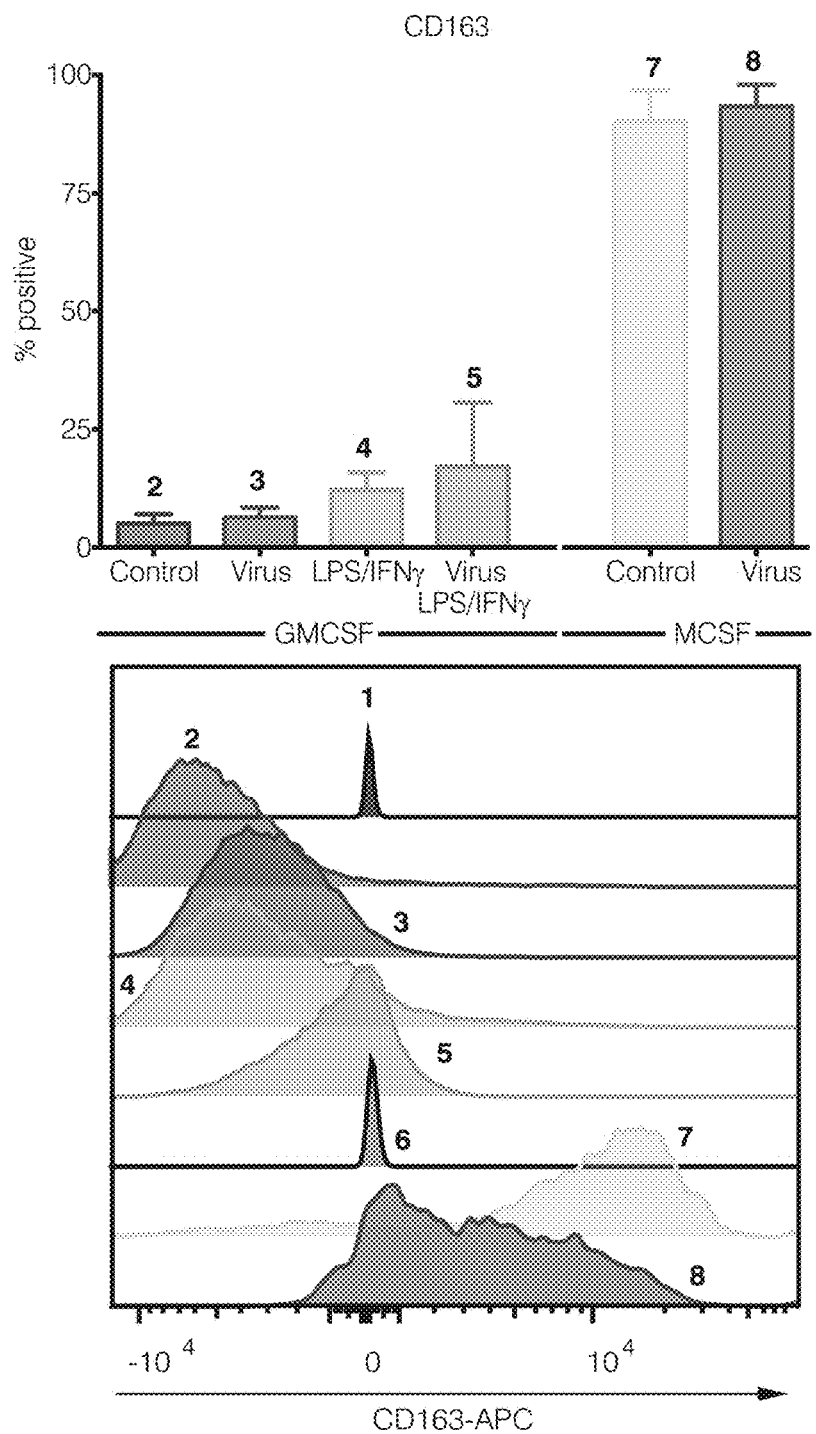
Figure 15C:
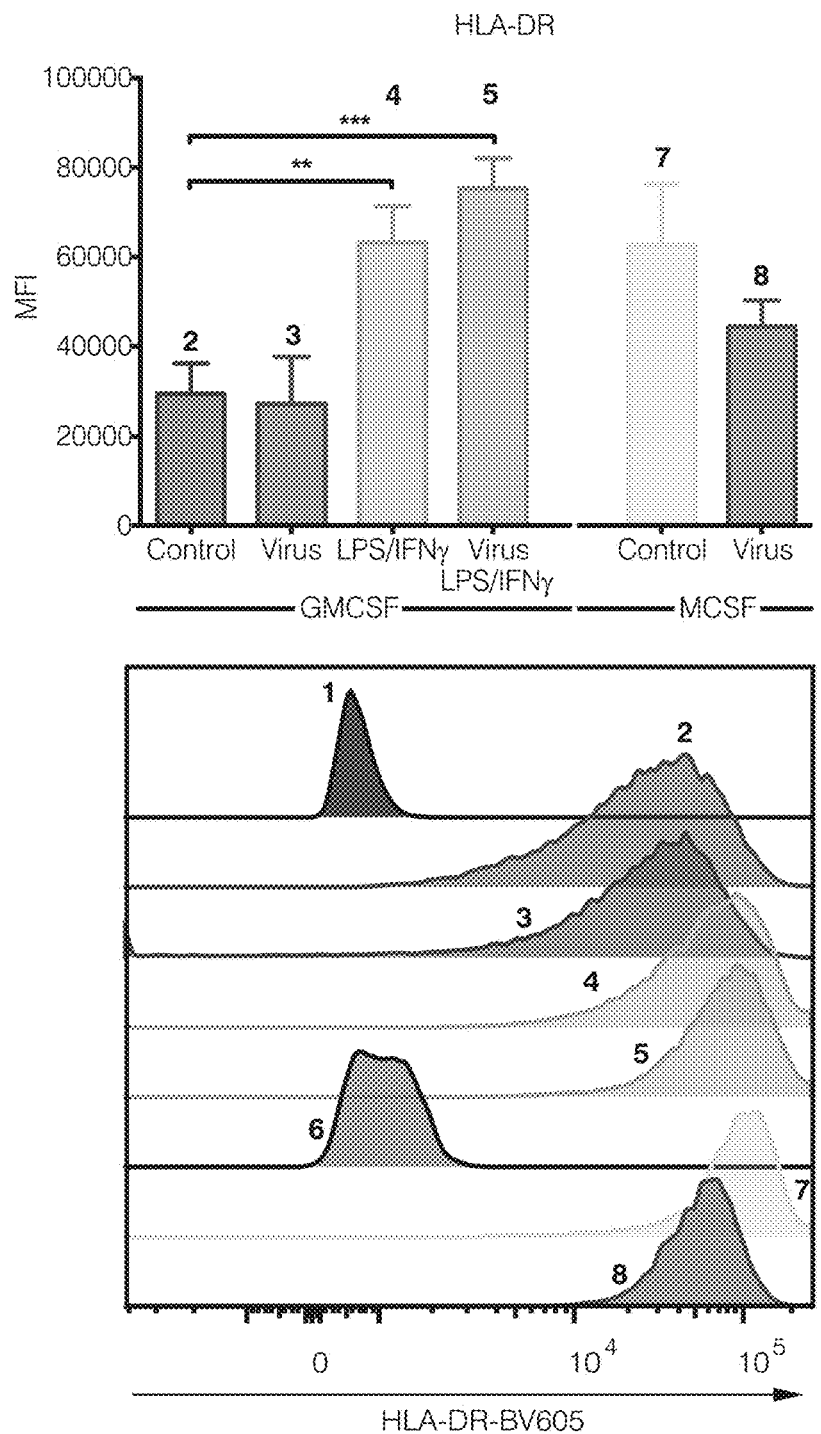
Figure 15D:
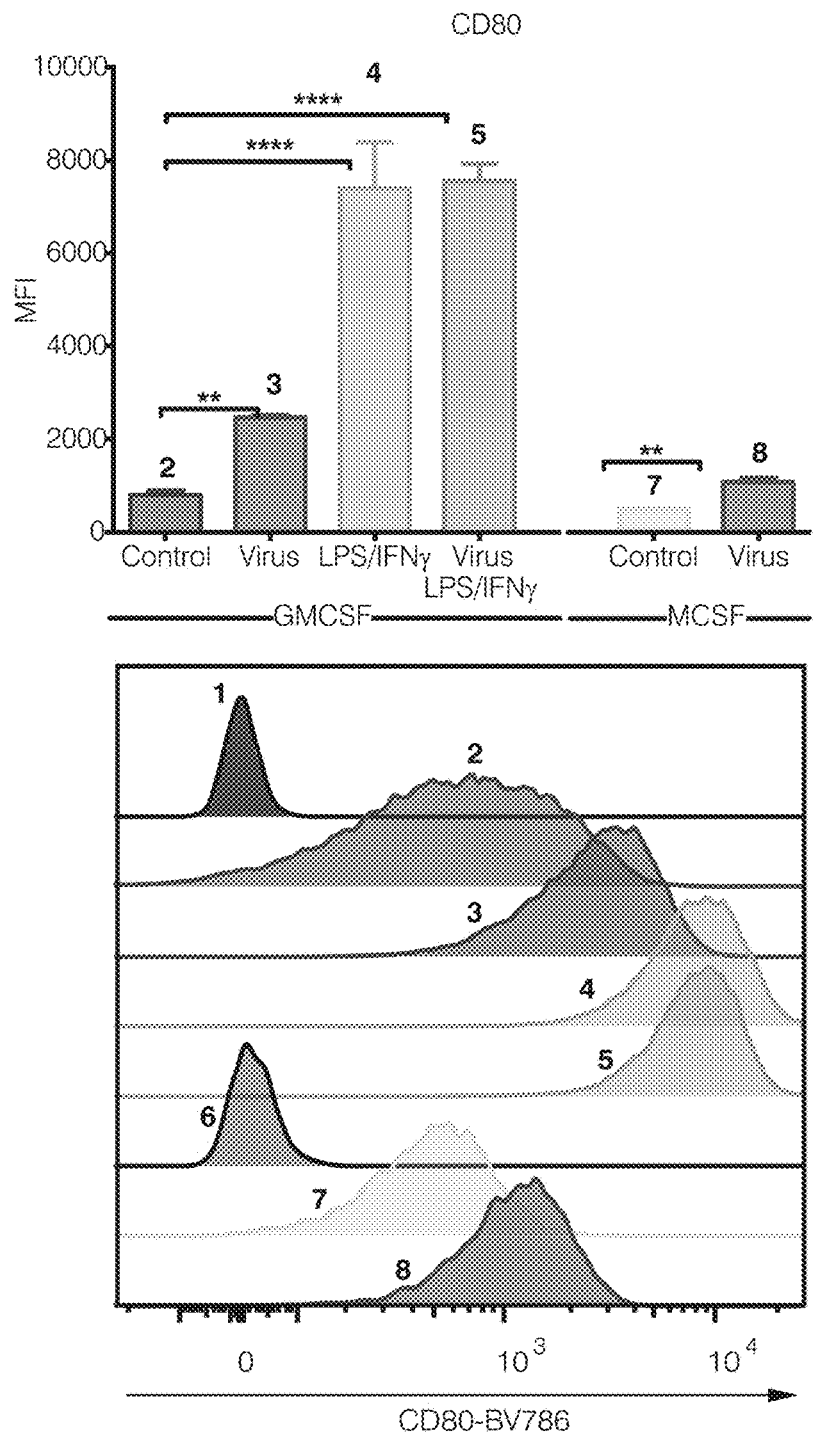
Figure 15E:
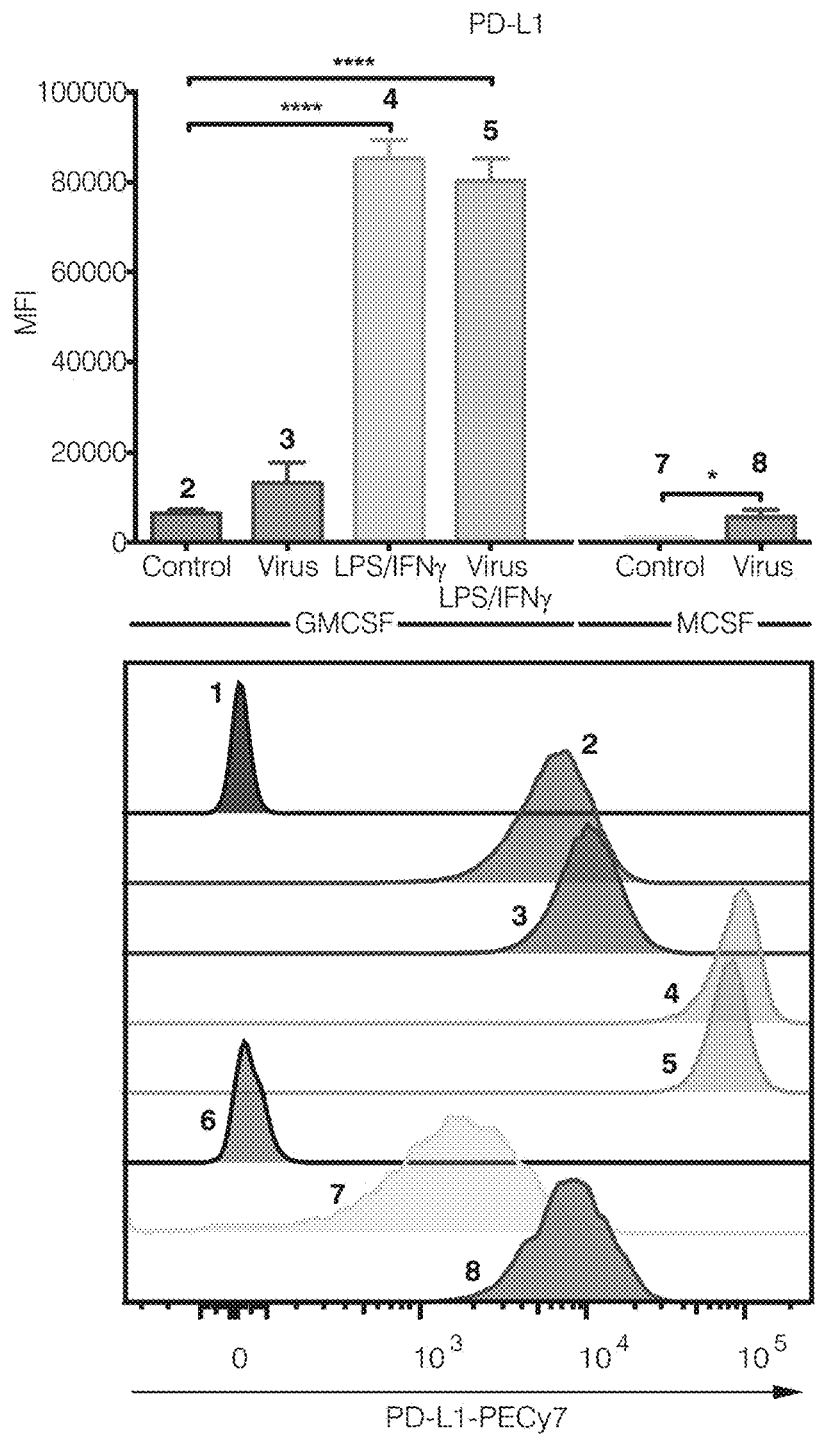
Figure 15F:
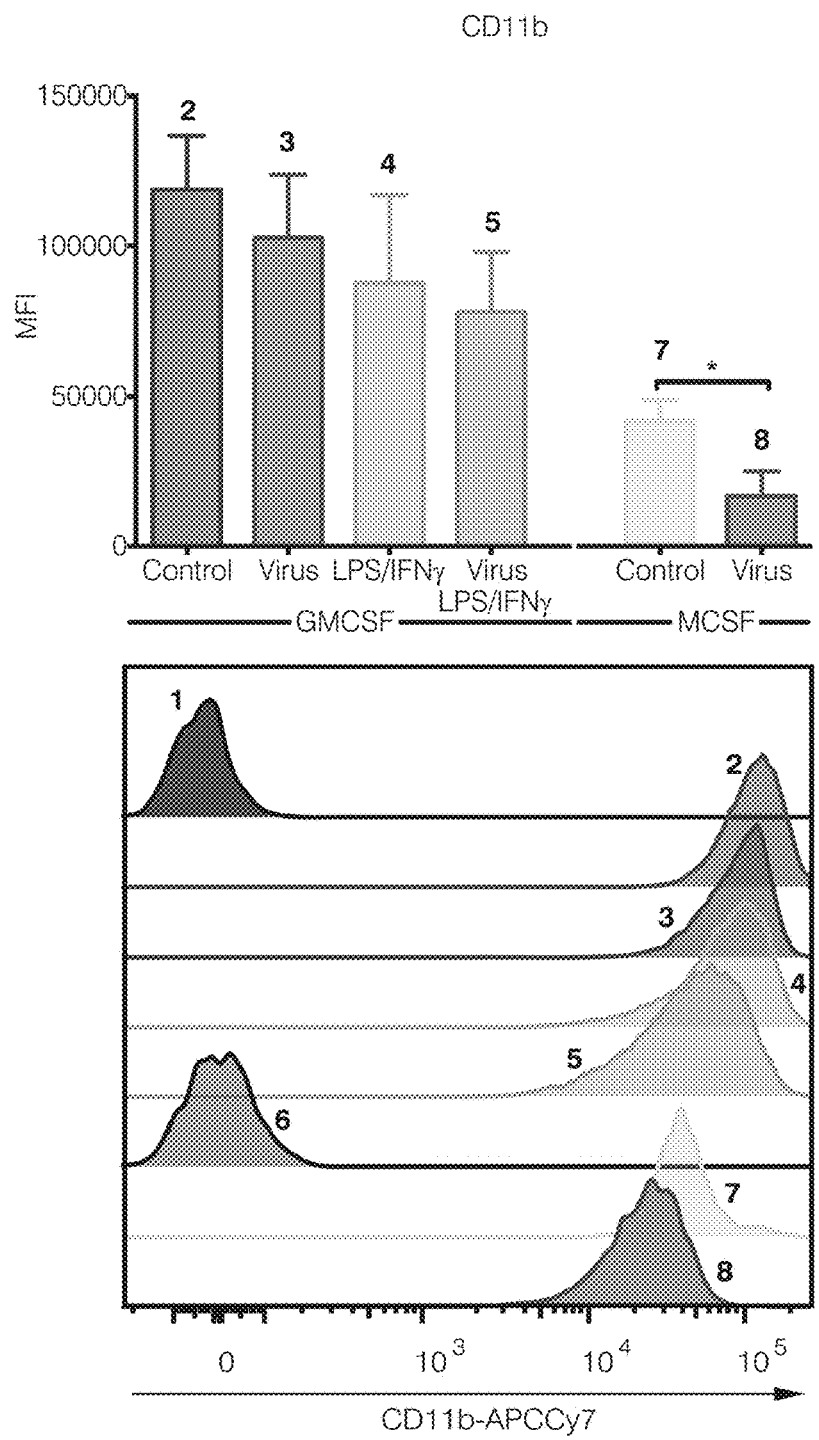
Figure 15G:
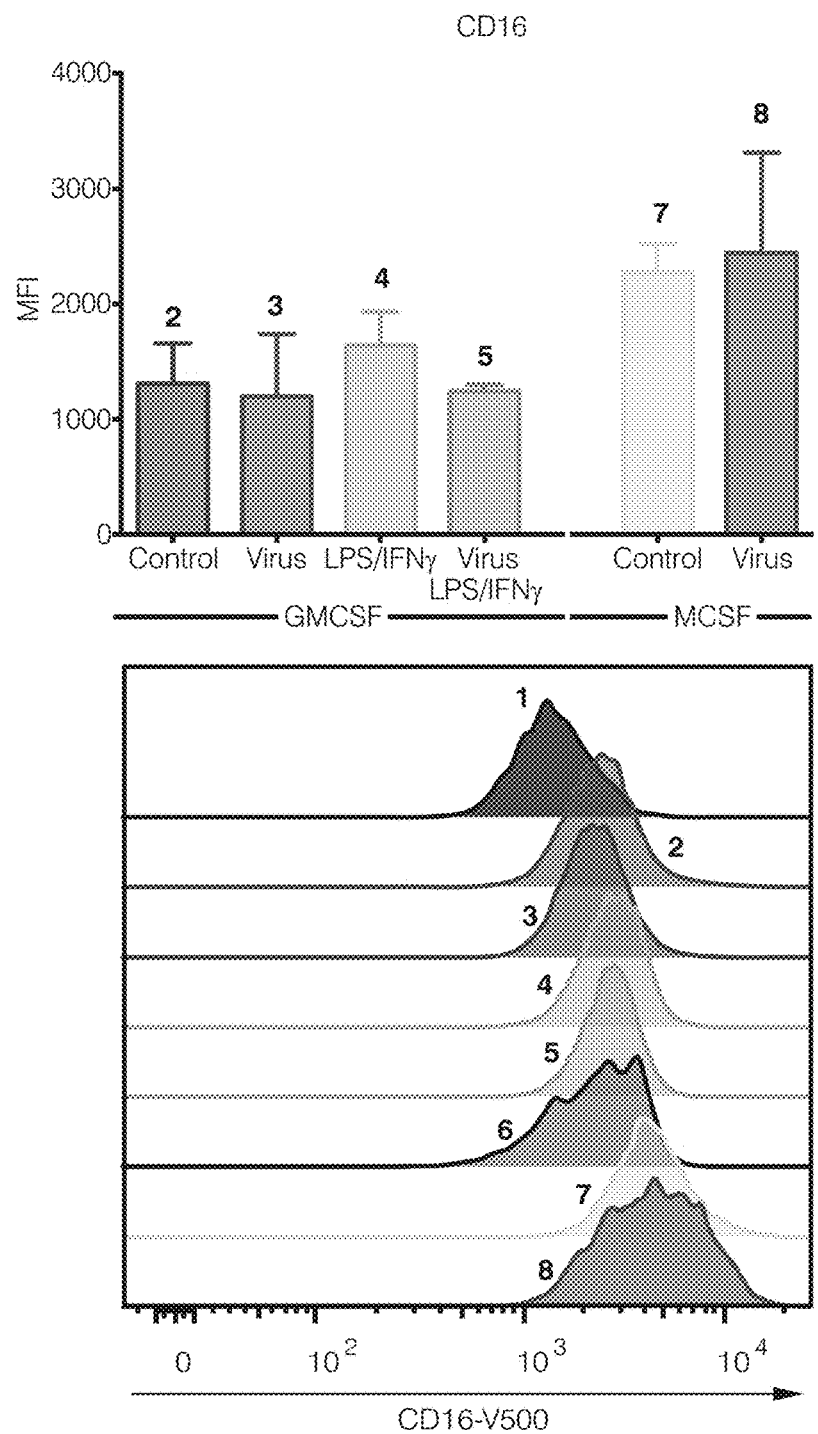

The next set of experiments were performed to determine if viral infection would impact differentiation of monocytes to pro or anti-inflammatory macrophages. In order to characterize the phenotype of both GM-CSF (FIG. 13A) and M-CSF GEMs monocytes (FIG. 13B) were transduced with epHIV7.2 lentivirus encoding the red fluorescent protein mCherry at a viral concentration of 250 LP/cell and concurrently differentiated the cells in GM-CSF or M-CSF. GEMs analyzed for mCherry expression using flow cytometry seven days later were 100% positive, regardless of differentiation conditions (FIG. 15A). GEMs were further analyzed by flow cytometry for surface expression of the common myeloid markers CD163, a scavenger receptor; HLA-DR, a receptor that presents internalized antigens to T cells; CD80, a co-stimulatory signal for T cells; PD-L1, a T cell inhibitory protein; CD11b, an integrin responsible for cell adhesion; CD16, an Fc receptor (FIG. 15B-G); CD80, which delivers a costimulatory signal to T cells, Major Histocompatibility Complex II (HLADR), which presents internalized antigens to T cells, the immunosuppressive protein PD-L1, and the scavenger receptor CD163 (FIG. 22C, FIG. 23A-23F). As expected, a higher fraction of M-CSF macrophages expressed the canonical anti-inflammatory macrophage marker CD163 than GM-CSF macrophages (90% vs 5%) (FIG. 15B). Importantly, GEMs are responsive to stimulation with the potent toll like receptor 4 (TLR4) agonist, LPS, and the pro-inflammatory cytokine, IFNγ, as evidenced by their up-regulation of proteins associated with improved antigen presentation, HLA-DR and CD80, as well as PD-L1, which is consistent with previous findings (FIG. 15C-E). Transduction with Vpx-containing virus did not have a significant impact on the expression of many of these markers, and CD16 was unaffected by any treatment (FIG. 15G). Interestingly, however, it was found that viral transduction resulted in a 60% decrease in CD11b expression in M-CSF differentiated GEMs (FIG. 15F), and 3-fold increase in CD80 in unstimulated, GM-CSF differentiated GEMs (FIG. 15D). The impact of increased CD80 expression on antigen presentation will be the subject of future investigations. The EF1a-Her2tG protein for TLR4 signaling is encoded by a sequence set forth in SEQ ID NO: 26

(GGCATTGANNGGTGCCTAGAGAAGGTGGCGCGGGGTAAACTGGGAAAGT

GATGTCGTGTACTGGCTCCGCCTTTTTCCCGAGGGTGGGGGAGAACCGTA

TATAAGTGCAGTAGTCGCCGTGAACGTTCTTTTTCGCAACGGGTTTGCCG

CCAGAACACAGCTGGGCTAGCATGTTGCTCCTCGTAACCTCCCTTTTGTT

GTGTGAGCTCCCTCACCCAGCTTTTCTGCTGATCCCGTGCCACCCTGAGT

GTCAACCACAGAATGGTAGCGTTACCTGCTTTGGGCCTGAAGCTGATCAG

TGCGTTGCATGTGCTCACTATAAGGATCCGCCATTTTGCGTGGCGCGGTG

CCCTTCGGGCGTGAAACCTGATCTAAGCTATATGCCGATCTGGAAGTTTC

CCGATGAGGAGGGGGCTTGCCAGCCATGTCCCATCAATTGTACACATAGC

TGCGTCGACTTAGATGACAAGGGGTGCCCGGCGGAACAACGCGCCTCGCC

CCTTACTGGAGGCGGATCGGGAGGCGGCTCAATAATATCAGCGGTAGTTG

GTATACTGCTGGTGGTGGTTCTCGGAGTAGTATTTGGGATATTGATAGGC

GGCGGAGAGGGCAGAGGAAGTCTTCTAACATGCGGTGACGTGGAGGAGAA

-continued

```
TCCCGGCCCTAGGATGTGCCGAGCCATCTCTCTTANGCGCTTGCTGCTGC

TGCTGCTGCAGCTGTCACAACTCCTAGCTGTCACTCAAGGGAAGACGCTG

GTGCTGGGGAAGGAAGGGGAATCAGCAGAACTGCCCTGCGAGAGTTCCCA

GAAGAAGATCACAGTCTTCACCTGNAAGTTCTCTGACCAGANGAAGATTC

TGGGGCAGCATGGNAAAGTGTATTAATTAGAGGAGGTTCGCCTTCGCAGT

TTGATCGTTTTGATTCCAAAAAAGGGCATGGGANNAAAGGATCGTTTCCN

NTCATCATCAATAAACTTNAGATGGAAGANTCTCAGACTTANNNNNNTGTG

AGCTG)
```

Figure 31A:
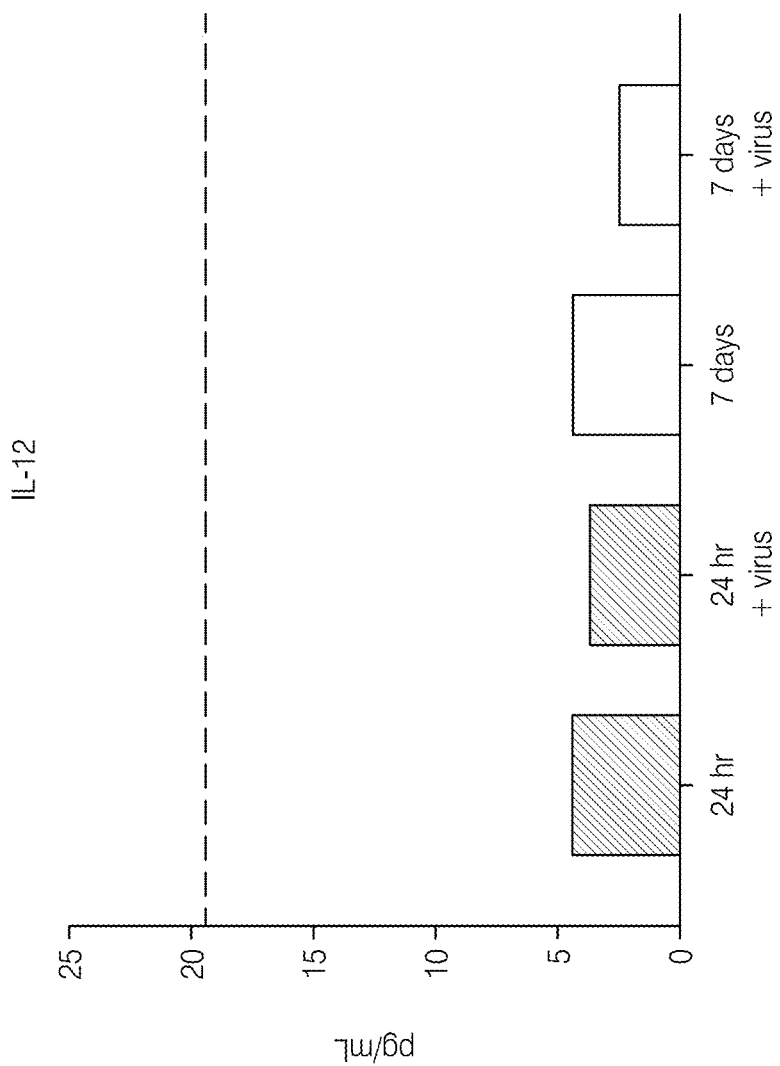
FIGS. 31A, 31B and 31C show cytokine production following viral transduction. Conditioned media samples from wild type (WT) and virally transduced monocytes were analyzed 24 hours or 7 days post-transduction by Luminex for (FIG. 31A) IL12 (p40/p70), (FIG. 31B) TNF, and (FIG. 31C) IFNα. All 3 analytes were below the limit of detection (dotted line), regardless of treatment.
Figure 31B:
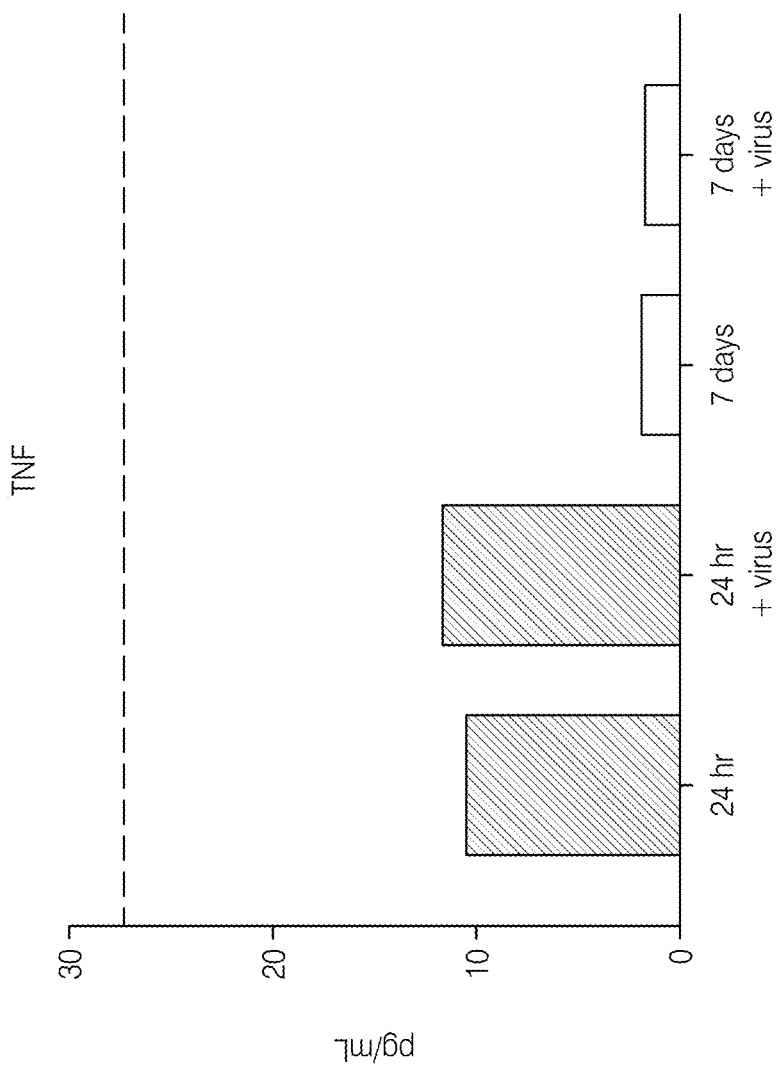
Figure 31C:
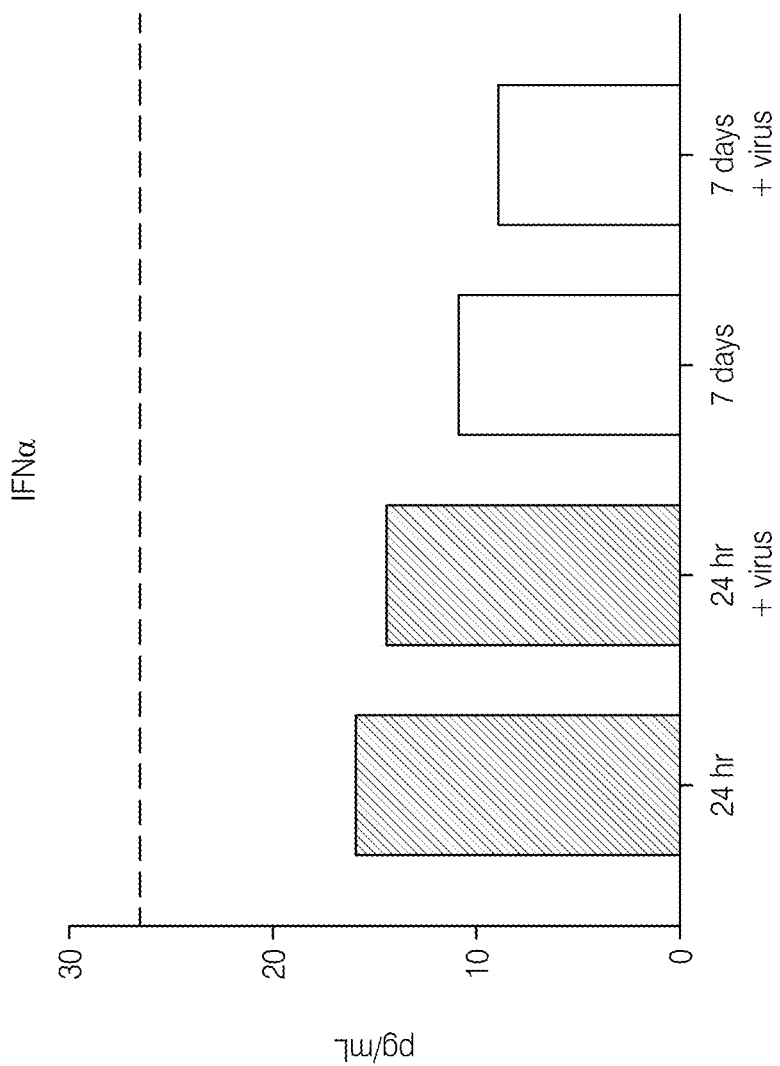

Because pattern recognition receptors such as TLR3 and TLR7 recognize viral RNA, and respond by up-regulating cytokines and chemokines to mount an immune response (Xagorari A, Chlichlia K. Toll-like receptors and viruses: induction of innate antiviral immune responses. Open Microbiol J 2008; 2:49-59; incorporated by reference in its entirety herein), it was desired to determine if viral infection impacted GEM secretion of canonical pro-inflammatory cytokines. To evaluate this, monocytes were infected on day 0 with 0 or 250 LP/cell mCherry Vpx+ lentivirus and differentiated in GM-CSF. Media was collected at 24 hours and 7 days post-transduction, for Luminex analysis of Tumor Necrosis Factor α (TNFα), IL-12, and Type I Interferons (FIGS. 31A-31C). All 3 analytes fell below the limit of detection for the assay, suggesting that lentiviral transduction does not induce pro-inflammatory cytokine secretion.

Genetically Engineered Macrophages Persist in Mouse Glioma Model

Figure 16A:
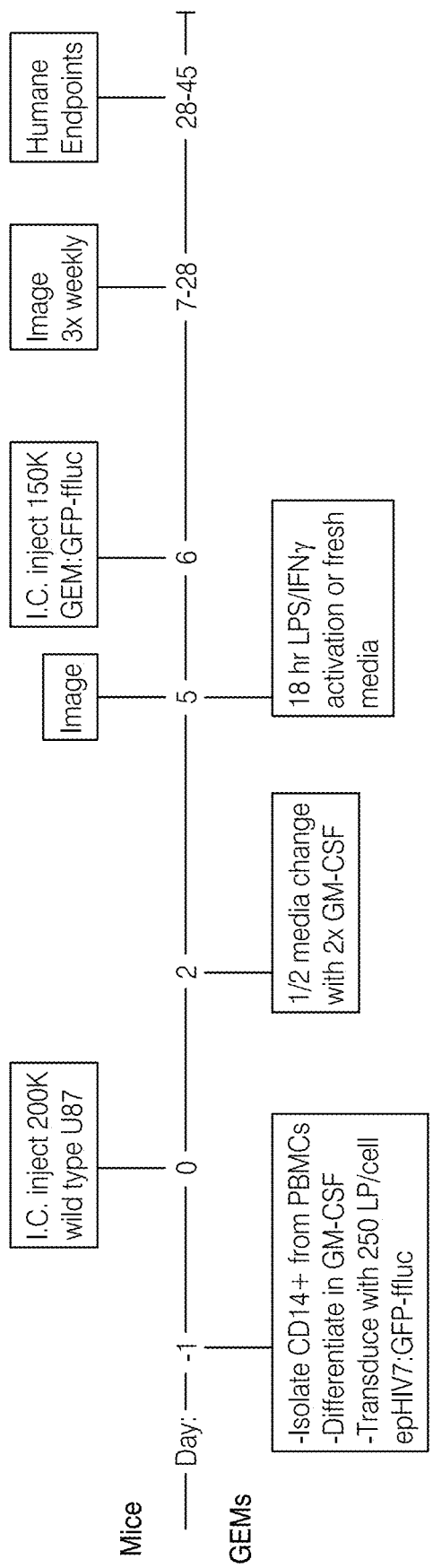
FIGS. 16A, 16B, 16C and 16D show that GEMs persist within a glioma xenograft model.
Figure 17A:
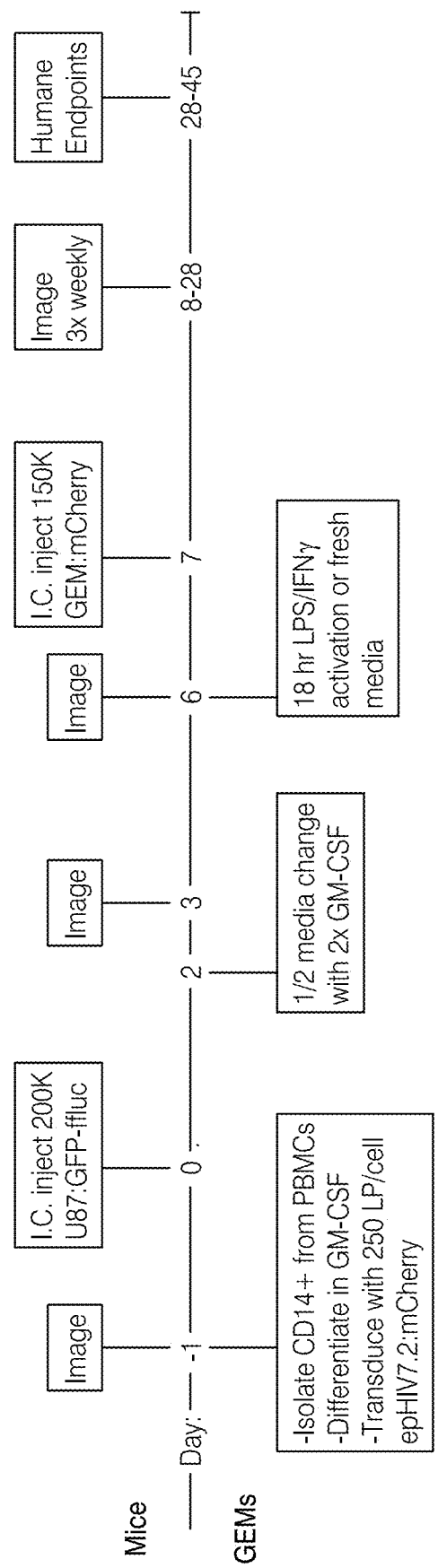
FIGS. 17A, 17B, 17C, 17D, 17E, 17F and 17G show that GEMs do not affect tumor growth in a glioma xenograft model.

These are the first tests to evaluate the therapeutic potential of adoptively transferred, lentivirally engineered macrophages derived from primary human monocytes. Evidence supporting the anti-tumor effect of pro-inflammatory macrophages comes from several mouse studies where locally or systemically administered TLR agonists overturn the tumor supportive program of TAMs and restore immune surveillance. Evidence supporting the anti-tumor effect of pro-inflammatory macrophages comes from several mouse studies where locally or systemically administered TLR agonists overturn the tumor supportive program of TAMs and restore immune surveillance (Peng J, Tsang J Y, Li D et al. Inhibition of TGF-beta signaling in combination with TLR7 ligation re-programs a tumoricidal phenotype in tumor-associated macrophages. Cancer Lett 2013; 331:239-249; Huang Z, Gan J, Long Z et al. Targeted delivery of let-7b to reprogramme tumor-associated macrophages and tumor infiltrating dendritic cells for tumor rejection. Biomaterials 2016; 90:72-84; Chang L S, Leng C H, Yeh Y C et al. Toll-like receptor 9 agonist enhances anti-tumor immunity and inhibits tumor-associated immunosuppressive cells numbers in a mouse cervical cancer model following recombinant lipoprotein therapy. Mol Cancer 2014; 13:60; Yu Q, Nie S P, Wang J Q et al. Toll-like receptor 4 mediates the antitumor host response induced by *Ganoderma atrum* polysaccharide. J Agric Food Chem 2015; 63:517-525; all incorporated by reference in their entireties herein). An ideal GEM is engineered to sustainably release factors such as IL-12 that are elicited by classical LPS/IFNγ activation and stimulate both the innate and adaptive immune systems (See FIG. 18A to 18CC) (Hao N B, Lu M H, Fan Y H et al. Macrophages in tumor microenvironments and the progression of tumors. Clin Dev Immunol 2012; 2012:948098; incorporated by reference in its entirety herein). Having demonstrated that GM-CSF-differentiated GEMs are responsive to LPS/IFNγ, it was desirable to test the feasibility of employing activated macrophages as a cellular therapeutic that is injected directly in to the brain. Specifically, it was desirable to determine if stimulated and unstimulated GEMs would survive in the TME, impact morbidity, or support tumor growth. To directly assess the behavior of GEMs, without the confounding effects of other immune cells, GEMs in the T and B lymphocyte-deficient NODSCID gamma (NSG) mouse were evaluated using an intracranial glioma xenograft model that has frequently been used for pre-clinical evaluations of cellular immunotherapies (Miao H, Choi B D, Suryadevara C M et al. EGFRvIII-specific chimeric antigen receptor T cells migrate to and kill tumor deposits infiltrating the brain parenchyma in an invasive xenograft model of glioblastoma. PLoS One 2014; 9:e94281; Kahlon K S, Brown C, Cooper L J et al. Specific recognition and killing of glioblastoma multiforme by inter-leukin 13-zetakine redirected cytolytic T cells. Cancer Res 2004; 64:9160-9166; Krenciute G, Krebs S, Torres D et al. Characterization and Functional Analysis of scFv-based Chimeric Antigen Receptors to Redirect T Cells to IL13Ralpha2-positive Glioma. Mol Ther 2016; 24:354-363; Shiina S, Ohno M, Ohka F et al. CAR T Cells Targeting Podoplanin Reduce Orthotopic Glioblastomas in Mouse Brains. Cancer Immunol Res 2016; 4:259-268; K K, Naik S, Kakarla S et al. T cells redirected to EphA2 for the immunotherapy of glioblastoma. Mol Ther 2013; 21:629-637; Hegde M, Corder A, Chow K K et al. Combinational targeting offsets antigen escape and enhances effector functions of adoptively transferred T cells in glioblastoma. Mol Ther 2013; 21:2087-2101; all incorporated by reference in their entireties herein). In these experiments 200,000 U87 cells were injected intracranially and allowed to establish tumor for six or seven days (FIG. 16A, 17A). For the initial experiment, freshly isolated monocytes were transduced with 250 LP/cell epHIV7:GFP-ffluc and differentiated them toward a pro-inflammatory phenotype in GM-CSF for six days (FIG. 16A). On the fifth day after differentiation and transduction, half of these GEMs were stimulated with LPS/IFNγ for 18 hours. 150,000 stimulated or unstimulated GEMs were injected into the established tumor and bioluminescence was monitored three times per week.

Figure 16B:
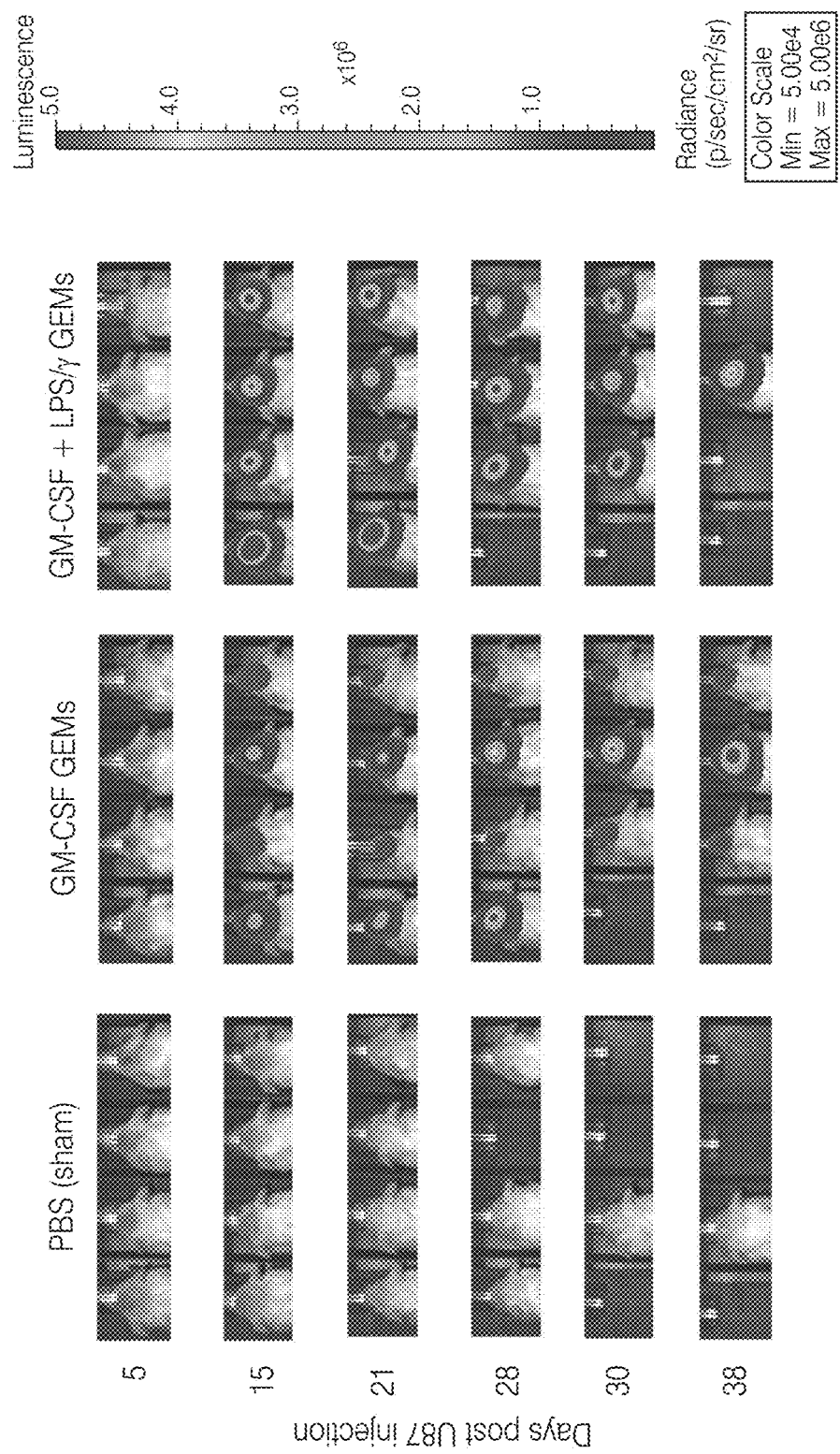
Figure 16C:
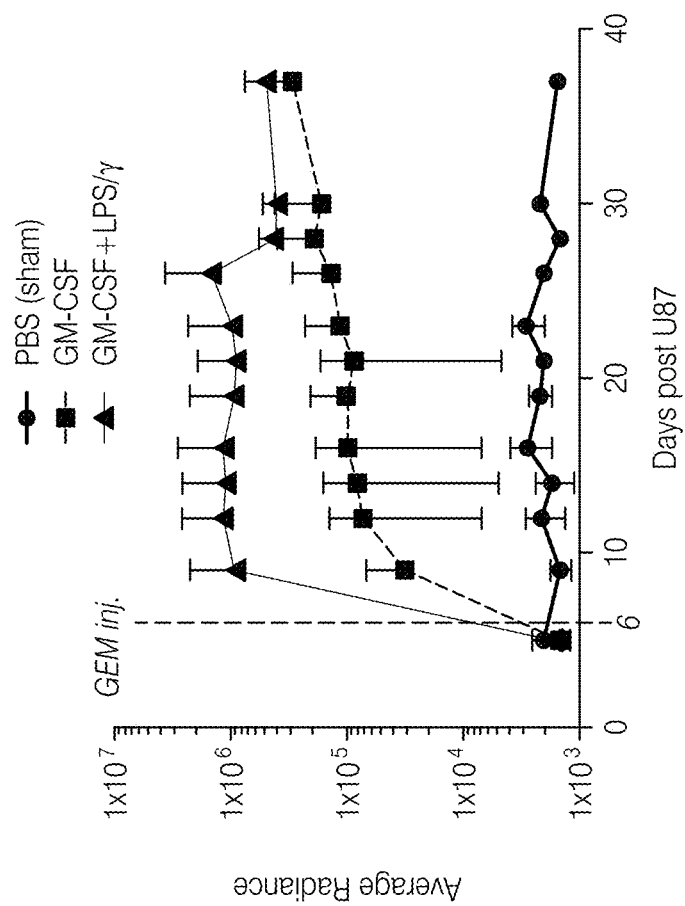
Figure 16D:
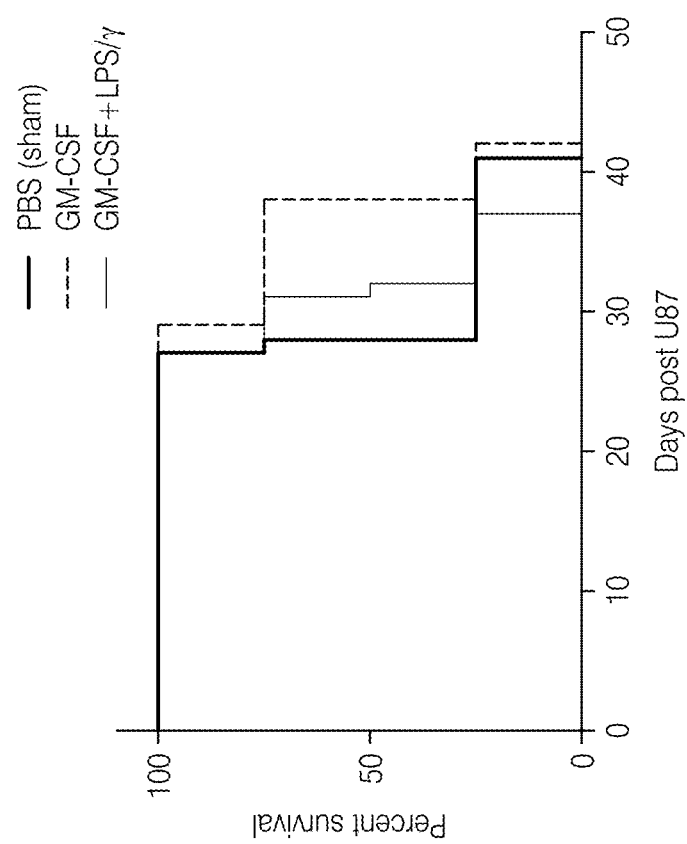
Figure 20:
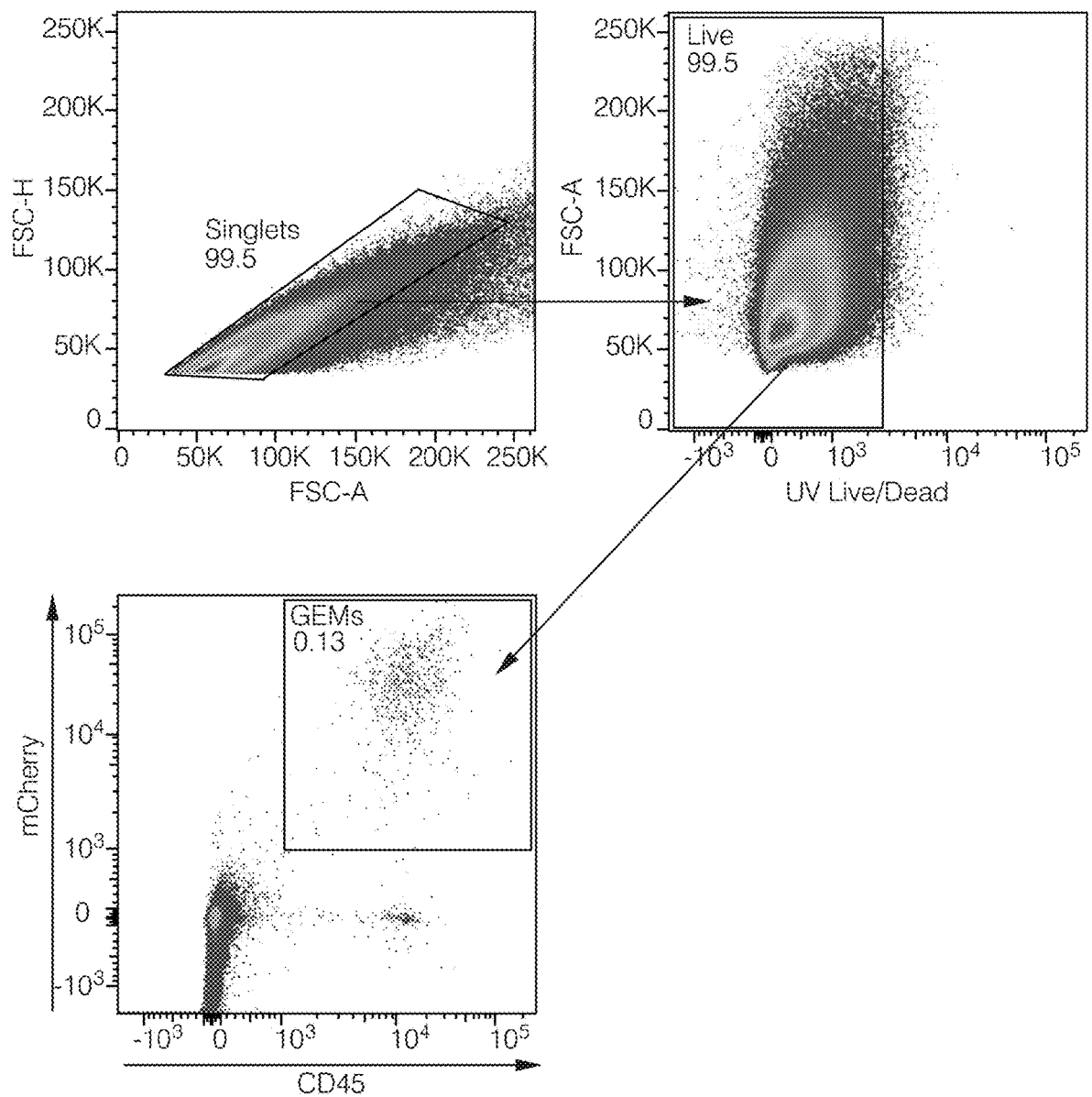
FIG. 20 shows that GEMs can be recovered from the brain following tumor dissociation. Human cells were isolated from brain tumor xenografts following animal euthanasia and stained for flow cytometry. After gating on singlets, and live cells, GEMs were identified as double positive for mCherry and CD45 expression.

The imaging data revealed that, once implanted, both GM-CSF-differentiated and GM-CSF differentiated, LPS/IFNγ-stimulated GEMs have a stable luciferin signal throughout the life of the animal (FIGS. 16B and 16C). Importantly, GEMs do not have a detrimental effect on animal survival, with no significant differences between groups (FIG. 16D, 17D), nor did they display outward signs of distress suggesting that even LPS/IFNγ-stimulated GEMs are well tolerated. Furthermore, GEMs do not enhance the growth of ffluc-expressing U87 tumors (FIG. 17B, C), and, despite being a rare cell population, can be recovered following enzymatic dissociation of tumor tissue (FIG. 20). Despite being a rare cell population, GEMs can also be detected within the tumor mass by immunostaining for human CD45 (FIGS. 17E-17G) and can be recovered following enzymatic dissociation of tumor tissue (FIG. 20). Collectively the data suggest that GEMs are capable of the long-term expression of transgenes in vivo, and neither support tumor growth nor reduce the survival of tumor-bearing animals. Future experiments will evaluate GEMs, which constitutively express activation signals to determine whether they are capable of supporting and endogenous anti-tumor response or whether safety concerns arise when they interact with other immune cells.

Figure 17B:
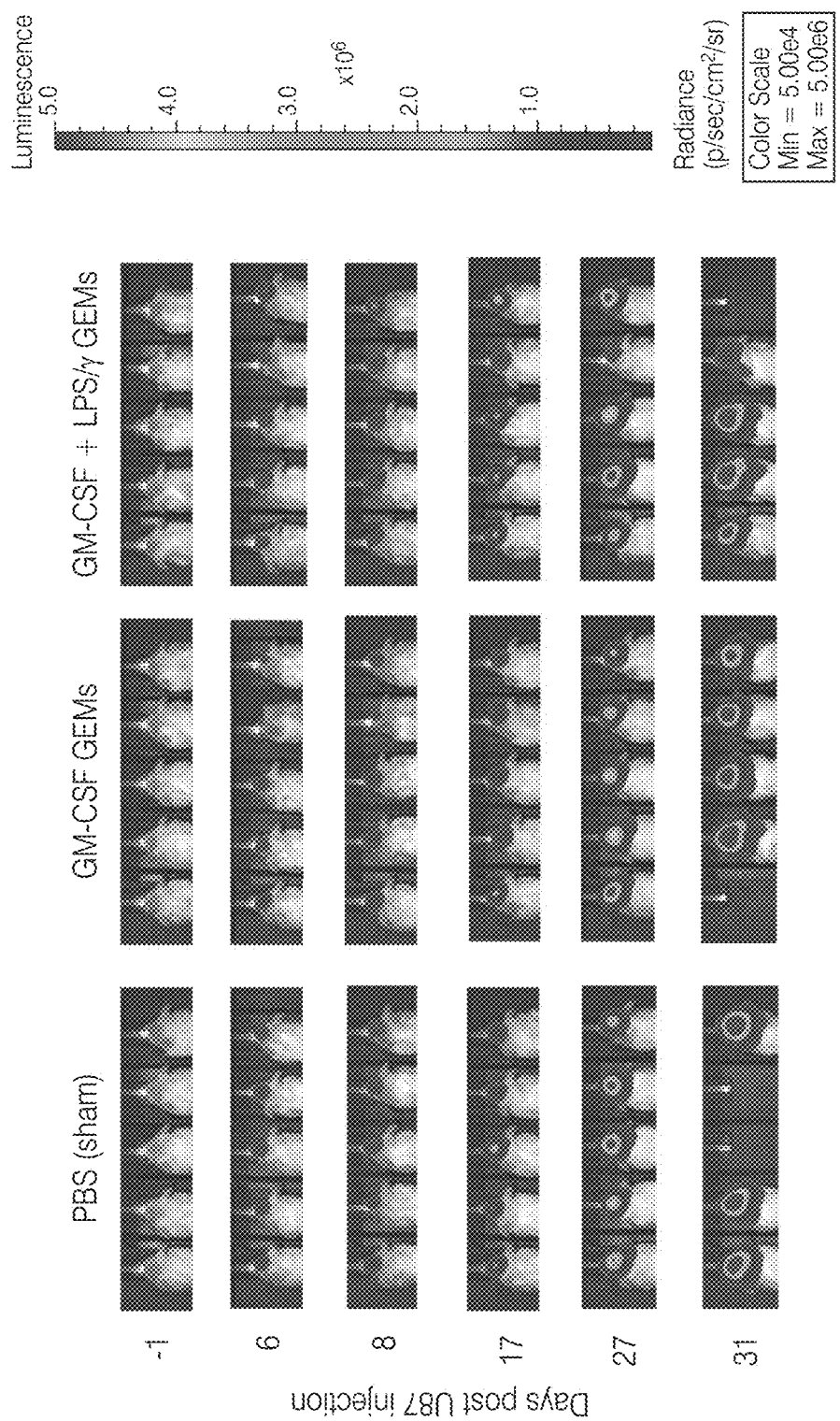
Figure 17C:
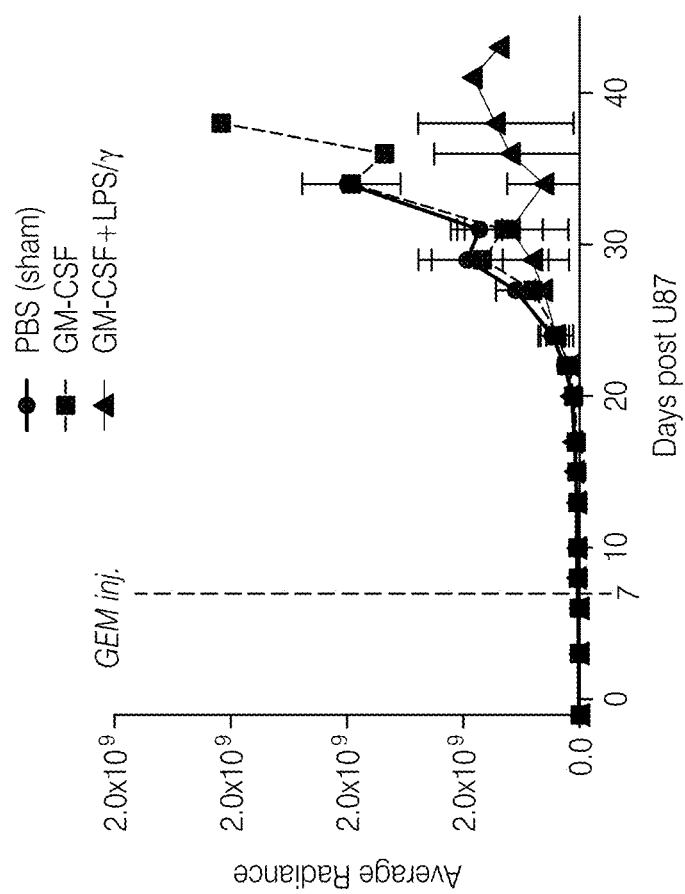
Figure 17D:
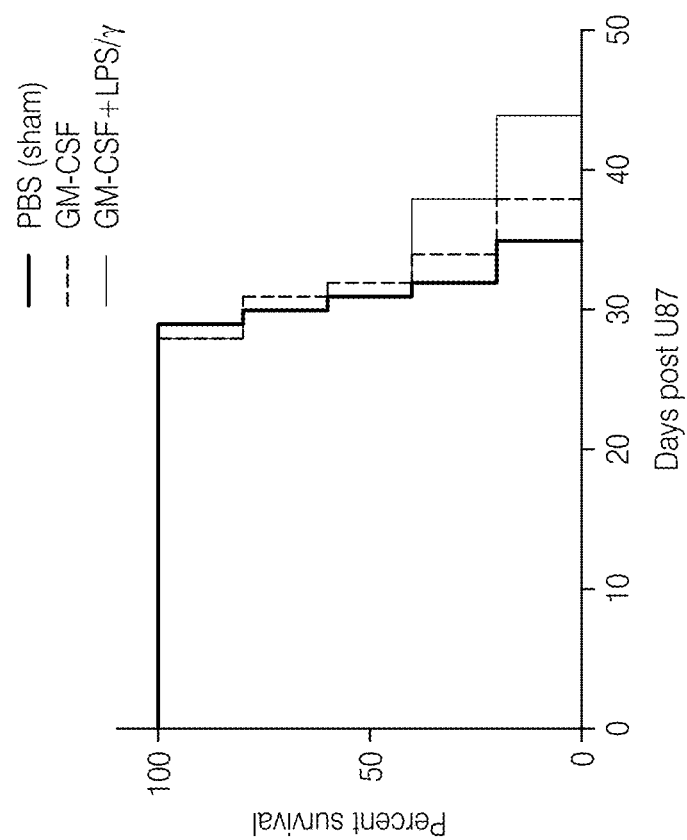
Figures 17E, 17F, 17G:
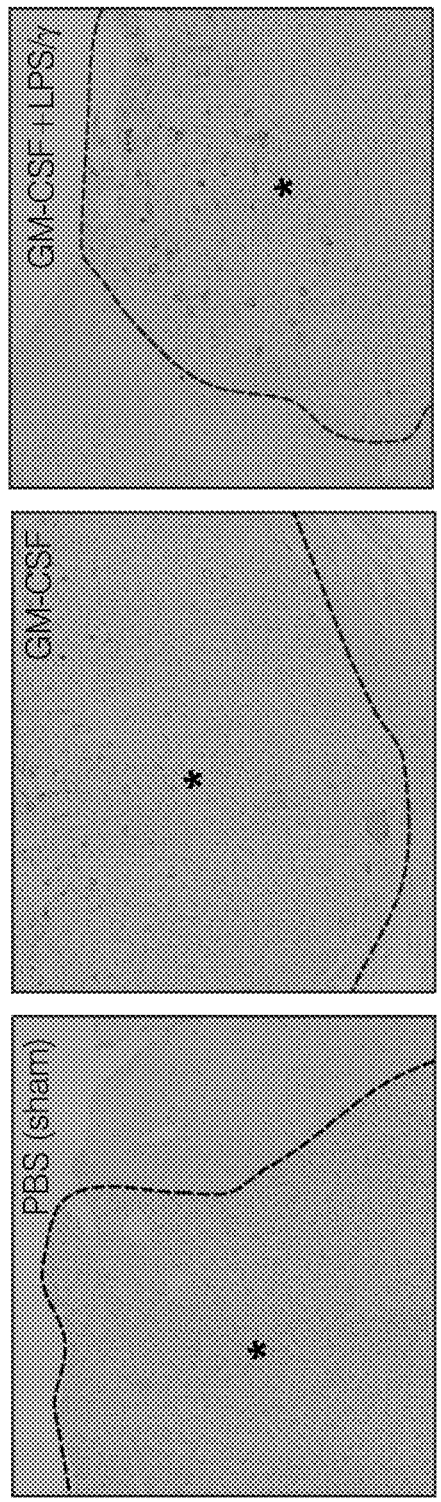

The imaging data revealed that GM-CSF differentiated GEMs have a stable luciferin signal throughout the life of the animal independent of stimulation using the potent TLR4 agonist LPS and the pro-inflammatory cytokine, IFNγ (FIG. 16A, 16B). As shown, the GEMs do not negatively affect the survival of the animal. (FIG. 16C, FIG. 17C). Furthermore, GEMs do not enhance the growth of ffluc-expressing U87 tumors (FIG. 17A, 17B). The data suggests that GEMs are capable of the long-term expression of transgenes in vivo, and do not support tumor growth or reduce the survival of tumor bearing animals.

GEMs can be Engineered to Counteract an Immunosuppressive TME

Figure 18A:
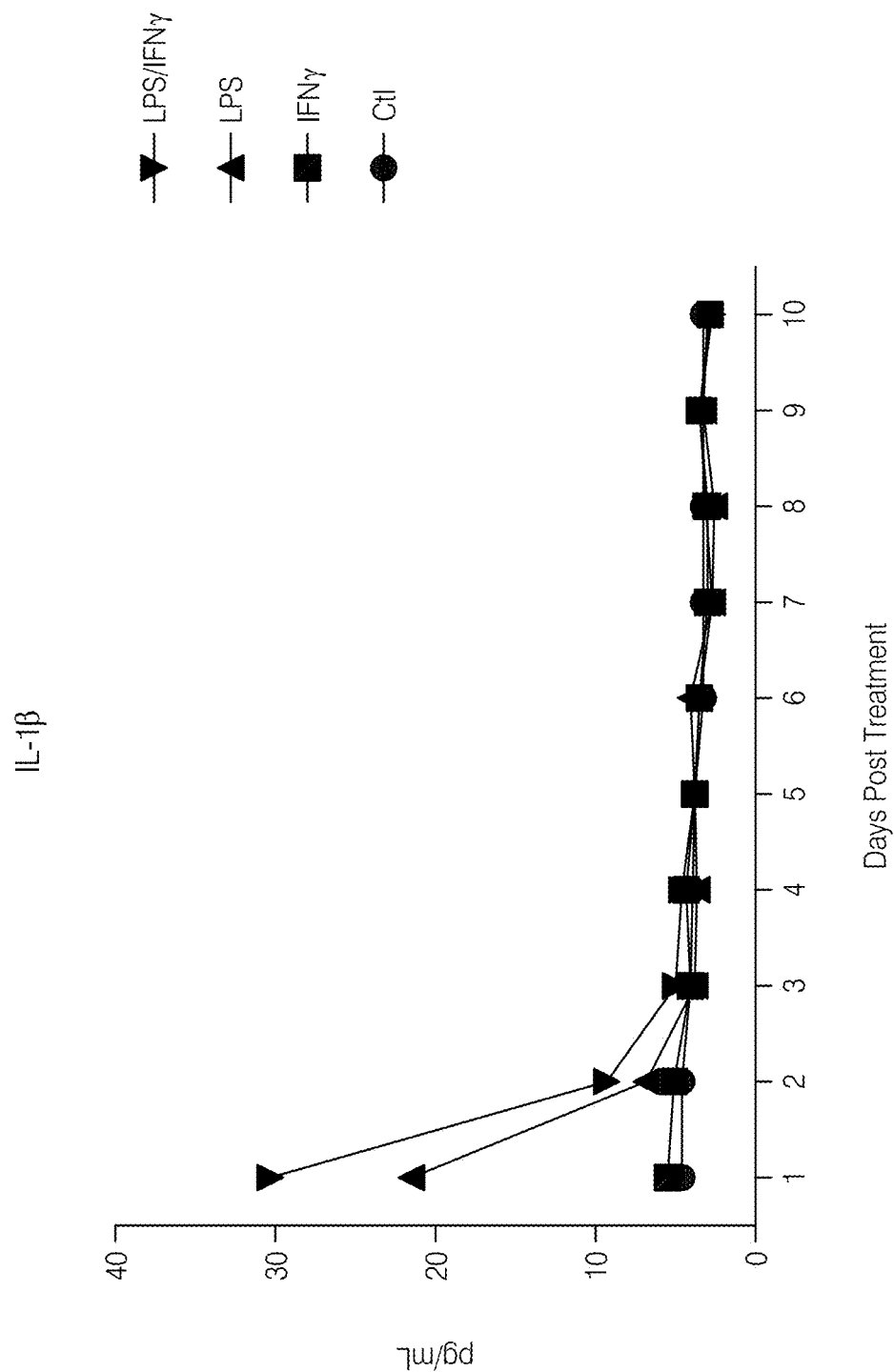
FIG. 18A to 18CC shows cytokine release following LPS/IFNγ stimulation persists for only 24-48 hours. Wild type, GM-CSF-differentiated macrophages seeded at 200,000 cells per well in a 24 well plate were stimulated with LPS (100 ng/mL), IFNγ (20 ng/mL), or LPS+IFNγ for 18 hours in 500 μL media. Conditioned media was collected at 18 h (Day 1) and replaced with fresh media without cytokines. Media was harvested every 24 hours for a total of 10 days. Cytokine release was detected using the Luminex human 30-plex cytokine kit (Life Tech). Most cytokines are detected only in the first 2 collections, with a steep decrease after 18 hours. Note that IL-10, IL-12, IL-17, IL-7, IP-10, and MIG remain elevated past the 2 day mark in the LPS+IFNγ condition. IFNγ alone has little impact but often potentiates the response to LPS.
Figure 18B:
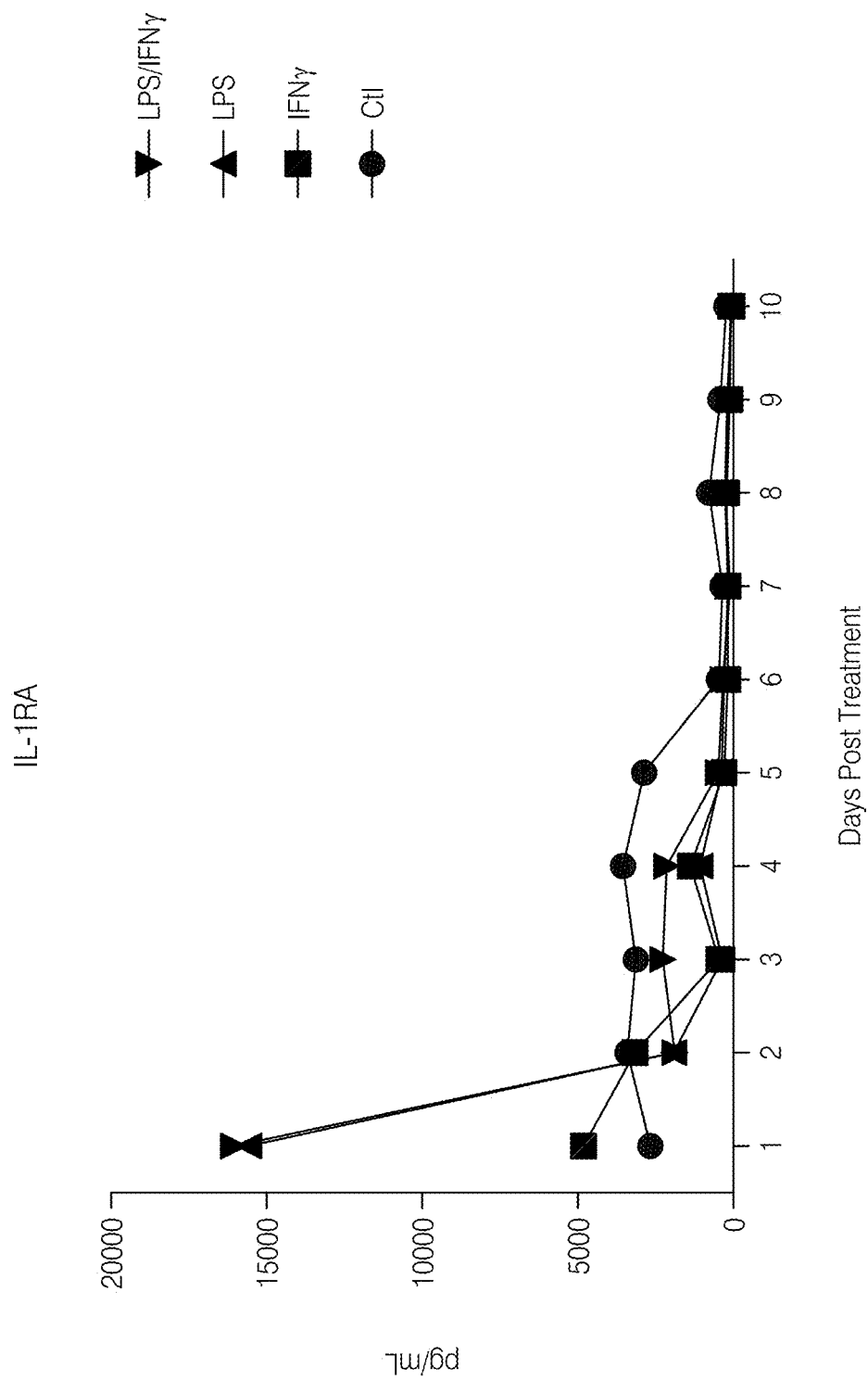
Figure 18C:
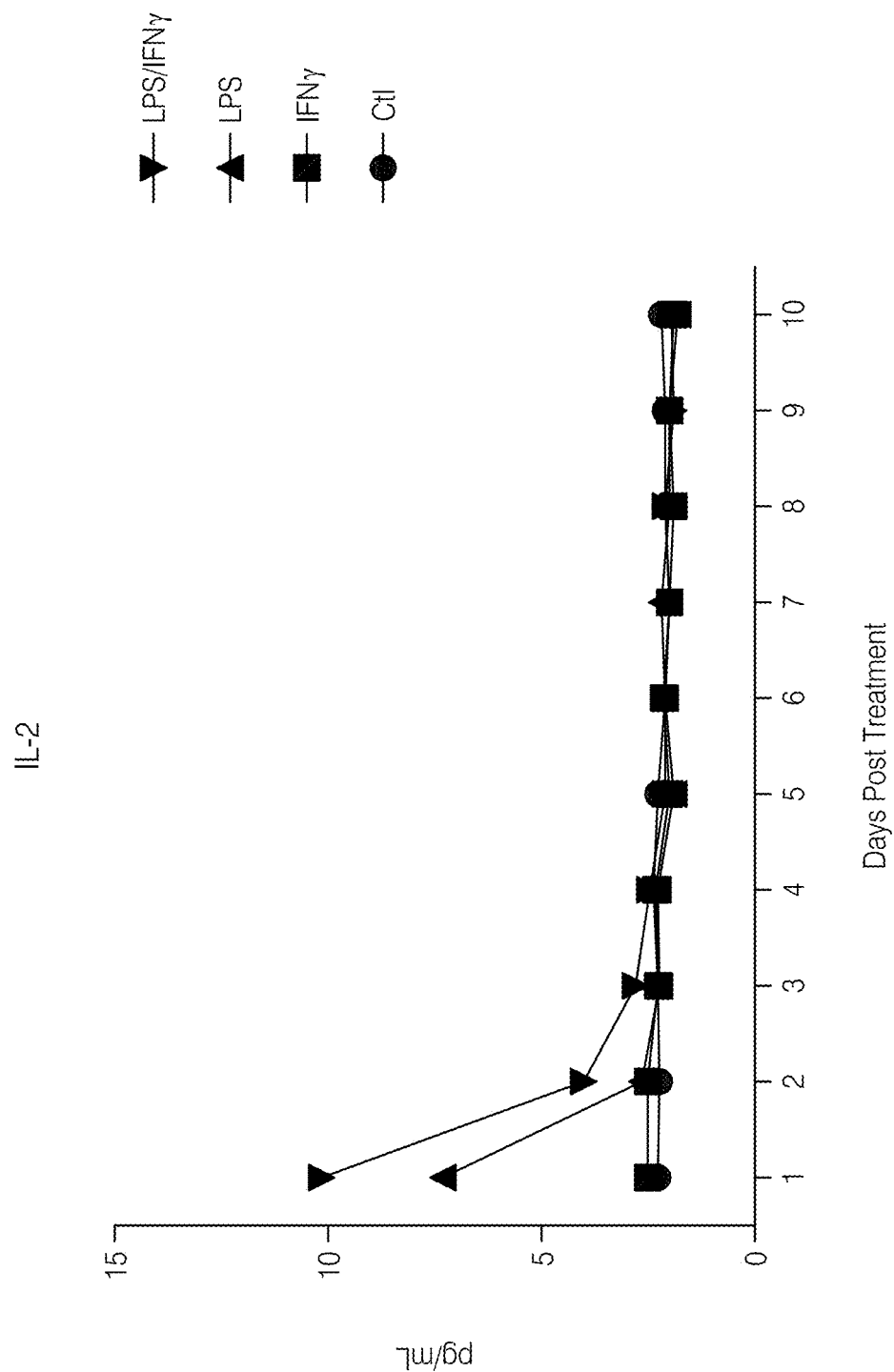
Figure 18D:
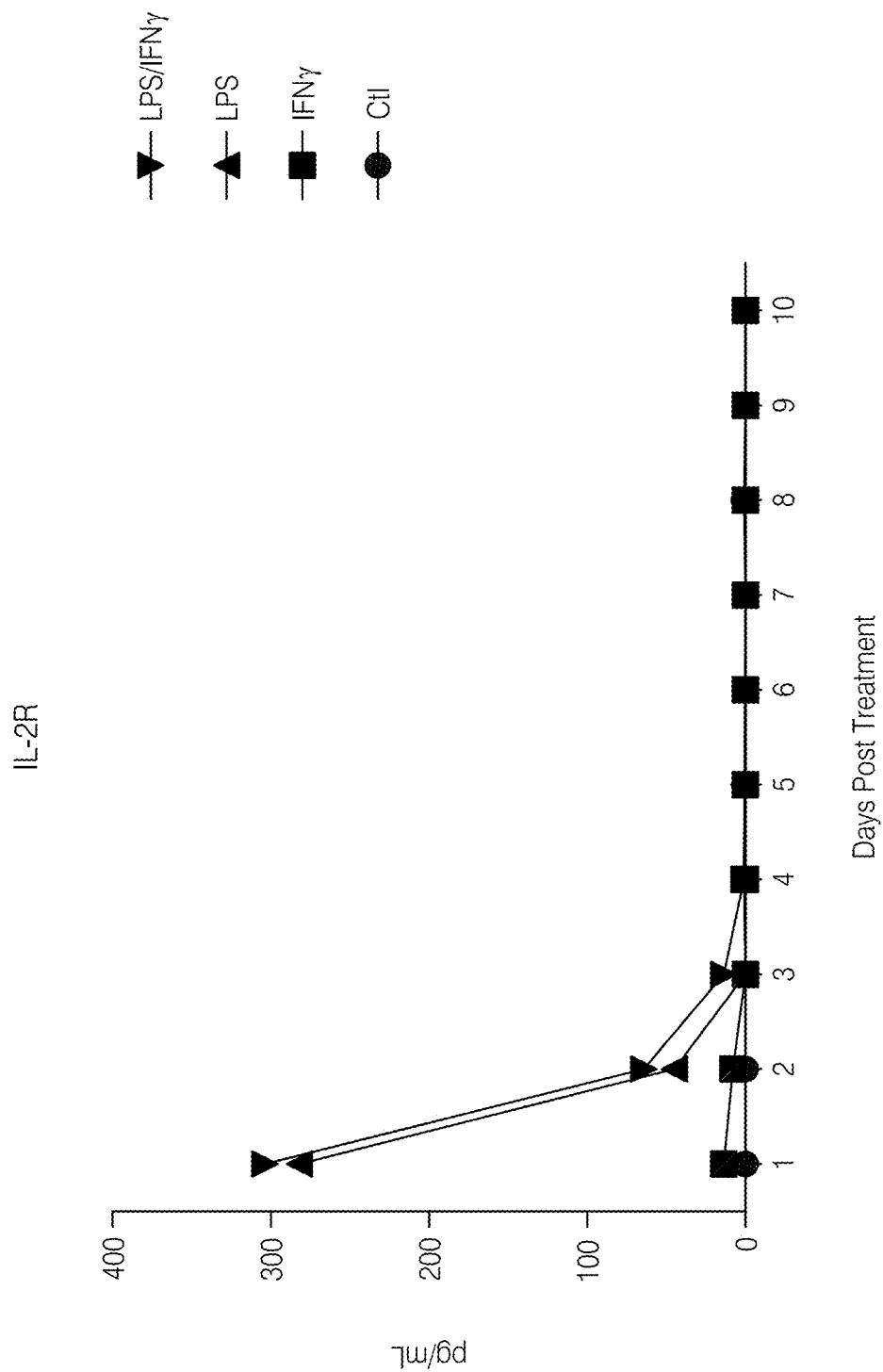
Figure 18E:
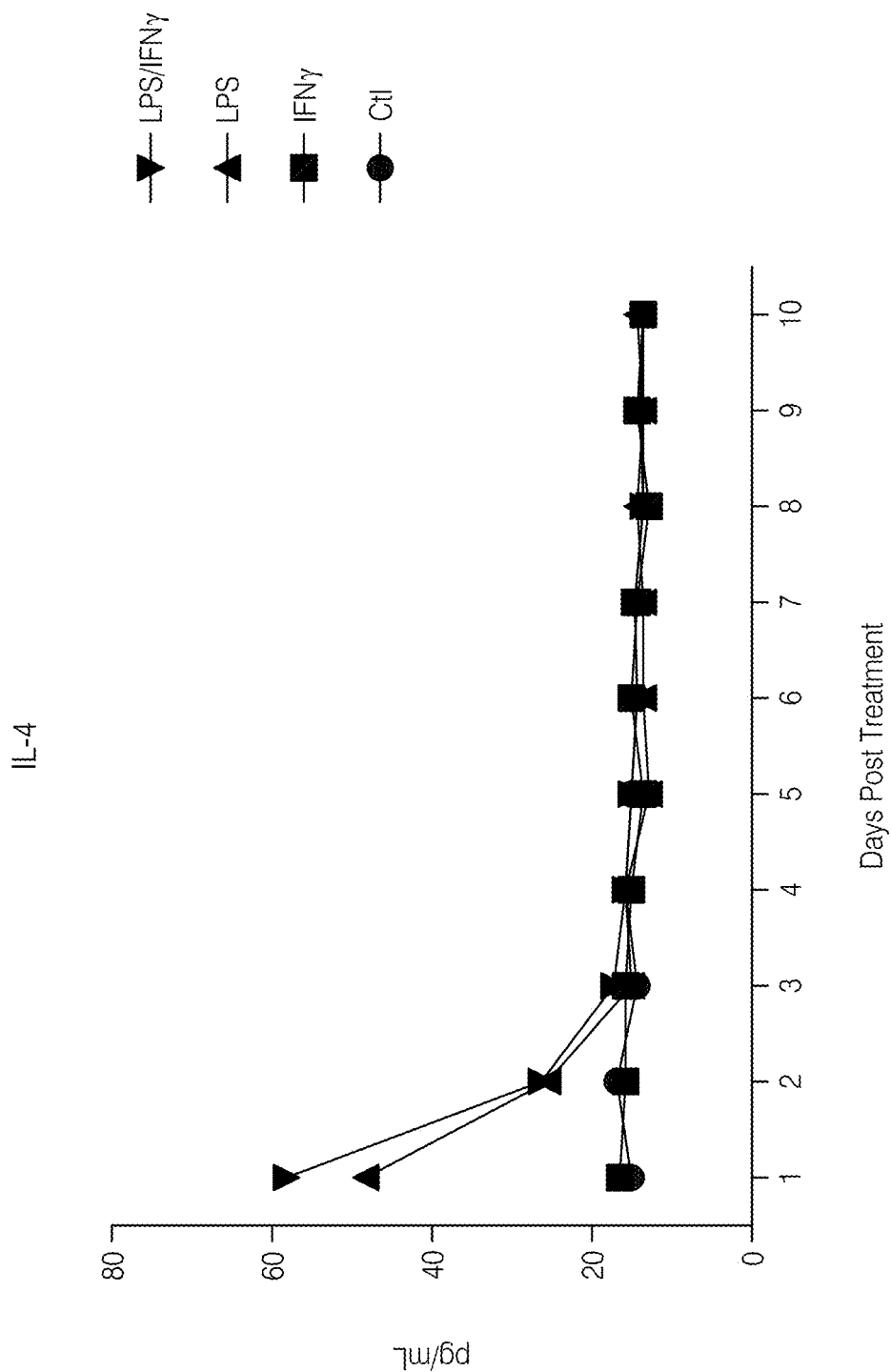
Figure 18F:
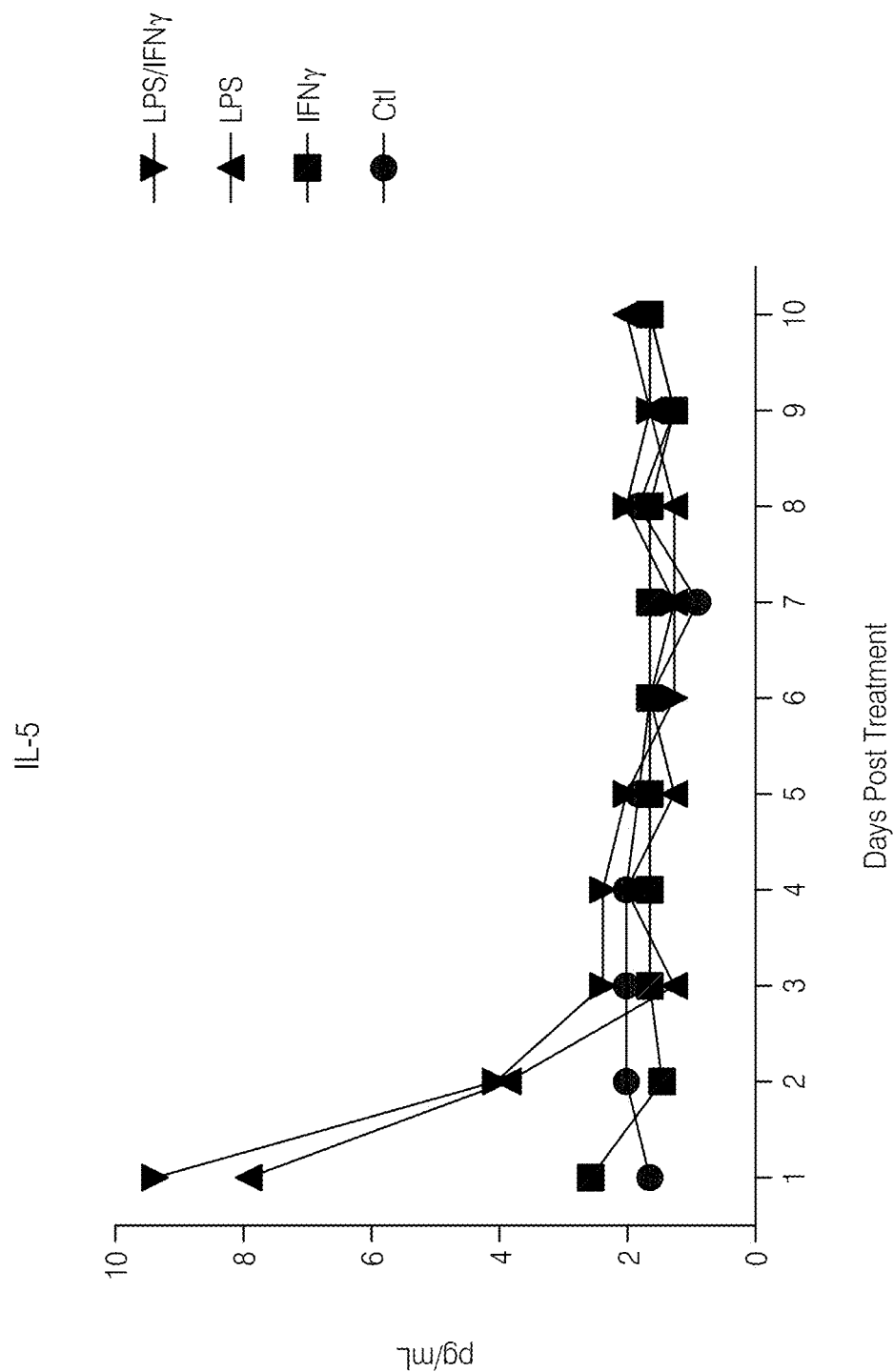
Figure 18G:
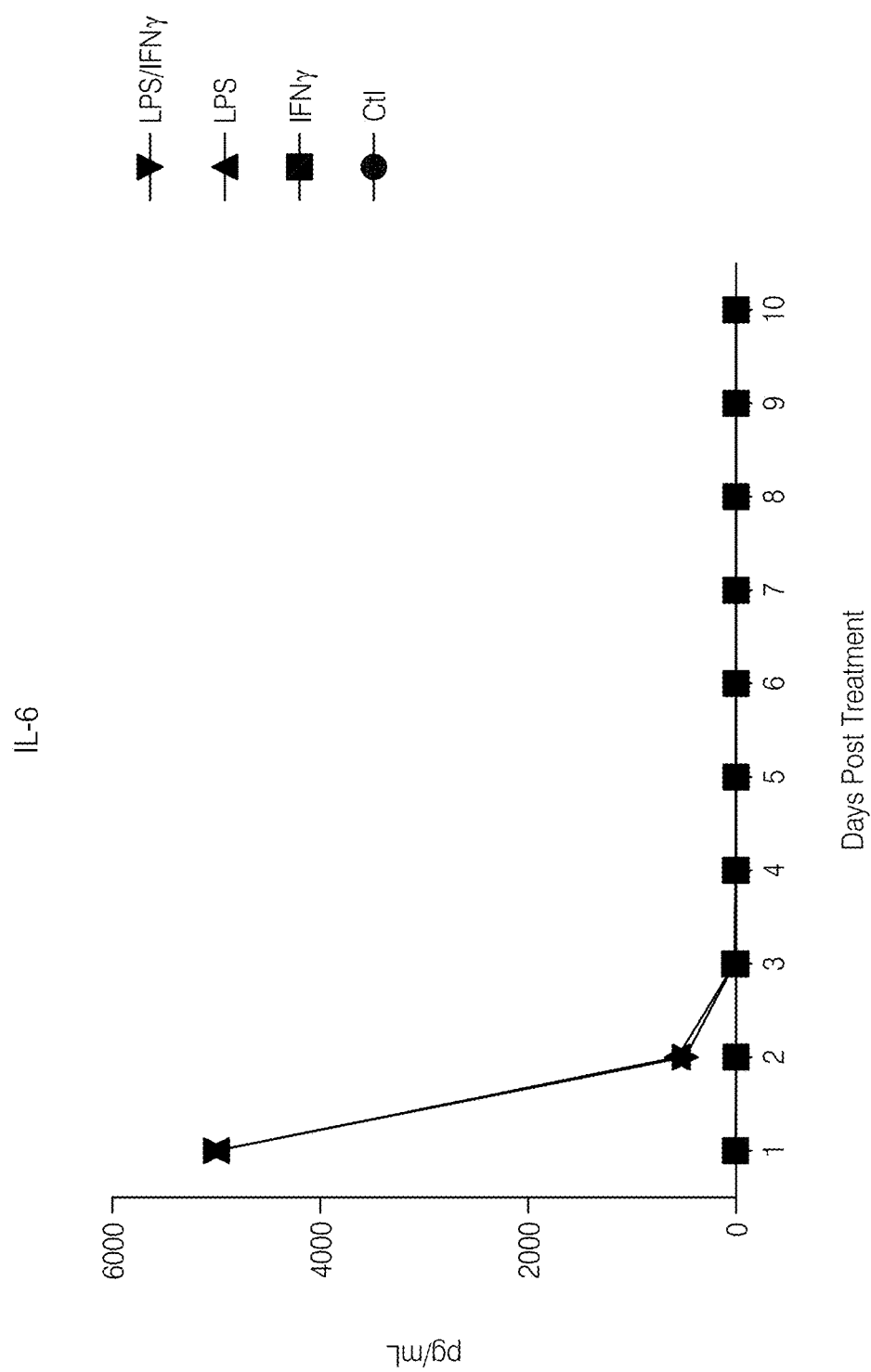
Figure 18H:
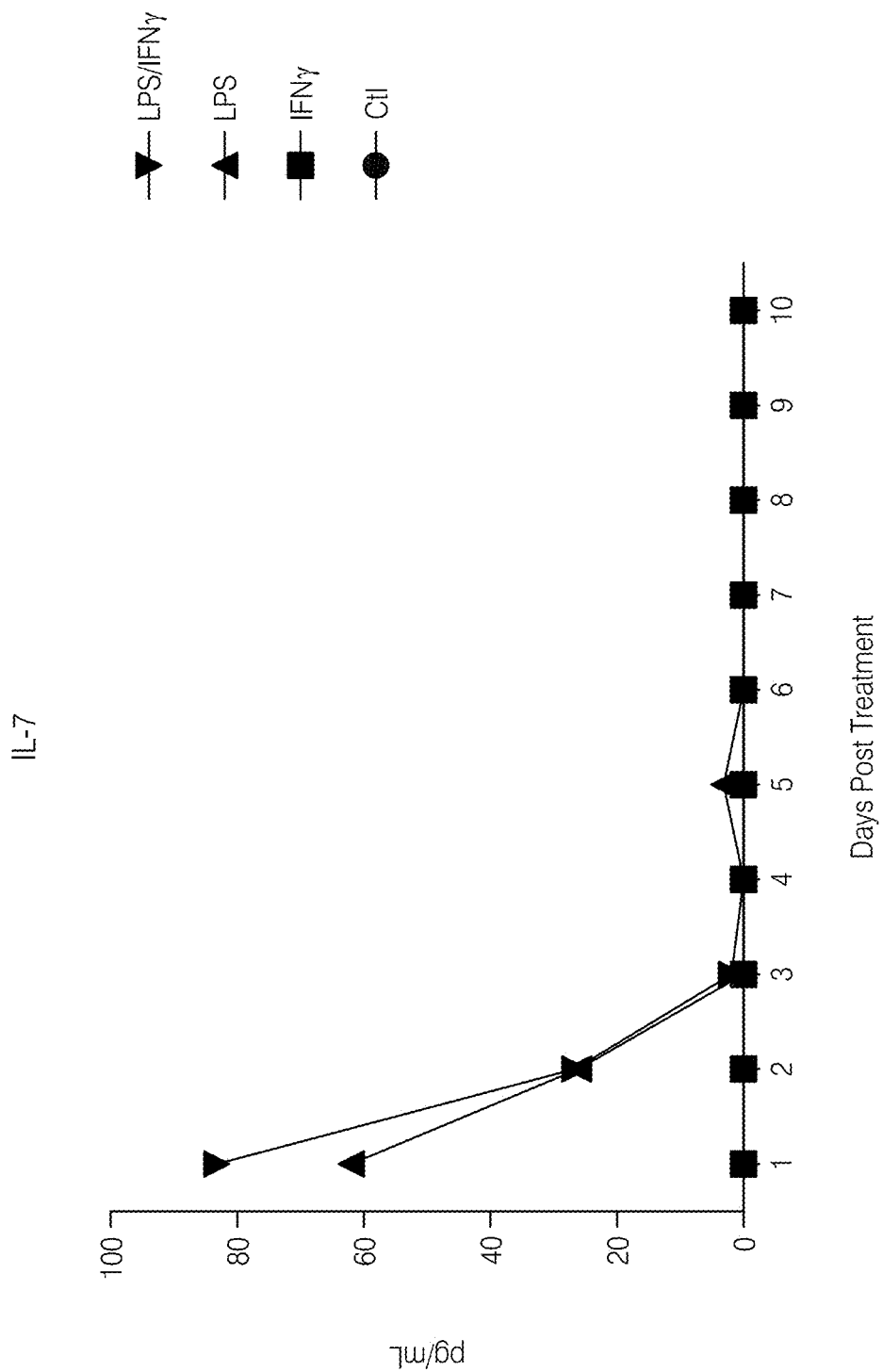
Figure 18I:
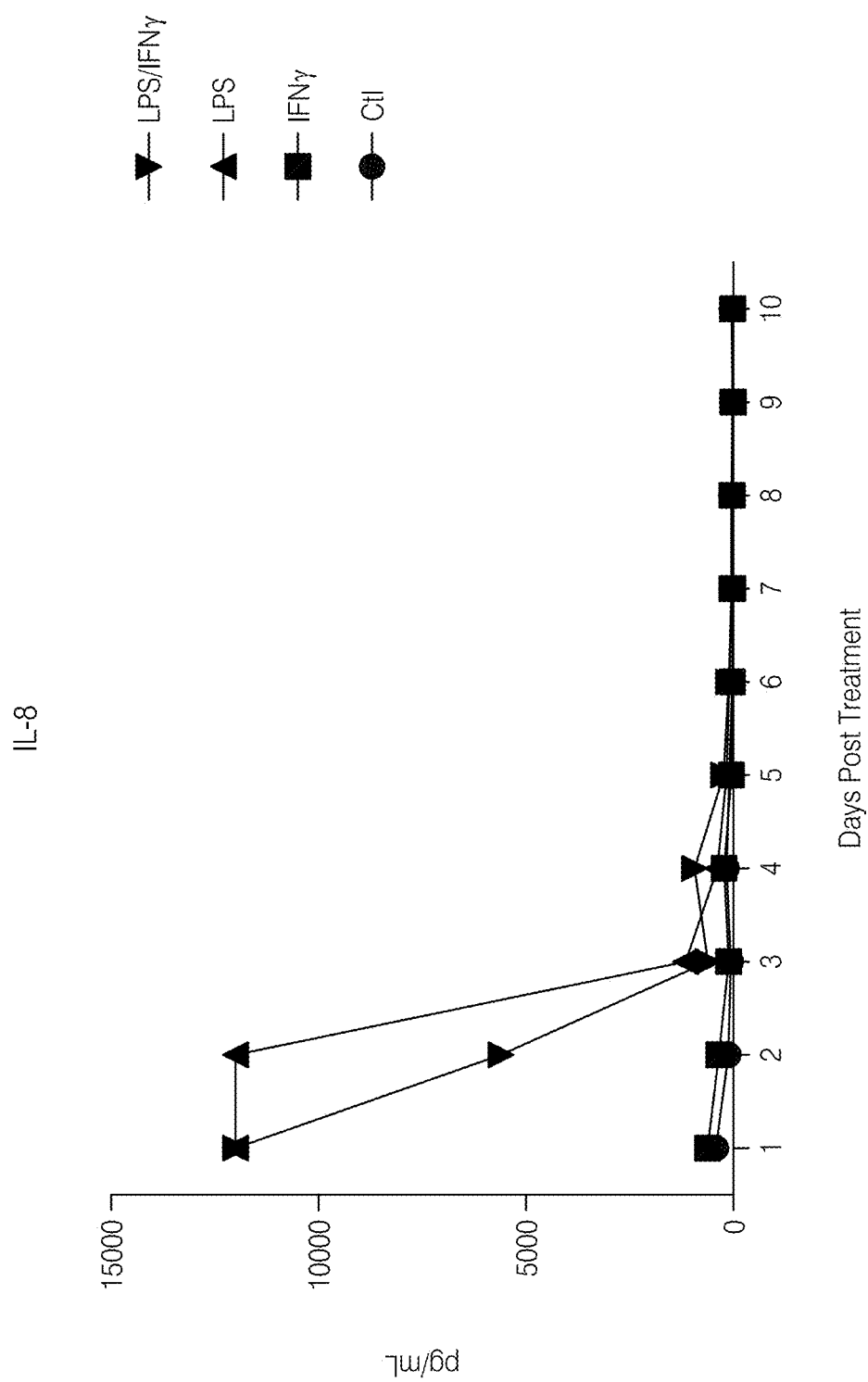
Figure 18J:
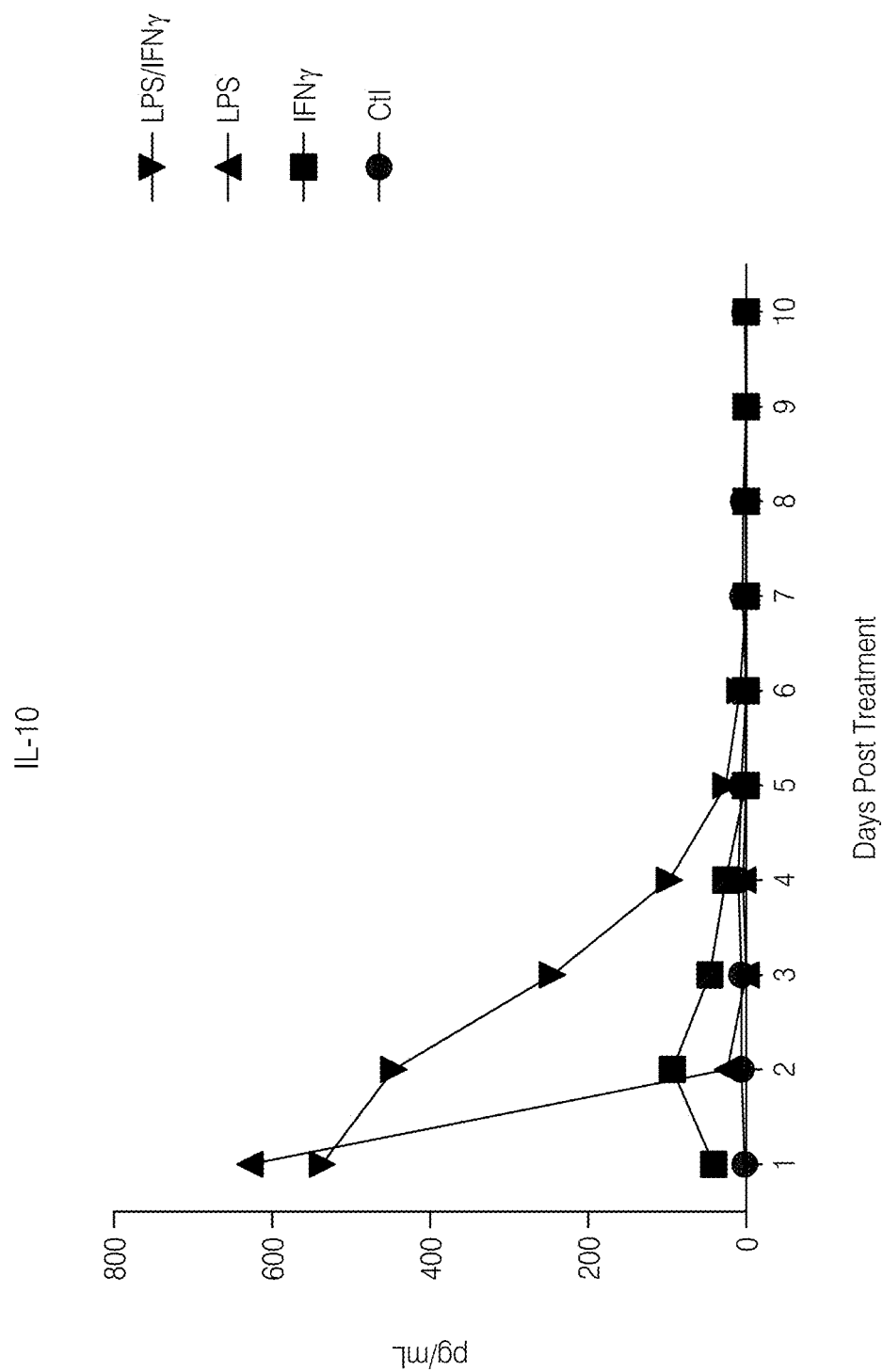
Figure 18K:
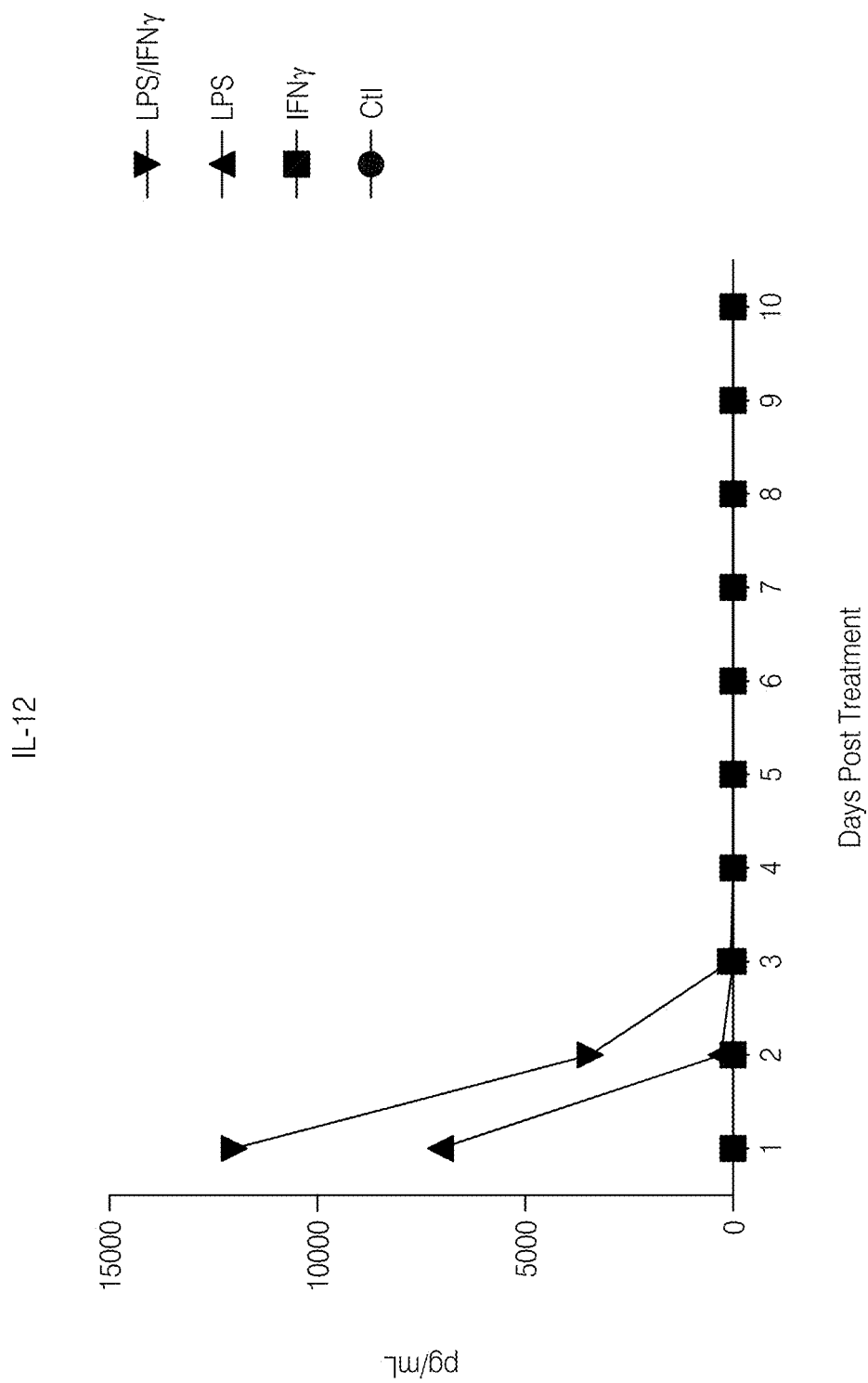
Figure 18L:
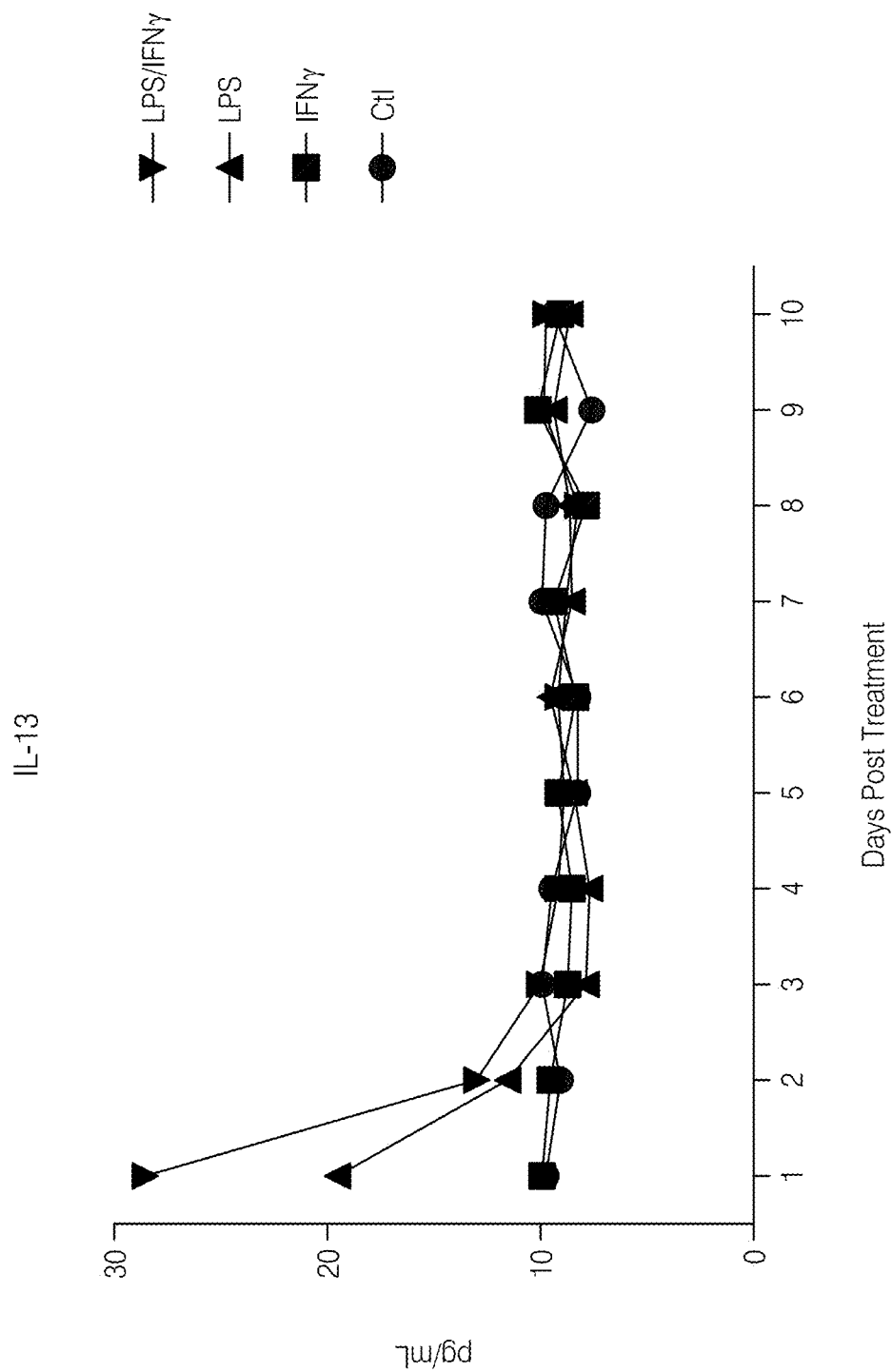
Figure 18M:
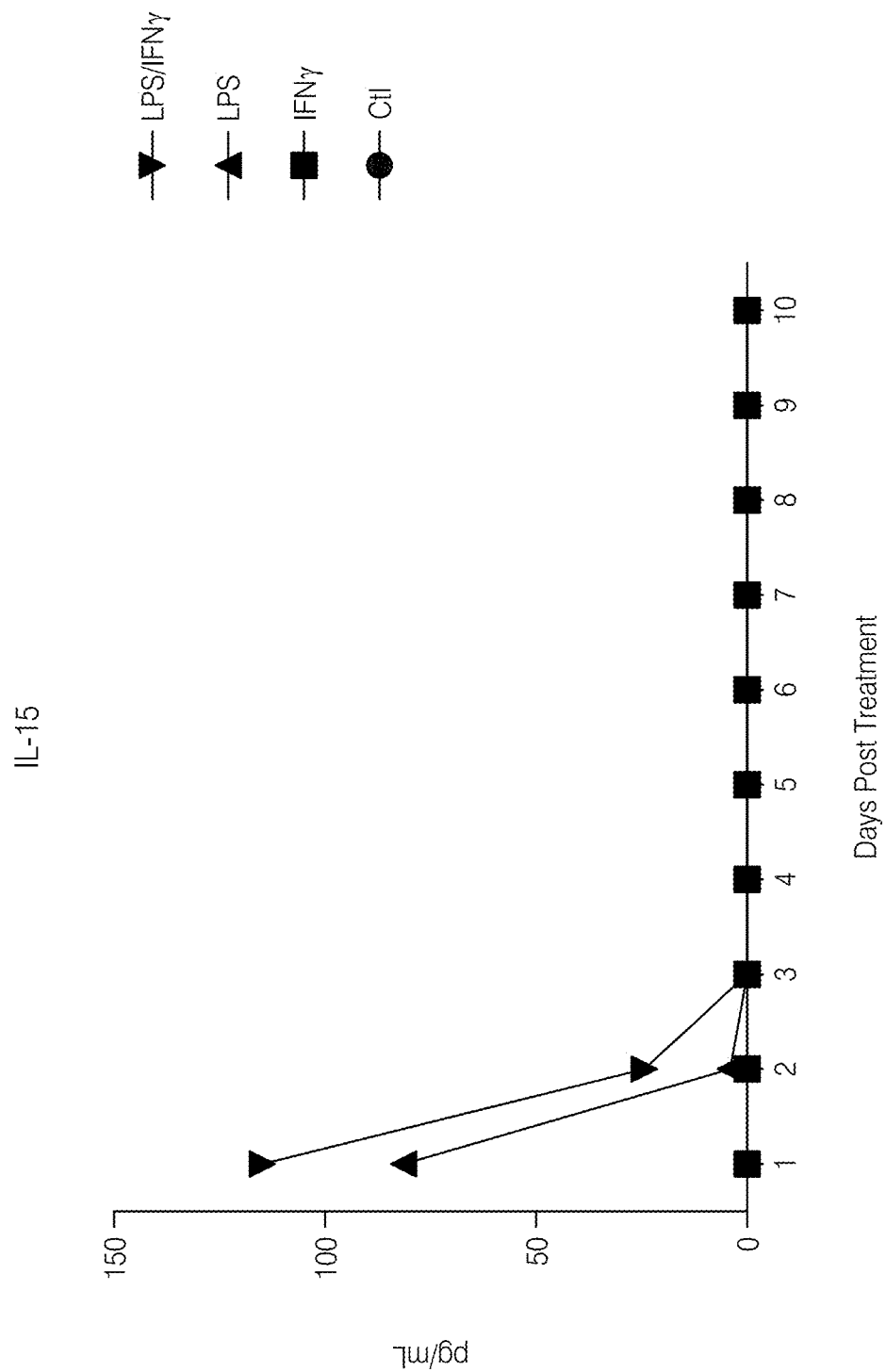
Figure 18N:
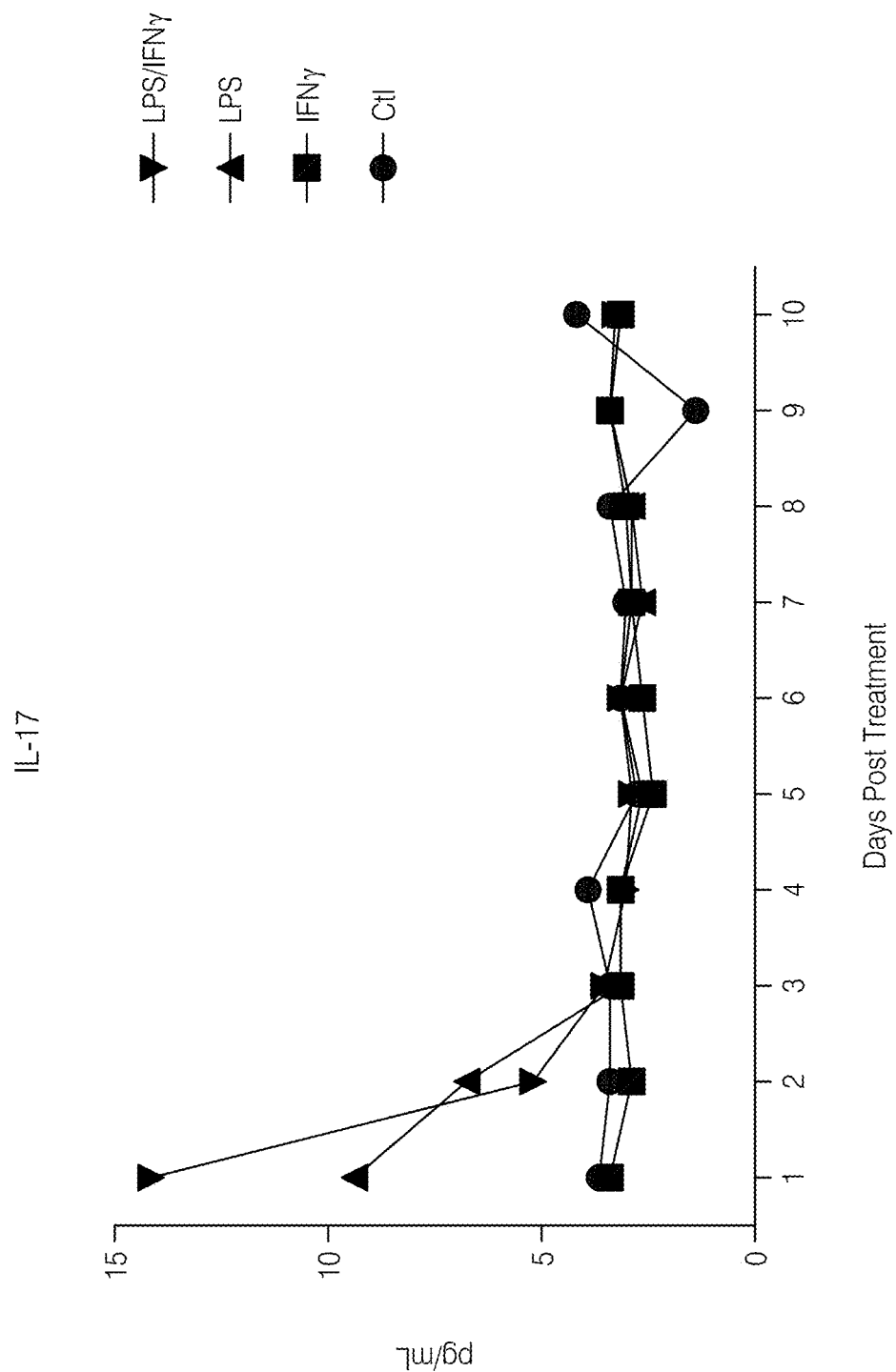
Figure 18O:
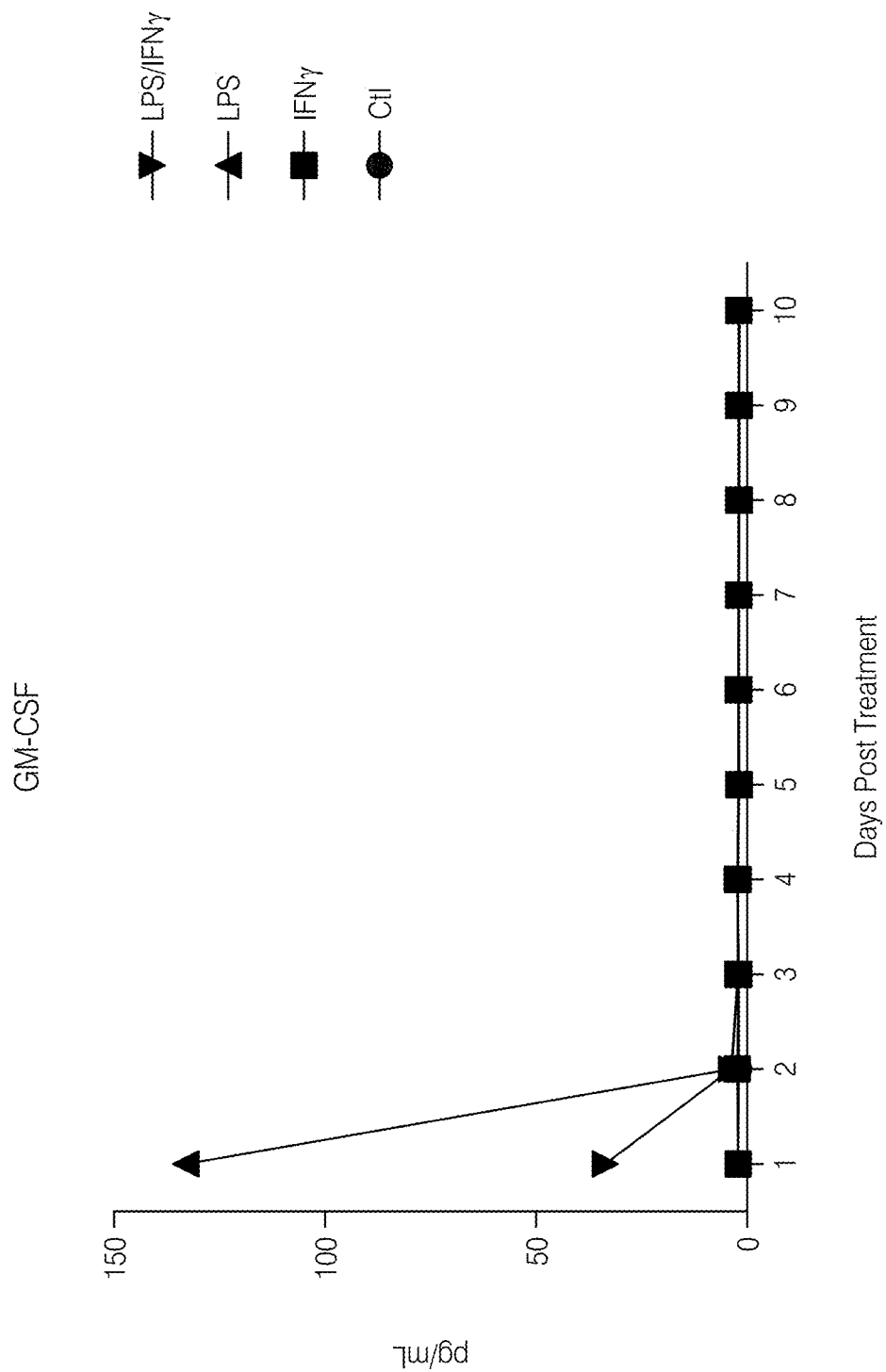
Figure 18P:
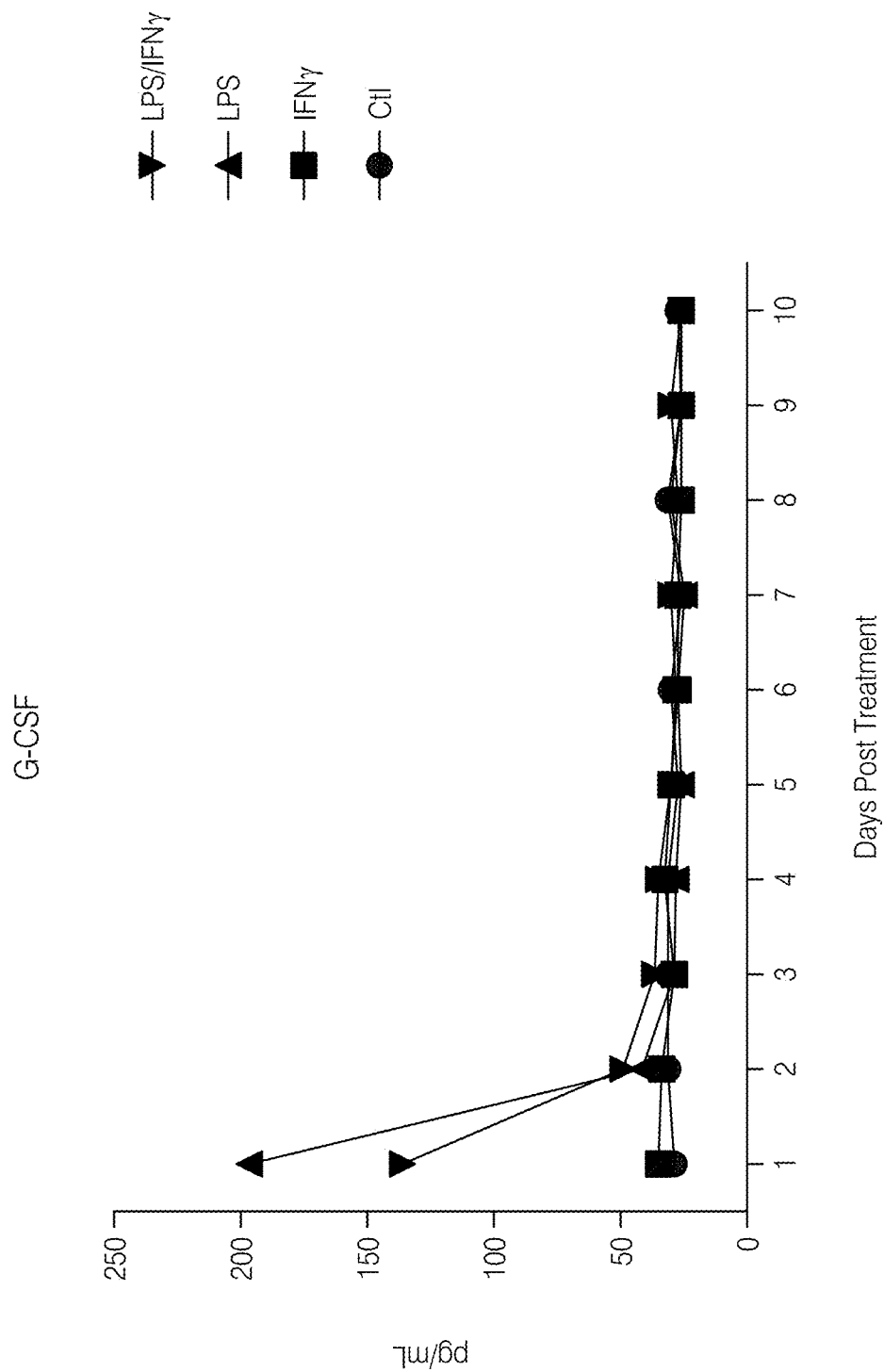
Figure 18Q:
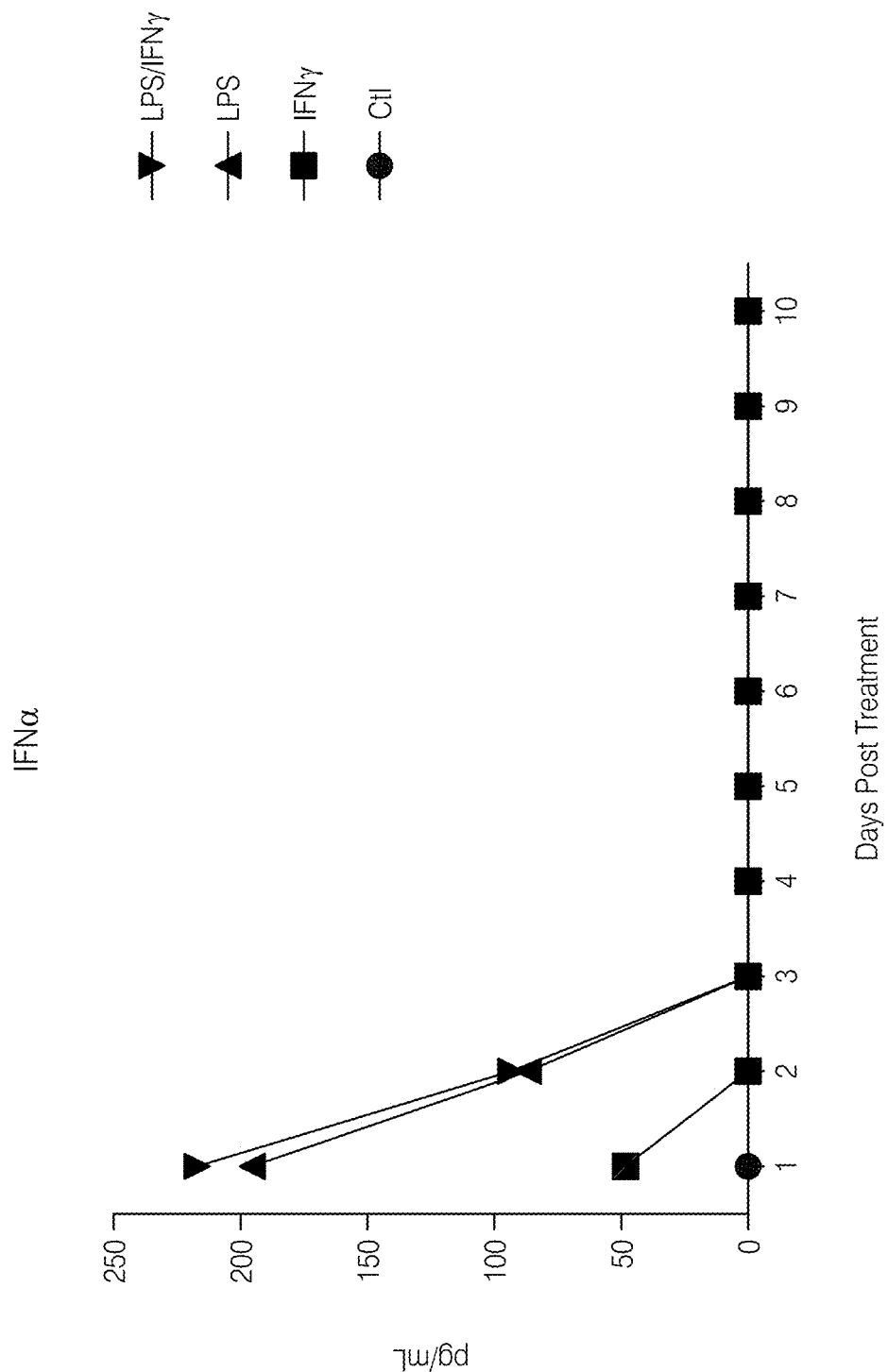
Figure 18R:
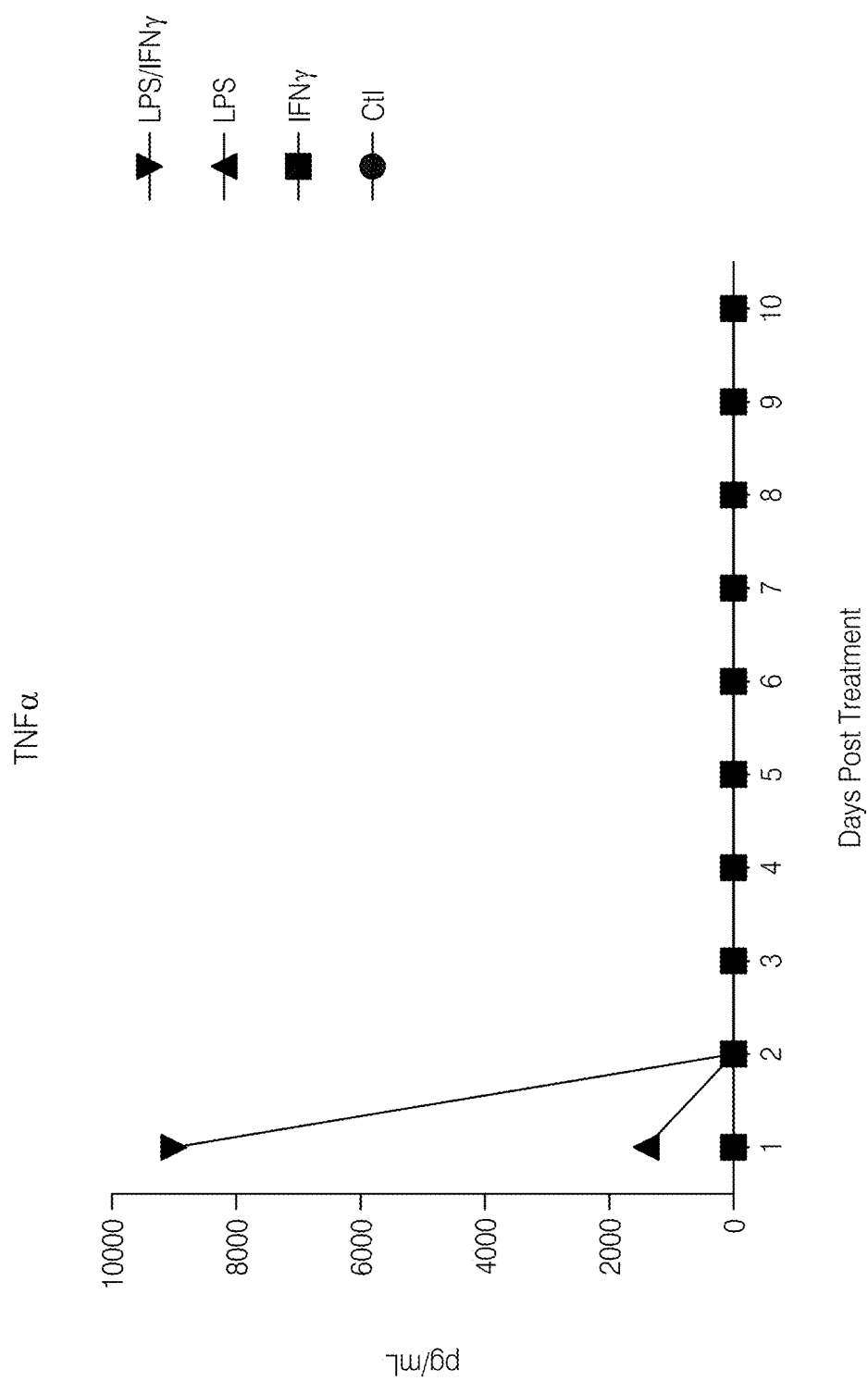
Figure 18S:
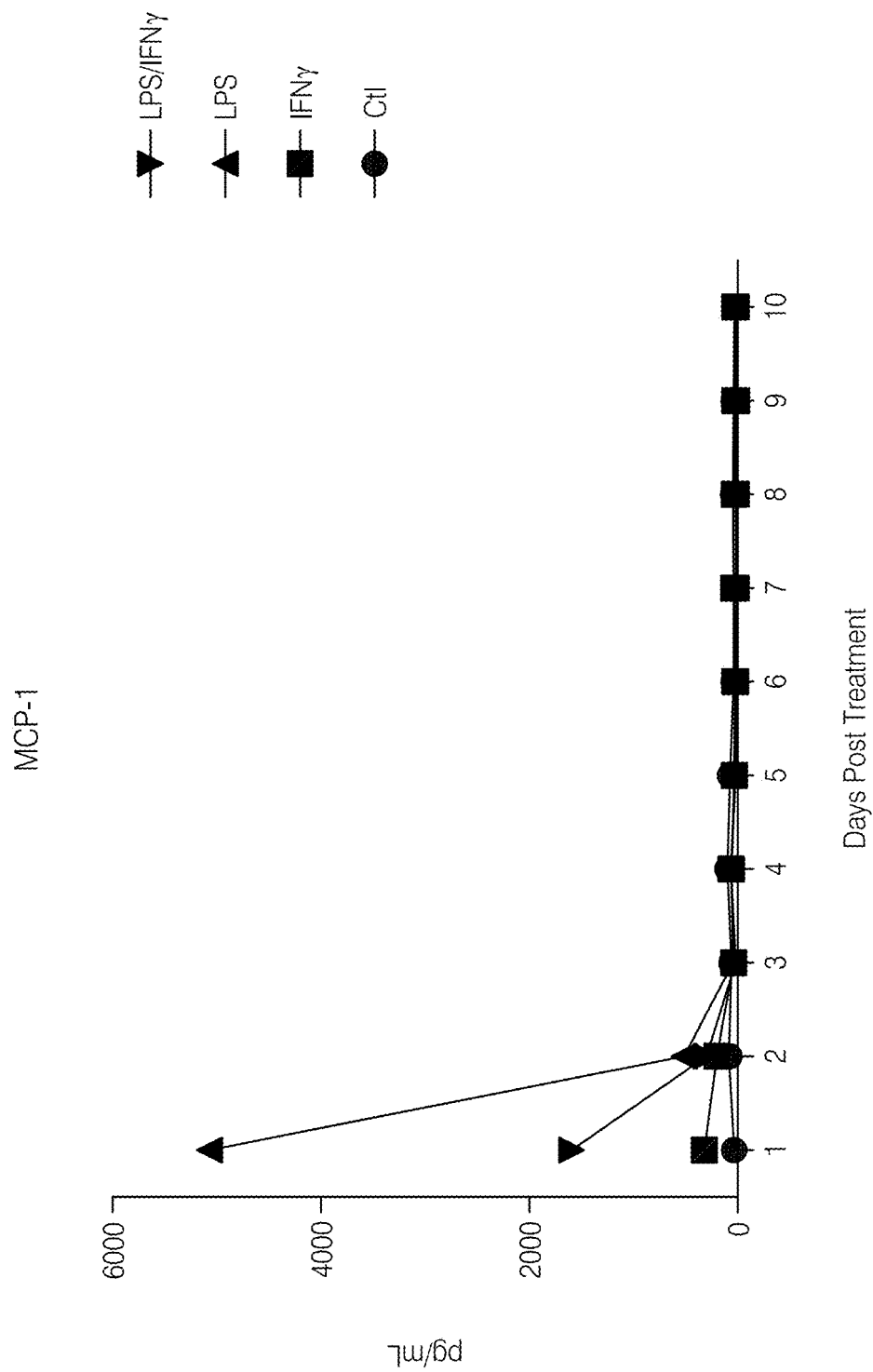
Figure 18T:
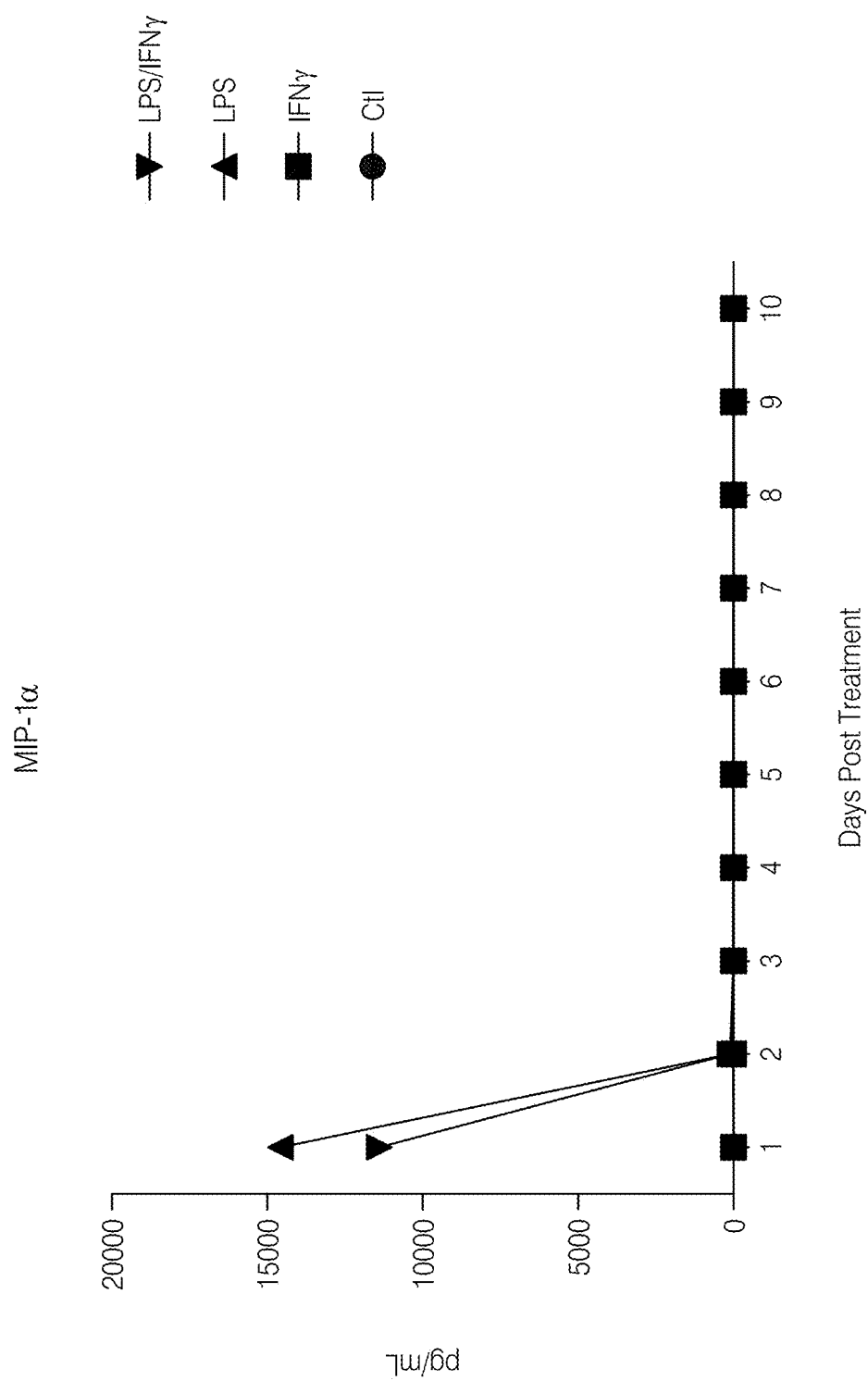
Figure 18U:
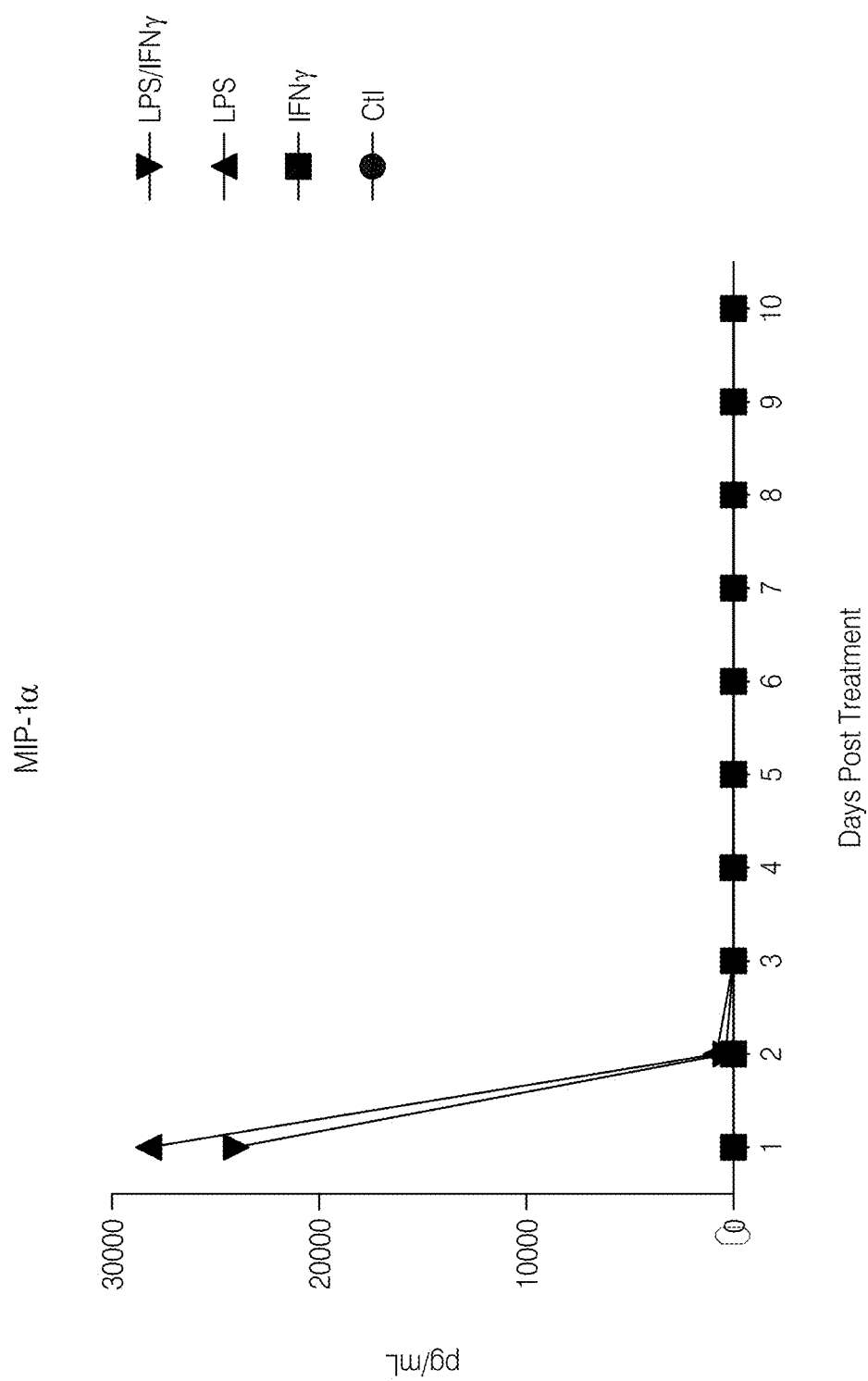
Figure 18V:
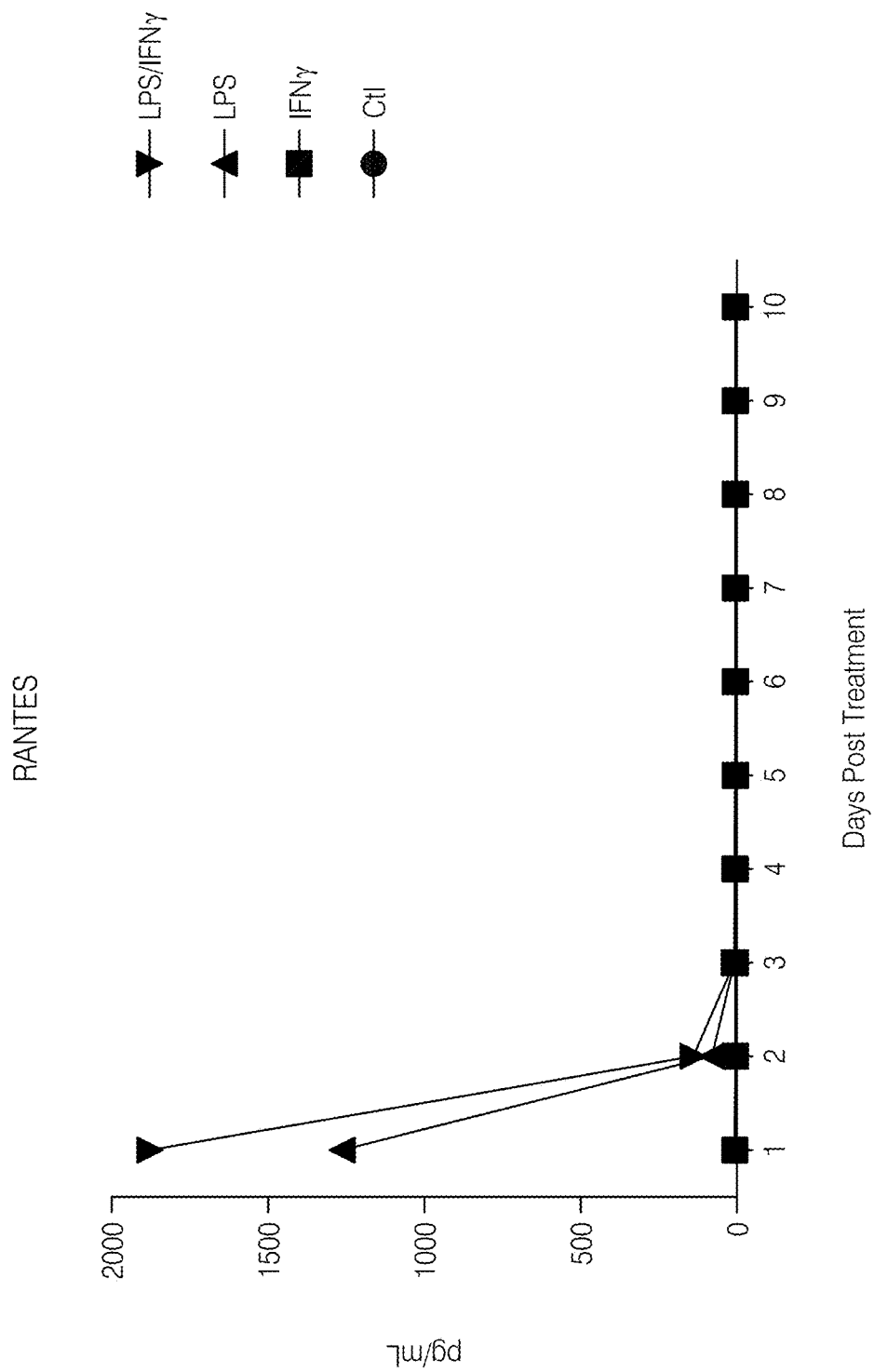
Figure 18W:
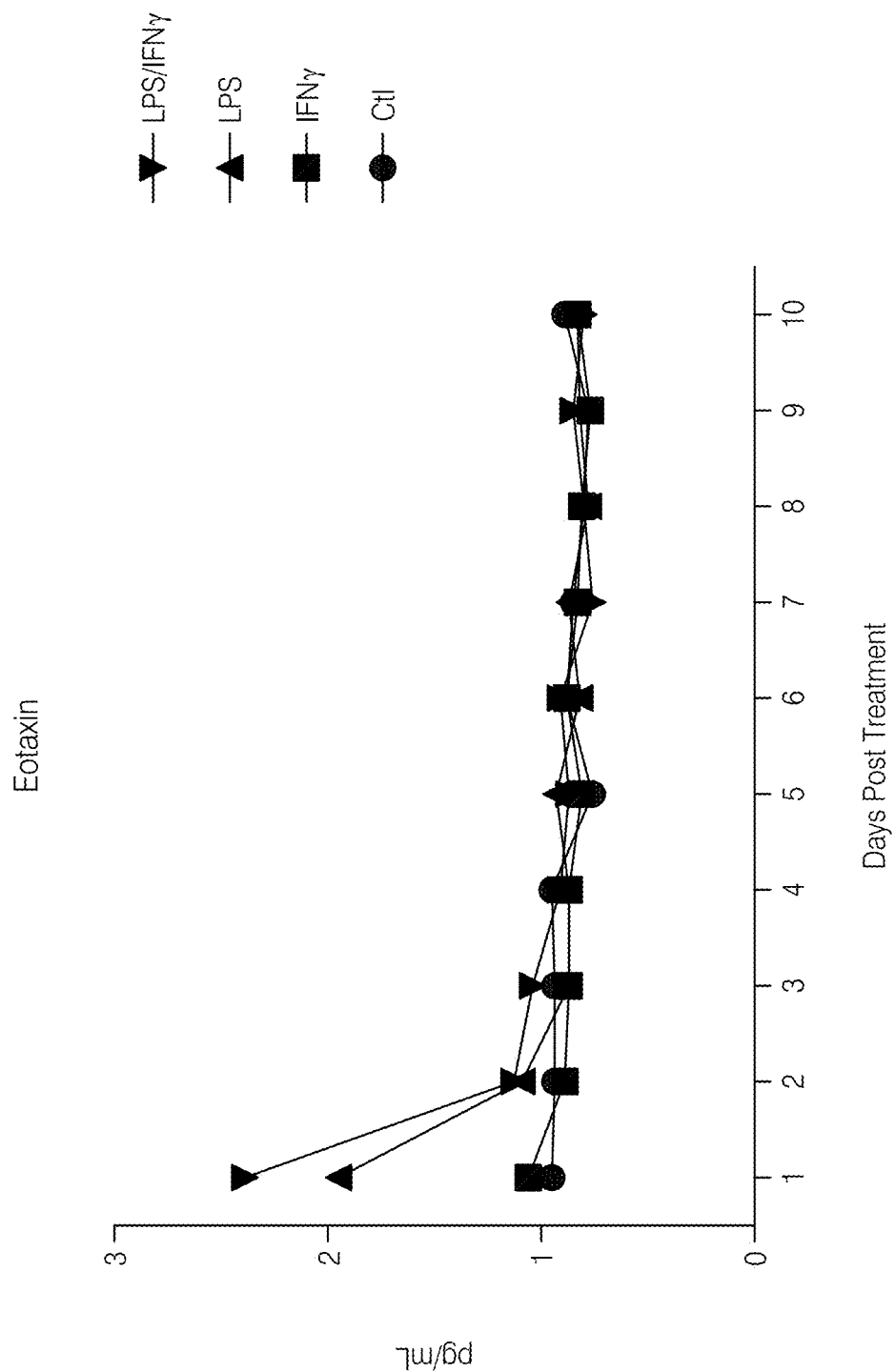
Figure 18X:
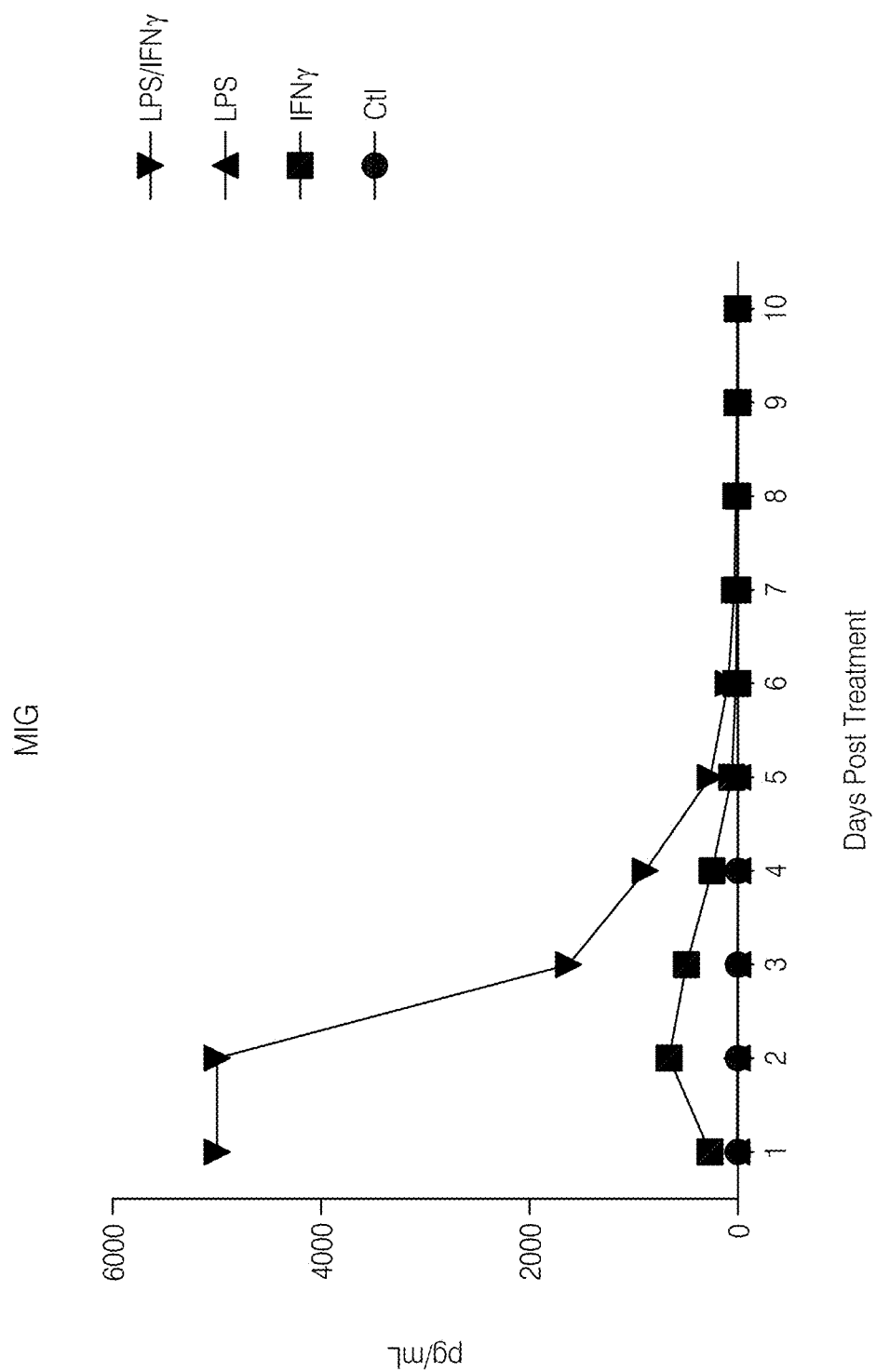
Figure 18Y:
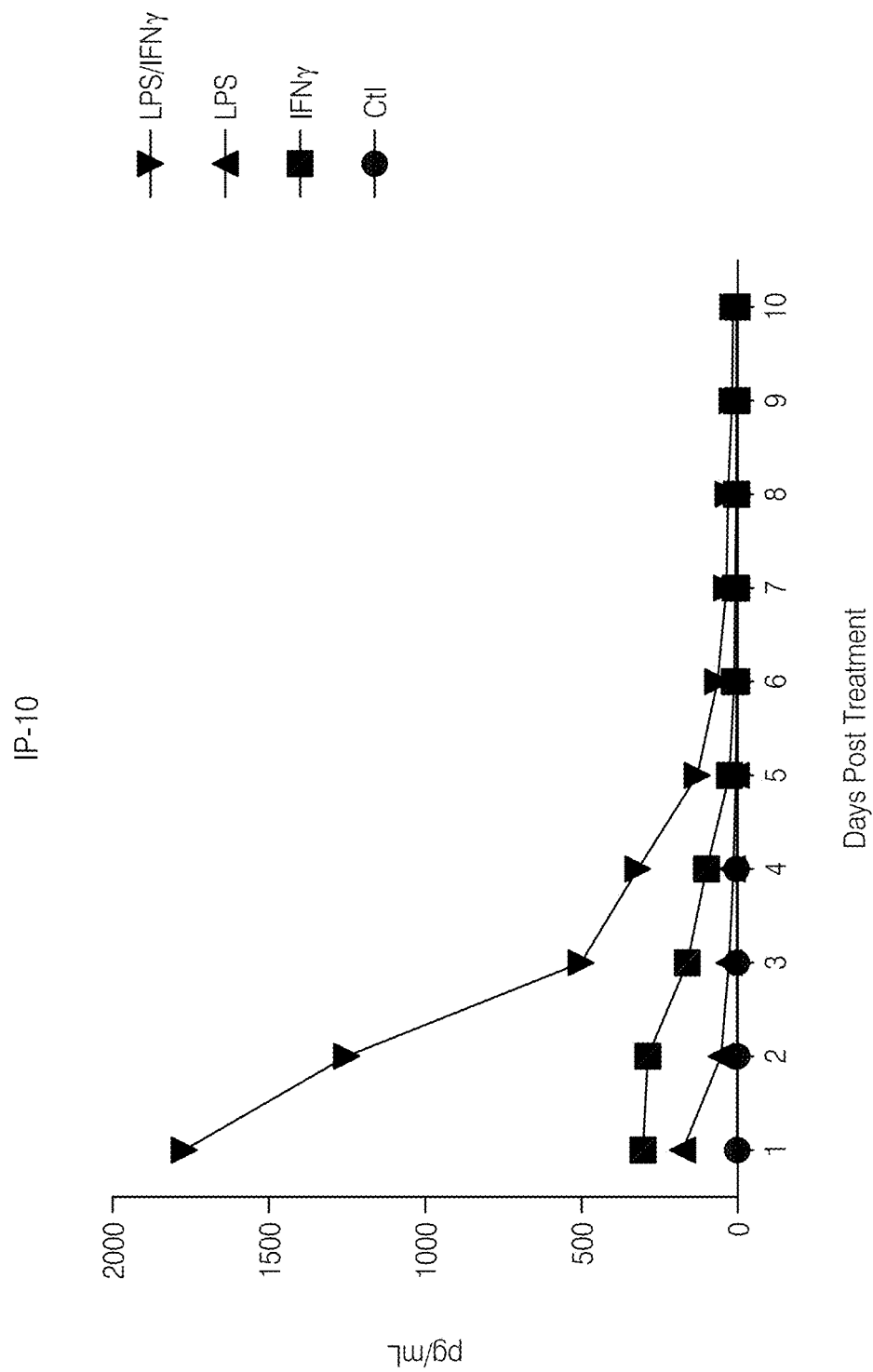
Figure 18Z:
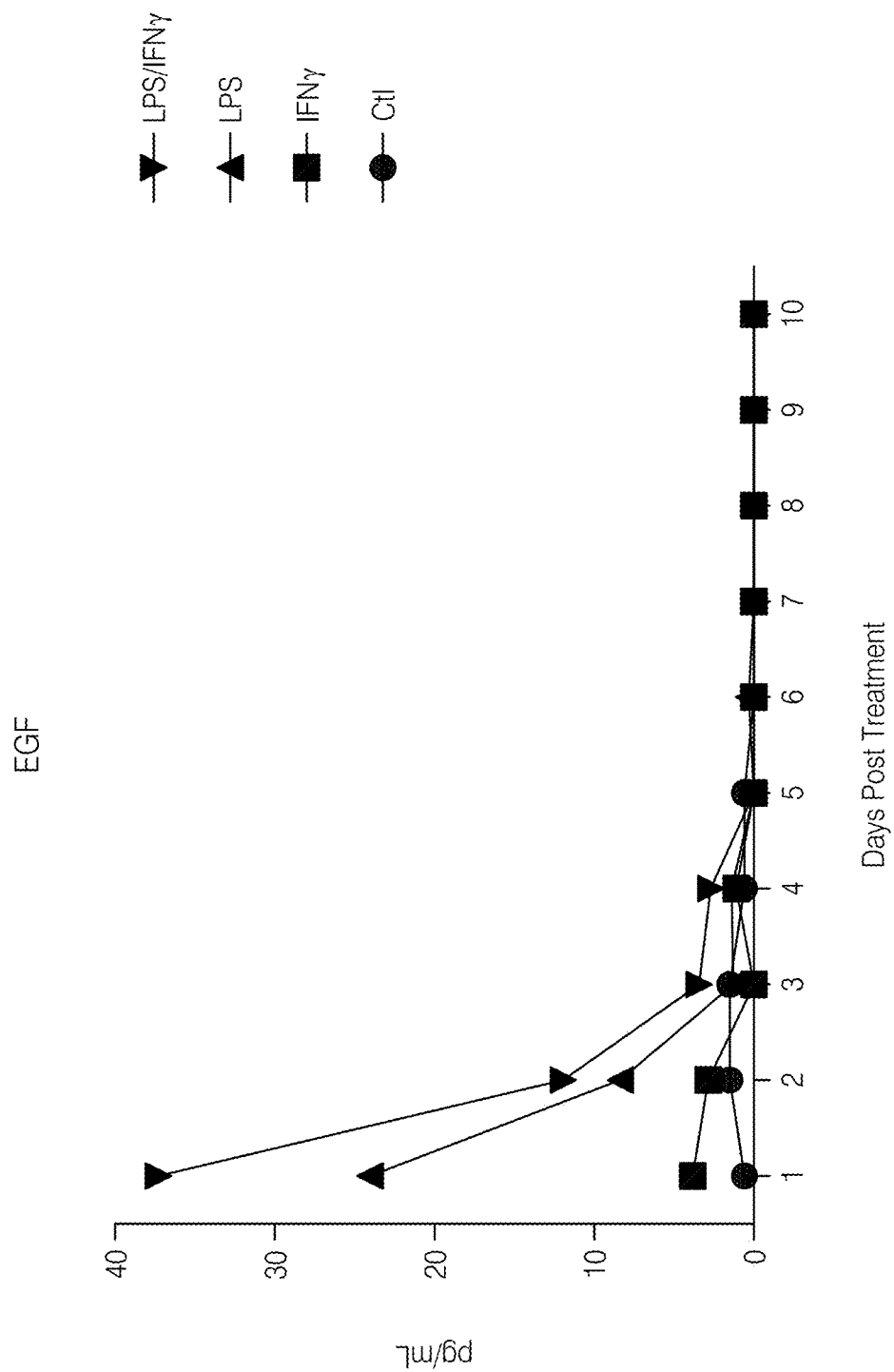
Figure 18A:
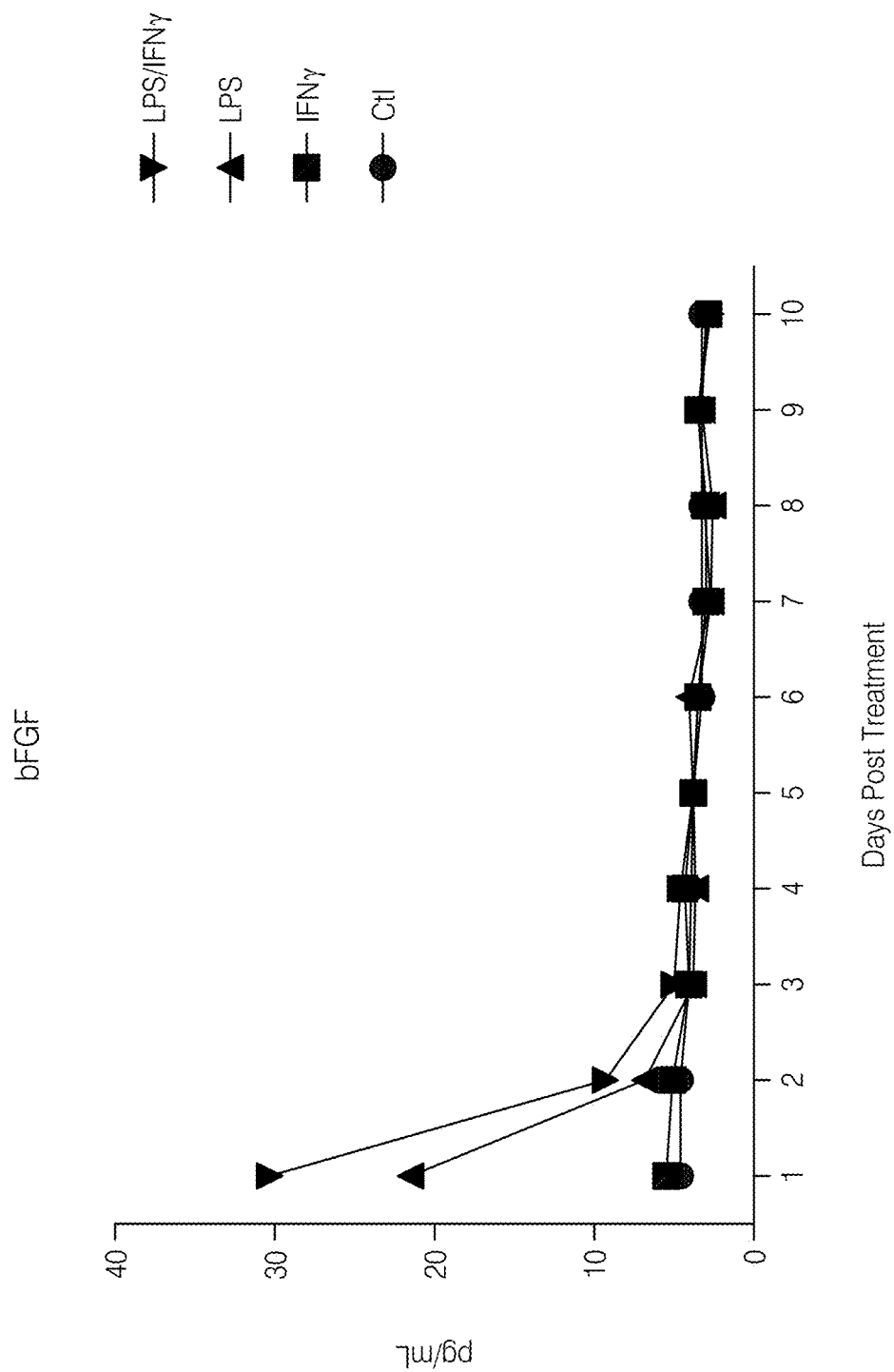
Figure 18B:
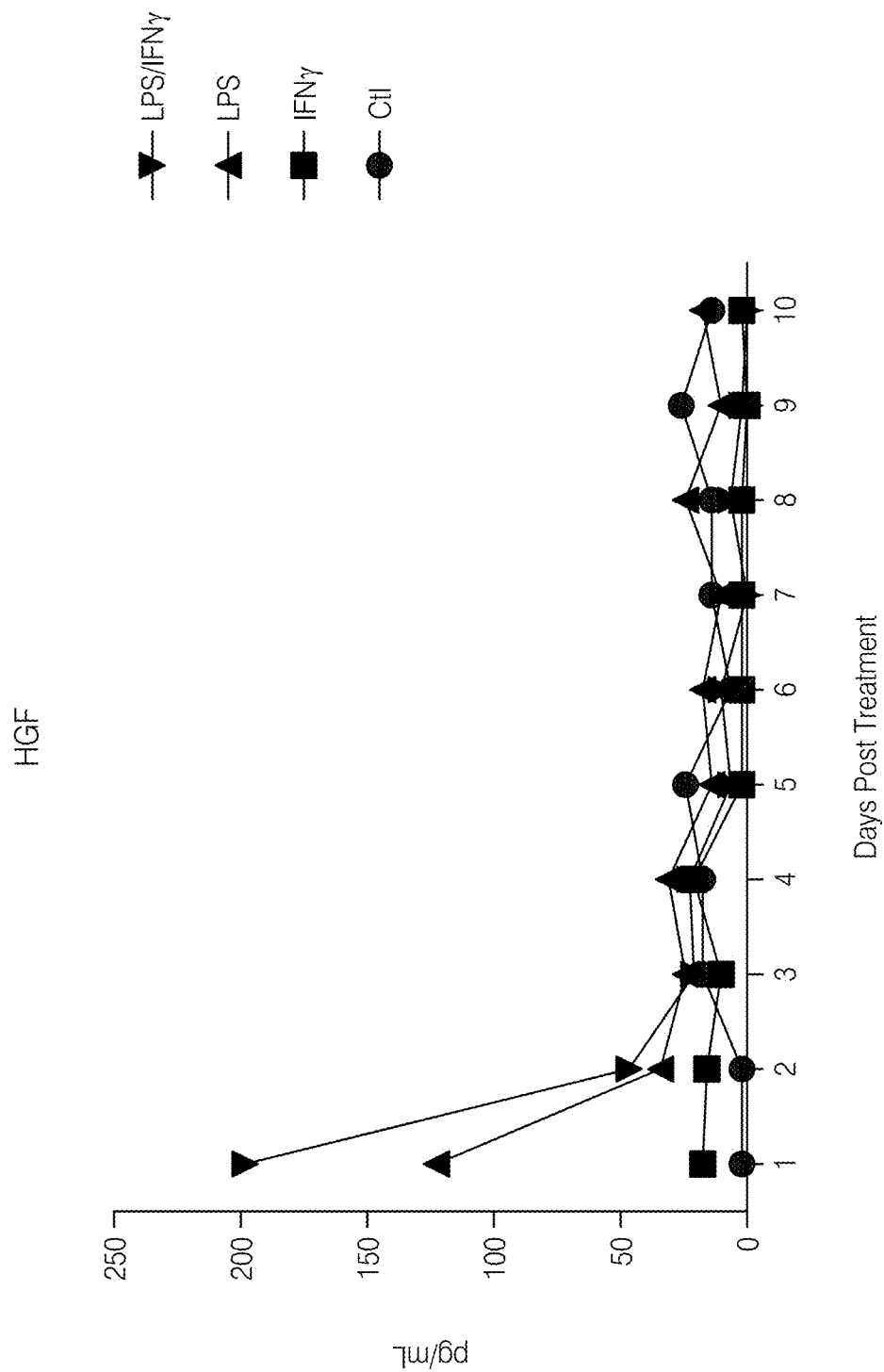
Figure 18C:
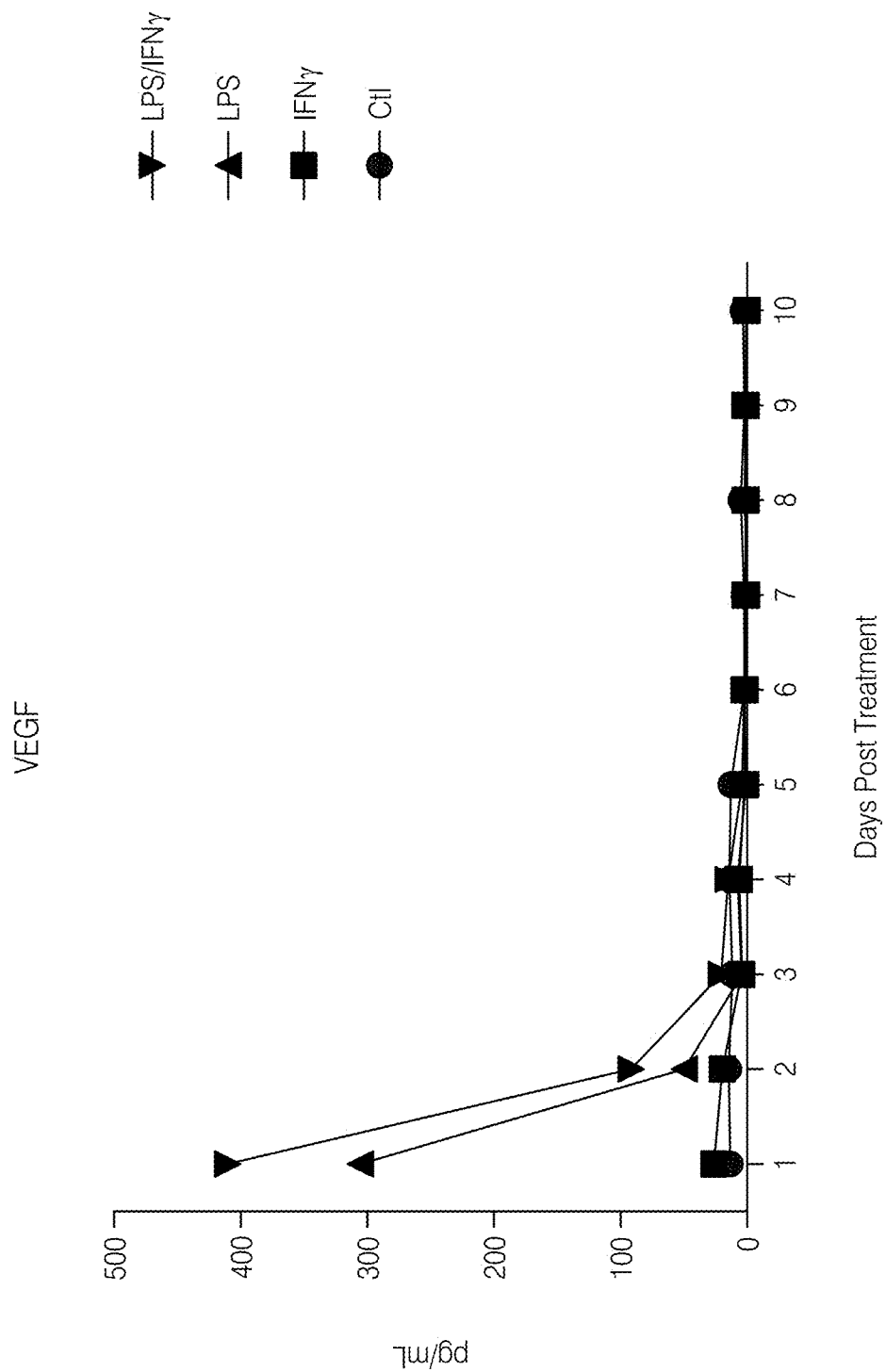

Given that the intracranial glioma model is in an animal lacking a complete immune system, and that these GEMs were not armed with anti-tumor factors, an impact on tumor growth or overall survival in tumor-bearing animals was not expected. However, human clinical trials from the 1990s, which evaluated IFNγ and/or LPS-stimulated macrophages showed a lack of efficacy, despite LPS/IFNγ stimulation supported antibody dependent cytotoxicity (ADCC), and increased Tumor necrosis factor (TNF) secretion in vitro following an 18 hour IFNγ stimulation (Andreesen, 1998). It is believed that the failure of macrophages to provide a survival benefit in this setting is partly due to diversion of macrophages by tumor cells to a pro-tumor or anti-inflammatory phenotype, absence or ineffectiveness of other cytotoxic immune cells, or lack of persistent inflammatory LPS/IFNγ signal, as it has been seen in vitro (FIG. 18A to 18CC). In fact, the use of a strong TLR4 agonist like LPS might have unintended anti-inflammatory consequences such as IL-10 secretion (FIG. 18J), or increased PD-L1 surface expression (FIG. 15B), two factors known to inhibit an effective immune response in tumors (refs). Therefore, subsequent experiments aimed to generate a GEM that may be resistant polarization to an anti-inflammatory phenotype by the tumor, while improving the efficacy of cytotoxic immune cells.

It was demonstrated that GEMs could be prevented from expressing TAM-associated factors that contribute to tumor immune evasion. Using the CRISPR/Cas9 system, the genes for IL-10 and PD-L1 were choose for deletion, as they are factors expressed by tumor associated macrophages in the tumor microenvironment that inhibit an effective anti-tumor response (Sica, Antonio, et al. Autocrine production of IL-10 mediates defective IL-12 production and NF-kappa B activation in tumor-associated macrophages. J Immunol. 2000 Jan. 15; 164(2):762-7; Bloch et al., Gliomas promote immunosuppression through induction of B7-H1 expression in tumor-associated macrophages; Clin Cancer Res. 2013 Jun. 15; 19(12):3165-75; references incorporated in their entirety herein).

Figure 19A:
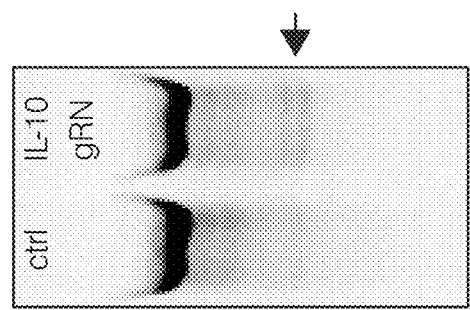
FIGS. 19A, 19B, 19C, 19D, 19E, 19F, 19G, 19H, and 19I show that GEMs can be engineered to resist the immunosuppressive tumor microenvironment and support an anti-tumor response.
Figure 19B:
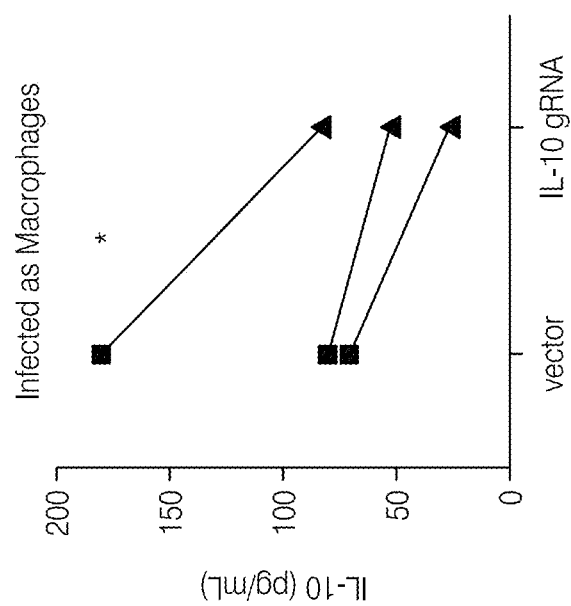
Figure 19C:
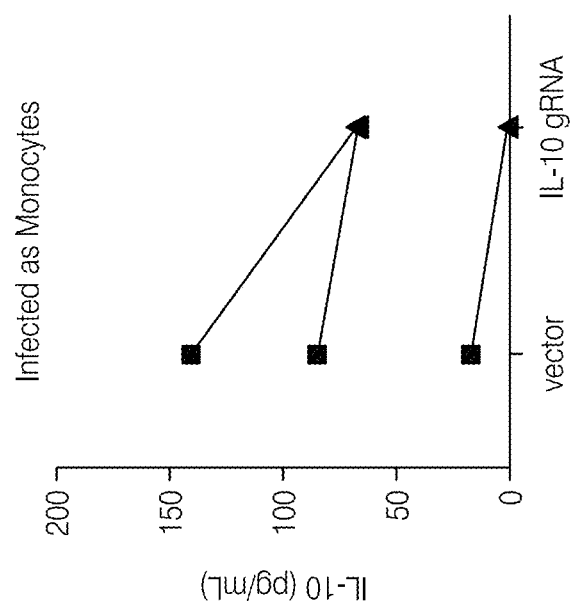
Figure 19D:
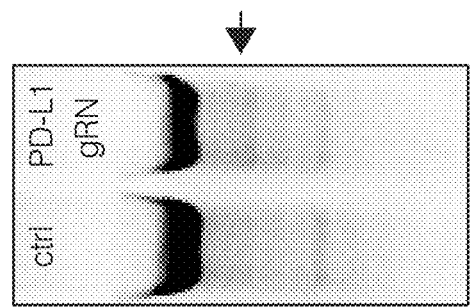
Figure 19E:
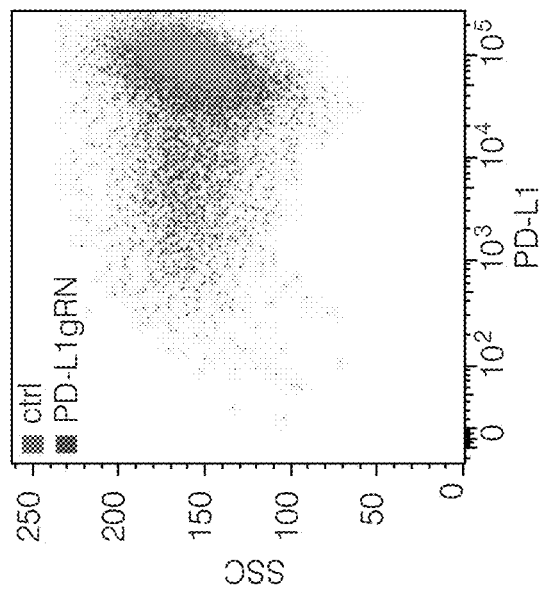
Figure 19F:
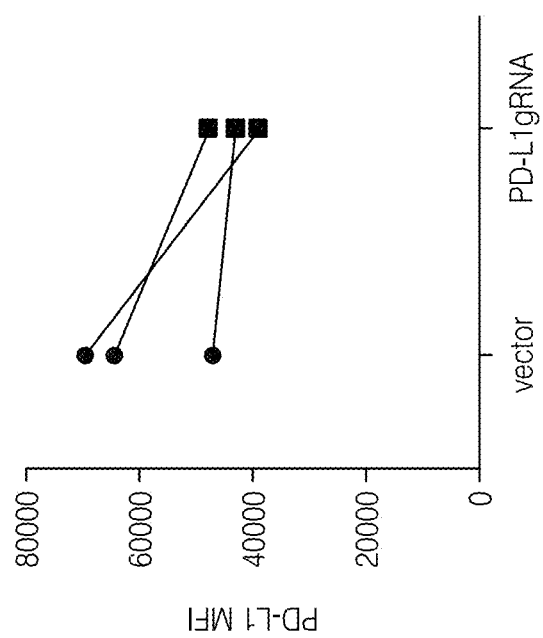

Using a lentiviral vector encoding Cas9 and specific guide RNAs (Sanjana Nat methods 2014), genomic interruption of the IL-10 and PD-L1 loci were introduced (FIGS. 19A and 19D). When introduced to either monocytes or GM-CSF differentiated macrophages, these genomic disruptions resulted in a reduction of LPS/IFNγ-induced IL-10 secretion (FIGS. 19A, 19B and 19C) and surface PD-L1 expression (FIGS. 19D, 19E and 19F).

Figure 19G:
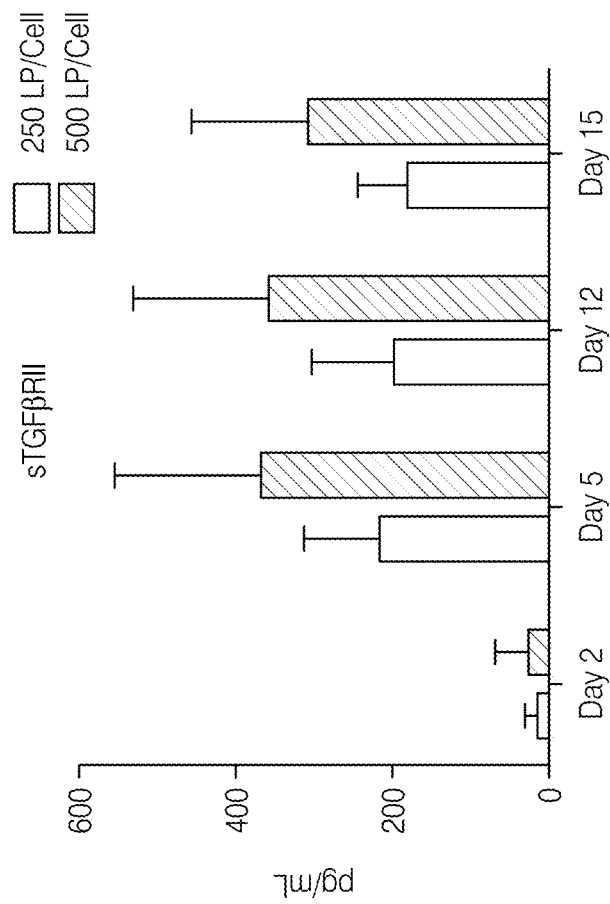
Figure 19H:
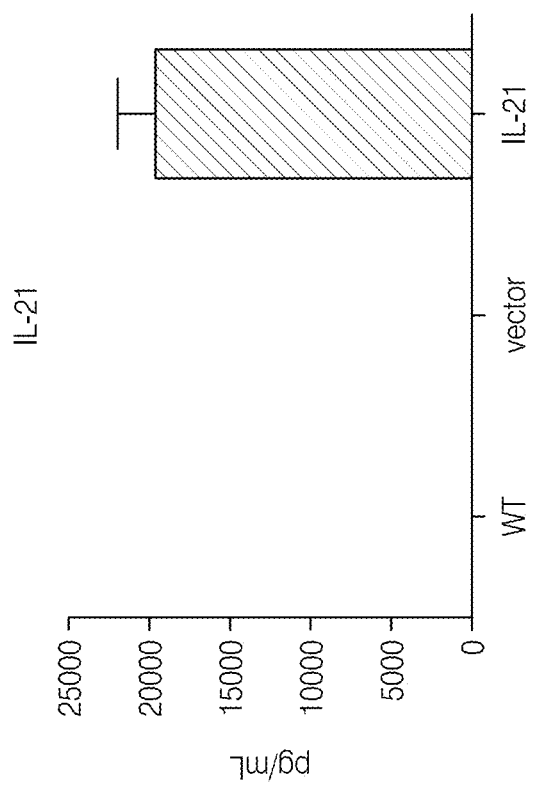
Figure 19I:
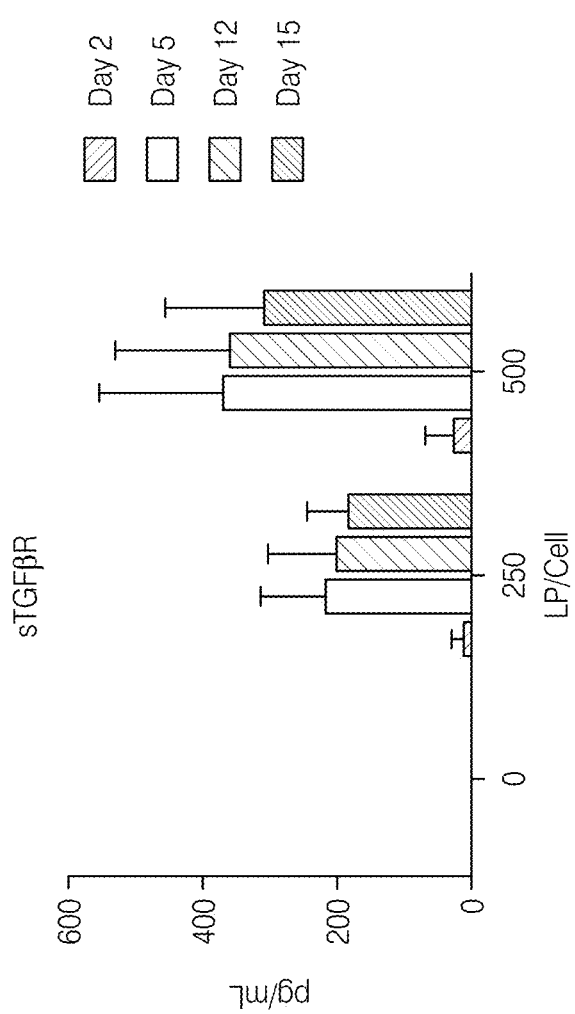

GEMs can further be programmed to resist and overturn the suppressive milieu in the TME and support the activation, proliferation, and/or survival of ineffective cytotoxic immune cells. For example, Tumor growth factor-beta (TGFβ) is a well-described tumor-derived factor that prevents a cytotoxic immune response in a variety of ways. Here it is demonstrated that GEMs can be engineered to secrete the soluble TGFβ receptor II (sTGFβRII) (FIGS. 19G and 19I), a decoy receptor that inhibits TGFβ signaling and SMAD activity. Additionally, GEMs can be employed to secrete cytokines that activate NK and T cells, and support ADCC, such as IL-21 (25961061) (FIG. 19H), a signaling molecule that is currently in multiple clinical trials as a cancer monotherapy or in combination with therapeutic antibodies. Although most commonly produced by CD4 helper T cells, IL-21 delivers potent proliferative and activating signals to cytotoxic lymphocytes, including T cell and natural killer cells. The data demonstrate that macrophages can be engineered to express and secrete significant concentrations of IL-21 suggest that impaired cytotoxic immune cell functions may be restored in the presence of GEMs. Together, these data provide evidence that GEMs can be engineered to express reduced anti-inflammatory proteins, or produce soluble factors that either interfere with immunosuppressive protein signaling or support pro-inflammatory protein production. In some alternatives of the GEMs, the GEMs can express reduced anti-inflammatory proteins, or produce soluble factors that either interfere with immunosuppressive protein signaling or support pro-inflammatory protein production in comparison to proteins that have not been transduced by said lentiviral vectors of the alternatives described herein. In some alternatives, the expressed protein or reduced anti-inflammatory protein is IL-21. In some alternatives the engineered GEMS can express reduced anti-inflammatory proteins, or produce soluble factors that either interfere with immunosuppressive protein signaling or support pro-inflammatory protein production at a higher expression level compared to wild type immune cells.

CRISPR Targeting of TAM Immunosuppressive Genes in GEMs

Figure 26A:
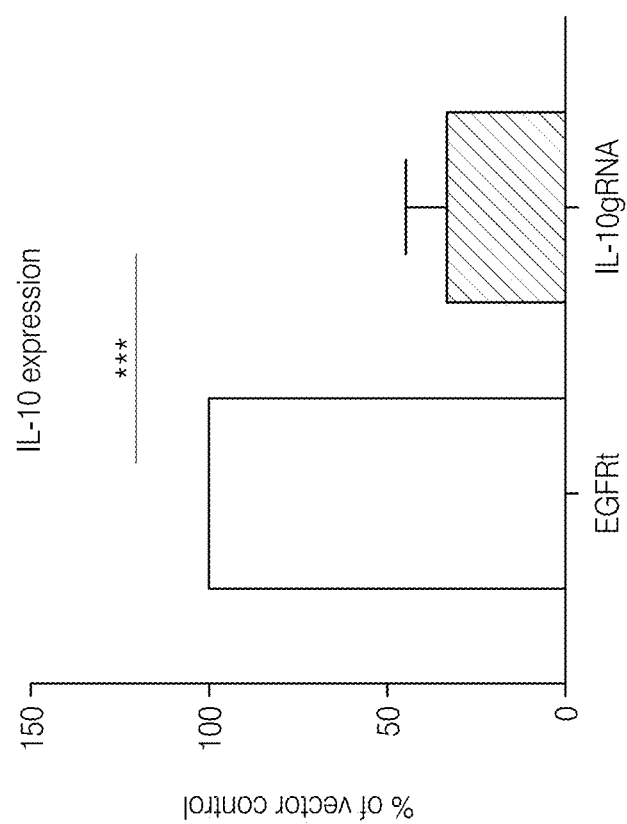
FIGS. 26A, 26B, 26C, 26D and 26E show that GEMs can be engineered to resist the immunosuppressive tumor microenvironment and support an anti-tumor response.
Figure 26B:
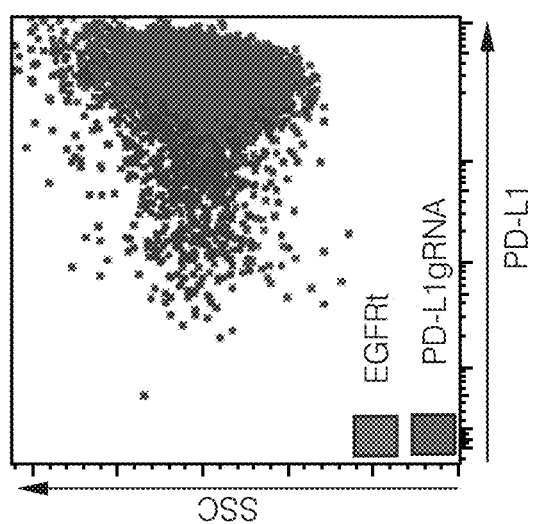
Figure 26C:
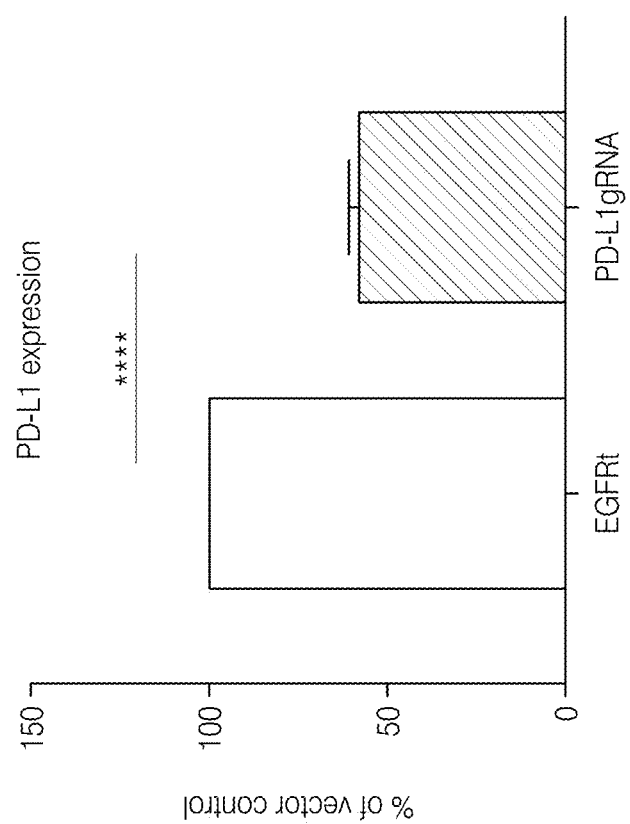

Given that the intracranial glioblastoma model lacks a complete immune system and that GEMs were not armed with functional payloads, nor do they express detectable levels of inflammatory cytokines (FIG. 31A-31C), it was not expected that there would be an impact on tumor growth or overall survival in xenograft-bearing animals. However, human clinical trials from the 1980s and 1990's, evaluating IFNγ and/or LPS ex vivo-stimulated macrophages for the treatment of patients with solid tumors, also showed no survival benefit, despite antibody dependent cell-mediate cytotoxicity (ADCC), and increased Tumor Necrosis Factor α (TNFα) secretion in vitro following an 18 hour IFNγ stimulation (Andreesen R, Hennemann B, Krause S W. Adoptive immunotherapy of cancer using monocyte-derived macrophages: rationale, current status, and perspectives. J Leukoc Biol 1998; 64:419-426; incorporated by reference in its entirety herein). It was believed that the failure of macrophages to provide a survival benefit in the setting of a complete immune system is due to: 1) diversion of macrophages by tumor cells to a pro-tumor or anti-inflammatory phenotype, or 2) absence or ineffectiveness of other cytotoxic immune cells, or 3) lack of persistent inflammatory LPS/IFNγ-induced cytokine release, as has been seen in vitro following 18 hour stimulation (FIGS. 19B and 19C). In fact, the use of a strong TLR4 agonist like LPS might have unintended anti-inflammatory consequences such as sustained IL-10 secretion (FIGS. 19B and 19C), or increased PD-L1 surface expression (FIG. 15E), two factors also known to be expressed by TAMs due to tumor-secreted signals (Bloch O, Crane C A, Kaur R et al. Gliomas promote immunosuppression through induction of B7-H1 expression in tumor-associated macrophages. Clin Cancer Res 2013; 19:3165-3175; incorporated by reference in its entirety herein). Therefore, using CRISPR/Cas9– mediated gene editing, it was aimed to prevent GEM expression of these factors that contribute to immune evasion (Sanjana N E, Shalem O, Zhang F. Improved vectors and genome-wide libraries for CRISPR screening. Nat Methods 2014; 11:783-784; Shalem O, Sanjana N E, Hartenian E et al. Genome-scale CRISPR-Cas9 knockout screening in human cells. Science 2014; 343:84-87; both incorporated by reference in their entireties herein). Using a lentiviral vector encoding Cas9 and specific guide RNAs19, the genomic loci for IL-10 and PD-L1 was interrupted. This is indicated by the generation of a cleavage product following incubation of the amplified and re-annealed genomic regions with the Surveyor endonuclease, which cleaves at mismatched base pairs (FIGS. 19A and 19D and FIGS. 24 A and B arrows) (Qiu P, Shandilya H, D'Alessio J M et al. Mutation detection using Surveyor nuclease. Biotechniques 2004; 36:702-707; incorporated by reference in its entirety herein). When introduced to either monocytes or GM-CSF-differentiated macrophages, disruption of the IL-10 locus resulted in a 60% reduction of LPS/IFNγ-induced IL-10 secretion (FIG. 26B-26C). Following infection of GM-CSF-differentiated macrophages with a virus encoding Cas9 and a PD-L1 guide RNA, surface PD-L1 expression as a result of LPS/IFNγ stimulation was reduced by 40% (FIG. 26B-26C). This is consistent with the findings of other investigators who report that the CRISPR system often modifies only one allele (Ran F A, Hsu P D, Wright J et al. Genome engineering using the CRISPR-Cas9 system. Nat Protoc 2013; 8:2281-2308; McComb S, Aguade-Gorgorio J, Harder L et al. Activation of concurrent apoptosis and necroptosis by SMAC mimetics for the treatment of refractory and relapsed ALL. Sci Transl Med 2016; 8:339ra370; all incorporated by reference in its entirety herein).

GEM Secretion of Anti-Inflammatory Blockades or Activating Cytokines

Figure 26D:
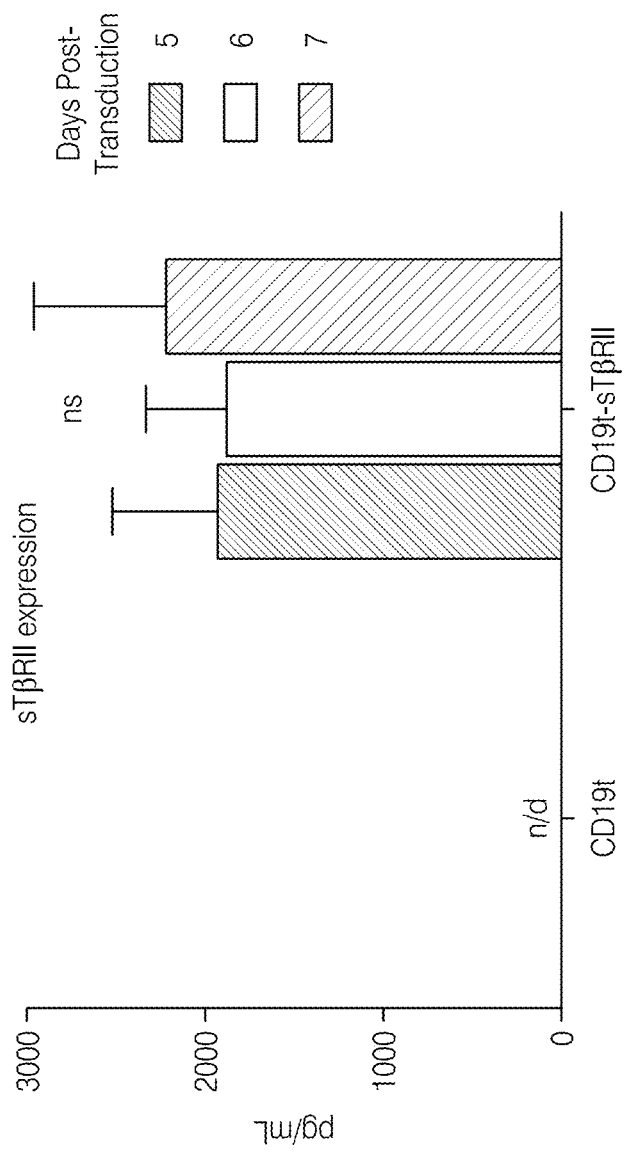
Figure 26E:
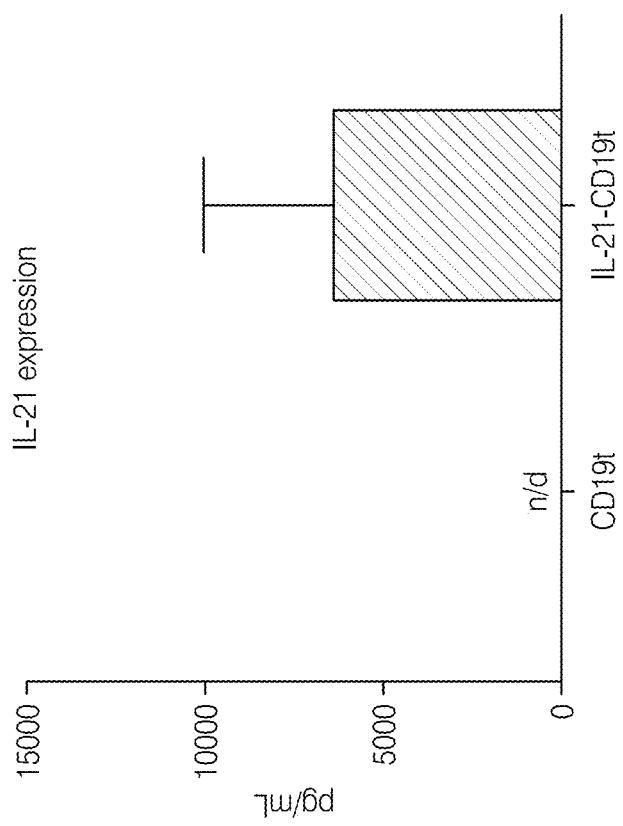

It was sought to evaluate whether GEMs could be programmed to resist the suppressive milieu in the TME and support the activation, proliferation, and survival of cytotoxic anti-tumor immune cells. For example, transforming growth factor-beta (TGFβ) is a well-described tumor-derived factor that prevents a cytotoxic immune response in a variety of ways (Crane C A, Han S J, Barry J J et al. TGF-beta downregulates the activating receptor NKG2D on NK cells and CD8+ T cells in glioma patients. Neuro Oncol 2010; 12:7-13; Smyth M J, Strobl S L, Young H A et al. Regulation of lymphokine-activated killer activity and pore-forming protein gene expression in human peripheral blood CD8+T lymphocytes. Inhibition by transforming growth factor-beta. J Immunol 1991; 146:3289-3297; Bright J J, Sriram S. TGF-beta inhibits IL-12-induced activation of Jak-STAT pathway in T lymphocytes. J Immunol 1998; 161:1772-1777; Peng Y, Laouar Y, Li M O et al. TGF-beta regulates in vivo expansion of Foxp3-expressing CD4+ CD25+ regulatory T cells responsible for protection against diabetes. Proc Natl Acad Sci USA 2004; 101:4572-4577; Gorelik L, Flavell R A. Immune-mediated eradication of tumors through the blockade of transforming growth factor-beta signaling in T cells. Nat Med 2001; 7:1118-1122; all incorporated by reference in their entireties herein). It was demonstrated that GEMs can be engineered to secrete the soluble TGFβ receptor II (sTGFβRII) (FIGS. 19G and 26D) to function as a decoy receptor for TGFβ and reduce TGFβ signaling as previously described (Rowland-Goldsmith M A, Maruyama H, Kusama T et al. Soluble type II transforming growth factor-beta (TGF-beta) receptor inhibits TGF-beta signaling in COLO-357 pancreatic cancer cells in vitro and attenuates tumor formation. Clin Cancer Res 2001; 7:2931-2940; included by reference in its entirety herein). GEMs were also engineered to secrete IL-21 (FIGS. 1911 and 26E), a cytokine normally expressed by CD4+ T cells that activates NK and T cells and supports ADCC44, and shifts the polarization of TAMs toward an M1 phenotype (Qiu P, Shandilya H, D'Alessio J M et al. Mutation detection using Surveyor nuclease. Biotechniques 2004; 36:702-707; Croce M, Rigo V, Ferrini S. IL-21: a pleiotropic cytokine with potential applications in oncology. J Immunol Res 2015; 2015:696578; Skak K, Frederiksen K S, Lundsgaard D. Interleukin-21 activates human natural killer cells and modulates their surface receptor expression. Immunology 2008; 123:575-583; Xu M, Liu M, Du X et al. Intratumoral Delivery of IL-21 Overcomes Anti-Her2/Neu Resistance through Shifting Tumor-Associated Macrophages from M2 to M1 Phenotype. J Immunol 2015; 194:4997-5006; all incorporated by reference in their entireties herein). Recombinant IL-21 is currently in multiple clinical trials either as a cancer monotherapy, or in combination with tyrosine kinase inhibitors or therapeutic antibodies (Croce M, Rigo V, Ferrini S. IL-21: a pleiotropic cytokine with potential applications in oncology. J Immunol Res 2015; 2015:696578; Spolski R, Leonard W J. Interleukin-21: a double-edged sword with therapeutic potential. Nat Rev Drug Discov 2014; 13:379-395; all incorporated by reference in their entireties herein). The observation that macrophages can be engineered to secrete significant concentrations of IL-21 provides evidence that impaired cytotoxic immune cell functions may be restored in the presence of IL-21-expressing GEMs. Together, the data demonstrate that GEMs can be engineered to express reduced levels of anti-inflammatory proteins, or produce soluble factors that either interfere with immunosuppressive signaling or support anti-tumor immune responses.

GEMs can Express Genes from Multiple Viruses

Figures 24A, 24B:
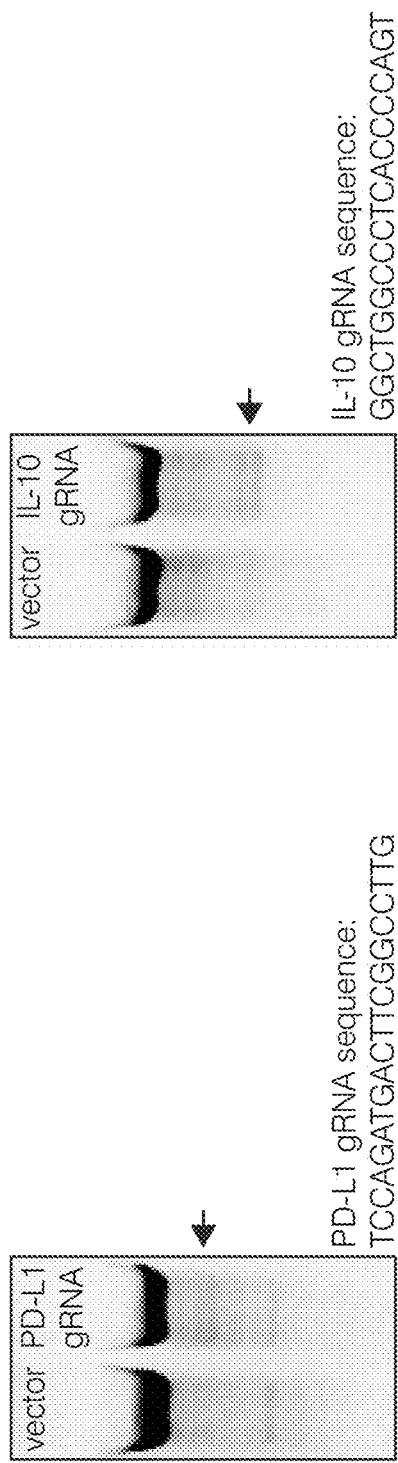
FIGS. 24A, 24B, 24C, 24D, 24E and 24F show that constructs used during functional analysis of GEMs. gRNA sequences encoding PD-L1 (FIG. 24A) and IL-10 (FIG. 24B) were screened for their ability to induce Cas9-mediated genomic DNA disruptions with the Surveyor assay. Successful sequences and the resultant cleavage are shown. Architecture of integrating region of (FIG. 24C) epHIV7.2 and (FIG. 24D) LentiCRISPRv2 lentiviral vectors used.
Figure 24C:
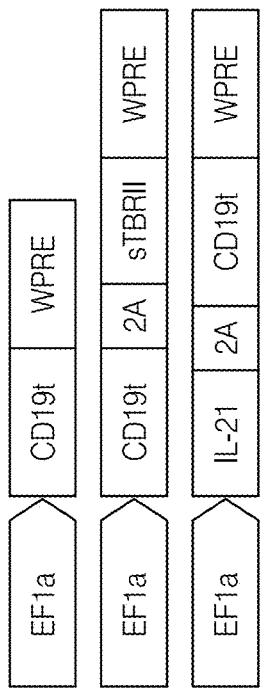
Figure 24D:
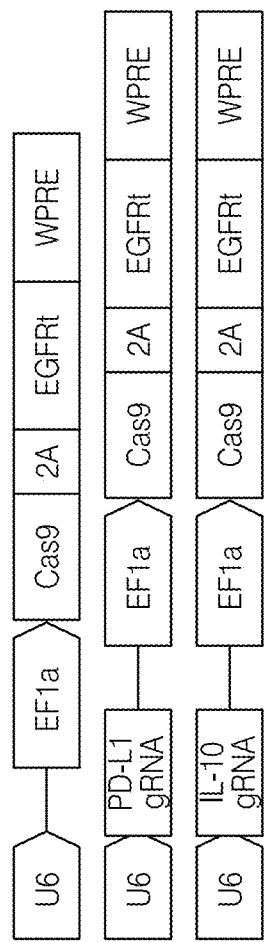
Figure 24E:
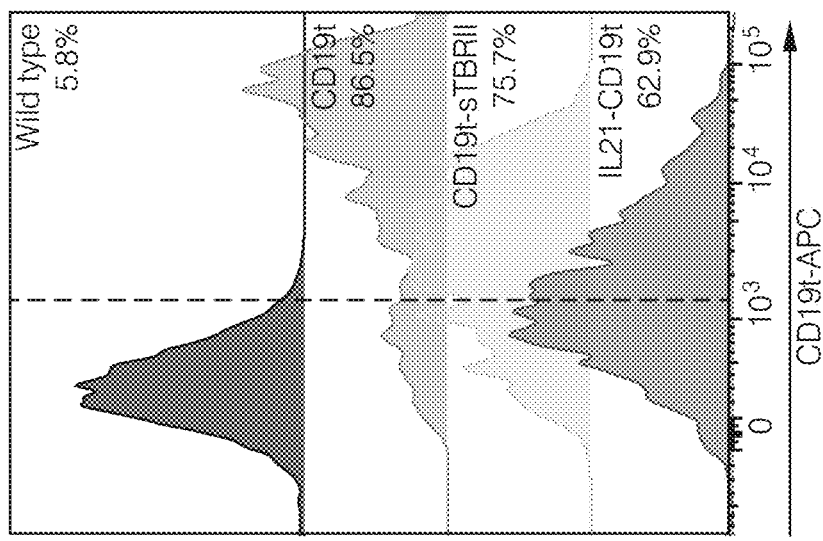
Figure 24F:
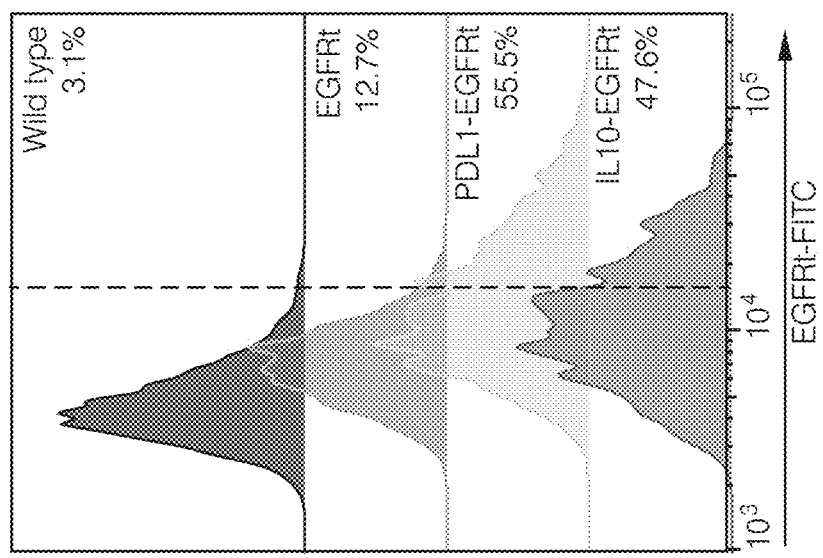
Figure 27A:
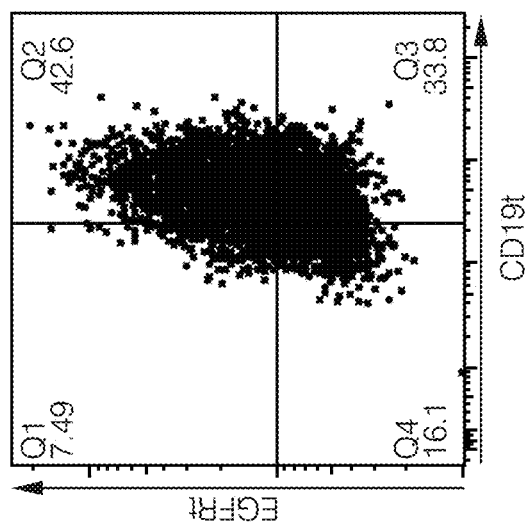
FIGS. 27A, 27B, 27C, 27D, 27E, 27F and 27G show GEMs can be engineered to have multiple functions.
Figure 27B:
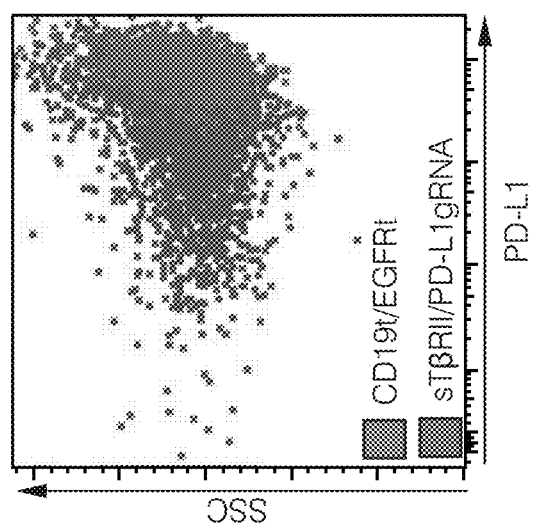
Figure 27C:
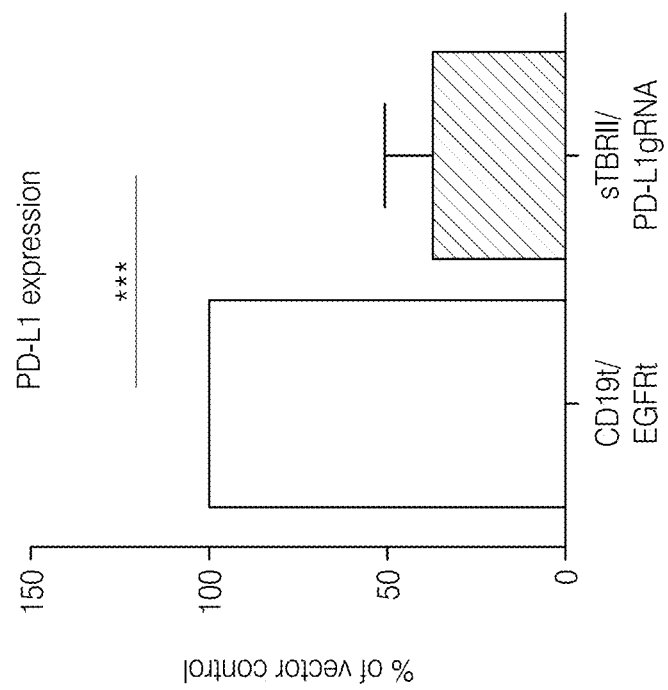
Figure 27D:
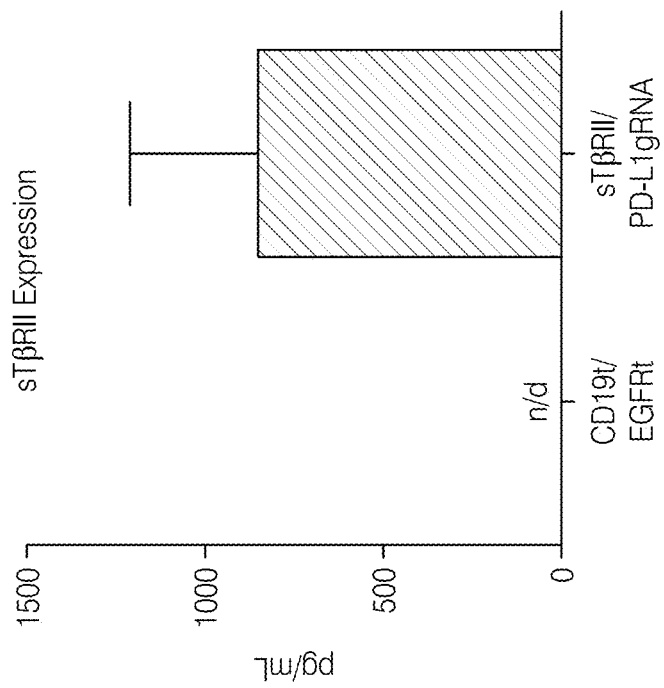
Figure 27E:
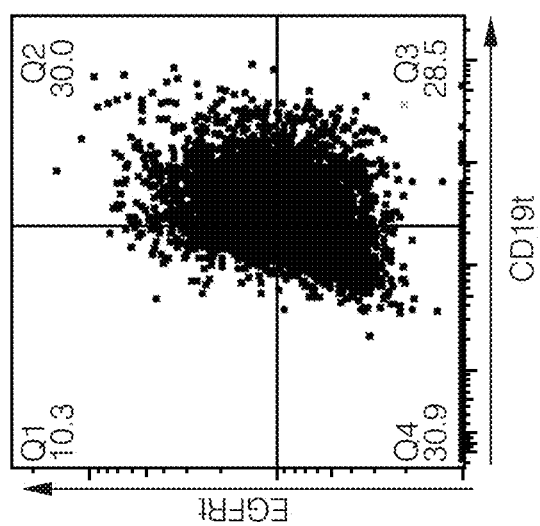
Figure 27F:
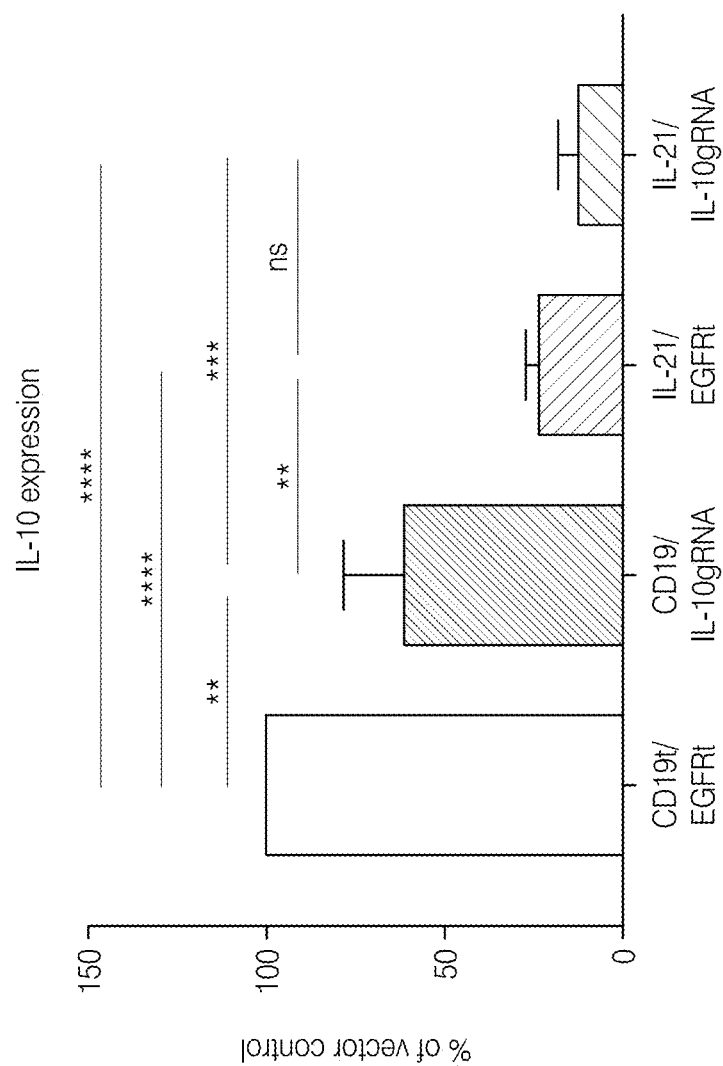
Figure 27G:
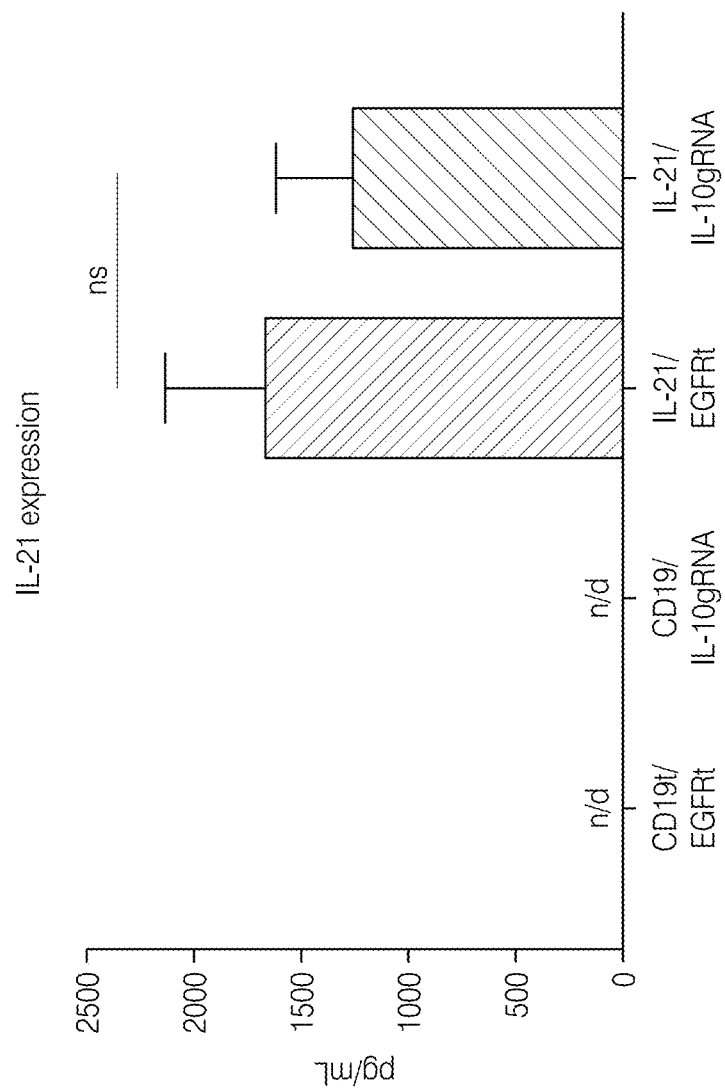

Due to the multiple challenges that arise as a result of the immunosuppressive milieu of the TME, it was sought to engineer macrophages that both resist the tumor microenvironment, through CRISPR-mediated gene disruption, as well as secrete sTβRII and IL-21. To this end, a truncated CD19 sequence was inserted into the epHIV7.2 vector (FIG. 24C) and added the epitope tag EGFRt to replace the puromycin sequence of the lentiCRISPRv2 vector (FIG. 24D). It was found that both epitope tags can be detected on macrophages infected with lentivirus encoding the respective sequences (FIGS. 24E and 24F). When GEMs are infected with both viruses, 30-45% cells were double positive by flow cytometry (FIGS. 27A and 27E). Furthermore, evaluation of PD-L1 expression on cells expressing both CD19t and EGFRt shows a 70% reduction in PD-L1 (FIG. 27C); these GEMs are also uncompromised in their expression of sTIβRII (FIG. 27D). Interestingly, IL-21 seems to prevent LPS-induced IL-10 expression. GEMs encoding IL-21 alone reduce IL-10 expression by 76.4% and when IL-21 is expressed in combination with IL-10gRNA, expression drops by 87.3%. These are significantly lower levels of expression than seen in the IL-10gRNA+CD19t vector control, 38.5%. (FIG. 27F). IL-21 expression was unchanged when IL-10 expression was targeted (FIG. 27G).

Human GEMs Disperse from the Injection Site and Infiltrate Tumor Tissue

Isolated CD14+ monocytes were plated in macrophage media (RPMI1640 medium (Gibco) supplemented with 10% FBS (Hyclone)) on tissue culture-treated plastic dishes (Corning) at a density not exceeding 250,000 cells/cm² in the presence of 10 ng/mL GM-CSF (R&D Systems) at 37° C., 5% $CO_2$. 72 hours after plating, half the medium was replaced with fresh macrophage media supplemented with 20 ng/mL GM-CSF. In epHIV7 the CMV promoter of pHIV7 has been replaced with the EF1 promoter. For epHIV7.2 the EF1 promoter has been replaced with a minimal EF1 (lacking the HTLV-1 domain) and the gene for ampicillin resistance has been exchanged for kanamycin resistance. The mCherry construct was created by cloning into the gene into HIV7.2. Eight week old male NOD.Cg-Prkdc$^{scid}$ Il2rg$^{tm1Wjt}$SzJ (NSG) mice were purchased from Jackson Laboratory. Ketamine/xylazine-anesthetized animals were immobilized in stereotactic apparatus (Stoelting), a 0.5 cm incision made on the skin covering the skull, and a burr hole drilled 2 mm lateral and 0.5 mm anterior to the bregma. 200,000 wild-type or GFP-ffluc-expressing U87 cells were injected in a 2 μL volume at a rate of 1 μL/minute at 2.5 and 2.25 mm beneath the dura, 1 μL at each location. After wound closure, mice received lactated Ringer's solution for fluid recovery and buprenorphine as an analgesic. Surgery for injection of GEMs was similar to that for U87s, except that 150,000 GEMs were injected in a 3 μL total volume at 3 steps of 2.5, 2.35, and 2.25 mm below the dura. Bioluminescent imaging of GEMs or U87s expressing ffluc was conducted three times weekly. Mice were anesthetized with isoflurane, injected with 150 μL of a 28.57 mg/mL solution of D-luciferin (Perkin Elmer) intraperitoneally or subcutaneously in the scruff. Bioluminescent images were collected with a Xenogen IVIS Spectrum Imaging System (Perkin Elmer) and Living Image Software (Perkin Elmer) used to analyze the data. 21 days after GEM injection, animals were euthanized, tumor harvested and dissociated. The single cell suspension was stained for CD45, gated on live cells and singlets, and evaluated for mCherry and CD45 expression by flow cytometry. See FIGS. 21A and 21B.

Provided herein is the validation of a lentivirus-based method to engineer primary human monocytes and macrophages with the goal of generating a novel immunotherapy for solid tumors. Previous studies report 80% infectivity rate when transducing DCs with 600 ng of p24 per 500,000 cells (Firat H, Zennou V, Garcia-Pons F et al. Use of a lentiviral flap vector for induction of CTL immunity against melanoma. Perspectives for immunotherapy. J Gene Med 2002; 4:38-45; incorporated by reference in its entirety herein). As demonstrated above, virus packaged with Vpx achieves nearly 100% efficiency at 250 LP/cell, equating to 10 ng p24, per 500,000 cells, 60 times less virus. This approach causes a higher number of genomic integration events than are observed in some engineered T cells used clinically. However, because the GEMs as described herein do not divide, as observed in the in vivo studies, and demonstrate a lack of GEM expansion, it is not anticipated that insertional mutagenesis will have an impact on the safety of a clinical product. Furthermore, if it is found that functions are affected, or that the insertion rate exceeds Food and Drug Administration regulations, vector copy number can be reduced by sorting for median gene expressers.

The flexibility of this approach has allowed CRISPR-mediated gene interruption for the important immunosuppressive factors IL-10 and PD-L1, and overexpression of sTβRII and IL-21, secreted proteins that will prevent intrinsic inhibitory signals and support the anti-tumor functions of NK and cytotoxic T cells. Interestingly, when co-expressing using two viral vectors, it was found that a significant percentage of GEMs express the epitope tags for both viruses, and that CRISPR mediated reduction of IL-10 was significantly augmented when GEMs also express IL-21.

This method of lentiviral modification of primary, human macrophages may serve as a novel type of cellular immunotherapy, which can be generated in as little as seven days from a patient's blood, using a clinically-approved lentiviral backbone. GEMs may be generated from a patient's monocyte population that is currently discarded during the preparation of therapeutic TCR or CAR T cells, reducing the time and cost associated with developing new infrastructure for a clinical product. It is anticipated that in the clinic, GEMs will be directly implanted into the tumor site immediately following surgical tumor resection. This approach has benefits over intravenous infusion, and non-specific systemic approaches that have been previously used in clinical trials, maximizing the likelihood that GEMs will interact with tumor cells and alleviating concerns that they may become trapped in narrow capillary beds during peripheral circulation.

The tumor microenvironment prevents immune responses through multiple redundant mechanisms (Razavi S M, Lee K E, Jin B E et al. Immune Evasion Strategies of Glioblastoma. Front Surg 2016; 3:11; Beavis P A, Slaney C Y, Kershaw M H et al. Reprogramming the tumor microenvironment to enhance adoptive cellular therapy. Semin Immunol 2016; 28:64-72; all incorporated by reference in their entireties herein), and it is believed that modulating immune suppression may be more effective to induce anti-tumor activity than a small molecule, antibody, or cellular therapy designed against a single target. The intracranial xenograft model will allow evaluation of the adjuvant properties of GEMs when used with other cellular therapies such as CAR T cells, and will be subsequently evaluated in an immune-competent model to determine the ability GEMs to function in a complex TME.

The concept of employing macrophages for anti-tumor therapy originated in 1974, when Fidler et al demonstrated that ex vivo stimulated macrophages could suppress pulmonary metastases in a B16 melanoma model (Fidler I J. Inhibition of pulmonary metastasis by intravenous injection of specifically activated macrophages. Cancer Res 1974; 34:1074-1078; incorporated by reference in its entirety herein). Subsequent studies confirmed these findings and laid the groundwork for several clinical trials that tested the safety and efficacy of adoptively transferred macrophages for the treatment of patients with various cancers, including ovarian, colorectal, and renal carcinomas (Andreesen R, Hennemann B, Krause S W. Adoptive immunotherapy of cancer using monocyte-derived macrophages: rationale, current status, and perspectives. J Leukoc Biol 1998; 64:419-426; incorporated by reference in its entirety herein). Dose escalation studies of autologous macrophages activated with IFNγ or LPS/IFNγ prior to infusion showed that the therapy was safe, inducing only flu-like symptoms, but had no clinical benefit (Andreesen R, Hennemann B, Krause S W. Adoptive immunotherapy of cancer using monocyte-derived macrophages: rationale, current status, and perspectives. J Leukoc Biol 1998; 64:419-426; incorporated by reference in its entirety herein). The failure to improve patient outcomes could be due to limited expression of LPS/IFNγ-induced factors, such as IL-12, TNFα, or IL-6, which support the cytotoxic function of effector cells (Hao N B, Lu M H, Fan Y H et al. Macrophages in tumor microenvironments and the progression of tumors. Clin Dev Immunol 2012; 2012: 948098; incorporated by reference in its entirety herein). Additionally, tumor-derived factors such as TGFβ, M-CSF, IL-4, and IL-10 may alter the polarization of the adoptively transferred macrophages, modifying their production of cytokines to promote the function of Tregs while inhibiting tumor-specific T cell responses (Glass R, Synowitz M. CNS macrophages and peripheral myeloid cells in brain tumours. Acta Neuropathol 2014; 128:347-362; incorporated by reference in its entirety herein).

Evidence supporting the efficacy of persistently polarized macrophages comes from recent animal studies in which adoptively transferred or tumor infiltrating macrophages, engineered to inhibit NFκB-mediated alternative activation or to overexpress IFNα, overturn an immunosuppressive TME, and inhibit tumor growth (Hagemann T, Lawrence T, McNeish I et al. "Re-educating" tumor-associated macrophages by targeting NF-kappaB. J Exp Med 2008; 205: 1261-1268; Escobar G, Gentner B, Naldini L et al. Engineered tumor-infiltrating macrophages as gene delivery vehicles for interferon-alpha activates immunity and inhibits breast cancer progression. Oncoimmunology 2014; 3:e28696; all incorporated by reference in their entireties herein). Additionally, reversing the anti-inflammatory phenotype of endogenous macrophages with an Ang2/VEGF bi-specific antibody (Kloepper J, Riedemann L, Amoozgar Z et al. Ang-2/VEGF bispecific antibody reprograms macrophages and resident microglia to anti-tumor phenotype and prolongs glioblastoma survival. Proc Natl Acad Sci USA 2016; 113:4476-4481; incorporated by reference in its entirety herein), antagonists of M-CSF (Pyonteck S M, Akkari L, Schuhmacher A J et al. CSF-1R inhibition alters macrophage polarization and blocks glioma progression. Nat Med 2013; 19:1264-1272; Ries C H, Cannarile M A, Hoves S et al. Targeting tumor-associated macrophages with anti-CSF-1R antibody reveals a strategy for cancer therapy. Cancer Cell 2014; 25:846-859; all incorporated by reference in their entireties herein), or agonists of CD40 (Beatty G L, Chiorean E G, Fishman M P et al. CD40 agonists alter tumor stroma and show efficacy against pancreatic carcinoma in mice and humans. Science 2011; 331:1612-1616; incorporated by reference in its entirety herein) or TLR pathways (Peng J, Tsang J Y, Li D et al. Inhibition of TGF-beta signaling in combination with TLR7 ligation re-programs a tumoricidal phenotype in tumor-associated macrophages. Cancer Lett 2013; 331:239-249; Huang Z, Gan J, Long Z et al. Targeted delivery of let-7b to reprogramme tumor-associated macrophages and tumor infiltrating dendritic cells for tumor rejection. Biomaterials 2016; 90:72-84; Yu Q, Nie S P, Wang J Q et al. Toll-like receptor 4 mediates the antitumor host response induced by *Ganoderma atrum* polysaccharide. J Agric Food Chem 2015; 63:517-525; El Andaloussi A, Sonabend A M, Han Y et al. Stimulation of TLR9 with CpG ODN enhances apoptosis of glioma and prolongs the survival of mice with experimental brain tumors. Glia 2006; 54:526-535; all incorporated by reference in their entireties herein) reduces tumor progression by inhibiting tumor-supportive behavior and restoring anti-tumor immune responses. Notably, these anti-tumor mechanisms may be either direct, such as the induction of tumoricidal activity by macrophages themselves (Peng J, Tsang J Y, Li D et al. Inhibition of TGF-beta signaling in combination with TLR7 ligation re-programs a tumoricidal phenotype in tumor-associated macrophages. Cancer Lett 2013; 331:239-249; Beatty G L, Chiorean E G, Fishman M P et al. CD40 agonists alter tumor stroma and show efficacy against pancreatic carcinoma in mice and humans. Science 2011; 331: 1612-1616; Hagemann T, Lawrence T, McNeish I et al. "Re-educating" tumor-associated macrophages by targeting NF-kappaB. J Exp Med 2008; 205:1261-1268; all incorporated by reference in their entireties herein), or indirect, through support of NK (Yu Q, Nie S P, Wang J Q et al. Toll-like receptor 4 mediates the antitumor host response induced by *Ganoderma atrum* polysaccharide. J Agric Food Chem 2015; 63:517-525; Hagemann T, Lawrence T, McNeish I et al. "Re-educating" tumor-associated macrophages by targeting NF-kappaB. J Exp Med 2008; 205: 1261-1268; all incorporated by reference in their entireties herein) and T cell-mediated cytotoxicity (Yu Q, Nie S P, Wang J Q et al. Toll-like receptor 4 mediates the antitumor host response induced by *Ganoderma atrum* polysaccharide. J Agric Food Chem 2015; 63:517-525; El Andaloussi A, Sonabend A M, Han Y et al. Stimulation of TLR9 with CpG ODN enhances apoptosis of glioma and prolongs the survival of mice with experimental brain tumors. Glia 2006; 54:526-535; all incorporated by reference in their entireties herein) or via activation of DCs (Van der Jeught K, Bialkowski L, Daszkiewicz L et al. Targeting the tumor microenvironment to enhance antitumor immune responses. Oncotarget 2015; 6:1359-1381; incorporated by reference in its entirety herein). Furthermore, studies demonstrating TLR3-mediated repolarization of tumor myeloid cells from GBM patients suggest that their inherent plasticity supports their potential to initiate local immune activation (Kees T, Lohr J, Noack J et al. Microglia isolated from patients with glioma gain antitumor activities on poly (I:C) stimulation. Neuro Oncol 2012; 14:64-78; incorporated by reference in its entirety herein). Accordingly, it is contemplated that macrophages can induce multi-faceted changes to the way the immune system responds to tumor, and underscore the power of harnessing this cell population to restructure the TME.

In support of this belief, several studies that evaluate the impact of innate immune cell activation in the TME indicate that this is an important component to clinical efficacy for patients with solid tumors. For example, DC-based cellular therapies are the first to receive approval by the Food and Drug Administration based on their ability to induce anti-tumor immune responses in patients with castration resistant prostate cancer (Kantoff P W, Higano C S, Shore N D et al. Sipuleucel-T immunotherapy for castration-resistant prostate cancer. N Engl J Med 2010; 363:411-422; incorporated by reference in its entirety herein). Other experimental studies seek to boost immunity using adjuvants (Crane C A, Han S J, Ahn B et al. Individual patient-specific immunity against high-grade glioma after vaccination with autologous tumor derived peptides bound to the 96 KD chaperone protein. Clin Cancer Res 2013; 19:205-214; incorporated by reference in its entirety herein), live oncolytic viruses (Suryadevara C M, Riccione K A, Sampson J H. Immunotherapy gone viral: Bortezomib and oHSV enhance antitumor NK cell activity. Clin Cancer Res 2016; incorporated by reference in its entirety herein), or those engineered to specifically infect tumor-resident APCs (Goyvaerts C, De Groeve K, Dingemans J et al. Development of the Nanobody display technology to target lentiviral vectors to antigen-presenting cells. Gene Ther 2012; 19:1133-1140; Cire S, Da Rocha S, Yao R et al. Immunization of mice with lentiviral vectors targeted to MHC class II+ cells is due to preferential transduction of dendritic cells in vivo. PLoS One 2014; 9:e101644; both incorporated by reference in their entireties herein). These approaches may likely result in significant innate immune cell activation, including their production of pro-inflammatory mediators, and support of cytotoxic immune cell functions in the tumor. Although these approaches demonstrate the impact of enhancing innate and adaptive immune cell crosstalk on clinical efficacy, the mechanisms underlying pleiotropic effects on the tumor microenvironment and anti-tumor immunity are not well defined. It is anticipated that use of a macrophage-based immunotherapy in animal studies and in clinical trials will synergize with these types of approaches to delineate the mechanisms that are critical to overcoming the suppressive and anti-inflammatory TME.

When injected directly into a brain tumor xenograft, GEMs stably produce lentivirally encoded firefly luciferase, and survive long-term without expanding or negatively impacting animal survival. The flexibility of this approach has allowed CRISPR-mediated gene interruption for the important immunosuppressive factors IL-10 and PD-L1, and overexpression of sTGFRβII and IL-21, secreted proteins that will prevent intrinsic inhibitory signals and support the anti-tumor functions of NK and T cells.

The concept of employing macrophages for anti-tumor therapy originated in 1974 when Fidler et al. demonstrated that ex vivo stimulated macrophages could suppress pulmonary metastases in a B16 melanoma model. Subsequent studies confirmed these findings and laid the groundwork for several clinical trials that tested the safety and efficacy of adoptively transferred macrophages for the treatment of patients with various cancers, including ovarian, colorectal, and renal carcinomas. Dose escalation studies of autologous macrophages activated with IFNγ or LPS/IFNγ prior to infusion showed that the therapy was safe, inducing only flu-like symptoms, but had no clinical benefit. The failure to improve patient outcomes could be due to limited expression of LPS/IFNγ-induced factors, such as IL-12, TNFα, or IL-6, which support the cytotoxic function of effector cells. Additionally, tumor-derived factors such as TGFβ, M-CSF, IL-4, and IL-10 may have altered the polarization of the adoptively transferred macrophages, modifying their production of cytokines to promote the function of Tregs while inhibiting tumor-specific T cell responses.

Evidence supporting the efficacy of persistently polarized macrophages comes from recent animal studies in which adoptively transferred or tumor infiltrating macrophages, engineered to inhibit NFκB-mediated alternative activation or to overexpress IFNα, overturn an immunosuppressive TME and inhibit tumor growth. Additionally, reversing the anti-inflammatory phenotype of endogenous macrophages with an Ang2/VEGF bi-specific antibody, antagonists of M-CSF or agonists of CD40 or TLR pathways reduces tumor progression by inhibiting tumor-supportive behavior and restoring anti-tumor immune responses. Notably, these anti-tumor mechanisms may be either direct, such as the induction of tumoricidal activity by macrophages themselves or indirect, through support of NK and T cell-mediated cytotoxicity. Furthermore, studies demonstrating TLR3-mediated repolarization of tumor myeloid cells from GBM patients suggest that their inherent plasticity supports their potential to initiate local immune activation. Accordingly, it is contemplated that macrophages alone can induce multi-faceted changes to the way the immune system responds to tumor, and underscore the power of harnessing this cell population as a tool to restructure the TME.

It was demonstrated for the first time that a novel macrophage-based immunotherapy can be generated in seven days from a patient's blood, using a clinically-approved lentiviral backbone. GEMs may be generated from a patient's monocyte population that is discarded during the preparation of therapeutic TCR or CAR T cells, reducing the time and cost associated with developing new infrastructure for a clinical product. It is anticipated that in the clinic, GEMs will be directly implanted into the tumor during surgical tumor resection. This approach has benefits over intravenous infusion previously employed in clinical trials as it maximizes the likelihood that GEMs will interact with tumor cells and alleviates concerns that they may become trapped in narrow capillary beds during peripheral circulation.

The tumor microenvironment prevents immune responses through multiple redundant mechanisms. Therefore, modulating immune suppression may be more effective to induce antitumor activity than a small molecule, antibody, or cellular therapy designed against a single target.

CD4 and CD8 T Cells Express EGFRvIII 806CAR and the Chimeric IL7 Receptor

Figure 32:
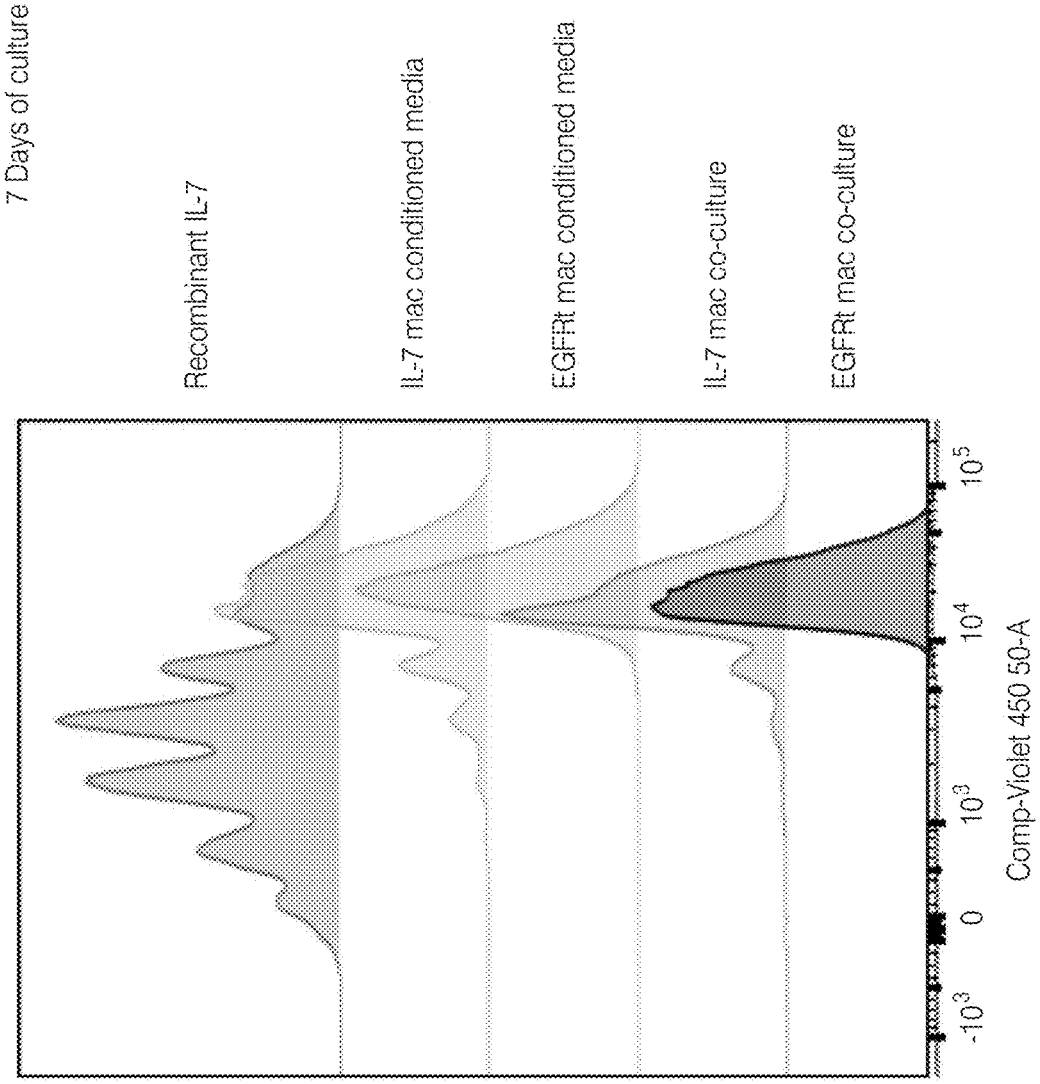
FIGS. 32 and 33 show expanded and cryogenically preserved CD4 and CD8 selected T cells were engineered to express the EGFRvIII 806CAR and the chimeric IL7 receptor (CD127) extracellular domain fused to the IL2 receptor (CD122) intracellular signaling domain and CD3/CD28 activated prior to freezing. Thawed CD4 or CD8 T cells were labeled with Cell Trace Violet, and cultured for 7 days with either recombinant IL-7 as a control (500 ng/ml), conditioned media frozen back from GEMs expressing either IL-7 or EGFRt (vector only), or co-cultured with autologous GEMs secreting IL-7 or EGFRt and analyzed using flow cytometry for CellTrace Violet dilution as a measure of proliferation. None of these were re-stimulated with CD3/CD28, nor did they receive any cytokines other than the IL-7.
Figure 33:
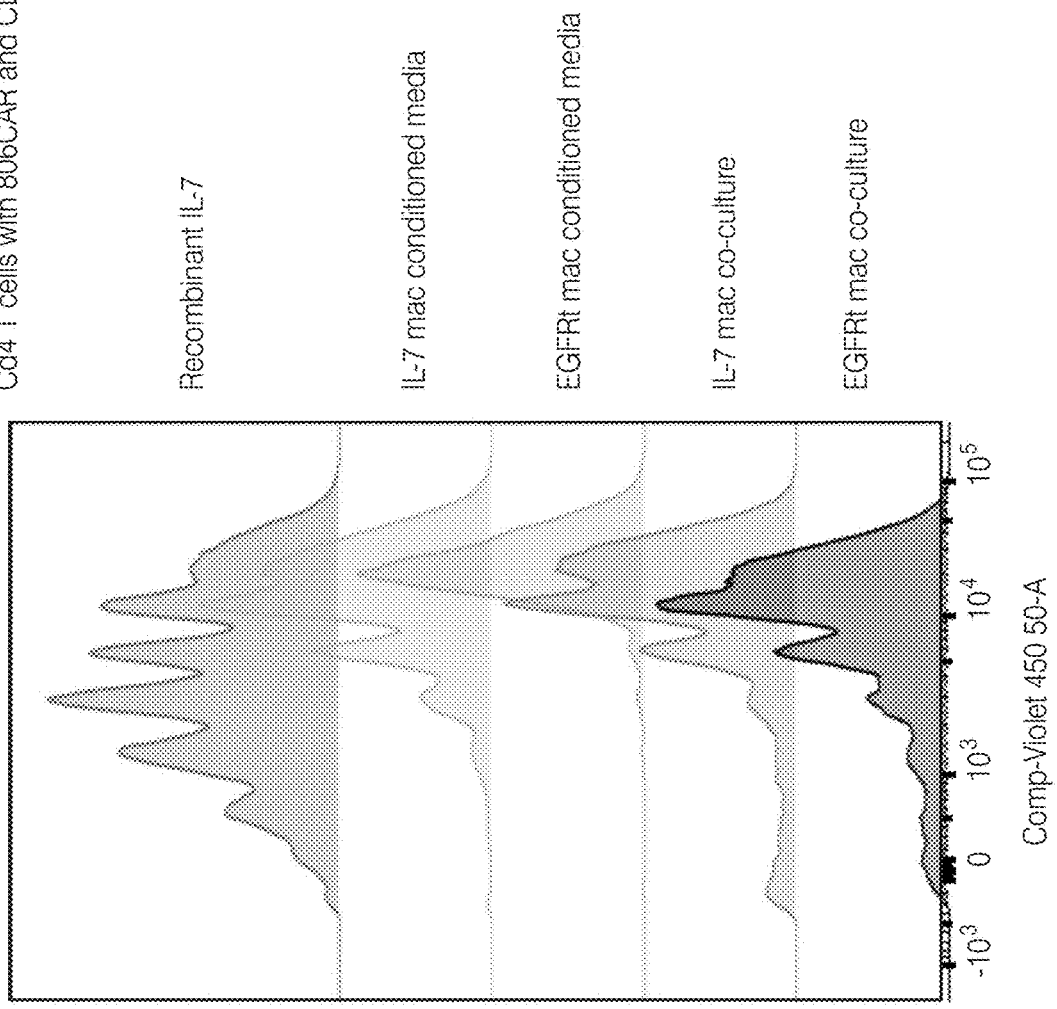

Expanded and cryogenically preserved CD4 and CD8 selected T cells were engineered to express the EGFRvIII 806CAR and the chimeric IL7 receptor (CD127) extracellular domain fused to the IL2 receptor (CD122) intracellular signaling domain and CD3/CD28 activated prior to freezing. Thawed CD4 or CD8 T cells were labeled with Cell Trace Violet, and cultured for 7 days with either recombinant IL-7 as a control (500 ng/ml), conditioned media frozen back from GEMs expressing either IL-7 or EGFRt (vector only), or co-cultured with autologous GEMs secreting IL-7 or EGFRt and analyzed using flow cytometry for CellTrace Violet dilution as a measure of proliferation. None of these were re-stimulated with CD3/CD28, nor did they receive any cytokines other than the IL-7. (See FIG. 32 and FIG. 33)

The IL-7 sequence, SEQ ID NO: 19 (Atgcttctcctggtgacaagccttctgctctgtgagttaacacaccagcat-tcctcctgatcccagattgtgatattgaaggtaaagat ggcaaacaatat-gagagtgttctaatggtcagcatcgatcaattattggacagcatgaaagaaat-tggtagcaattgcctgaataatgaa tttaacttttttaaaagacatatctgtgatgctaataaggaaggtatgtttttat-tccgtgctgctcgcaagttgaggcaatttcttaaaatgaat agcactggtgatttt-gatctccacttattaaaagtttcagaaggcacaacaatactgtt-gaactgcactggccaggttaaaggaagaaaa ccagctgccctgggtgaagcccaaccaacaaagagtttggaagaaaataaatctt-taaaggaacagaaaaaactgaatgacttgtgttt cctaaagagactatta-caagagataaaaacttgttggaataaaatttt-gatgggcactaaagaacacctcgagtga) was amplified using forward primer set forth in SEQ ID NO: 17 (atgcttctcctggtgacaagc) and reverse primer set forth in SEQ ID NO: 18

(gcagcccgggtctagagcggccgctcactcgaggtgttctttagtgc cc).

In some alternatives described herein, a method of making a genetically modified immune cell for modifying a tumor microenvironment (TME) is provided, the method comprising: delivering a first vector to an immune cell, wherein the first vector comprises a nucleic acid encoding a protein that induces T-cell proliferation, promotes persistence and/or activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the T-cell is a genetically modified T-cell. In some alternatives, the genetically modified T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the method further comprises delivering to the immune cell, a fourth vector, wherein the fourth vector encodes a Cas9 VP64 fusion protein to activate transcription and translation of a second protein and delivering to the immune cell a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, IL-15 is encoded by a sequence set forth in SEQ ID NO: 35. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene encodes IL-12p40, IL-15, IL-6, IL-1 beta, TNF-alpha, IFN-alpha/beta/gamma, IL-12, IL-18, IL-23 or GM-CSF. In some alternatives, IL-15 is encoded by a sequence set forth in SEQ ID NO: 35. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the immune cell is selected from the group consisting of a macrophage, allogeneic cell, myeloid cell and a monocyte. In some alternatives, the method further comprises differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor. In some alternatives, the T-cells that are proliferated are selected from the group consisting of T-helper Cells, memory T-cells, cytotoxic T-cells, suppressor T-cells, natural killer T cells, and gamma delta T-cells. In some alternatives small designer proteins are used to occupy the PD-1 binding site without delivery of an agonist signal. Additionally in some alternatives, single chain antibody-like proteins generated using the sequence of monoclonal antibodies developed to inhibit PD-1 signaling can be used to prevent complex agonist activity and is described in U.S. Pat. No. 8,008,449 B2 (incorporated by reference in its entirety). In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokines are selected from the group consisting of EGF, Eotaxin, FGF-2, FLT-3L, Fractalkine, G-CSF, GM-CSF, GRO, IL-10, IL-12(p40), IL-12(p70), IL-13, IL-13, IL-15, Il18A, IL-1RA, Il-1a, IL-1b, Il-2, Il-3, Il-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, 1309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the method further comprises delivering to the cell, a second vector, wherein the second vector comprises a nucleic acid encoding a Cas9 endonuclease and delivering to the cell a nucleic acid encoding a CRISPR guide RNA, wherein the CRISPR guide RNA is complimentary to at least one target gene in in the cell, and wherein said nucleic acid is present on the second vector or a third vector. In some alternatives, the second vector is an mRNA. In some alternatives, the target gene in the cell encodes TGF-beta or IL-10. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the method further comprises delivering to the cell, a fourth vector, wherein the fourth vector encodes a Cas9 protein fused to a transcriptional activator domain to activate transcription and translation of a second protein and delivering to the cell a fifth vector, wherein the fifth vector comprises a CRISPR guide RNA complimentary to at least one target gene in the cell. In some alternatives the transcriptional activation domain comprises a VP16, VP64 or a p65 activation domain. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives the at least one target gene is an endogenous pro-inflammatory gene. In some alternatives, the pro-inflammatory gene encodes IL-12p40, IL-15, IL-6, IL-1 beta, TNF-alpha, IFN-alpha/beta/gamma, IL-12, IL-18, IL-23 or GM-CSF. In some alternatives, IL-15 is encoded by a sequence set forth in SEQ ID NO: 35. In some alternatives, codon optimizing is done by OptimumGene', GeneGPS® algorithms and other programs known to those skilled in the art.

In some alternatives, a genetically modified immune cell comprising a first vector that comprises a nucleic acid encoding a protein that induces T-cell proliferation, promotes persistence and/or activation of endogenous or adoptively transferred NK or T cells and/or induces production of an interleukin, an interferon, a PD-1checkpoint binding protein, HMGB1, MyD88, or a cytokine is provided. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCA-GATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCT-CACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, IL-15 is encoded by a sequence set forth in SEQ ID NO: 35. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives small designer proteins are used to occupy the PD-1 binding site without delivery of an agonist signal. In some alternatives, the PD-L1 protein comprising residues 62-136 is used to block binding. In some alternatives, the protein is a fusion of PD-1 checkpoint binding protein and interferon alpha, interferon beta, or interferon gamma. In some alternatives, the cytokine is IL-2, IL-1β, IFNγ, IL-1, IL-7, IL-15, IL12, IL-18, IL-21 or IL-33. In some alternatives, the protein is TGFBRII, IL-1, IL-6, IL-7, IL-15, IL-2, IL-12, IL-18 or IL-21. In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the chemokines are selected from the group consisting of EGF, Eotaxin, FGF-2, FLT-3L, Fractalkine, G-CSF, GM-CSF, GRO, IL-10, IL-12(p40), IL-12 (p70), IL-13, IL-13, IL-15, Il18A, IL-1RA, Il-1a, IL-1b, Il-2, Il-3, Il-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, 1309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, IL-15 is encoded by a sequence set forth in SEQ ID NO: 35. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the second vector is an mRNA. In some alternatives, the target gene in the cell encodes TGF-beta or IL-10. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 protein fused to a transcriptional activator domain to activate transcription and translation of a second protein and a fifth vector, wherein the fifth vector comprises a CRISPR guide RNA complimentary to at least one target gene in the cell. In some alternatives the transcriptional activation domain comprises a VP16, VP64 or a p65 activation domain. More alternatives concern any one or more of the aforementioned genetically modified immune cells, alone or in combination, for use as a medicament e.g., to treat or inhibit a cancer such as a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122.

In some alternatives a composition is provided, wherein the composition comprises any one or more of the genetically modified immune cells of any one or more of the alternatives described herein and a carrier, anti-cancer therapeutic, anti-infection therapeutic, antibacterial therapeutic, anti-viral therapeutic, or anti-tumoral therapeutic. In some alternatives, the T-cells that are proliferated are selected from the group consisting of T-helper Cells, memory T-cells, cytotoxic T-cells, suppressor T-cells, natural killer T cells, and gamma delta T-cells.

In some alternatives, a composition is provided. The composition can comprise any one or more of the genetically modified immune cells of any one or more of the alternatives described herein and a carrier, anti-cancer therapeutic, anti-infection therapeutic, antibacterial therapeutic, anti-viral therapeutic, or anti-tumoral therapeutic. In some alternatives, the genetically modified immune cell comprises a first vector that comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine o, is provided. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, IL-15 is encoded by a sequence set forth in SEQ ID NO: 35. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives small designer proteins are used to occupy the PD-1 binding site without delivery of an agonist signal. In some alternatives, the PD-L1 protein comprising residues 62-136 is used to block binding. In some alternatives, the protein is a fusion of PD-1 checkpoint binding protein and interferon alpha, interferon beta, or interferon gamma. In some alternatives, the cytokine is IL-2, IL-1β, IFNγ, IL-1, IL-7, IL-15, IL12, IL-18, IL-21 or IL-33. In some alternatives, the protein is TGFBRII, IL-1, IL-6, IL-7, IL-15, IL-2, IL-12, IL-18 or IL-21. In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, IL-15 is encoded by a sequence set forth in SEQ ID NO: 35. In some alternatives, the chemokines are selected from a group consisting of EGF, Eotaxin, FGF-2, FLT-3L, Fractalkine, G-CSF, GM-CSF, GRO, IL-10, IL-12(p40), IL-12(p70), IL-13, IL-13, IL-15, Il18A, IL-1RA, Il-1a, IL-1b, Il-2, Il-3, Il-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, I309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the second vector is an mRNA. In some alternatives, the target gene in the cell encodes TGF-beta or IL-10. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 protein fused to a transcriptional activator domain to activate transcription and translation of a second protein and a fifth vector, wherein the fifth vector comprises a CRISPR guide RNA complimentary to at least one target gene in the cell. In some alternatives the transcriptional activation domain comprises a VP16, VP64 or a p65 activation domain.

In some alternatives, a method of modulating the suppression of the immune response in a tumor microenvironment of a subject in need thereof e.g., a human is provided, wherein the method comprises administering any one or more of the genetically modified immune cells of any one or more of the alternatives described herein or any one or more the compositions of any one of the alternatives described herein to a subject in need thereof and, optionally, selecting or identifying said subject to receive said genetically modified immune cells and/or measuring a modulation of suppression of the immune response in the tumor microenvironment of said subject after administration of said genetically modified immune cells. In some alternatives, the genetically modified immune cell comprises a first vector that comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, or a cytokine is provided. In some alternatives, the protein is a fusion of PD-1 checkpoint binding protein and interferon alpha, interferon beta, or interferon gamma. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the protein is a T-cell or NK-cell chemokine. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, IL-15 is encoded by a sequence set forth in SEQ ID NO: 35. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives small designer proteins are used to occupy the PD-1 binding site without delivery of an agonist signal. In some alternatives, the PD-L1 protein comprising residues 62-136, is used to block binding. In some alternatives, the protein is a fusion of PD-1 checkpoint binding protein and interferon alpha, interferon beta, or interferon gamma. In some alternatives, the cytokine is IL-2, IL-1β, IFNγ, IL-1, IL-7, IL-15, IL12, IL-18, IL-21 or IL-33. In some alternatives, the protein is TGFBRII, IL-1, IL-6, IL-7, IL-15, IL-2, IL-12, IL-18 or IL-21. In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, IL-15 is encoded by a sequence set forth in SEQ ID NO: 35. In some alternatives, the chemokines are selected from the group consisting of EGF, Eotaxin, FGF-2, FLT-3L, Fractalkine, G-CSF, GM-CSF, GRO, IL-10, IL-12(p40), IL-12(p70), IL-13, IL-13, IL-15, Il18A, IL-1RA, Il-1a, IL-1b, Il-2, Il-3, Il-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, 1309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the second vector is an mRNA. In some alternatives, the target gene in the cell encodes TGF-beta or IL-10. In some alternatives, the target gene is PD-L1, TGF-beta, IL-10, Arginase, HIF-1 alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 protein fused to a transcriptional activator domain to activate transcription and translation of a second protein and a fifth vector, wherein the fifth vector comprises a CRISPR guide RNA complimentary to at least one target gene in the cell. In some alternatives the transcriptional activation domain comprises a VP16, VP64 or a p65 activation domain. In some alternatives, the administering is performed by adoptive cell transfer. In some alternatives, the genetically modified immune cells are administered by direct delivery to a tumor bed by injection. In some alternatives, the subject in need suffers from cancer. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122. In some alternatives, the method further comprises administering a cellular therapy to the subject in need thereof before, after or simultaneous to introducing, providing, or administering any one or more of the cells of any one of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any one of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Gancirclovir, FK506 or a chemical inducer of dimerization. In some alternatives, the method further comprises administering to the subject a drug before, after or simultaneous to introducing, providing, or administering any one or more of the cells of any one of the alternatives described herein. In some alternatives, the drug is tamoxifen and/or its metabolites. In some alternatives, the subject is identified or selected to receive anti-cancer therapy, anti-infection therapy, antibacterial therapy, anti-viral therapy, or anti-tumoral therapy. In some alternatives, the method further comprises further comprising introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of any one of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragments thereof is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In some alternatives, a method of minimizing the proliferation of tumor and suppressive cells in a subject in need thereof is provided, wherein the method comprises administering any one or more of the genetically modified immune cells of any one or more of the alternatives described herein or any one or more the compositions of any one of the alternatives described herein to a subject in need thereof and, optionally, selecting or identifying said subject to receive said genetically modified immune cells and/or measuring the proliferation of tumor and suppressive cells in said subject after administration of said genetically modified immune cells. In some alternatives, the genetically modified immune cell comprises a first vector that comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, or a cytokine is provided. In some alternatives, the protein is a fusion of PD-1 checkpoint binding protein and interferon alpha, interferon beta, or interferon gamma. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, IL-15 is encoded by a sequence set forth in SEQ ID NO: 35. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives small designer proteins are used to occupy the PD-1 binding site without delivery of an agonist signal. In some alternatives, the PD-L1 protein comprising residues 62-136, is used to block binding. In some alternatives, the protein is a fusion of PD-1 checkpoint binding protein and interferon alpha, interferon beta, or interferon gamma. In some alternatives, the cytokine is IL-2, IL-1β, IFNγ, IL-1, IL-7, IL-15, IL12, IL-18, IL-21 or IL-33. In some alternatives, the protein is TGFBRII, IL-1, IL-6, IL-7, IL-15, IL-2, IL-12, IL-18 or IL-21. In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, IL-15 is encoded by a sequence set forth in SEQ ID NO: 35. In some alternatives, the chemokines are selected from the group consisting of EGF, Eotaxin, FGF-2, FLT-3L, Fractalkine, G-CSF, GM-CSF, GRO, IL-10, IL-12(p40), IL-12(p70), IL-13, IL-13, IL-15, Il18A, IL-1RA, Il-1a, IL-1b, Il-2, IL-3, Il-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, 1309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the second vector is an mRNA. In some alternatives, the target gene in the cell encodes TGF-beta or IL-10. In some alternatives, the target gene is PD-L1, TGF-beta, IL-10, Arginase, HIF-1 alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 protein fused to a transcriptional activator domain to activate transcription and translation of a second protein and a fifth vector, wherein the fifth vector comprises a CRISPR guide RNA complimentary to at least one target gene in the cell. In some alternatives the transcriptional activation domain comprises a VP16, VP64 or a p65 activation domain. In some alternatives, the composition comprises any one or more of the genetically modified immune cells of any one or more of the alternative genetically modified immune cells described herein and a carrier, anti-cancer therapeutic, anti-infection therapeutic, antibacterial therapeutic, anti-viral therapeutic, or anti-tumoral therapeutic. In some alternatives, the administering is performed by adoptive cell transfer. In some alternatives, the genetically modified immune cells are administered by direct delivery to a tumor bed by injection. In some alternatives, the subject in need suffers from cancer. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122. In some alternatives, the method further comprises administering a cellular therapy to the subject in need thereof before, after or simultaneous to introducing, providing, or administering any one or more of the cells of any one of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any one of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of any one of the alternatives described herein. In some alternatives, the drug is tamoxifen and/or its metabolites. In some alternatives, the subject is identified or selected to receive anti-cancer therapy, anti-infection therapy, antibacterial therapy, anti-viral therapy, or anti-tumoral therapy. In some alternatives, the method further comprises further comprising introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of any one of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In some alternatives, a method of increasing the efficiency of an anti-cancer therapy, anti-infection therapy, antibacterial therapy, anti-viral therapy, or anti-tumoral therapy in a subject e.g., a human in need thereof is provided, wherein the method comprises administering any one or more of the genetically modified immune cells of any one or more of the alternatives described herein or any one or more the compositions of any one of the alternatives described herein to a subject in need thereof and, optionally, selecting or identifying said subject to receive said genetically modified immune cells and/or measuring the proliferation of the cancer, infection, bacteria, virus, or tumor in said subject after administration of said genetically modified immune cells. In some alternatives, the genetically modified immune cell comprises a first vector that comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, or a cytokine is provided. In some alternatives, the protein is a fusion of PD-1 checkpoint binding protein and interferon alpha, interferon beta, or interferon gamma. In some alternatives, the T-cell is a modified T-cell. In some alternatives, the T-cell genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, IL-15 is encoded by a sequence set forth in SEQ ID NO: 35. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives small designer proteins are used to occupy the PD-1 binding site without delivery of an agonist signal. In some alternatives, the PD-L1 protein comprising residues 62-136, is used to block binding. In some alternatives, the protein is a fusion of PD-1 checkpoint binding protein and interferon alpha, interferon beta, or interferon gamma. In some alternatives, the cytokine is IL-2, IL-1β, IFNγ, IL-1, IL-7, IL-15, IL12, IL-18, IL-21 or IL-33. In some alternatives, the protein is TGFBRII, IL-1, IL-6, IL-7, IL-15, IL-2, IL-12, IL-18 or IL-21. In some alternatives, the chemokine is CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, IL-15 is encoded by a sequence set forth in SEQ ID NO: 35. In some alternatives, the chemokines are selected from the group consisting of EGF, Eotaxin, FGF-2, FLT-3L, Fractalkine, G-CSF, GM-CSF, GRO, IL-10, IL-12(p40), IL-12(p70), IL-13, IL-13, IL-15, 1118A, IL-1RA, Il-1a, IL-1b, Il-2, Il-3, IL-4, Il-5, Il-6, Il-7, IL-8, IL-9, INF-α2, INFγ, IP-10, MCP-1, MCP-3, MDC, MIP-1a, MIP-1b, PDGF-AA, PDGF-BB, RANTES, TGF-α, TGF-β, VEGF, sCD401, 6CKINE, BCA-1, CTACK, ENA78, Eotaxin-2, Eotaxin-3, 1309, IL-16, IL-20, IL-21, IL-23, IL-28a, IL-33, LIF, MCP-2, MCP-4, MIP-1d, SCF, SDF-1atb, TARC, TPO, TRAIL, TSLP, CCL1ra/HCC-1, CCL19/MIP beta, CCL20/MIP alpha, CXCL11/1-TAC, CXCL6/GCP2, CXCL7/NAP2, CXCL9/MIG, IL-11, IL-29/ING-gamma, M-CSF and XCL1/Lymphotactin. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the second vector is an mRNA. In some alternatives, the target gene in the cell encodes TGF-beta or IL-10. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the genetically modified immune cell further comprises a fourth vector, wherein the fourth vector encodes a Cas9 protein fused to a transcriptional activator domain to activate transcription and translation of a second protein and a fifth vector, wherein the fifth vector comprises a CRISPR guide RNA complimentary to at least one target gene in the cell. In some alternatives the transcriptional activation domain comprises a VP16, VP64 or a p65 activation domain. In some alternatives, the composition comprises any one or more of the genetically modified immune cells of any one or more of the alternative genetically modified immune cells described herein and a carrier, anti-cancer therapeutic, anti-infection therapeutic, antibacterial therapeutic, anti-viral therapeutic, or anti-tumoral therapeutic. In some alternatives, the administering is performed by adoptive cell transfer. In some alternatives, the genetically modified immune cells are administered by direct delivery to a tumor bed by injection. In some alternatives, the subject in need suffers from cancer. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122. In some alternatives, the method further comprises administering a cellular therapy to the subject in need thereof before, after or simultaneous to introducing, providing, or administering any one or more of the cells of any one of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any one of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of any one of the alternatives described herein. In some alternatives, the drug is tamoxifen and/or its metabolites. In some alternatives, the subject is identified or selected to receive anti-cancer therapy, anti-infection therapy, antibacterial therapy, anti-viral therapy, or anti-tumoral therapy. In some alternatives, the method further comprises further comprising introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of any one of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragments thereof is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In some alternatives, a method of making a genetically modified immune cell for modifying a tumor microenvironment (TME) of a tumor is provided. The method can include delivering a first vector to an immune cell, wherein the first vector comprises a nucleic acid encoding a protein that induces T-cell proliferation, promotes persistence and activation of endogenous or adoptively transferred NK or T cells and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein fragment, and wherein binding of the PD-L1 protein fragment does not cause an agonist signal upon binding PD-1. In some alternatives, the protein comprises a PD-1 protein fragment, wherein the PD-1 protein fragment binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1(KNIIQFVHGEEDLKVQHSSYRQRARLLKDQLSLGNAALQITDVKLQDAGVYRCM ISYGGADYKRITVKVNAPYNKI; SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the immune cell is selected from the group consisting of a macrophage, allogeneic cell, myeloid cell, a monocyte and a human monocyte. In some alternatives, the immune cell is a T cell. In some alternatives, the immune cell is an NK cell. In some alternatives, the immune cell is a genetically modified NK cell. In some alternatives, the T-cell is a genetically modified T-cell. In some alternatives, the genetically modified T-cell is genetically modified to express a chimeric antigen receptor (CAR) or T-cell receptor (Tcr). In some alternatives, the immune cell is a myeloid cell. In some alternatives, the myeloid cell is a macrophage. In some alternatives, the myeloid cell is a microglial cell. In some alternatives, the tumor is a glioma. In some alternatives, the tumor is a glioblastoma. In some alternatives, the method further comprises delivering to the immune cell, a second vector, wherein the second vector comprises a nucleic acid encoding a Cas9 endonuclease and delivering to the immune cell a nucleic acid encoding a CRISPR guide RNA, wherein the CRISPR guide RNA is complimentary to at least one target gene in in the cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the method further comprises delivering to the immune cell, a fourth vector, wherein the fourth vector encodes a Cas9 VP64 fusion protein to activate transcription and translation of a second protein and delivering to the immune cell a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the pro-inflammatory gene encodes IL-12p40, IL-15, IL-6, IL-1 beta, TNF-alpha, IFN-alpha/beta/gamma, IL-12, IL-18, IL-23 or GM-CSF. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the method further comprises differentiating the immune cells. In some alternatives, the immune cells are differentiated to a pro-inflammatory phenotype by culturing the cells with granulocyte macrophage colony stimulating factor. In some alternatives, the cells are differentiated to an anti-inflammatory phenotype by culturing the cells with a macrophage colony stimulating factor. In some alternatives, the composition comprises any one or more of the genetically modified immune cells of any one or more of the alternative genetically modified immune cells described herein and a carrier, anti-cancer therapeutic, anti-infection therapeutic, antibacterial therapeutic, anti-viral therapeutic, or anti-tumoral therapeutic.

In some alternatives, a genetically modified immune cell is provided for use as a medicament. The genetically modified immune cell can comprise a first vector wherein the first vector comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from a group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCA-GATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCT-CACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, IL-15 is encoded by a sequence set forth in SEQ ID NO: 35. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, a composition is provided. The composition can comprise any one or more of the genetically modified immune cells of any of the alternatives described herein and a carrier, anti-cancer therapeutic, anti-infection therapeutic, antibacterial therapeutic, anti-viral therapeutic, or anti-tumoral therapeutic. The genetically modified immune cell can comprise a first vector that comprises a nucleic acid encoding a protein that induces T-cell proliferation, promotes persistence and activation of endogenous or adoptively transferred NK or T cells and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/

CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid is present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

In some alternatives, a method of modulating the suppression of the immune response in a tumor microenvironment of a subject in need thereof e.g., a human is provided the method can comprise administering any one or more of the genetically modified immune cells of any one or more of the alternatives described herein or any of the compositions of any one or more of the alternatives described herein and a carrier, anti-cancer therapeutic, anti-infection therapeutic, antibacterial therapeutic, anti-viral therapeutic, or anti-tumoral therapeutic. The genetically modified immune cell can comprise a first vector that comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, IL-15 is encoded by a sequence set forth in SEQ ID NO: 35. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 binding and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCA-GATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCA-GATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCT-CACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the composition comprises any one or more of the genetically modified immune cells of any one or more of the alternative genetically modified immune cells described herein and a carrier, anti-cancer therapeutic, anti-infection therapeutic, antibacterial therapeutic, anti-viral therapeutic, or anti-tumoral therapeutic. In some alternatives, the administering is performed by adoptive cell transfer. In some alternatives, the genetically modified immune cells are administered by direct delivery to a tumor bed by injection. In some alternatives, the subject in need suffers from cancer or a subject having cancer is selected to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122. In some alternatives, the method further comprises administering a cellular therapy to the subject in need thereof before, after or simultaneous to introducing, providing, or administering any one or more of the cells of any of the alternatives described herein or the composition of any of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any of the alternatives described herein or the composition of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of anyone of the alternatives described herein or the composition of anyone of the alternatives described herein. In some alternatives, the subject is identified or selected to receive anti-cancer therapy, anti-infection therapy, antibacterial therapy, anti-viral therapy, or anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of anyone of the alternatives described herein or the composition of anyone of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragments thereof is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In some alternatives, a method of minimizing the proliferation of tumor and suppressive cells in a subject in need thereof is provided. The method can comprise administering any one or more of the genetically modified immune cells or any of the compositions of any one or more of the alternatives described herein to a subject in need thereof and, optionally, selecting or identifying said subject to receive said genetically modified immune cells and/or measuring the proliferation of tumor and suppressive cells in said subject after administration of said genetically modified immune cells. The genetically modified immune cell can comprise a first vector that comprises a nucleic acid encoding a protein that promotes persistence and activation of endogenous or adoptively transferred NK or T cells, induces T-cell proliferation and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from a group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. In some alternatives, the protein comprises interferon alpha, interferon beta, or interferon gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 binding and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCAGATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCAGATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCTCACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, IL-15 is encoded by a sequence set forth in SEQ ID NO: 35. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the composition comprises any one or more of the genetically modified immune cells of any one or more of the alternative genetically modified immune cells described herein and a carrier, anti-cancer therapeutic, anti-infection therapeutic, antibacterial therapeutic, anti-viral therapeutic, or anti-tumoral therapeutic. In some alternatives, the administering is performed by adoptive cell transfer. In some alternatives, the genetically modified immune cells are administered by direct delivery to a tumor bed by injection. In some alternatives, the subject in need suffers from cancer or a subject having cancer is selected to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122. In some alternatives, the method further comprises administering a cellular therapy to the subject in need thereof before, after or simultaneous to introducing, providing, or administering any one or more of the cells of any of the alternatives described herein or the composition of any of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any of the alternatives described herein or the composition of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the method further comprises administering to the subject a drug before, after or simultaneous to introducing, providing, or administering any one or more of the cells of anyone of the alternatives described herein or the composition of anyone of the alternatives described herein. In some alternatives, the subject is identified or selected to receive anti-cancer therapy, anti-infection therapy, antibacterial therapy, anti-viral therapy, or anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of anyone of the alternatives described herein or the composition of anyone of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragments thereof is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor.

In some alternatives, a method of increasing the efficiency of an anti-cancer therapy, anti-infection therapy, antibacterial therapy, anti-viral therapy, or anti-tumoral therapy in a subject in need thereof is provided. The method can comprise administering any one or more of the genetically modified immune cells or any of the compositions of any one or more of the alternatives described herein to a subject in need thereof and, optionally, selecting or identifying said subject to receive said genetically modified immune cells and/or measuring the proliferation of the cancer, infection, bacteria, virus, or tumor in said subject after administration of said genetically modified immune cells. In some alternatives, the composition comprises any one or more of the genetically modified immune cells of any one or more of the alternative genetically modified immune cells described herein and a carrier, anti-cancer therapeutic, anti-infection therapeutic, antibacterial therapeutic, anti-viral therapeutic, or anti-tumoral therapeutic. The genetically modified immune cell can comprise a first vector that comprises a nucleic acid encoding a protein that promotes persistence and activation of endogenous or adoptively transferred NK or T cells, induces T-cell proliferation and/or induces production of an interleukin, an interferon, a PD-1checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from the group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell antitumor activity. In some alternatives, the protein is TGFBRII, IL-1, IL-6, IL-7, IL-15, IL-2, IL-12, IL-18 or IL-21. In some alternatives, the protein comprises interferon alpha, interferon beta, or interferon gamma. In some alternatives, IL-15 is encoded by a sequence set forth in SEQ ID NO: 35. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 binding and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCA-GATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCA-GATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCT-CACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, IL-15 is encoded by a sequence set forth in SEQ ID NO: 35. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from a group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor. In some alternatives, the administering is performed by adoptive cell transfer. In some alternatives, the genetically modified immune cells are administered by direct delivery to a tumor bed by injection. In some alternatives, the subject in need suffers from cancer or a subject having cancer is selected to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the genetically modified immune cell expresses EGFRvIII 806 CAR and a chimeric IL7 receptor fused to CD122. In some alternatives, the method further comprises administering a cellular therapy to the subject in need thereof before, after or simultaneous to introducing, providing, or administering any one or more of the cells of any of the alternatives described herein or the composition of any of the alternatives described herein. In some alternatives, the cellular therapy is CAR T-cell therapy. In some alternatives, the method further comprises delivering antibodies or binding fragments thereof, small molecules, heat shock protein-peptide complexes or oncolytic polio virus to the subject in need thereof before, after, or simultaneous to introducing, providing, or administering any one or more of the cells of any of the alternatives described herein or the composition of any of the alternatives described herein into the subject for therapy. In some alternatives, the antibodies or binding fragments thereof are specific for alphafetoprotein, carcinoembryonic antigen, CA-125, MUC-1, Epithelial tumor antigen, Tyrosinase, Melanoma associated antigen (MAGE), HER2, and/or abnormal products of ras or p53. In some alternatives, the method further comprises administering to the subject in need a prodrug. In some alternatives, the prodrug is Erbitux, Herceptin, Ganciclovir, FK506 or a chemical inducer of dimerization. In some alternatives, the subject is identified or selected to receive anti-cancer therapy, anti-infection therapy, antibacterial therapy, antiviral therapy, or anti-tumoral therapy. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, after or simultaneous to introducing, providing, or administering any one or more of the cells of anyone of the alternatives described herein or the composition of anyone of the alternatives described herein. In some alternatives, the additional therapeutic agent is an anti-cancer therapy comprising a hormone blocking therapy, chemotherapy, a small molecule, monoclonal antibodies or binding fragments thereof, and/or radiation. In some alternatives, the monoclonal antibody or binding fragments thereof is specific for Her2, CD52, CD20, CD25, VEGF or EGRF. In some alternatives, the hormone blocking therapy comprises delivery of tamoxifen, anastrozole, and/or letrozole. In some alternatives, the small molecule comprises a tyrosine kinase inhibitor, a small molecule drug conjugates, a serine kinase inhibitor and/or a threonine kinase inhibitor. More alternatives concern any one or more of the aforementioned genetically modified immune cells, alone or in combination, for use as a medicament.

In some alternatives, the genetically modified immune cell of any one of the alternatives described herein is for use as a medicament e.g., to treat or inhibit a cancer. The genetically modified immune cell can comprise a first vector wherein the first vector comprises a nucleic acid encoding a protein that promotes persistence and activation of endogenous or adoptively transferred NK or T cells, induces T-cell proliferation and/or induces production of an interleukin, an interferon, a PD-1 checkpoint binding protein, HMGB1, MyD88, a cytokine or a chemokine. In some alternatives, the protein is a fusion of PD-1 checkpoint binding protein and interferon alpha, interferon beta, or interferon gamma. In some alternatives, the immune cell is a T-cell. In some alternatives, the immune cell is a modified T-cell. In some alternatives, the immune cell is genetically modified to express a chimeric antigen receptor (CAR) or T-cell receptor (Tcr). In some alternatives, the immune cell is an NK cell. In some alternatives, the immune cell is a genetically modified NK cell. In some alternatives, the immune cell is a myeloid cell. In some alternatives, the myeloid cell is a macrophage. In some alternatives, the myeloid cell is a microglial cell. In some alternatives, the immune cell is selected from a group consisting of a macrophage, allogeneic cell, myeloid cell, a monocyte and a human monocyte. In some alternatives, the first vector is a viral vector. In some alternatives, the viral vector is a lentiviral vector. In some alternatives, the lentiviral vector is packaged with a Vpx protein. In some alternatives, the protein supports or promotes T-cell and/or NK-cell anti-tumor activity. In some alternatives, the protein is TGFBRII, IL-1, IL-6, IL-7, IL-15, IL-2, IL-12, IL-18 or IL-21. In some alternatives, IL-15 is encoded by a sequence set forth in SEQ ID NO: 35. IL-15 can be amplified with a forward cloning primer comprising the sequence set forth in SEQ ID NO: 36 and a reverse cloning primer comprising a sequence set forth in SEQ ID NO: 37. In some alternatives, the protein comprises interferon alpha, beta, or gamma. In some alternatives, the protein comprises a PD-1 checkpoint binding inhibitor. In some alternatives, the PD-1 checkpoint binding inhibitor is a PD-L1 protein or active fragment thereof, and wherein binding of the PD-L1 protein or active fragment thereof does not cause an agonist signal upon binding PD-1. In some alternatives, the protein comprises a PD-1 protein fragment, wherein the PD-1 protein binds PD-L1 or PD-L2 expressed by tumor cells and/or associated macrophages, and wherein binding of the PD-1 protein fragment to PD-L1 or PD-L2 does not cause an agonist signal upon binding. In some alternatives, the PD-L1 protein fragment comprises amino acids 62-136 of PD-L1 (SEQ ID NO: 7). In some alternatives, the protein is a fusion of PD-1 checkpoint binding protein and interferon alpha, interferon beta, or interferon gamma. In some alternatives, the protein is a T-cell or NK-cell chemokine. In some alternatives, the chemokine comprises CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13 or CXCL15. In some alternatives, the genetically modified immune cell further comprises a second vector, wherein the second vector comprises a nucleic acid encoding a Cas9 endonuclease and a nucleic acid encoding a CRISPR guide RNA, wherein the CRISPR guide RNA is complimentary to at least one target gene in the immune cell, and wherein said nucleic acid can be present on the second vector or a third vector. In some alternatives, the second vector is an mRNA. In some alternatives, the Cas9 is codon optimized for expression in a eukaryotic cell, such as a human cell. In some alternatives, the target gene is PD-L1, TGF-beta, IL-10, Arginase, HIF-1alpha, RAGE, CD206, IL-4, CCL22, CCL17, VEGF, EGF, WNT7beta, or PGE. In some alternatives, the primers for small guide RNAs for PDL1 CRISPR deletion comprise a forward primer comprising a sequence set forth in SEQ ID NO: 20 (CACCGGTCCA-GATGACTTCGGCCTT) and a reverse primer comprising a sequence set form in SEQ ID NO: 21 (AAACAAGGCCGAAGTCATCTGGACC). In some alternatives, the PD-L1 small guide RNA sequence comprises a sequence set forth in SEQ ID NO: 22 (TCCA-GATGACTTCGGCCTTG). In some alternatives, the primers for the IL-10 small guide RNA sequence comprises a forward primer comprising a sequence set forth in SEQ ID NO: 23 (AGGAACACGCGAATGAGAACCC) and a reverse primer comprising a sequence set forth in SEQ ID NO: 24 (TGCAAGGCATGGGGAGCATCTT). In some alternatives, the IL-10 small guide RNA sequence comprises a sequence set forth in SEQ ID NO: 25 (GGCTGGCCCT-CACCCCAGT). In some alternatives, the genetically modified immune cell further comprises a fourth vector, wherein the fourth vector encodes a Cas9 VP64 fusion protein to activate transcription and translation of a second protein and a fifth vector, wherein the fifth vector comprises a CRISPR guide RNA complimentary to at least one target gene in the cell. In some alternatives, the second protein is IL-12p40, IL-15, IL-6, IL-1 beta, TNF-alpha, IFN-alpha/beta/gamma, IL-12, IL-18, IL-23 or GM-CSF. In some alternatives, the fourth vector is an mRNA. In some alternatives, the mRNA is codon optimized for expression in a eukaryotic cell, such as a human cell. In some alternatives, the at least one target gene is an endogenous pro-inflammatory gene. In some alternatives, the at least one target gene encodes for TGF-beta, IL-10, Arginase, HIF-1alpha, RAGE, CD206, IL-4, CCL22, CCL17, VEGF, EGF, WNT7beta, or PGE. In some alternatives, the first vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the nucleic acid encoding said protein is under the control of a regulatory element. In some alternatives, the regulatory element is a promoter that is inducible by a drug. In some alternatives, the regulatory element is a promoter that is inducible by a steroid, such as a ligand for the estrogen receptor. In some alternatives, the regulatory element is a promoter inducible by tamoxifen and/or its metabolites. In some alternatives, the cell is selected from the group consisting of a macrophage, allogeneic cell, myeloid cell, a monocyte and a primary human monocyte. In some alternatives, the cell is a primary human monocyte. In some alternatives, the immune cells are differentiated. In some alternatives, the immune cells are differentiated to a pro-inflammatory phenotype by culturing the cells with granulocyte macrophage colony stimulating factor. In some alternatives, the immune cells are differentiated to an anti-inflammatory phenotype by culturing the cells with a macrophage colony stimulating factor.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

---

What is claimed is:

1. A method of making a genetically modified immune cell, comprising:
delivering a first vector to an immune cell, wherein the first vector comprises a VPX protein and a nucleic acid encoding a payload protein; and
differentiating the immune cell concurrently with delivering a first vector to an immune cell.

2. The method of claim 1, wherein the first vector is a lentiviral vector.

3. The method of claim 1, wherein the differentiating the immune cell comprises contacting the immune cell with (i) GM-CSF in the absence of IL-4, or (ii) M-CSF.

4. The method of claim 1, wherein the immune cell is selected from the group consisting of a macrophage, a monocyte-derived macrophage, a myeloid cell, a monocyte, a dendritic cell, and a microglial cell.

5. The method of claim 1, wherein the delivering comprises contacting the immune cell with the first vector at a multiplicity of infection (MOI) of 250 or less.

6. The method of claim 1, wherein the delivering comprises contacting the immune cell with the first vector at a multiplicity of infection (MOI) of 15 or less.

7. The method of claim 1, wherein the nucleic acid encodes a payload protein selected from the group consisting of IL-1, IL-6, IL-7, IL-15, IL-2, IL-12, IL-18, IL-21, interferon alpha, interferon beta, interferon gamma, a T-cell chemokine, NK-cell chemokine, a PD1-checkpoint binding inhibitor, and a PD-1 fusion.

8. The method of claim 1, wherein the payload protein comprises (i) a fusion protein comprising: a PD-1 checkpoint binding protein, and a protein selected from interferon alpha, interferon beta, or interferon gamma; (ii) a PD-1 protein fragment capable of binding to a PD-L1 protein or a PD-L2 protein, and wherein the PD-1 protein fragment lacks activity to cause an agonist signal on binding to the PD-L1 protein or the PD-L2 protein: (iii) a cell surface selectable marker selected from a truncated EGFR polypeptide (EGFRt), and a truncated CD19 polypeptide (CD19t); or (iv) a chimeric antigen receptor (CAR).

9. The method of claim 8, wherein the PD-1 protein fragment comprises amino acids 62-136 of the amino acid sequence set forth in SEQ ID NO: 7.

10. The method of claim 1, wherein the first vector further comprises a nucleic acid encoding a suicide gene system.

11. The method of claim 1, wherein the nucleic acid encoding a payload protein is operably linked to an inducible promoter.

12. The method of claim 1, further comprising:
delivering a second vector to the immune cell, wherein the second vector comprises a nucleic acid encoding a Cas9 endonuclease; and
delivering a first polynucleotide to the immune cell, wherein the first polynucleotide encodes a CRISPR guide RNA.

13. The method of claim 12, wherein the CRISPR guide RNA is complimentary to a target gene selected from the group consisting of TGF-beta, IL-10, Arginase, HIF-1alpha, RAGE, CD206, IL-4, CCL22, CCL17, VEGF, EGF, WNT7beta, and PGE.

14. The method of claim 1, further comprising:
delivering an additional vector to the immune cell, wherein the additional vector comprises a nucleic acids encoding a Cas9 VP64 fusion protein; and
delivering a second polynucleotide to the immune cell, wherein the second polynucleotide comprises a CRISPR guide RNA.

15. The method of claim 14, wherein the Cas9 VP64 fusion protein is capable of activating transcription or translation of a protein selected from the group consisting of is IL-12p40, IL-15, IL-6, IL-1 beta, TNF-alpha, IFN-alpha, ILN-beta, IFN-gamma, IL-12, IL-18, IL-23, and GM-CSF.

16. The method of claim 1, wherein the immune cell is human.

17. The method of claim 1, wherein the immune cell is a primary monocyte.

18. A method of making a genetically modified immune cell, comprising:
(i) delivering a vector to a primary monocyte, wherein the vector comprises a VPX protein and a nucleic acid encoding a payload; and
(ii) differentiating the primary monocyte, wherein step (ii) is performed concurrently with step (i).

19. The method of claim 18, wherein the differentiating comprises contacting the immune cell with GM-CSF in the absence of IL-4.

20. The method of claim 4, wherein the immune cell is selected from the group consisting of a macrophage, a monocyte-derived macrophage, and a monocyte.

* * * * *